(12) United States Patent
Mevellec et al.

(10) Patent No.: US 10,202,387 B2
(45) Date of Patent: *Feb. 12, 2019

(54) HETEROCYCLYL LINKED IMIDAZOPYRIDAZINE DERIVATIVES AS PI3KB INHIBITORS

(71) Applicant: Janssen Pharmaceutica NV, Beerse (BE)

(72) Inventors: Laurence Anne Mevellec, Louviers (FR); Lieven Meerpoel, Beerse (BE); Sophie Coupa, Belbeuf (FR); Virginie Sophie Poncelet, Le Manoir sur Seine (FR); Isabelle Noelle Constance Pilatte, Louviers (FR); Elisabeth Therese Jeanne Pasquier, Val de Reuil (FR); Didier Jean-Claude Berthelot, La Neuville Chant d'Oisel (FR); Olivier Alexis Georges Querolle, Saint Vigor (FR); Christophe Meyer, Les Authieux sur le Port St Ouen (FR); Patrick Rene Angibaud, Saint Pierre d'Autils (FR); Christophe Gabriel Marcel Demestre, Saint Jean du Thenney (FR); Guillaume Jean Maurice Mercey, Montaure (FR)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/537,619

(22) PCT Filed: Dec. 18, 2015

(86) PCT No.: PCT/EP2015/080623
§ 371 (c)(1),
(2) Date: Jun. 19, 2017

(87) PCT Pub. No.: WO2016/097359
PCT Pub. Date: Jun. 23, 2016

(65) Prior Publication Data
US 2018/0057496 A1 Mar. 1, 2018

(30) Foreign Application Priority Data
Dec. 19, 2014 (EP) ..................................... 14199344

(51) Int. Cl.
*A61K 31/5377* (2006.01)
*C07D 487/04* (2006.01)
*C07D 405/10* (2006.01)
*C07B 59/00* (2006.01)
*C07D 519/00* (2006.01)

(52) U.S. Cl.
CPC ........ *C07D 487/04* (2013.01); *A61K 31/5377* (2013.01); *C07B 59/002* (2013.01); *C07D 405/10* (2013.01); *C07D 519/00* (2013.01); *C07B 2200/05* (2013.01)

(58) Field of Classification Search
None
See application file for complete search history.

(56) References Cited

U.S. PATENT DOCUMENTS

| 2013/0157977 A1 | 6/2013 | Rivero et al. |
| 2014/0187545 A1* | 7/2014 | Lin ..................... C07D 487/04 514/230.8 |

FOREIGN PATENT DOCUMENTS

| WO | 2007038314 | 4/2007 |
| WO | 2008008539 A2 | 1/2008 |
| WO | 2008014219 | 1/2008 |
| WO | 2008030579 | 3/2008 |
| WO | 2009060197 A2 | 7/2009 |
| WO | 2009091374 A2 | 7/2009 |
| WO | 2011022439 | 2/2011 |
| WO | 2011058109 | 5/2011 |
| WO | 2011123751 | 10/2011 |

(Continued)

OTHER PUBLICATIONS

B.Vanhasesbroeck et al, Signaling by distinct classes of phosphoinositide 3-kinases, Experimental Cell Research, 1999, pp. 239-254, 253.

(Continued)

*Primary Examiner* — Samantha L Shterengarts

(57) ABSTRACT

The present invention relates to heterocyclyl linked imidazopyridazine derivatives of Formula (I)

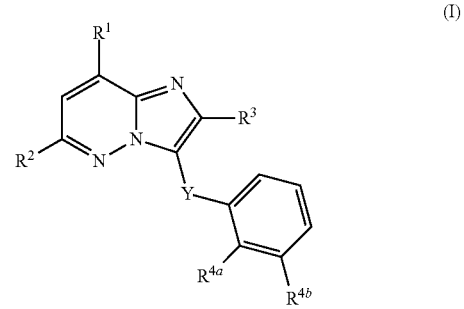

wherein the variables have the meaning defined in the claims. The compounds according to the present invention are useful as PI3Kβ inhibitors. The invention further relates to processes for preparing such novel compounds, pharmaceutical compositions comprising said compounds as an active ingredient as well as the use of said compounds as a medicament.

14 Claims, No Drawings

(56) References Cited

FOREIGN PATENT DOCUMENTS

| WO | 2012047538 | 4/2012 |
| WO | 2012116237 | 8/2012 |
| WO | 2013028263 | 2/2013 |
| WO | 2013095761 A1 | 6/2013 |
| WO | 2014078211 | 5/2014 |

OTHER PUBLICATIONS

David Stokoe et al, Dual role of phosphatidylinositol-3,4,5-trisposphate in the activation of protein kinase B, Science, Jul. 25, 1997, pp. 567-570, 277.

Dr Calnan et al, The FoxO code, Oncogene, 2008, pp. 2276-2288, 27.

Kevin D. Courtney En Al, The PI3K pathways as drug target in human cancer, Journal of clinical oncology, Feb. 20, 2010, pp. 1075-1083, 28.

L Zhao et al, Class I PI3K in oncogenic cellular transformation, Oncogene, 2008. pp. 5486-5496, 27.

Michael P. Meyers et al, The lipid phosphatase activity of PTEN is critical for its tumor supressor function, Proc. Natl.Acad.Sci.USA, Nov. 1998, pp. 13513-13518, 95.

Rute B. Marques et al, High Efficacy of Combination Therapy Using PI3K/AKT inhibitors with Androgen Deprivation in Prostate Cancer Preclinical Models, European Urology, 2014, pp. 1177-1185, 67.

Shaun P. Jackson, PI 3-kinase p. 110b a new target for antithrombotic therapy, Nature medicine, May 2005, pp. 507-514, 11.

Shidong Jia et al, Essential roles of PI(3)K-p110Bin cell growth metabolism and tuniorgenesis, Nature, August, pp. 776-779, 454.

Susan Wee et al, PTEN-deficient cancers depend on PIL3CB, PNAS, Sep. 2, 2008, pp. 13057-13082, 105.

* cited by examiner

HETEROCYCLYL LINKED IMIDAZOPYRIDAZINE DERIVATIVES AS PI3KB INHIBITORS

CROSS REFERENCE TO RELATED APPLICATIONS

This application is a national stage application of International Patent Application No. PCT/EP2015/080623, filed 18 Dec. 2015, which claims priority from EP Application 1419344.4 filed 19 Dec. 2014. The complete disclosures of the aforementioned related patent applications are hereby incorporated herein by reference for all purposes.

FIELD OF THE INVENTION

The present invention relates to heterocyclyl linked imidazopyridazine derivatives useful as PI3Kβ inhibitors. The invention further relates to processes for preparing such compounds, pharmaceutical compositions comprising said compounds as an active ingredient as well as the use of said compounds as a medicament.

BACKGROUND OF THE INVENTION

There are three classes of phosphoinositide-3-kinases (PI3Ks): class I, class II and class III. Class I PI3Ks are the most associated with human cancer [K. D Courtney, R. B. Corcoran and J. A. Engelman (2010), *Journal of Clinical Oncology.*, 28; 1075]. The class I phosphoinositide-3-kinases (PI3Ks) are divided into 2 subclasses: class $I_A$, composed of a p110 catalytic subunit (p110a, p110b or p110d) and a p85 regulatory subunit (p85a, p55a and p50a, p85b or p55g) and class $I_B$ PI3K represented by the p110g catalytic subunit and the p101 and p84 regulatory subunits [B. Vanhaesebroeck and M. D. Waterfield (1999) *Experimental Cell Research.*, 253, 239-254]. The class $I_A$ PI3Ks are activated in a variety of solid and non-solid tumors via mutation or deletion of the tumor suppressor PTEN (phosphatase and tensin homolog) or in the case of p110a by activating mutations [K. D Courtney, R. B. Corcoran and J. A. Engelman (2010), *Journal of Clinical Oncology*, 28; 1075]. PI3Ks can also be activated by receptor tyrosine kinases (RTKs); p110b can be activated by G-protein coupled receptors [K. D Courtney, R. B. Corcoran and J. A. Engelman (2010), *Journal of Clinical Oncology.*, 28; 1075]. Once activated the phosphoinositide-3-kinases catalyze the phosphorylation of phosphatidyl 4,5-diphosphate leading to the generation of phosphatidyl, 3,4,5-triphosphate (PIP3) [Zhao L., Vogt P. K. (2008) Oncogene 27, 5486-5496]. PTEN antagonizes the activity of the PI3Ks through the dephosphorylation PIP3 [Myers M. P., Pass I., Batty I. H., Van der Kaay J., Stolarov J. P., Hemmings B. A., Wigler M. H., Downes C. P., Tonks N. K. (1998) *Proc. Natl. Acad. Sci. U.S.A.* 95, 13513-13518]. The PIP3 generated by activation of PI3K or sustained by the inactivation of PTEN binds to a subset of lipid-binding domains in downstream targets such as the pleckstrin homology domain of the oncogene Akt thereby recruiting it to the plasma membrane [Stokoe D., Stephens L. R., Copeland T., Gaffney P. R., Reese C. B., Painter G. F., Holmes A. B., McCormick F., Hawkins P. T. (1997) *Science* 277, 567-570]. Once at the plasma membrane Akt phosphorylates several effector molecules that are involved in numerous biologically relevant processes such as metabolism, differentiation, proliferation, longevity and apoptosis [D. R. Calnan and A. Brunet (2008) *Oncogene* 27; 2276)].

Several studies suggest a key role for p110b in PTEN-deficient tumors. For example the genetic knockout of p110b, but not p110a, is able to block tumor formation and Akt activation driven by Pten loss in the anterior prostate in a mouse model [Jia S, Liu Z, Zhang S. Liu P, Zhang L, Lee S H, Zhang J, Signoretti S, Loda M, Roberts T M, Zhao J J. *Nature* 2008; 454:776-9]. Furthermore other studies have shown that a subset of PTEN-deficient human tumor cell lines is sensitive to inactivation of p110b rather than p110a [Wee S. Wiederschain D. Maira S M, Loo A, Miller C, deBeaumont R, Stegmeier F, Yao Y M, Lengauer C (2008) *Proc. Natl. Acad. Sci* (USA); 105 13057]. PTEN deficiency either by genetic inactivation or reduced expression frequently occurs in human cancers such as GBM, endometrial, lung, breast cancers and prostate cancer among others [K. D Courtney, R. B. Corcoran and J. A. Engelman (2010), *Journal of Clinical Oncology.*, 28; 1075].

These studies suggest that treatment of PTEN-deficient cancer with agents that inhibition p110b may be therapeutically beneficial. In addition to its role in cancer, p110b may be a target for antithrombotic therapy. It has been reported in mouse models that PI3Kb inhibition can prevent stable integrin $a_{IIb}b_3$ adhesion contacts that eliminates occulusive thrombus formation without prolongation of bleed time [S. P. Jackson et al. (2005) *Nature Medicine.*, 11, 507-514].

Furthermore, the phosphatidylinositol-4,5-bisphosphate 3-kinase (PI3K)/AKT pathway is frequently activated during prostate cancer (PCa) progression through loss or mutation of the phosphatase and tensin homolog (PTEN) gene. Following the androgen receptor (AR) pathway, it is the second major driver of PCa growth. Combination with hormonal therapy improved efficacy of PI3K/AKT-targeted agents in PTEN-negative PCa models. Upregulation of AR-target genes upon PI3K/AKT inhibition suggests a compensatory crosstalk between the PI3K-AR pathways which, for optimal efficacy treatment, could require cotargeting of the AR axis [Marques R B, et al., High Efficacy of Combination Therapy Using PI3K/AKT Inhibitors with Androgen Deprivation in Prostate Cancer Preclinical Models. *Eur Urol* (2014), http://dx.doi.org/10.1016/j.eururo.2014.08.053]. Therefore PI3Kβ inhibitors can be advantageously combined with anti-androgen therapies including androgen receptor antagonists and inhibitors of androgen biosynthesis in PTEN-negative prostate cancers.

WO 2009/060197 discloses imidazopyridazines for use as protein kinase inhibitors.

WO 2012/116237 discloses heterocyclic entitites that modulate PI3 kinase activity.

WO 2011/123751 describes heterocyclic compounds as selective inhibitors of PI3K activity.

WO 2011/058109 relates to a series of fused bicyclic pyrrole and imidazole derivatives as kinase inhibitors.

WO 2011/022439 discloses heterocyclic entities that modulate PI3 kinase activity.

WO 2008/014219 describes thiozolidinedione derivatives as PI3 kinase inhibitors.

WO 2013/028263 relates to pyrazolopyrimidine derivatives as PI3 kinase inhibitors.

WO 2012/047538 relates to benzimidazole derivatives as PI3 kinase inhibitors.

WO 2013/095761 relates to imidazopyridine derivatives as PI3 kinase inhibitors.

US 2013/0157977 relates to benzimidazole boronic acid derivatives as PI3 kinase inhibitors.

WO2007/038314 discloses heterocyclic compounds useful as kinase modulators.

WO2008/030579 describes modulators of IRAK kinase.

WO2009/091374 and WO2008/008539 relate to fused heterocyclic derivatives for prophylaxis and treatment of diseases, such as HGF mediated diseases.

WO 2014/078211 discloses heteroaromatic compounds as PI3 kinase modulators.

WO 2008/138834 relates to substituted imidazopyridazines as PI3K lipid kinase inhibitors.

WO 2010/007099 describes 2-aminoimidazo[1,2-b]pyridazine derivatives as PI3K inhibitors.

WO 2011/047770 discloses pyrazolopyrimidine derivatives as PI3K inhibitors.

There is thus a strong need for novel PI3Kβ kinase inhibitors thereby opening new avenues for the treatment or prevention of cancer, in particular PTEN-deficient cancers, more in particular prostate cancer. It is accordingly an object of the present invention to provide such compounds.

SUMMARY OF THE INVENTION

It has been found that the compounds of the present invention are useful as PI3Kβ inhibitors. The compounds according to the invention and compositions thereof, may be useful for the treatment or prevention, in particular for the treatment, of diseases such as cancer, autoimmune disorders, cardiovascular diseases, inflammatory diseases, neurodegenerative diseases, allergy, pancreatitis, asthma, multiorgan failure, kidney diseases, platelet aggregation, sperm motility, transplantation rejection, graft rejection, lung injuries and the like.

This invention concerns compounds of Formula (I)

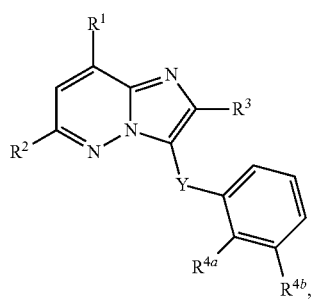

(I)

tautomers and stereoisomeric forms thereof, wherein
$R^1$ represents —C(=O)OH, —C(=O)NH$_2$, —NH$_2$,

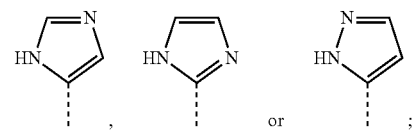

or $R^2$ represents

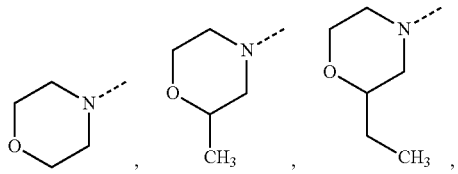

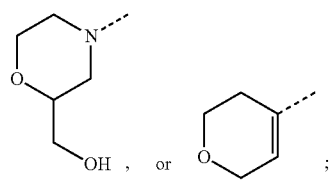

$R^3$ represents $C_{1-4}$alkyl substituted with one substituent selected from the group consisting of Het$^1$, —O—C(=O)—$C_{1-4}$alkyl-Het$^1$, —C(=O)-Het$^1$, and —NH—C(=O)-Het$^1$; —CH(OH)—CH$_2$-Het$^1$; or $C_{1-4}$alkyl substituted on the same carbon atom with one —OH and with one Het$^1$;

Het$^1$ represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of halo, —NH$_2$, $C_{1-4}$alkyl, —S(=O)$_2$—$C_{1-6}$alkoxy, —$C_{1-4}$alkyl-S(=O)$_2$—$C_{1-6}$alkyl, hydroxy and $C_{1-4}$alkyl substituted with one hydroxy; or two substituents on the same carbon atom of said 4-, 5- or 6-membered saturated heterocyclyl are taken together to form together with the common carbon atom to which they are attached Ring A;

Ring A represents cyclobutyl, cyclopentyl, cyclohexyl or a 4-, 5- or 6-membered saturated heterocyclyl containing at least one heteroatom each independently selected from O, S, S(=O)$_p$ and N; said cyclobutyl, cyclopentyl, cyclohexyl or 4-, 5- or 6-membered saturated heterocyclyl is optionally substituted with one or two substituents, with one $C_{1-4}$alkyl and one hydroxy substituent, or with one hydroxy substituent;

Y represents —CH$_2$— or —NH—;

$R^{4a}$ represents hydrogen, $C_{1-4}$alkyl, Het$^a$, or $C_{1-4}$alkyl substituted with one or more substituents each independently selected from the group consisting of —OH, —NR$^5$R$^6$ and Het$^a$;

$R^{4b}$ represents hydrogen, halo, $C_{1-4}$alkyl, or $C_{1-4}$alkyl substituted with one or more halo substituents;

or $R^{4a}$ and $R^{4b}$ are taken together to form together with the phenyl ring to which they are attached a structure of Formula (a-1), (a-2), (a-3), (a-4) or (a-5):

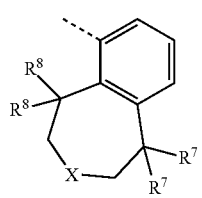

(a-1)

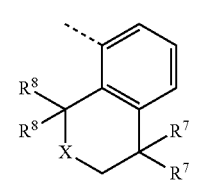

(a-2)

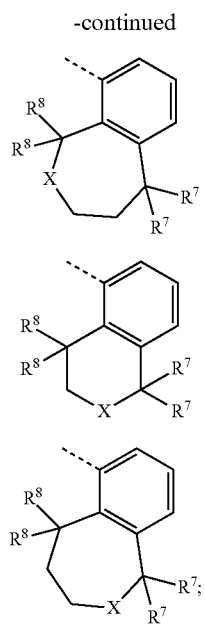

X represents —NH—, —O— or —N($C_{1-3}$alkyl)-;
both $R^7$ substituents are the same and are selected from the group consisting of hydrogen, fluoro and methyl; or both $R^7$ substituents are taken together to form together with the common carbon atom to which they are attached a cyclopropyl, cyclobutyl or oxetanyl;
both $R^8$ substituents are the same and are selected from the group consisting of hydrogen and methyl; or both $R^8$ substituents are taken together to form together with the common carbon atom to which they are attached a cyclopropyl, cyclobutyl or oxetanyl;
$R^5$ represents hydrogen, $C_{1-6}$alkyl, or $C_{1-6}$alkyl substituted with one OH;
$R^6$ represents hydrogen, $C_{1-6}$alkyl, or $C_{1-6}$alkyl substituted with one OH;
each $Het^a$ independently represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of $C_{1-4}$alkyl, —S(=O)$_2$—$C_{1-6}$alkyl, hydroxy, —$C_{1-4}$alkyl-S(=O)$_2$—$C_{1-6}$ alkyl, and $C_{1-4}$alkyl substituted with one hydroxy; or two substituents on the same carbon atom of said 4-, 5- or 6-membered saturated heterocyclyl are taken together to form together with the common carbon atom to which they are attached Ring B;
Ring B represents cyclobutyl, cyclopentyl, cyclohexyl or a 4-, 5- or 6-membered saturated heterocyclyl containing at least one heteroatom each independently selected from O, S, S(=O)$_p$ and N; said cyclobutyl, cyclopentyl, cyclohexyl or 4-, 5- or 6-membered saturated heterocyclyl is optionally substituted with one or two $C_{1-4}$alkyl substituents, with one $C_{1-4}$alkyl and one hydroxy substituent, or with one hydroxy substituent;
p represents 1 or 2;
and the N-oxides, the pharmaceutically acceptable addition salts, and the solvates thereof.

The present invention also concerns methods for the preparation of compounds of the present invention and pharmaceutical compositions comprising them.

The compounds of the present invention were found to inhibit PI3Kβ, and therefore may be useful in the treatment or prevention, in particular in the treatment, of diseases such as cancer, autoimmune disorders, cardiovascular diseases, inflammatory diseases, neurodegenerative diseases, allergy, pancreatitis, asthma, multiorgan failure, kidney diseases, platelet aggregation, sperm motility, transplantation rejection, graft rejection, lung injuries and the like.

Some of the compounds of the present invention may undergo metabolism to a more active form in vivo (prodrugs).

In view of the aforementioned pharmacology of the compounds of Formula (I) and N-oxides, pharmaceutically acceptable addition salts, and solvates thereof, it follows that they may be suitable for use as a medicament.

In particular the compounds of Formula (I) and N-oxides, pharmaceutically acceptable addition salts, and solvates thereof may be suitable in the treatment or prevention, in particular in the treatment, of cancer.

The present invention also concerns the use of compounds of Formula (I) and N-oxides, pharmaceutically acceptable addition salts, and solvates thereof, for the manufacture of a medicament for the inhibition of PI3Kβ, for the treatment or prevention of cancer. The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

When any variable occurs more than one time in any constituent or in any formula (e.g. Formula (I)), its definition in each occurrence is independent of its definition at every other occurrence.

Whenever the term "substituted" is used in the present invention, it is meant, unless otherwise is indicated or is clear from the context, to indicate that one or more hydrogens, in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The skilled person will understand that the term "optionally substituted" means that the atom or radical indicated in the expression using "optionally substituted" may or may not be substituted (this means substituted or unsubstituted respectively).

When two or more substituents are present on a moiety they may, unless otherwise is indicated or is clear from the context, replace hydrogens on the same atom or they may replace hydrogen atoms on different atoms in the moiety.

It will be clear for the skilled person that, unless otherwise is indicated or is clear from the context, a substituent on a heterocyclyl group may replace any hydrogen atom on a ring carbon atom or on a ring heteroatom.

The prefix "$C_{x-y}$" (where x and y are integers) as used herein refers to the number of carbon atoms in a given group. Thus, a $C_{1-6}$alkyl group contains from 1 to 6 carbon atoms, a $C_{1-4}$alkyl group contains from 1 to 4 carbon atoms, a $C_{1-3}$alkyl group contains from 1 to 3 carbon atoms and so on.

The term "halo" as a group or part of a group is generic for fluoro, chloro, bromo, iodo unless otherwise is indicated or is clear from the context.

The term "$C_{1-6}$alkyl" as a group or part of a group refers to a hydrocarbyl radical of Formula $C_nH_{2n+1}$ wherein n is a number ranging from 1 to 6. $C_{1-6}$alkyl groups comprise from 1 to 6 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl includes all linear, or branched alkyl groups with between 1 and 6 carbon atoms, and thus includes such as for example methyl, ethyl, n-propyl, i-propyl, 2-methyl-ethyl, butyl and its isomers (e.g. n-butyl, isobutyl and tert-butyl), pentyl and its isomers, hexyl and its isomers, and the like.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl groups may be linear or branched and may be substituted as indicated herein. When a subscript is used herein following a carbon atom, the subscript refers to the number of carbon atoms that the named group may contain. $C_{1-4}$alkyl includes all linear, or branched alkyl groups with between 1 and 4 carbon atoms, and thus includes methyl, ethyl, n-propyl, i-propyl, 2-methyl-ethyl, butyl and its isomers (e.g. n-butyl, isobutyl and tert-butyl)), and the like.

The term "$C_{1-3}$alkyl" as a group or part of a group refers to a hydrocarbyl radical of Formula $C_nH_{2n+1}$ wherein n is a number ranging from 1 to 3. $C_{1-3}$alkyl groups comprise from 1 to 3 carbon atoms, preferably 1 to 2 carbon atoms. $C_{1-3}$alkyl groups may be linear or branched and may be substituted as indicated herein. When a subscript is used herein following a carbon atom, the subscript refers to the number of carbon atoms that the named group may contain. $C_{1-3}$alkyl includes all linear, or branched alkyl groups with between 1 and 3 carbon atoms, and thus includes methyl, ethyl, n-propyl, i-propyl, 2-methyl-ethyl, and the like.

A 4-, 5- or 6-membered saturated heterocyclyl containing at least one heteroatom each independently selected from O, S, $S(=O)_p$ and N (as occuring for example in the definitions of $Het^1$, $Het^a$, Ring A and Ring B); in a particular embodiment is a 4-, 5- or 6-membered saturated heterocyclyl containing 1, 2 or 3 heteroatoms selected from O, S, $S(=O)_p$ and N; in a more particular embodiment a 4-, 5- or 6-membered saturated heterocyclyl containing 1 or 2 heteroatoms selected from O, S, $S(=O)_p$ and N.

Examples of a 4-, 5- or 6-membered saturated heterocyclyl containing at least one heteroatom each independently selected from O, S, $S(=O)_p$ and N, include, but are not limited to azetidinyl, morpholinyl, piperidinyl, pyrrolidinyl, 1,1-dioxido-thietanyl, 1,1-dioxido-thiomorpholinyl, piperazinyl, dioxolanyl, oxazolidinyl, oxetanyl, tetrahydrofuranyl, and the like.

$Het^1$ and $Het^a$ may be attached to the remainder of the molecule of Formula (I) through any available ring carbon atom or ring heteroatom as appropriate, if not otherwise specified.

It will be clear that when two substituents on the same carbon atom in the $Het^1$ or $Het^a$ definition are taken together to form together with the common carbon atom to which they are attached Ring A or Ring B respectively, a spiro moiety is formed.

For example, when $Het^1$ represents 1-piperidinyl wherein two substituents on the carbon atom in position β are taken together to form together with the common carbon atom to which they are attached ring A, the following spiro moiety is formed:

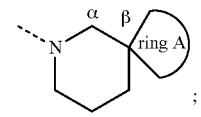

in particular if in the above example ring A represents 3-azetidinyl, the following spiro moiety is formed:

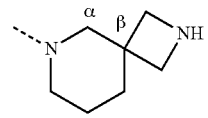

Examples of such Spiro moieties, include, but are not limited to

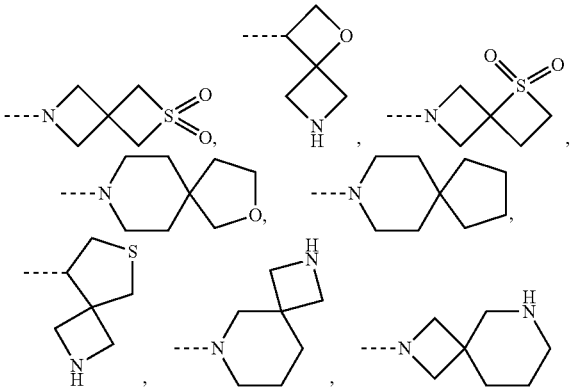

and the like.

Whenever substituents are represented by chemical structure, "—" represents the bond of attachment to the remainder of the molecule of Formula (I).

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compounds of the invention" as used herein, is meant to include the compounds of Formula (I) and N-oxides, pharmaceutically acceptable addition salts, and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Whenever one of the ring systems, is substituted with one or more substituents, those substituents may replace, unless otherwise is indicated or is clear from the context, any hydrogen atom bound to a carbon or nitrogen atom of the ring system.

Hereinbefore and hereinafter, the term "compound of Formula (I)" is meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds of Formula (I) may also exist in their tautomeric form. Such forms in so far as they may exist, are intended to be included within the scope of the present invention. It follows that a single compound may exist in both stereoisomeric and tautomeric form.

For example, it will be clear for the skilled person that when R¹ represents

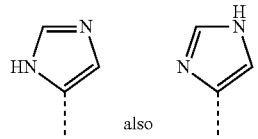

is included in the scope of the invention.

For therapeutic use, salts of the compounds of Formula (I), N-oxides and solvates thereof, are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove or hereinafter are meant to comprise the therapeutically active non-toxic acid and base addition salt forms which the compounds of Formula (I), N-oxides and solvates thereof, are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I), N-oxides and solvates thereof containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D- glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of Formula (I) are able to form, as well as N-oxides and pharmaceutically acceptable addition salts thereof. Examples of such forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and N-oxides, pharmaceutically acceptable addition salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, an element, in particular when mentioned in relation to a compound of Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^2$H, $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^2$H, $^3$H, $^{11}$C and $^{18}$F. More preferably, the radioactive isotope is $^2$H. In particular, deuterated compounds are intended to be included within the scope of the present invention In an embodiment, the present invention concerns novel compounds of Formula (I), tautomers and stereoisomeric forms thereof, wherein $R^1$ represents C(=O)OH, —C(=O)NH$_2$,

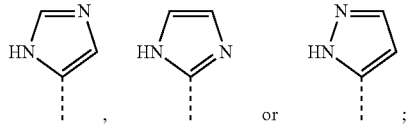

or ;

$R^2$ represents

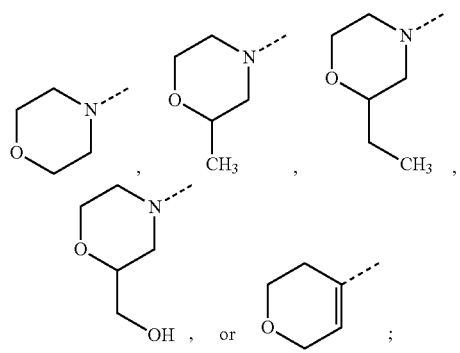

$R^3$ represents $C_{1-4}$alkyl substituted with one substituent selected from the group consisting of Het$^1$, —C(=O)-Het$^1$, and —NH—C(=O)-Het$^1$; or
$C_{1-4}$alkyl substituted on the same carbon atom with one —OH and with one Het$^1$;

Het$^1$ represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of halo, —NH$_2$, $C_{1-4}$alkyl, —S(=O)$_2$—$C_{1-6}$alkyl, —$C_{1-4}$alkyl-S(=O)$_2$—$C_{1-6}$alkyl, hydroxy and $C_{1-4}$alkyl substituted with one hydroxy; or two substituents on the same carbon atom of said 4-, 5- or 6-membered saturated heterocyclyl are taken together to form together with the common carbon atom to which they are attached Ring A;

Ring A represents cyclobutyl, cyclopentyl, cyclohexyl or a 4-, 5- or 6-membered saturated heterocyclyl containing at least one heteroatom each independently selected from O, S, S(=O)$_p$ and N; said cyclobutyl, cyclopentyl, cyclohexyl or 4-, 5- or 6-membered saturated heterocyclyl is optionally substituted with one or two $C_{1-4}$alkyl substituents, with one $C_{1-4}$alkyl and one hydroxy substituent, or with one hydroxy substituent;

Y represents —CH$_2$— or —NH—;

$R^{4a}$ represents hydrogen, $C_{1-4}$alkyl, Het$^a$, or $C_{1-4}$alkyl substituted with one or more substituents each independently selected from the group consisting of —OH, —NR$^5$R$^6$ and Het$^a$;

$R^{4b}$ represents hydrogen, halo, $C_{1-4}$alkyl, or $C_{1-4}$alkyl substituted with one or more halo substituents;

or $R^{4a}$ and $R^{4b}$ are taken together to form together with the phenyl ring to which they are attached a structure of Formula (a-1), (a-2), (a-3), (a-4) or (a-5):

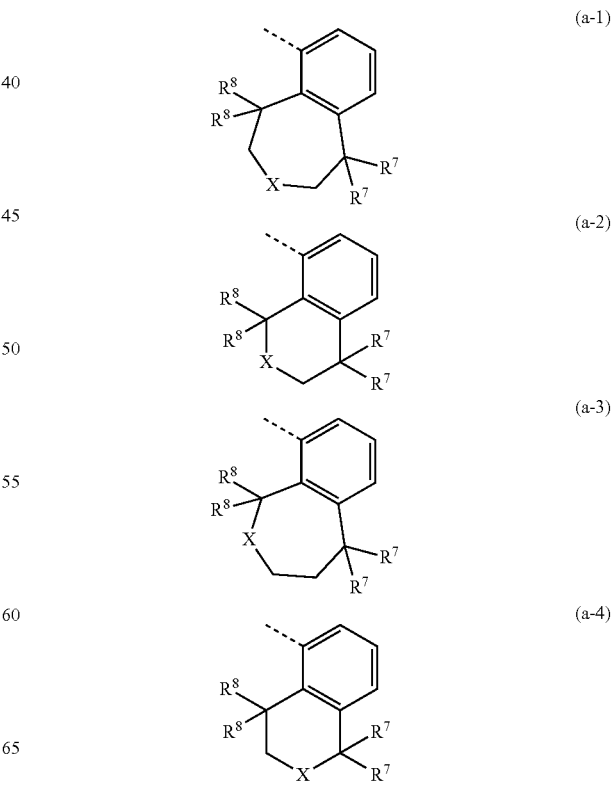

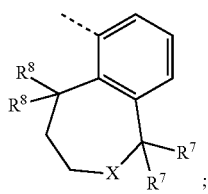

(a-5)

X represents —NH—, —O— or —N(C$_{1-3}$alkyl)-;

both R$^7$ substituents are the same and are selected from the group consisting of hydrogen, fluoro and methyl; or both R$^7$ substituents are taken together to form together with the common carbon atom to which they are attached a cyclopropyl, cyclobutyl or oxetanyl;

both R$^8$ substituents are the same and are selected from the group consisting of hydrogen and methyl; or both R$^8$ substituents are taken together to form together with the common carbon atom to which they are attached a cyclopropyl, cyclobutyl or oxetanyl;

R$^5$ represents hydrogen, C$_{1-6}$alkyl, or C$_{1-6}$alkyl substituted with one OH;

R$^6$ represents hydrogen, C$_{1-6}$alkyl, or C$_{1-6}$alkyl substituted with one OH;

each Het$^a$ independently represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of C$_{1-4}$alkyl, —S(=O)$_2$—C$_{1-6}$alkyl, hydroxy, —C$_{1-4}$alkyl-S(=O)$_2$—C$_{1-6}$ alkyl, and C$_{1-4}$alkyl substituted with one hydroxy; or two substituents on the same carbon atom of said 4-, 5- or 6-membered saturated heterocyclyl are taken together to form together with the common carbon atom to which they are attached Ring B;

Ring B represents cyclobutyl, cyclopentyl, cyclohexyl or a 4-, 5- or 6-membered saturated heterocyclyl containing at least one heteroatom each independently selected from O, S, S(=O)$_p$ and N; said cyclobutyl, cyclopentyl, cyclohexyl or 4-, 5- or 6-membered saturated heterocyclyl is optionally substituted with one or two C$_{1-4}$alkyl substituents, with one C$_{1-4}$alkyl and one hydroxy substituent, or with one hydroxy substituent;

p represents 1 or 2;

and the N-oxides, the pharmaceutically acceptable addition salts, and the solvates thereof.

In an embodiment, the present invention concerns novel compounds of Formula (I), tautomers and stereoisomeric forms thereof, wherein R$^1$ represents —C(=O)OH, —C(=O)NH$_2$, —NH$_2$,

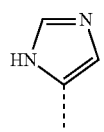 , 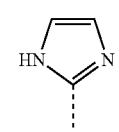 or 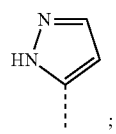 ;

R$^2$ represents

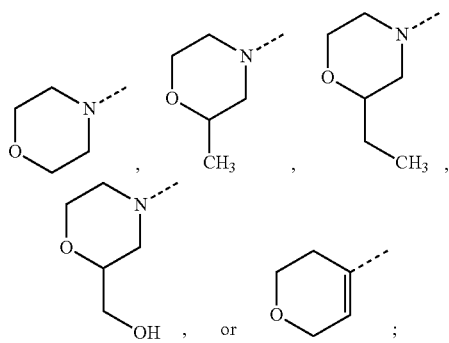

R$^3$ represents C$_{1-4}$alkyl substituted with one substituent selected from the group consisting of Het$^1$, —O—C(=O)—C$_{1-4}$alkyl-Het$^1$, —C(=O)-Het$^1$, and —NH—C(=O)-Het$^1$; —CH(OH)—CH$_2$-Het$^1$; or C$_{1-4}$alkyl substituted on the same carbon atom with one —OH and with one Het$^1$;

Het$^1$ represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of halo, —NH$_2$, C$_{1-4}$alkyl, —S(=O)$_2$—C$_{1-6}$alkyl, —C$_{1-4}$alkyl-S(=O)$_2$—C$_{1-6}$alkyl, hydroxy and C$_{1-4}$alkyl substituted with one hydroxy; or two substituents on the same carbon atom of said 4-, 5- or 6-membered saturated heterocyclyl are taken together to form together with the common carbon atom to which they are attached Ring A;

Ring A represents cyclobutyl, cyclopentyl, cyclohexyl or a 4-, 5- or 6-membered saturated heterocyclyl containing at least one heteroatom each independently selected from O, S, S(=O)$_p$ and N; said cyclobutyl, cyclopentyl, cyclohexyl or 4-, 5- or 6-membered saturated heterocyclyl is optionally substituted with one or two C$_{1-4}$alkyl substituents, with one C$_{1-4}$alkyl and one hydroxy substituent, or with one hydroxy substituent;

Y represents —CH$_2$— or —NH—;

R$^{4a}$ represents hydrogen, C$_{1-4}$alkyl, or C$_{1-4}$alkyl substituted with one or more —NR$^5$R$^6$ substituents;

R$^5$ represents hydrogen, C$_{1-6}$alkyl, or C$_{1-6}$alkyl substituted with one OH;

R$^6$ represents hydrogen, C$_{1-6}$alkyl, or C$_{1-6}$alkyl substituted with one OH;

p represents 1 or 2;

and the N-oxides, the pharmaceutically acceptable addition salts, and the solvates thereof.

In an embodiment, the present invention concerns novel compounds of Formula (I), tautomers and stereoisomeric forms thereof, wherein R$^1$ represents —C(=O)OH, —C(=O)NH$_2$, —NH$_2$,

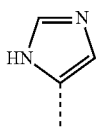 , 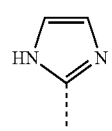 or 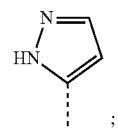 ;

$R^2$ represents

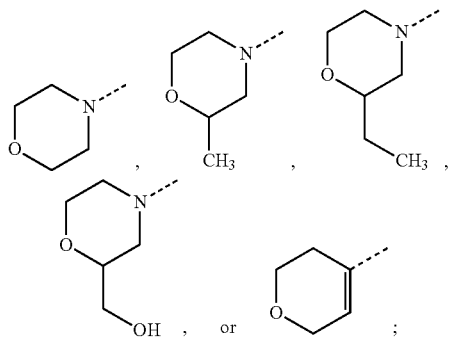

$R^3$ represents $C_{1-4}$alkyl substituted with one substituent selected from the group consisting of Het$^1$, —C(=O)-Het$^1$, and —NH—C(=O)-Het$^1$; or $C_{1-4}$alkyl substituted on the same carbon atom with one —OH and with one Het$^1$;

Het$^1$ represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of halo, —NH$_2$, $C_{1-4}$alkyl, —S(=O)$_2$—$C_{1-6}$alkyl, —$C_{1-4}$alkyl-S(=O)$_2$—$C_{1-6}$alkyl, hydroxy and $C_{1-4}$alkyl substituted with one hydroxy; or two substituents on the same carbon atom of said 4-, 5- or 6-membered saturated heterocyclyl are taken together to form together with the common carbon atom to which they are attached Ring A;

Ring A represents cyclobutyl, cyclopentyl, cyclohexyl or a 4-, 5- or 6-membered saturated heterocyclyl containing at least one heteroatom each independently selected from O, S, S(=O)$_p$ and N; said cyclobutyl, cyclopentyl, cyclohexyl or 4-, 5- or 6-membered saturated heterocyclyl is optionally substituted with one or two $C_{1-4}$alkyl substituents, with one $C_{1-4}$alkyl and one hydroxy substituent, or with one hydroxy substituent;

Y represents —CH$_2$— or —NH—;

$R^{4a}$ represents hydrogen, $C_{1-4}$alkyl, or $C_{1-4}$alkyl substituted with one or more —NR$^5$R$^6$ substituents;

$R^{4b}$ represents hydrogen, halo, $C_{1-4}$alkyl, or $C_{1-4}$alkyl substituted with one or more halo substituents;

$R^5$ represents hydrogen, $C_{1-6}$alkyl, or $C_{1-6}$alkyl substituted with one OH;

$R^6$ represents hydrogen, $C_{1-6}$alkyl, or $C_{1-6}$alkyl substituted with one OH;

p represents 1 or 2;

and the N-oxides, the pharmaceutically acceptable addition salts, and the solvates thereof.

In an embodiment, the present invention concerns novel compounds of Formula (I), tautomers and stereoisomeric forms thereof, wherein $R^1$ represents —C(=O)OH, —C(=O)NH$_2$, —NH$_2$,

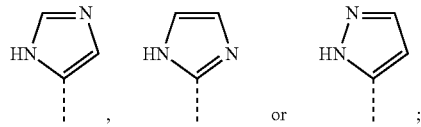

$R^2$ represents

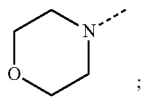

$R^3$ represents $C_{1-4}$alkyl substituted with one substituent selected from the group consisting of Het$^1$, —O—C(=O)—$C_{1-4}$alkyl-Het$^1$, —C(=O)-Het$^1$, and —NH—C(=O)-Het$^1$; or —CH(OH)—CH$_2$-Het$^1$;

Het$^1$ represents a 4-, 5- or 6-membered saturated heterocyclyl containing at least one heteroatom each independently selected from S(=O)$_p$ and N; said 4-, 5- or 6-membered saturated heterocyclyl is optionally substituted with one or two substituents each independently selected from the group consisting of halo, —NH$_2$, $C_{1-4}$alkyl, —S(=O)$_2$—$C_{1-6}$alkyl, —$C_{1-4}$alkyl-S(=O)$_2$—$C_{1-6}$alkyl, hydroxy and $C_{1-4}$alkyl substituted with one hydroxy; or two substituents on the same carbon atom of said 4-, 5- or 6-membered saturated heterocyclyl are taken together to form together with the common carbon atom to which they are attached Ring A;

Ring A represents cyclobutyl, cyclopentyl, cyclohexyl or a 4-, 5- or 6-membered saturated heterocyclyl containing at least one heteroatom each independently selected from S(=O)$_p$ and N; said cyclobutyl, cyclopentyl, cyclohexyl or 4-, 5- or 6-membered saturated heterocyclyl is optionally substituted with one hydroxy substituent;

Y represents —CH$_2$— or —NH—;

$R^{4a}$ represents $C_{1-4}$alkyl;

$R^{4b}$ represents $C_{1-4}$alkyl substituted with one or more halo substituents;

p represents 2;

and the N-oxides, the pharmaceutically acceptable addition salts, and the solvates thereof.

In an embodiment, the present invention concerns novel compounds of Formula (I), tautomers and stereoisomeric forms thereof, wherein $R^1$ represents —NH$_2$;

$R^2$ represents

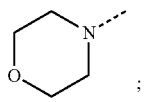

$R^3$ represents $C_{1-4}$alkyl substituted with one substituent selected from the group consisting of —O—C(=O)—$C_{1-4}$alkyl-Het$^1$, and —NH—C(=O)-Het$^1$; or —CH(OH)—CH$_2$-Het$^1$;

Het$^1$ represents a 4-, 5- or 6-membered saturated heterocyclyl containing one or two heteroatoms each independently selected from S(=O)$_p$ and N; said 4-, 5- or 6-membered saturated heterocyclyl is optionally substituted with one or two substituents each independently selected from the group consisting of $C_{1-4}$alkyl, and hydroxy; or two substituents on the same carbon atom of said 4-, 5- or 6-membered saturated heterocyclyl are taken together to form together with the common carbon atom to which they are attached Ring A;

Ring A represents a 4-, 5- or 6-membered saturated heterocyclyl containing one or two heteroatoms each independently selected from S(=O)$_p$ and N;

Y represents —CH$_2$—;

$R^{4a}$ represents $C_{1-4}$alkyl;

$R^{4b}$ represents $C_{1-4}$alkyl substituted with one or more halo substituents;

p represents 2;

and the N-oxides, the pharmaceutically acceptable addition salts, and the solvates thereof.

In an embodiment, the present invention concerns novel compounds of Formula (I), tautomers and stereoisomeric forms thereof, wherein $R^1$ represents —C(=O)NH$_2$, —NH$_2$,

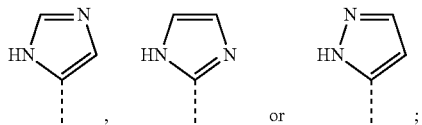

$R^2$ represents

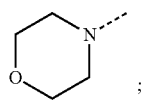

$R^3$ represents $C_{1-4}$alkyl substituted with one substituent selected from the group consisting of Het$^1$ and —C(=O)-Het$^1$;

Het$^1$ represents a 4-, 5- or 6-membered saturated heterocyclyl containing at least one heteroatom each independently selected from $S(=O)_p$ and N; said 4-, 5- or 6-membered saturated heterocyclyl is optionally substituted with one or two substituents each independently selected from the group consisting of —NH$_2$, $C_{1-4}$alkyl, —S(=O)$_2$—C$_{1-6}$alkyl, hydroxy and $C_{1-4}$alkyl substituted with one hydroxy; or two substituents on the same carbon atom of said 4-, 5- or 6-membered saturated heterocyclyl are taken together to form together with the common carbon atom to which they are attached Ring A;

Ring A represents a 4-, 5- or 6-membered saturated heterocyclyl containing at least one heteroatom each independently selected from $S(=O)_p$ and N;

Y represents —CH$_2$— or —NH—;

$R^{4a}$ represents $C_{1-4}$alkyl;

$R^{4b}$ represents $C_{1-4}$ alkyl substituted with one or more halo substituents;

p represents 2;

and the N-oxides, the pharmaceutically acceptable addition salts, and the solvates thereof.

Another embodiment of the present invention relates to those compounds of Formula (I) and the N-oxides, the pharmaceutically acceptable addition salts, and the solvates thereof, or any subgroup thereof as mentioned in any of the other embodiments wherein one or more of the following restrictions apply:

(i) $R^2$ represents

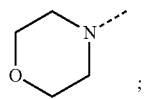

(ii) $R^3$ represents $C_{1-4}$alkyl substituted with one substituent selected from the group consisting of Het$^1$, —O—C(=O)—C$_{1-4}$alkyl-Het$^1$, —C(=O)-Het$^1$, and —NH—C(=O)-Het$^1$; or —CH(OH)—CH$_2$-Het$^1$;

in particular $R^3$ represents $C_{1-4}$alkyl substituted with one substituent selected from the group consisting of Het$^1$, —C(=O)-Het$^1$, and —NH—C(=O)-Het$^1$;

(iii) Het$^1$ represents a 4-, 5- or 6-membered saturated heterocyclyl containing at least one heteroatom each independently selected from $S(=O)_p$ and N; said 4-, 5- or 6-membered saturated heterocyclyl is optionally substituted with one or two substituents each independently selected from the group consisting of halo, —NH$_2$, $C_{1-4}$alkyl, —S(=O)$_2$—C$_{1-6}$alkyl, —C$_{1-4}$alkyl-S(=O)$_2$—C$_{1-5}$alkyl, hydroxy and $C_{1-4}$alkyl substituted with one hydroxy; or two substituents on the same carbon atom of said 4-, 5- or 6-membered saturated heterocyclyl are taken together to form together with the common carbon atom to which they are attached Ring A;

(iv) Ring A represents cyclobutyl, cyclopentyl, cyclohexyl or a 4-, 5- or 6-membered saturated heterocyclyl containing at least one heteroatom each independently selected from $S(=O)_p$ and N; said cyclobutyl, cyclopentyl, cyclohexyl or 4-, 5- or 6-membered saturated heterocyclyl is optionally substituted with one hydroxy substituent;

(v) $R^{4a}$ represents $C_{1-4}$alkyl;

(vi) $R^{4b}$ represents $C_{1-4}$alkyl substituted with one or more halo substituents;

(vii) p represents 2.

Another embodiment of the present invention relates to those compounds of Formula (I) and the N-oxides, the pharmaceutically acceptable addition salts, and the solvates thereof, or any subgroup thereof as mentioned in any of the other embodiments wherein one or more of the following restrictions apply:

(i) $R^1$ represents —C(=O)NH$_2$, —NH$_2$,

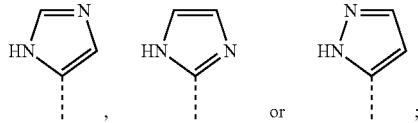

(ii) $R^2$ represents

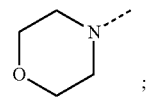

(iii) $R^3$ represents $C_{1-4}$alkyl substituted with one substituent selected from the group consisting of Het$^1$ and —C(=O)-Het$^1$;

(iv) Het$^1$ represents a 4-, 5- or 6-membered saturated heterocyclyl containing at least one heteroatom each independently selected from $S(=O)_p$ and N; said 4-, 5- or 6-membered saturated heterocyclyl is optionally substituted with one or two substituents each independently selected from the group consisting of —NH$_2$, $C_{1-4}$alkyl, —S(=O)$_2$—C$_{1-6}$alkyl, hydroxy and $C_{1-4}$alkyl substituted with one hydroxy; or two substituents on the same carbon atom of said 4-, 5- or 6-membered saturated heterocyclyl are taken together to form together with the common carbon atom to which they are attached Ring A;

(v) Ring A represents a 4-, 5- or 6-membered saturated heterocyclyl containing at least one heteroatom each independently selected from $S(=O)_p$ and N;

(vi) $R^{4a}$ represents $C_{1-4}$-alkyl;

(vii) $R^{4b}$ represents $C_{1-4}$alkyl substituted with one or more halo substituents;
(viii) p represents 2.

Another embodiment of the present invention relates to those compounds of Formula (I) and the N-oxides, the pharmaceutically acceptable addition salts, and the solvates thereof, or any subgroup thereof as mentioned in any of the other embodiments wherein one or more of the following restrictions apply:

(i) $R^1$ represents —$NH_2$, or

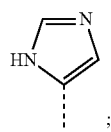
;

(ii) $R^2$ represents

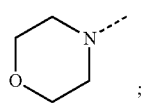
;

(iii) R represents $C_{1-4}$alkyl substituted with one $Het^1$;
(iv) $Het^1$ represents

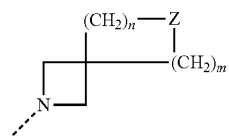

Z represents —NH—, —S—, —O— or —S(O)$_2$—;
n represents 0, 1 or 2;
m represents 1, 2 or 3; provided however that m does not have value 1 when n is 0;
in particular $Het^1$ represents

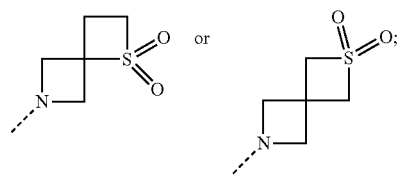

more in particular $Het^1$ represents

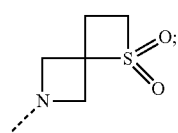

(v) $R^{4a}$ represents $C_{1-4}$alkyl; in particular $CH_3$;
(vi) $R^{4b}$ represents $C_{1-4}$alkyl substituted with one or more halo substituents; in particular $CF_3$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^1$ represents —C(=O)$NH_2$, —$NH_2$,

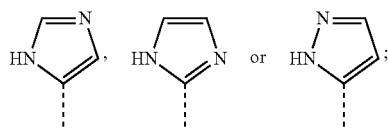

in particular $R^1$ represents

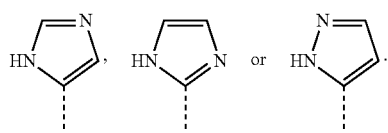

In an embodiment, the present invention relates to those compounds of Formula (I) and the N-oxides, the pharmaceutically acceptable addition salts, and the solvates thereof, or any subgroup thereof as mentioned in any of the other embodiments, wherein Y represents —NH—; and
$R^1$ represents

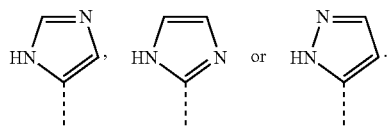

In an embodiment, the present invention relates to those compounds of Formula (I) and the N-oxides, the pharmaceutically acceptable addition salts, and the solvates thereof, or any subgroup thereof as mentioned in any of the other embodiments, wherein Y represents —$CH_2$—; and
$R^1$ represents

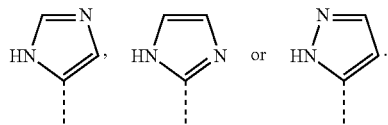

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^1$ represents —C(=O)$NH_2$, —$NH_2$,

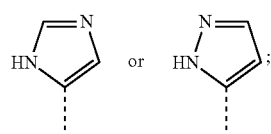

in particular $R^1$ represents

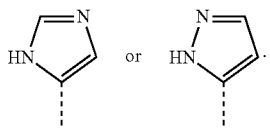

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^1$ represents —NH$_2$, or

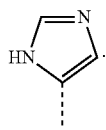

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^3$ represents C$_{1-4}$alkyl substituted with one substituent selected from the group consisting of Het$^{1a}$, —C(=O)-Het$^1$, and —NH—C(=O)-Het$^{1b}$; or
C$_{1-4}$alkyl substituted on the same carbon atom with one —OH and with one Het$^{1b}$;
Het$^1$ represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of halo, —NH$_2$, C$_{1-4}$alkyl, —S(=O)$_2$—C$_{1-6}$alkyl, —C$_{1-4}$alkyl-S(=O)$_2$—C$_{1-6}$alkyl, hydroxy and C$_{1-4}$alkyl substituted with one hydroxy; or two substituents on the same carbon atom of said 4-, 5- or 6-membered saturated heterocyclyl are taken together to form together with the common carbon atom to which they are attached Ring A;
Het$^{1a}$ is defined as Het$^{1a}$ provided however that Het$^{1a}$ is always attached to the remainder of R$^3$ through a ring nitrogen atom;
Het$^{1b}$ is defined as Het$^1$ provided however that Het$^{1b}$ is always attached to the remainder of R$^3$ through a ring carbon atom.

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^3$ represents C$_{1-4}$alkyl substituted with one substituent selected from the group consisting of Het$^{1a}$, —O—C(=O)—C$_{1-4}$-alkyl-Het$^1$, —C(=O)-Het$^1$, and —NH—C(=O)-Het$^{1b}$; —CH(OH)—CH$_2$-Het$^{1a}$; or C$_{1-4}$alkyl substituted on the same carbon atom with one —OH and with one Het$^{1b}$;
Het$^1$ represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of halo, —NH$_2$, C$_{1-4}$alkyl, —S(=O)$_2$—C$_{1-6}$alkyl, —C$_{1-4}$alkyl-S(=O)$_2$—C$_{1-6}$alkyl, hydroxy and C$_{1-4}$alkyl substituted with one hydroxy; or two substituents on the same carbon atom of said 4-, 5- or 6-membered saturated heterocyclyl are taken together to form together with the common carbon atom to which they are attached Ring A;
Het$^{1a}$ is defined as Het$^1$ provided however that Het$^{1a}$ is always attached to the remainder of R$^3$ through a ring nitrogen atom;
Het$^{1b}$ is defined as Het$^1$ provided however that Het$^{1b}$ is always attached to the remainder of R$^3$ through a ring carbon atom.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^1$ represents —C(=O)NH$_2$ or —NH$_2$; in particular $R^1$ represents NH$_2$.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^1$ represents other than —C(=O)OH.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^2$ represents

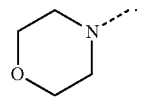

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^2$ represents

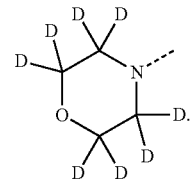

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^3$ represents C$_{1-4}$alkyl substituted with one substituent selected from the group consisting of Het$^1$, —C(=O)-Het$^1$, and —NH—C(=O)-Het$^1$; or
C$_{1-4}$alkyl substituted on the same carbon atom with one —OH and with one Het$^1$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ represents $C_{1-4}$alkyl substituted with one substituent selected from the group consisting of $Het^1$, —C(=O)-$Het^1$, and —NH—C(=O)-$Het^1$; —CH(OH)—$CH_2$-$Het^1$; or $C_{1-4}$alkyl substituted on the same carbon atom with one —OH and with one $Het^1$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ represents $C_{1-4}$alkyl substituted with one substituent selected from the group consisting of $Het^1$, —O—C(=O)—$C_{1-4}$alkyl-$Het^1$, —C(=O)-$Het^1$, and —NH—C(=O)-$Het^1$; or —CH(OH)—$CH_2$-$Het^1$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ represents $C_{1-4}$alkyl substituted with one substituent selected from the group consisting of $Het^1$, —C(=O)-$Het^1$, and —NH—C(=O)-$Het^1$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ represents $C_{1-4}$alkyl substituted with one substituent selected from the group consisting of $Het^1$ and —C(=O)-$Het^1$;

in particular $R^1$ represents $C_{1-4}$alkyl substituted with one $Het^1$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ represents $C_{1-4}$alkyl substituted with one substituent selected from the group consisting of $Het^1$, —C(=O)-$Het^1$, and —NH—C(=O)-$Het^1$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ represents $C_{1-4}$alkyl substituted with one $Het^1$ substituent; in particular $R^3$ represents $C_{1-4}$alkyl substituted with one $Het^{1a}$ substituent wherein $Het^{1a}$ is defined as $Het^1$ provided however that $Het^{1a}$ is always attached to $C_{1-4}$alkyl through a ring nitrogen atom.

In an embodiment, the present invention relates to those compounds of Formula (I) and the N-oxides, the pharmaceutically acceptable addition salts, and the solvates thereof, or any subgroup thereof as mentioned in any of the other embodiments, wherein the following proviso is applicable: when Y represents —NH—, then $R^3$ represents $C_{1-4}$alkyl substituted with one $Het^1$ substituent; in particular when Y represents —NH—, then $R^3$ represents $C_{1-4}$alkyl substituted with one $Het^{1a}$ substituent wherein $Het^{1a}$ is defined as $Het^1$ provided however that $Het^{1a}$ is always attached to $C_{1-4}$alkyl through a ring nitrogen atom.

In an embodiment, the present invention relates to those compounds of Formula (I) and the N-oxides, the pharmaceutically acceptable addition salts, and the solvates thereof, or any subgroup thereof as mentioned in any of the other embodiments, wherein $Het^1$ represents a 4-, 5- or 6-membered saturated heterocyclyl containing at least one heteroatom each independently selected from $S(=O)_p$ and N; said 4-, 5- or 6-membered saturated heterocyclyl is optionally substituted with one or two substituents each independently selected from the group consisting of —$NH_2$, $C_{1-4}$alkyl, —$S(=O)_2$—$C_{1-6}$alkyl, hydroxy and $C_{1-4}$alkyl substituted with one hydroxy; or two substituents on the same carbon atom of said 4-, 5- or 6-membered saturated heterocyclyl are taken together to form together with the common carbon atom to which they are attached Ring A.

In an embodiment, the present invention relates to those compounds of Formula (I) and the N-oxides, the pharmaceutically acceptable addition salts, and the solvates thereof, or any subgroup thereof as mentioned in any of the other embodiments, wherein $Het^1$ represents a 4-, 5- or 6-membered saturated heterocyclyl containing at least one heteroatom each independently selected from $S(=O)_p$ and N; said 4-, 5- or 6-membered saturated heterocyclyl is optionally substituted with one or two substituents each independently selected from the group consisting of —$NH_2$, $C_{1-4}$alkyl, —$S(=O)_2$—$C_{1-6}$alkyl, hydroxy and $C_{1-4}$alkyl substituted with one hydroxy.

In an embodiment, the present invention relates to those compounds of Formula (I) and the N-oxides, the pharmaceutically acceptable addition salts, and the solvates thereof, or any subgroup thereof as mentioned in any of the other embodiments, wherein $Het^1$ represents a 4-, 5- or 6-membered saturated heterocyclyl containing at least one heteroatom each independently selected from $S(=O)_p$ and N; said 4-, 5- or 6-membered saturated heterocyclyl is optionally substituted with one or two substituents each independently selected from the group consisting of halo, —$NH_2$, $C_{1-4}$alkyl, —$S(=O)_2$—$C_{1-6}$alkyl, —$C_{1-4}$alkyl-$S(=O)_2$—$C_{1-6}$alkyl, hydroxy and $C_{1-4}$alkyl substituted with one hydroxy; or two substituents on the same carbon atom of said 4-, 5- or 6-membered saturated heterocyclyl are taken together to form together with the common carbon atom to which they are attached Ring A.

In an embodiment, the present invention relates to those compounds of Formula (I) and the N-oxides, the pharmaceutically acceptable addition salts, and the solvates thereof, or any subgroup thereof as mentioned in any of the other embodiments, wherein $Het^1$ represents a 4-, 5- or 6-membered saturated heterocyclyl containing at least one heteroatom each independently selected from $S(=O)_p$ and N; said 4-, 5- or 6-membered saturated heterocyclyl is optionally substituted with one or two substituents each independently selected from the group consisting of halo, —$NH_2$, $C_{1-4}$alkyl, —$S(=O)_2$—$C_{1-6}$alkyl, —$C_{1-4}$alkyl-$S(=O)_2$—$C_{1-6}$alkyl, hydroxy and $C_{1-4}$alkyl substituted with one hydroxy.

In an embodiment, the present invention relates to those compounds of Formula (I) and the N-oxides, the pharmaceutically acceptable addition salts, and the solvates thereof, or any subgroup thereof as mentioned in any of the other embodiments, wherein Ring A represents a 4-, 5- or 6-membered saturated heterocyclyl containing at least one heteroatom each independently selected from $S(=O)_p$ and N.

In an embodiment, the present invention relates to those compounds of Formula (I) and the N-oxides, the pharmaceutically acceptable addition salts, and the solvates thereof, or any subgroup thereof as mentioned in any of the other embodiments, wherein Ring A represents cyclobutyl, cyclopentyl, cyclohexyl or a 4-, 5- or 6-membered saturated heterocyclyl containing at least one heteroatom each independently selected from $S(=O)_p$ and N; said cyclobutyl, cyclopentyl, cyclohexyl or 4-, 5- or 6-membered saturated heterocyclyl is optionally substituted with one hydroxy substituent.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^{4a}$ represents $C_{1-4}$alkyl; and
$R^{4b}$ represents $C_{1-4}$alkyl substituted with one or more halo substituents.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^{4a}$ represents $CH_3$; and $R^{4b}$ represents $CF_3$.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^{4a}$ represents hydrogen, $C_{1-4}$alkyl, or $C_{1-4}$alkyl substituted with one or more substituents each independently selected from the group consisting of —$NR^5R^6$ and $Het^a$;
$R^{4b}$ represents hydrogen, halo, $C_{1-4}$alkyl, or $C_{1-4}$alkyl substituted with one or more halo substituents.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^{4a}$ represents $C_{1-4}$alkyl; in particular $R^{4a}$ represents methyl.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^{4a}$ represents hydrogen, $C_{1-4}$alkyl, $Het^a$, or $C_{1-4}$alkyl substituted with one substituent selected from the group consisting of —OH, —$NR^5R^6$ and $Het^a$.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^{4b}$ represents $C_{1-4}$alkyl substituted with one or more halo substituents; in particular $R^{4b}$ represents $CF_3$.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^{4a}$ and $R^{4b}$ are other than hydrogen.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^{4a}$ represents $C_{1-4}$alkyl, $Het^a$, or $C_{1-4}$alkyl substituted with one or more substituents each independently selected from the group consisting of —OH, —$NR^5R^6$ and $Het^a$;
$R^{4b}$ represents $C_{1-4}$alkyl, or $C_{1-4}$alkyl substituted with one or more halo substituents.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^{4a}$ represents $C_{1-4}$alkyl, $Het^a$, or $C_{1-4}$alkyl substituted with one or more substituents each independently selected from the group consisting of —OH, —$NR^5R^6$ and $Het^a$;
$R^{4b}$ represents $C_{1-4}$alkyl.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^{4a}$ represents $C_{1-4}$alkyl; and $R^{4b}$ represents $C_{1-4}$alkyl.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^{4a}$ represents $C_{1-4}$alkyl, $Het^a$, or $C_{1-4}$alkyl substituted with one or more substituents each independently selected from the group consisting of —OH, —$NR^5R^6$ and $Het^a$;
$R^{4b}$ represents $C_{1-4}$alkyl, or $C_{1-4}$alkyl substituted with one or more halo substituents;
or $R^{4a}$ and $R^{4b}$ are taken together to form together with the phenyl ring to which they are attached a structure of Formula (a-2) or (a-4).

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^{4a}$ and $R^{4b}$ are taken together to form together with the phenyl ring to which they are attached a structure of Formula (a-1), (a-2), (a-3), (a-4) or (a-5); in particular a structure of Formula (a-2).

In an embodiment, the present invention relates to those compounds of Formula (I) and the N-oxides, the pharmaceutically acceptable addition salts, and the solvates thereof, or any subgroup thereof as mentioned in any of the other embodiments, wherein p represents 2.

In an embodiment, the present invention relates to those compounds of Formula (I) and the N-oxides, the pharmaceutically acceptable addition salts, and the solvates thereof, or any subgroup thereof as mentioned in any of the other embodiments, wherein $Het^1$ represents a 4-, 5- or 6-membered saturated heterocyclyl containing at least one heteroatom each independently selected from O, S, S($=$O)$_p$ and N; and 2 substituents on the same carbon atom of said 4-, 5- or 6-membered saturated heterocyclyl are taken together to form together with the common carbon atom to which they are attached Ring A.

In an embodiment, the present invention relates to those compounds of Formula (I) and the N-oxides, the pharmaceutically acceptable addition salts, and the solvates thereof, or any subgroup thereof as mentioned in any of the other embodiments, wherein $Het^1$ represents a 4-, 5- or 6-membered saturated heterocyclyl containing at least one heteroatom each independently selected from O, S, S($=$O)$_p$ and N; said 4-, 5- or 6-membered saturated heterocyclyl s optionally substituted with one or two substituents each independently selected from the group consisting of —$NH_2$, $C_{1-4}$alkyl, —S($=$O)$_2$—$C_{1-6}$alkyl, —$C_{1-4}$alkyl-S($=$O)$_2$—$C_{1-6}$alkyl, hydroxy and $C_{1-4}$alkyl substituted with one hydroxy.

In an embodiment, the present invention relates to those compounds of Formula (I) and the N-oxides, the pharmaceutically acceptable addition salts, and the solvates thereof, or any subgroup thereof as mentioned in any of the other embodiments, wherein Het¹ represents a 4-, 5- or 6-membered saturated heterocyclyl containing at least one heteroatom each independently selected from O, S, S(=O)$_p$ and N; p represents 2.

In an embodiment, the present invention relates to those compounds of Formula (I) and the N-oxides, the pharmaceutically acceptable addition salts, and the solvates thereof, or any subgroup thereof as mentioned in any of the other embodiments, wherein Het¹ represents a 4-, 5- or 6-membered saturated heterocyclyl containing one S(=O)$_p$ and also containing one N; p represents 2.

In an embodiment, the present invention relates to those compounds of Formula (I) and the N-oxides, the pharmaceutically acceptable addition salts, and the solvates thereof, or any subgroup thereof as mentioned in any of the other embodiments, wherein Het¹ represents a 4-, 5- or 6-membered saturated heterocyclyl containing one S(=O)$_p$ and also containing one N; said 4-, 5- or 6-membered saturated heterocyclyl is optionally substituted with one or two substituents each independently selected from the group consisting of —NH$_2$, $C_{1-4}$alkyl, —S(=O)$_2$—$C_{1-6}$alkyl, —$C_{1-4}$alkyl-S(=O)$_2$—$C_{1-6}$alkyl, hydroxy and $C_{1-4}$alkyl substituted with one hydroxy;

p represents 2.

In an embodiment, the present invention relates to those compounds of Formula (I) and the N-oxides, the pharmaceutically acceptable addition salts, and the solvates thereof, or any subgroup thereof as mentioned in any of the other embodiments, wherein Het¹ represents

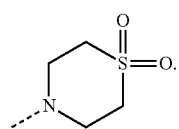

In an embodiment, the present invention relates to those compounds of Formula (I) and the N-oxides, the pharmaceutically acceptable addition salts, and the solvates thereof, or any subgroup thereof as mentioned in any of the other embodiments, wherein Het¹ represents

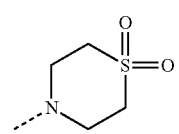

optionally substituted with one or two substituents each independently selected from the group consisting of —NH$_2$, $C_{1-4}$alkyl, —S(=O)$_2$—$C_{1-6}$alkyl, —$C_{1-4}$alkyl-S(=O)$_2$—$C_{1-6}$alkyl, hydroxy and $C_{1-4}$alkyl substituted with one hydroxy.

In an embodiment, the present invention relates to those compounds of Formula (I) and the N-oxides, the pharmaceutically acceptable addition salts, and the solvates thereof, or any subgroup thereof as mentioned in any of the other embodiments, wherein Het¹ represents

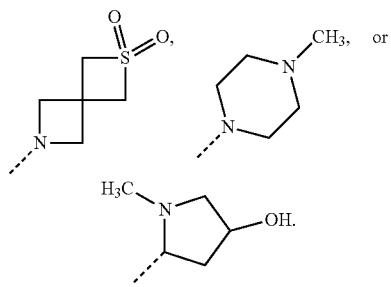

In an embodiment, the present invention relates to those compounds of Formula (I) and the N-oxides, the pharmaceutically acceptable addition salts, and the solvates thereof, or any subgroup thereof as mentioned in any of the other embodiments, wherein Het¹ represents

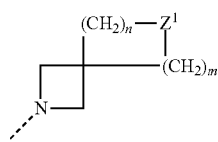

$Z^1$ represents —NH—, —S—, —O— or —S(O)$_2$—; in particular $Z^1$ represents —S(O)$_2$—;
n represents 0, 1 or 2;
m represents 1, 2 or 3; provided however that in does not have value 1 when n is 0.

In an embodiment, the present invention relates to those compounds of Formula (I) and the N-oxides, the pharmaceutically acceptable addition salts, and the solvates thereof, or any subgroup thereof as mentioned in any of the other embodiments, wherein Het¹ represents

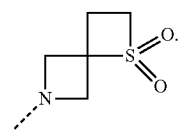

In an embodiment, the present invention relates to those compounds of Formula (I) and the N-oxides, the pharmaceutically acceptable addition salts, and the solvates thereof, or any subgroup thereof as mentioned in any of the other embodiments, wherein Het$^a$ represents

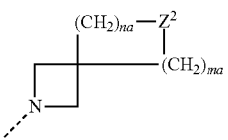

$Z^2$ represents —NH—, —S—, —O— or —S(O)$_2$—; in particular $Z^2$ represents —S(O)$_2$—:
na represents 0, 1 or 2;
ma represents 1, 2 or 3; provided however that m does not have value 1 when n is 0.

In an embodiment, the present invention relates to those compounds of Formula (I) and the N-oxides, the pharmaceutically acceptable addition salts, and the solvates thereof, or any subgroup thereof as mentioned in any of the other embodiments, wherein Het$^a$ represents

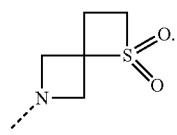

In an embodiment, the present invention relates to those compounds of Formula (I) and the N-oxides, the pharmaceutically acceptable addition salts, and the solvates thereof, or any subgroup thereof as mentioned in any of the other embodiments, wherein each Het$^a$ independently represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of C$_{1-4}$alkyl, —S(=O)$_2$—C$_{1-6}$alkyl, hydroxy, —C$_{1-4}$alkyl-S(=O)$_2$—C$_{1-6}$alkyl, and C$_{1-4}$alkyl substituted with one hydroxy.

In a particular embodiment, the present invention relates to those compounds of Formula (I) and the N-oxides, the pharmaceutically acceptable addition salts, and the solvates thereof, or any subgroup thereof as mentioned in any of the other embodiments, wherein Het$^1$ is attached to the remainder of the molecule of Formula (I) through a nitrogen atom.

In a particular embodiment, the present invention relates to those compounds of Formula (I) and the N-oxides, the pharmaceutically acceptable addition salts, and the solvates thereof, or any subgroup thereof as mentioned in any of the other embodiments, wherein Het$^1$ is attached to the remainder of the molecule of Formula (I) through a carbon atom.

In an embodiment, the present invention relates to those compounds of Formula (I) and the N-oxides, the pharmaceutically acceptable addition salts, and the solvates thereof, or any subgroup thereof as mentioned in any of the other embodiments, wherein Y represents —CH$_2$—.

In an embodiment, the present invention relates to those compounds of Formula (I) and the N-oxides, the pharmaceutically acceptable addition salts, and the solvates thereof, or any subgroup thereof as mentioned in any of the other embodiments, wherein Y represents —NH—.

In an embodiment, the present invention relates to those compounds of Formula (I) and the N-oxides, the pharmaceutically acceptable addition salts, and the solvates thereof, or any subgroup thereof as mentioned in any of the other embodiments, wherein
R$^1$ represents —C(=O)NH$_2$, —NH$_2$,

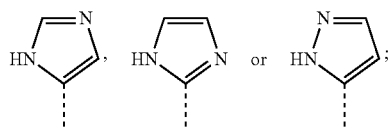

in particular R$^1$ represents —C(=O)NH$_2$, —NH$_2$,

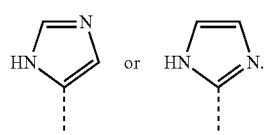

In an embodiment, the present invention relates to those compounds of Formula (I) and the N-oxides, the pharmaceutically acceptable addition salts, and the solvates thereof, or any subgroup thereof as mentioned in any of the other embodiments, wherein each Het$^a$ independently represents

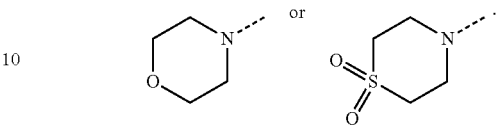

In an embodiment, the present invention relates to those compounds of Formula (I) and the N-oxides, the pharmaceutically acceptable addition salts, and the solvates thereof, or any subgroup thereof as mentioned in any of the other embodiments, wherein both R$^7$ substituents are hydrogen; and wherein both R$^8$ substituents are hydrogen.

In an embodiment, the present invention relates to those compounds of Formula (I) and the N-oxides, the pharmaceutically acceptable addition salts, and the solvates thereof, or any subgroup thereof as mentioned in any of the other embodiments, wherein both R$^7$ substituents are the same and are selected from the group consisting of hydrogen, fluoro and methyl; and wherein both R$^8$ substituents are the same and are selected from the group consisting of hydrogen and methyl.

In an embodiment, the present invention relates to a subgroup of Formula (I) and the N-oxides, the pharmaceutically acceptable addition salts, and the solvates thereof, as defined in the general reaction schemes.

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^2$ represents

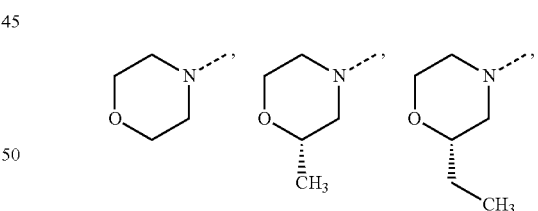

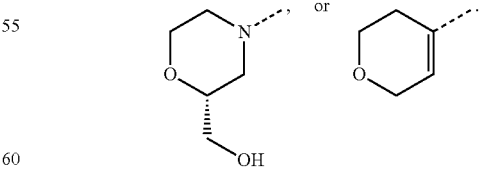

In an embodiment, the present invention relates to those compounds of Formula (I) and the N-oxides, the pharmaceutically acceptable addition salts, and the solvates thereof, or any subgroup thereof as mentioned in any of the other embodiments, wherein R² represents

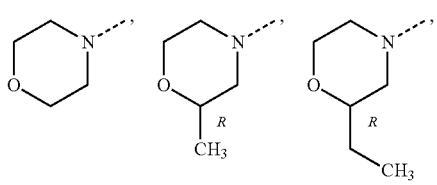

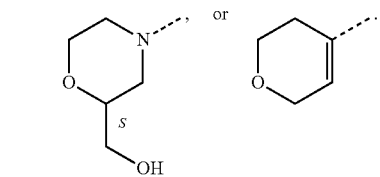

In an embodiment, the present invention relates to those compounds of Formula (I) and the N-oxides, the pharmaceutically acceptable addition salts, and the solvates thereof, or any subgroup thereof as mentioned in any of the other embodiments, wherein R² representing

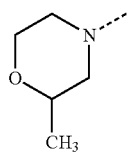

is limited to

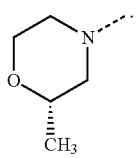

In an embodiment, the present invention relates to those compounds of Formula (I) and the N-oxides, the pharmaceutically acceptable addition salts, and the solvates thereof, or any subgroup thereof as mentioned in any of the other embodiments, wherein R² representing

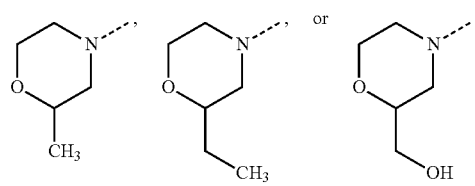

are limited respectively to

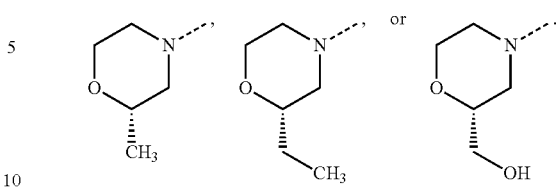

In an embodiment the compound of Formula (I) is selected from the group consisting of compounds 1, 2, and 7, tautomers and stereoisomeric forms thereof, and the N-oxides, the pharmaceutically acceptable addition salts, and the solvates thereof.

All possible combinations of the above-indicated embodiments are considered to be embraced within the scope of this invention.

Methods for the Preparation of Compounds of Formula (I)

In this section, as in all other sections unless the context indicates otherwise, references to Formula (I) also include all other sub-groups and examples thereof as defined herein.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry.

The skilled person will realize that in the reactions described in the Schemes, it may be necessary to protect reactive functional groups, for example hydroxy, amino, or carboxy groups, where these are desired in the final product, to avoid their unwanted participation in the reactions. Conventional protecting groups can be used in accordance with standard practice. This is illustrated in the specific examples. The protecting groups may be removed at a convenient subsequent stage using methods known from the art.

The skilled person will realize that in the reactions described in the Schemes, it may be advisable or necessary to perform the reaction under an inert atmosphere, such as for example under $N_2$-gas atmosphere.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the Schemes below, may also result in the desired compound of Formula (I).

The skilled person will realize that intermediates and final compounds shown in the schemes below may be further functionalized according to methods well-known by the person skilled in the art.

In the general schemes below, Het$^{1a}$ is defined as Het$^1$ provided however that Het$^{1a}$ is always attached to the remainder of R³ through a ring nitrogen atom;

Het[1b] is defined as Het[1] provided however that Het[1b] is always attached to the remainder of R[3] through a ring carbon atom.

As mentioned before, the prefix "$C_{x-y}$" (where x and y are integers) as used herein refers to the number of carbon atoms in a given group. The skilled person will realize that $C_0$ corresponds to a covalent bond. Thus the term "$C_{0-3}$alkyl" as a group or part of a group refers to a covalent bond ($C_0$) and a hydrocarbyl radical of Formula $C_nH_{2n+1}$ wherein n is a number ranging from 1 to 3.

In general, compounds of Formula (I) wherein R[1] is —NH$_2$, and wherein the other variables are as shown in Formula (Ia); and compounds of Formula (I) wherein R[1] is restricted to R[1a] being

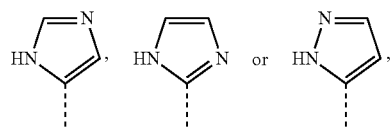

and wherein the other variables are as shown in Formula (Ib), can be prepared according to the following reaction Scheme 1 wherein PG is a protecting group such as for example 2-tetrahydropyran, N,N-dimethylsulfonamide. In scheme I, halo[1] is defined as Cl, Br or I and R[1a] is as defined above. All other variables in Scheme 1 are defined according to the scope of the present invention. Het[1a] is defined as above.

Scheme 1

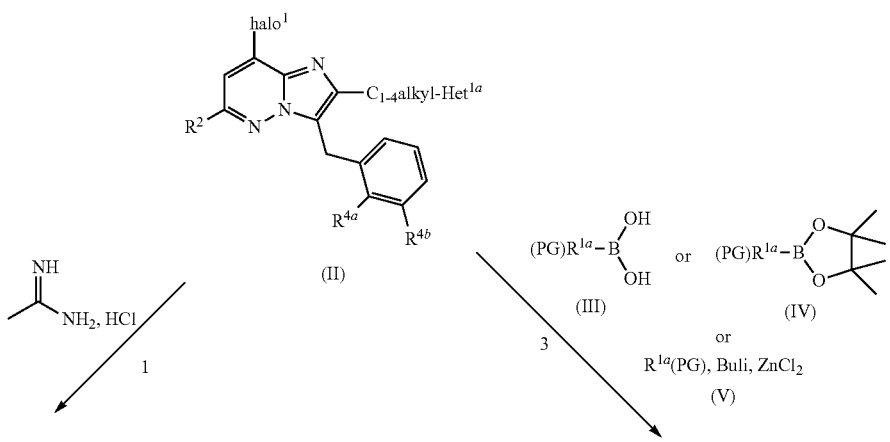

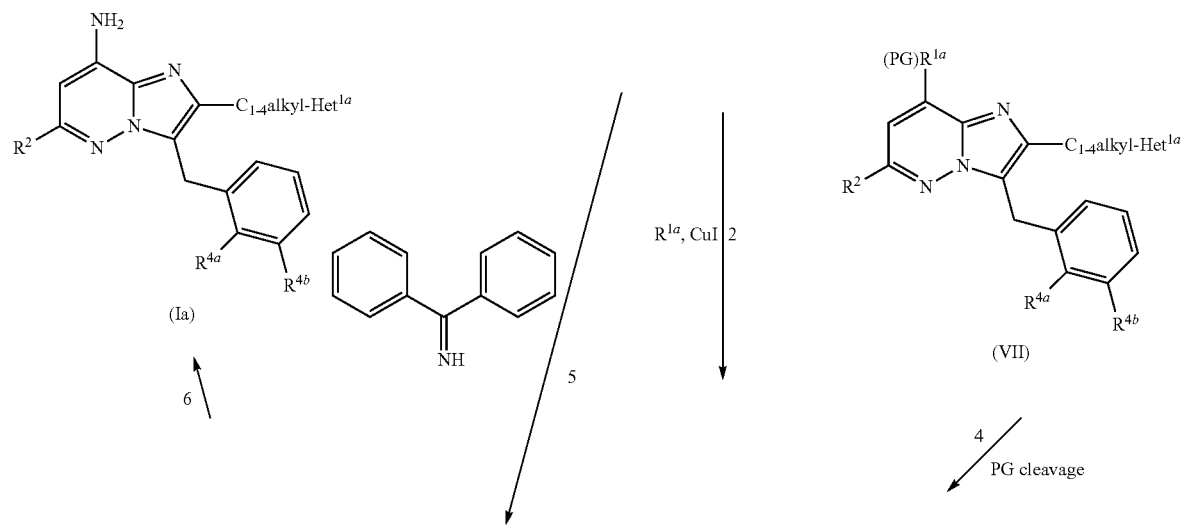

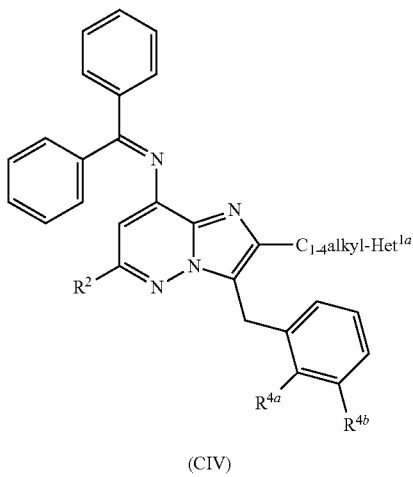

(CIV)

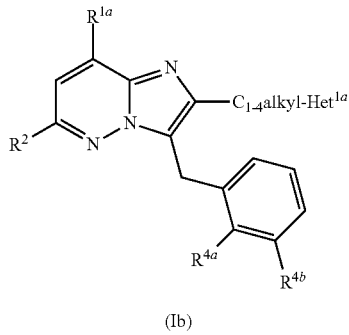

(Ib)

In Scheme 1, the following reaction conditions apply:

1: in the presence of a suitable catalyst such as for example copper iodide, a suitable ligand such as for example L-proline, a suitable base such as for example cesium carbonate, a suitable solvent such as for example N,N-dimethylformamide, at a suitable temperature such as 110° C. in a sealed vessel;

2: in the presence of copper iodide, a suitable catalyst such as for example palladium acetate, in a microwave, and a suitable solvent such as dimethylformamide, at a suitable temperature such as for example 185° C.;

3: in case of $(PG)R^{1a}B(OH)_2$ or $(PC)R^{1a}$(4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium carbonate, and a suitable solvent such as for example a mixture of dioxane and water, at a suitable temperature such as for example at 100° C.;

In case of $R^{1a}(PG)$, first, in the presence of zinc chloride, a suitable deprotonating agent such as for example butyl lithium, a suitable solvent such as for example THF, at a suitable temperature such as for example −78° C., followed by addition (of/to) this solution (to) a mixture of intermediate (II), optionally in solution in THF, and a suitable catalyst such as for example tetrakis(triphenylphosphine) palladium $Pd(PPh_3)_4$, heating at a suitable temperature ranging from 60 to 100° C.;

4: in the presence of a suitable acid such as for example p-toluenesulfonic acid hydrochloric acid or trifluoroacetic acid, in a suitable solvent such as for example dioxane or methanol (MeOH), at a suitable temperature such as for example 50 or 100° C.;

5: in the presence of a suitable catalyst such as for example palladium acetate, in the presence of a suitable ligand such as for example racemic-2,2'-bis(diphenylphosphino)-1,1'-binaphtyl, in the presence of a suitable base such as for example cesium carbonate, and in a suitable solvent such as for example toluene at a temperature of 100° C., in a sealed vessel;

6: in the presence of a suitable acid such as for example hydrochloric acid, in a suitable solvent such as for example methyltetrahydrofuran (Me-THF), at a suitable temperature such as for example room temperature.

In general, compounds of Formula (I) wherein $R^1$ is —C(=O)OH, and wherein the other variables are as shown in Formula (Ic); and compounds of Formula (I) wherein $R^1$ is —C(=O)NH$_2$, and wherein the other variables are as shown in Formula (Id), can be prepared according to the following reaction Scheme 2 wherein all variables in Scheme 2 are defined as above or according to the scope of the present invention.

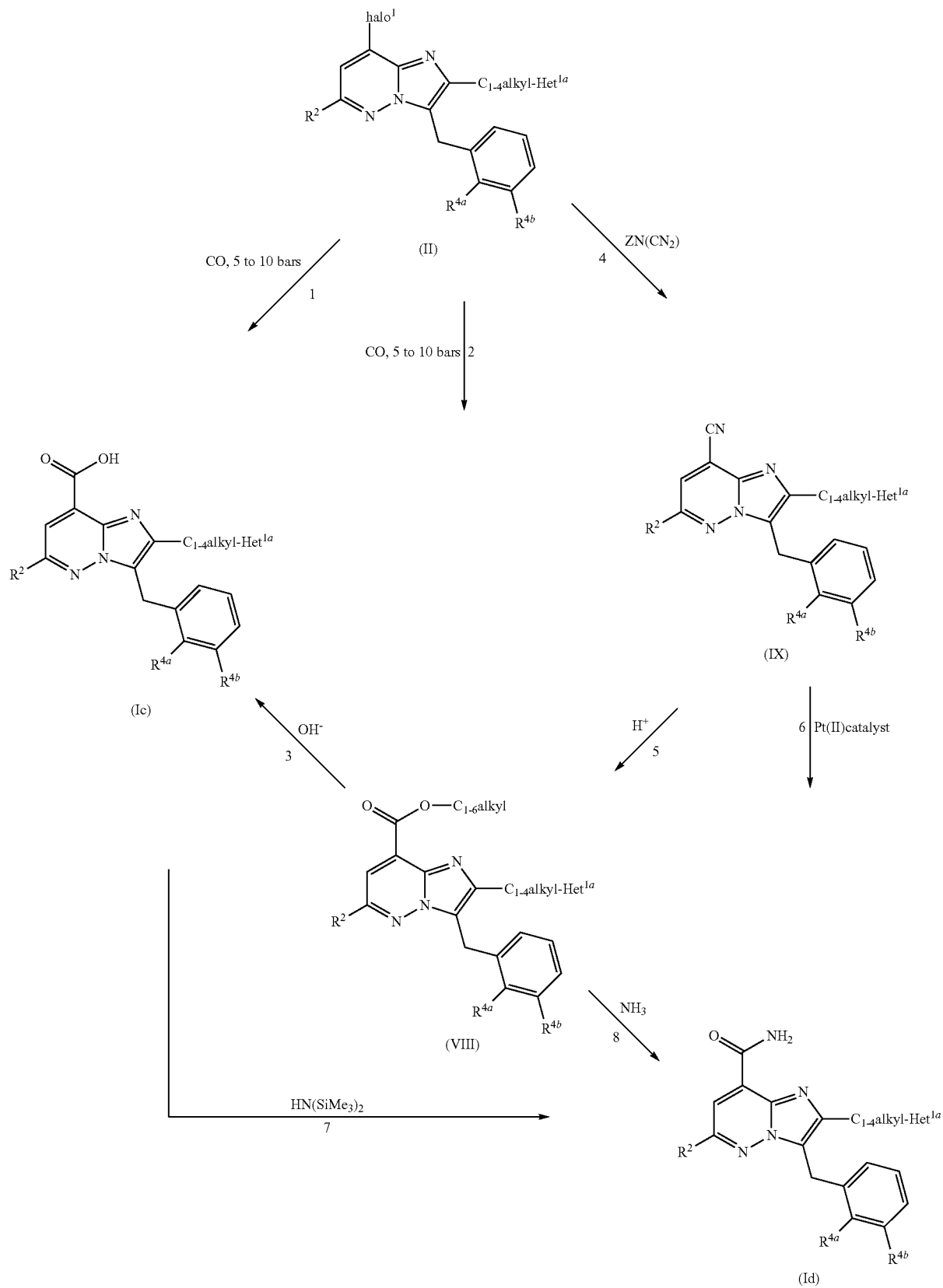

In Scheme 2, the following reaction conditions apply:

1: in the presence of a suitable catalyst such as for example Pd(PPh$_3$)$_4$, a suitable base such as for example an aqueous solution of Na$_2$CO$_3$, and a suitable solvent such as for example N,N-dimethylformamide, at a suitable temperature such as for example at 120° C.;

2: in the presence of a suitable catalyst such as for example Pd(PPh$_3$)$_4$, a suitable base such as for example triethylamine (Et$_3$N), and a suitable solvent such as for example methanol or ethanol, at a suitable temperature such as for example at 100° C. or 120° C.;

3: in the presence of a suitable base such as lithium hydroxide monohydrate, and a suitable solvent or a mixture of solvents such as for example a mixture of THF/water or MeOH/water;

4: in the presence of a suitable catalyst such as for example Pd(PPh$_3$)$_4$, and a suitable solvent such as a for example N,N-dimethylformamide (DMF), at a suitable temperature such as for example at 100° C.;

5: in the presence of a suitable acid such as for example sulphuric acid, and a suitable solvent such as methanol, at a suitable temperature such as for example at 100° C.;

6: in the presence of a suitable catalyst such as for example hydrido(dimethylphosphinous acid-kP)[hydrogen bis(dimethylphosphinito-kP)]platinum(II), and a suitable solvent or a mixture of solvents such as for example a mixture of THF/water, at a suitable temperature such as for example at 95° C.;

7: in the presence of a suitable peptidic coupling reagent such as 1-[bis(dimethylamino)methylene]-1H-[1,2,3]triazolo[4,5-b]pyridin-1-ium 3-oxide hexafluorophosphate (HATU), in the presence of a suitable base such as for example diisopropylamine, and a suitable solvent such as for example DMF;

8: in a suitable solvent such as for example methanol, at a suitable temperature such as for example at 100° C., in a sealed vessel.

Intermediates of Formula (II) used in the above Schemes 1 and 2 can be prepared according to the following reaction Scheme 3. In Scheme 3, R$^x$ and R$^y$ represent C$_{1-4}$alkyl, and R$^z$ represent C$_{1-4}$alkyl or phenyl, for instance R$^x$ and R$^y$ represent CH$_3$ and R$^z$ represents C(CH$_3$)$_3$ or phenyl. All the other variables are defined as above or according to the scope of the present invention.

Scheme 3

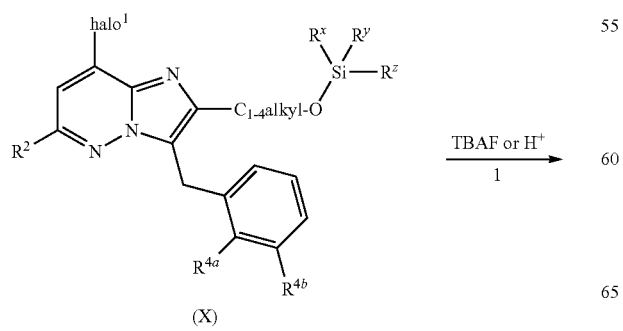

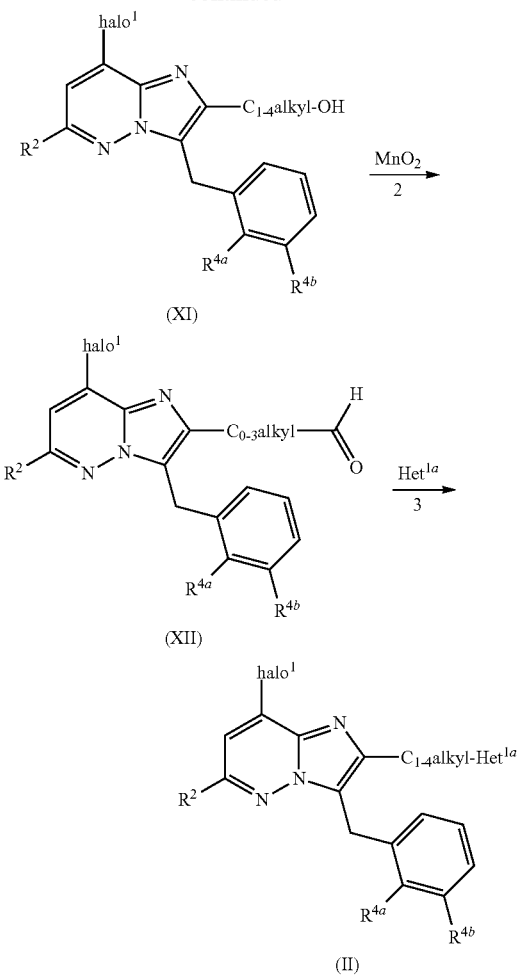

In Scheme 3, the following reaction conditions apply:

1: in the presence of a suitable reagent such as for example tetrabutylammonium fluoride, hydrochloric acid or trifluoroacetic acid in a suitable solvent such as THF, dioxane or dichloromethane:

2: at a suitable temperature such as for example 80° C. in the presence of a suitable oxidative reagent such as for example manganese dioxide, in a suitable solvent such as for example dioxane;

3: in the presence of a suitable reducing agent such as for example sodium triacetoxyborohydride, a suitable additive such as for example sodium acetate, and in a suitable solvent such as for example dichloromethane.

Intermediates of Formula (X) used in the above Schemes 3 can be prepared according to the following reaction Scheme 4. In Scheme 4, W and W$_1$ are a leaving group such as F, Cl, Br or I; W$_2$ represent a suitable leaving group, such as for example halo, e.g. bromo, chloro and iodo. All the other variables are defined as above or according to the scope of the present invention.

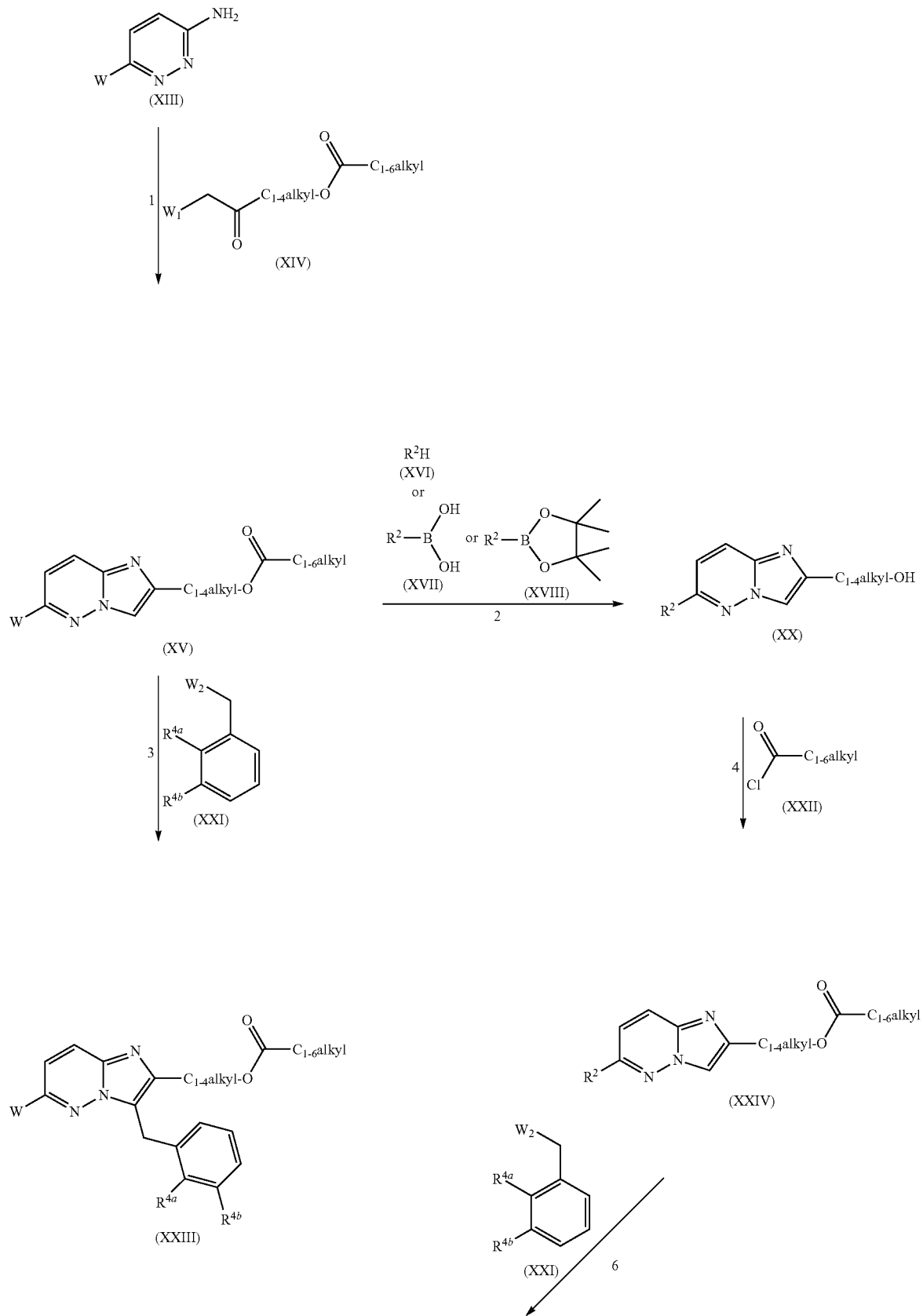

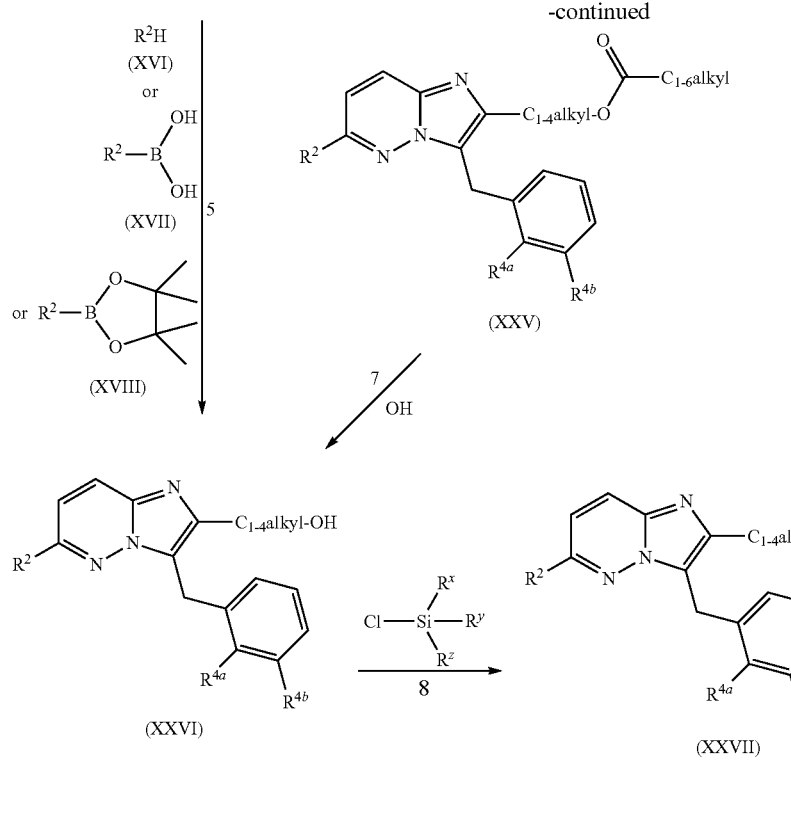

In Scheme 4, the following reaction conditions apply:

1: at a suitable temperature such as for example 90° C. in the presence of a suitable solvent such as for example N,N-dimethylformamide or dimethoxy ethane;

2: in case of $R^2H$:
Without any solvent at a suitable temperature such as 105° C.
Alternatively in the presence of a suitable ligand such as 2-dicyclohexylphosphino-2',6'-diisopropoxybiphenyl (Ruphos), a suitable catalyst such as for example tris(dibenzylideneacetone)dipalladium ($Pd_2dba_3$), a suitable base such as for example $Cs_2CO_3$, and a suitable solvent such as for example 2-methyl-2-butanol, at a suitable temperature such as for example between 100 and 120° C.;
in case of $R^2B(OH)_2$ or $R^2$(4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium phosphate, and a suitable solvent such as for example a mixture dioxane and water, at a suitable temperature such as for example at 80° C.;

3: in the presence of a suitable catalyst such as for example palladium acetate, a suitable ligand such as triphenylphosphine, a suitable base such as for example $K_2CO_3$, a suitable solvent such as for example dioxane, and a suitable temperature such as for example 100° C., optionally in a sealed vessel;

4: in the presence of a suitable base such as for example triethylamine and a suitable solvent such as for example dichloromethane;

5: in case of $R^2H$:
Without any solvent at a suitable temperature such as 120° C.
Alternatively in the presence of a suitable ligand such as Ruphos, a suitable catalyst such as for example $Pd_2dba_3$, a suitable base such as for example $Cs_2CO_3$, and a suitable solvent such as for example 2-methyl-2-butanol, at a suitable temperature such as for example between 100 and 120° C.;
in case of $R^2B(OH)_2$ or $R^2$(4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium phosphate, and a suitable solvent such as for example a mixture dioxane and water, at a suitable temperature such as for example at 80° C.;

6: in the presence of a suitable catalyst such as for example palladium acetate, a suitable ligand such as triphenylphosphine, a suitable base such as for example $K_2CO_3$, a suitable solvent such as for example dioxane, and a suitable temperature such as for example 100° C., optionally in a sealed vessel;

7: in the presence of a suitable base such as for example lithium hydroxide monohydrate, a suitable solvent such as for example a mixture of methanol and water;

8: in the presence of a suitable activating agent such as for example imidazole and a suitable solvent such as for example N,N-dimethylformamide;

9: in the presence of a suitable base, such as for example lithium diisopropylamide, and a suitable solvent such as for example tetrahydrofuran (THF), at a suitable temperature such as for example at −70° C.

Intermediates of Formula (XX) and (XXVI) depicted in the above Scheme 4 can alternatively be prepared according to the following reaction Scheme 5, wherein all variables are defined as above or according to the scope of the present invention.

Scheme 5

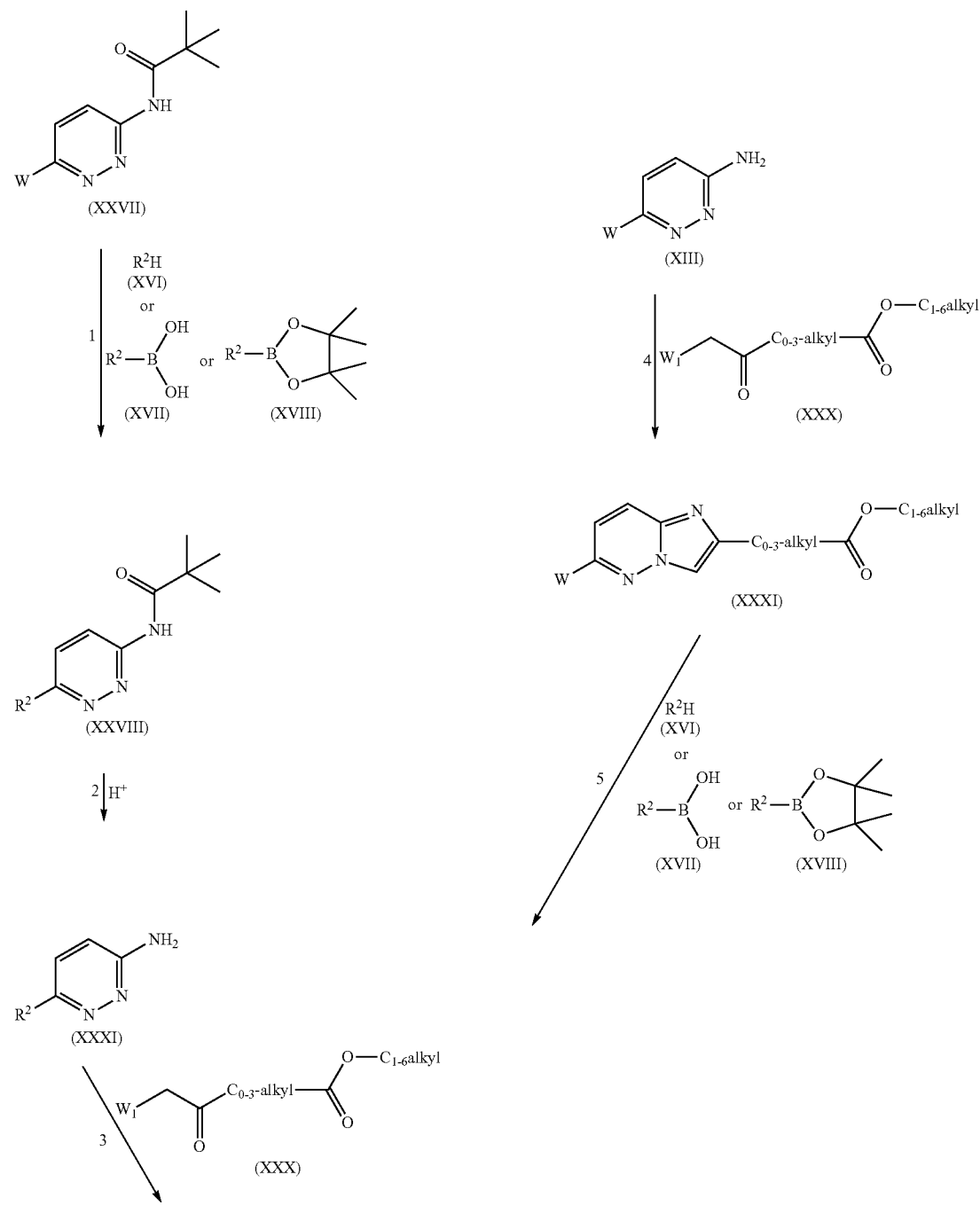

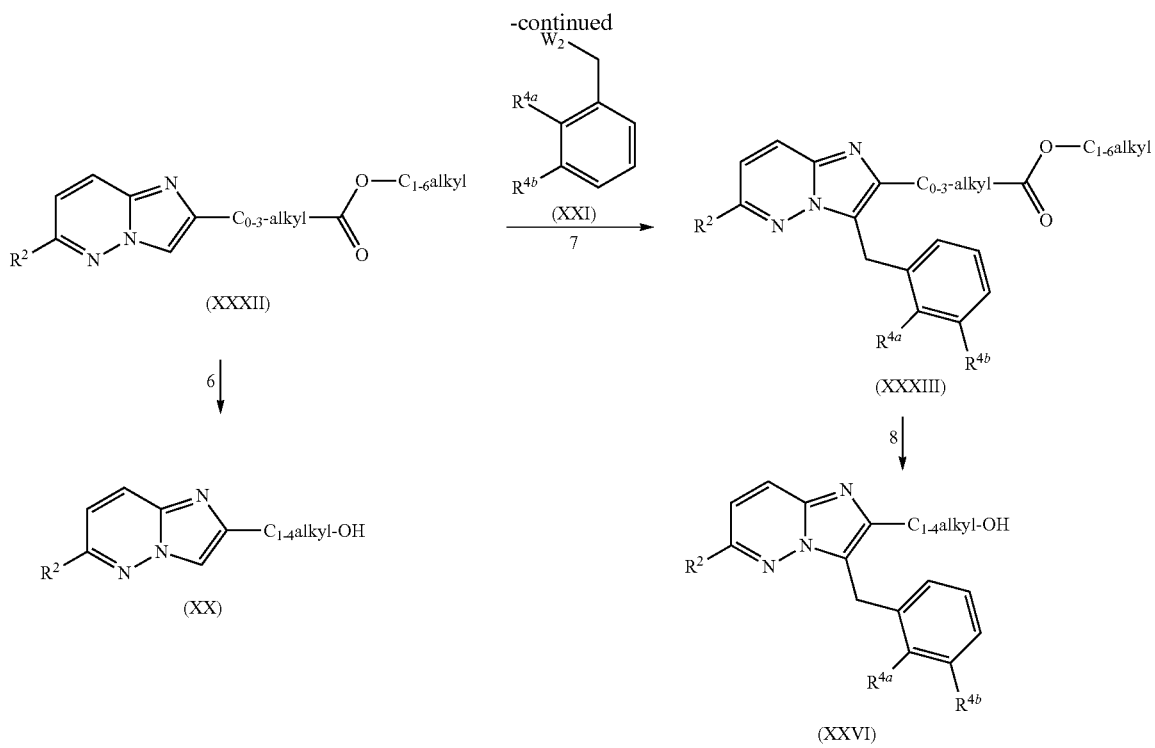

In Scheme 5, the following reaction conditions apply:
1: in case of R₂H:
Without any solvent at a suitable temperature such as 120° C.
Alternatively in the presence of a suitable ligand such as Ruphos, a suitable catalyst such as for example Pd₂dba₃, a suitable base such as for example Cs₂CO₃, and a suitable solvent such as for example 2-methyl-2-butanol, at a suitable temperature such as for example between 100 and 120° C.;
in case of R₂B(OH)₂ or R₂(4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium phosphate, and a suitable solvent such as for example a mixture dioxane and water, at a suitable temperature such as for example at 80° C.;
2: in the presence of a suitable acid such as for example hydrochloric acid, a suitable solvent such as for example dioxane, and a suitable temperature such as for example 70° C.:
3: at a suitable temperature such as for example 70° C. or 90° C., in the presence of a suitable solvent such as for example ethanol, N,N-dimethylformamide or dimethoxyethane;
4: at a suitable temperature such as for example 70° C. or 90° C., in the presence of a suitable solvent such as for example ethanol, N,N-dimethylformamide or dimethoxyethane;

5: in case of R₂H, without any solvent at a suitable temperature such as 90° C.;
in case of R₂B(OH)₂ or R₂(4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium phosphate, and a suitable solvent such as for example a mixture dioxane and water, at a suitable temperature such as for example at 80° C.;
6: in the presence of a suitable reducing reagent such as for example potassium borohydride or lithium aluminium hydride, optionally a suitable additive such as for example lithium chloride, a suitable solvent such as for example THF or and a suitable temperature such as 0° C. or solvent reflux based on the reducing reagent;
7: in the presence of a suitable catalyst such as for example palladium acetate, a suitable ligand such as triphenylphosphine, a suitable base such as for example K₂CO₃, a suitable solvent such as for example dioxane, and a suitable temperature such as for example 100° C., optionally in a sealed vessel;
8: in the presence of a suitable reducing reagent such as for example lithium aluminium hydride, a suitable solvent such as for example THF or and a suitable temperature such as 0° C.

Intermediates of Formula (VII) and compounds (Ib) depicted in the above Scheme 1 can alternatively be prepared according to the following reaction Scheme 6, wherein all variables are defined as above or according to the scope of the present invention.

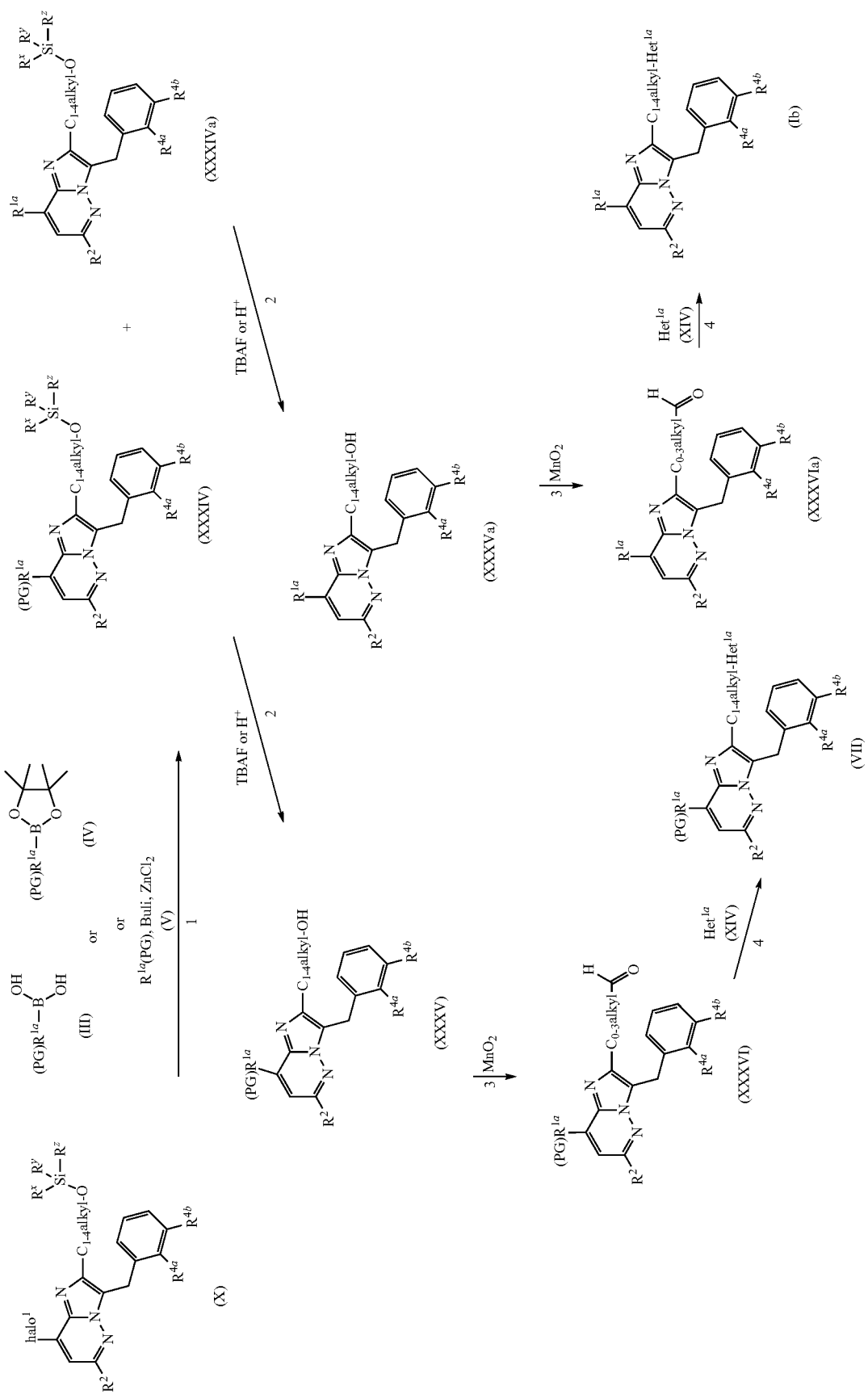

In Scheme 6, the following reaction conditions apply:

1: in case of (PG)R$^{1a}$B(OH)$_2$ or (PG)R$^{1a}$ (4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium carbonate, and a suitable solvent such as for example a mixture of dioxane and water, at a suitable temperature such as for example at 100° C.;

In case of R$^{1a}$ (PG), first, in the presence of zinc chloride, a suitable deprotonating agent such as for example butyl lithium, a suitable solvent such as for example THF, at a suitable temperature such as for example −78° C., followed by addition (of/to) this solution (to) a mixture of intermediate (X), optionally in solution in THF, and a suitable catalyst such as for example Pd(PPh$_3$)$_4$, healing at a suitable temperature ranging from 60 to 100° C.;

2: in the presence of a suitable reagent such as for example tetrabutylammonium fluoride, in a suitable solvent such as THF;

3: at a suitable temperature such as for example 100° C., in the presence of a suitable oxidative reagent such as for example manganese dioxide, in a suitable solvent such as for example dioxane;

4: in the presence of a suitable reducing agent such as for example sodium triacetoxyborohydride, and in a suitable solvent such as for example methanol.

Intermediates of Formula (VIII) depicted in the above Scheme 2 can alternatively be prepared according to the following reaction Scheme 7, wherein all variables are defined as above or according to the scope of the present invention.

Scheme 7

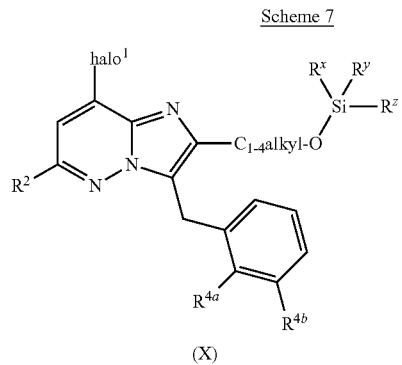

(X)

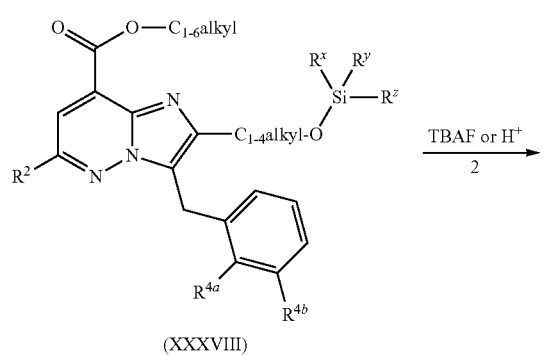

(XXXVIII)

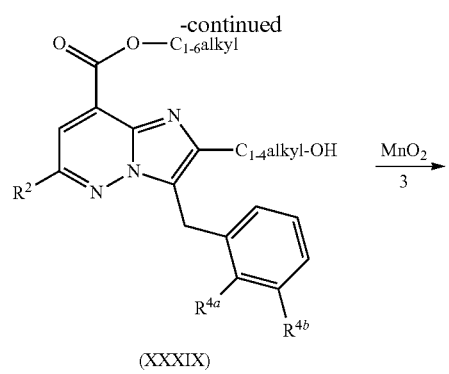

(XXXIX)

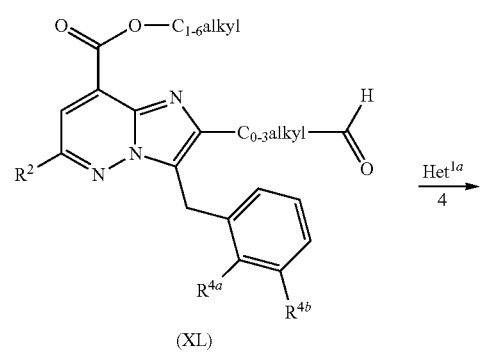

(XL)

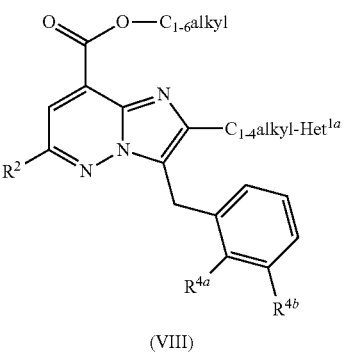

(VIII)

In Scheme 7, the following reaction conditions apply:

1: in the presence of a suitable catalyst such as for example Pd(PPh$_3$)$_4$, a suitable base such as for example triethylamine (Et$_3$N), and a suitable solvent such as for example methanol or ethanol, at a suitable temperature such as for example at 100° C. or 120° C.;

2: in the presence of a suitable reagent such as for example tetrabutylammonium fluoride, hydrochloric acid or trifluoroacetic acid in a suitable solvent such as THF, dioxane or dichloromethane;

3: at a suitable temperature such as for example 100° C., in the presence of a suitable oxidative reagent such as for example manganese dioxide, in a suitable solvent such as for example dioxane;

4: in the presence of a suitable reducing agent such as for example sodium triacetoxyborohydride, a suitable additive such as for example sodium acetate, and in a suitable solvent such as for example dichloromethane.

Intermediates of Formula (IX) depicted in the above Scheme 2 can alternatively be prepared according to the following reaction Scheme 8, wherein all variables are defined as above or according to the scope of the present invention.

Scheme 8

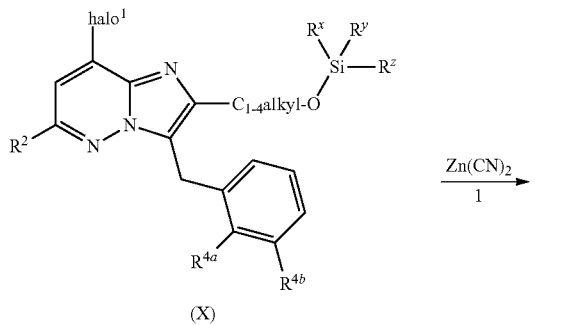

(X)

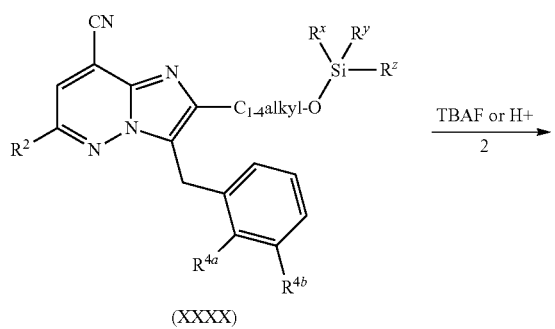

(XXXX)

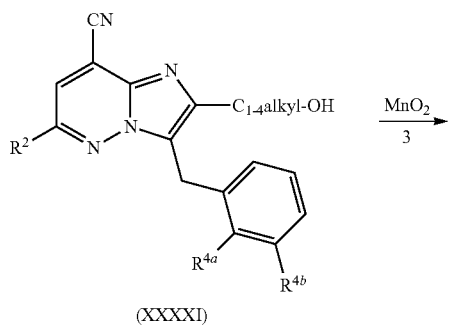

(XXXXI)

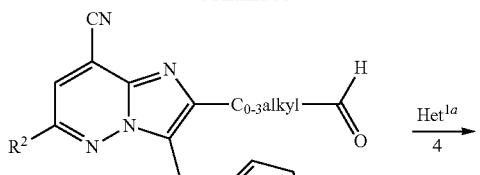

(XXXXII)

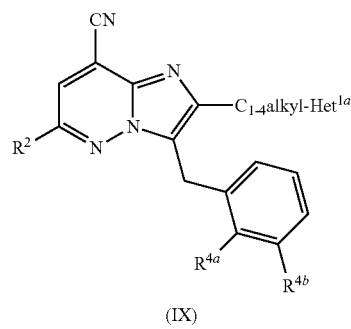

(IX)

In Scheme 8, the following reaction conditions apply:

1: in the presence of a suitable catalyst such as for example Pd(PPh$_3$)$_4$, and a suitable solvent such as a for example N,N-dimethylformamide (DMF), at a suitable temperature such as for example at 100° C.;

2: in the presence of a suitable reagent such as for example tetrabutylammonium fluoride, hydrochloric acid or trifluoroacetic acid in a suitable solvent such as THF, dioxane or dichloromethane;

3: at a suitable temperature such as for example 100° C., in the presence of a suitable oxidative reagent such as for example manganese dioxide, in a suitable solvent such as for example dioxane;

4: in the presence of a suitable reducing agent such as for example sodium triacetoxyborohydride, a suitable additive such as for example sodium acetate, and in a suitable solvent such as for example dichloromethane.

In general, compounds of Formula (I) wherein R$^1$ is —NH$_2$, and wherein the other variables are as shown in Formula (Ie); and compounds of Formula (I) wherein R$^1$ is restricted to R$^{1a}$ being

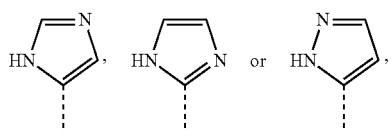

and wherein the other variables are as shown in Formula (If), can be prepared according to the following reaction Scheme 9. Het$^{1b}$ is defined as above. All other variables in Scheme 9 are defined as above or according to the scope of the present invention.

Scheme 9
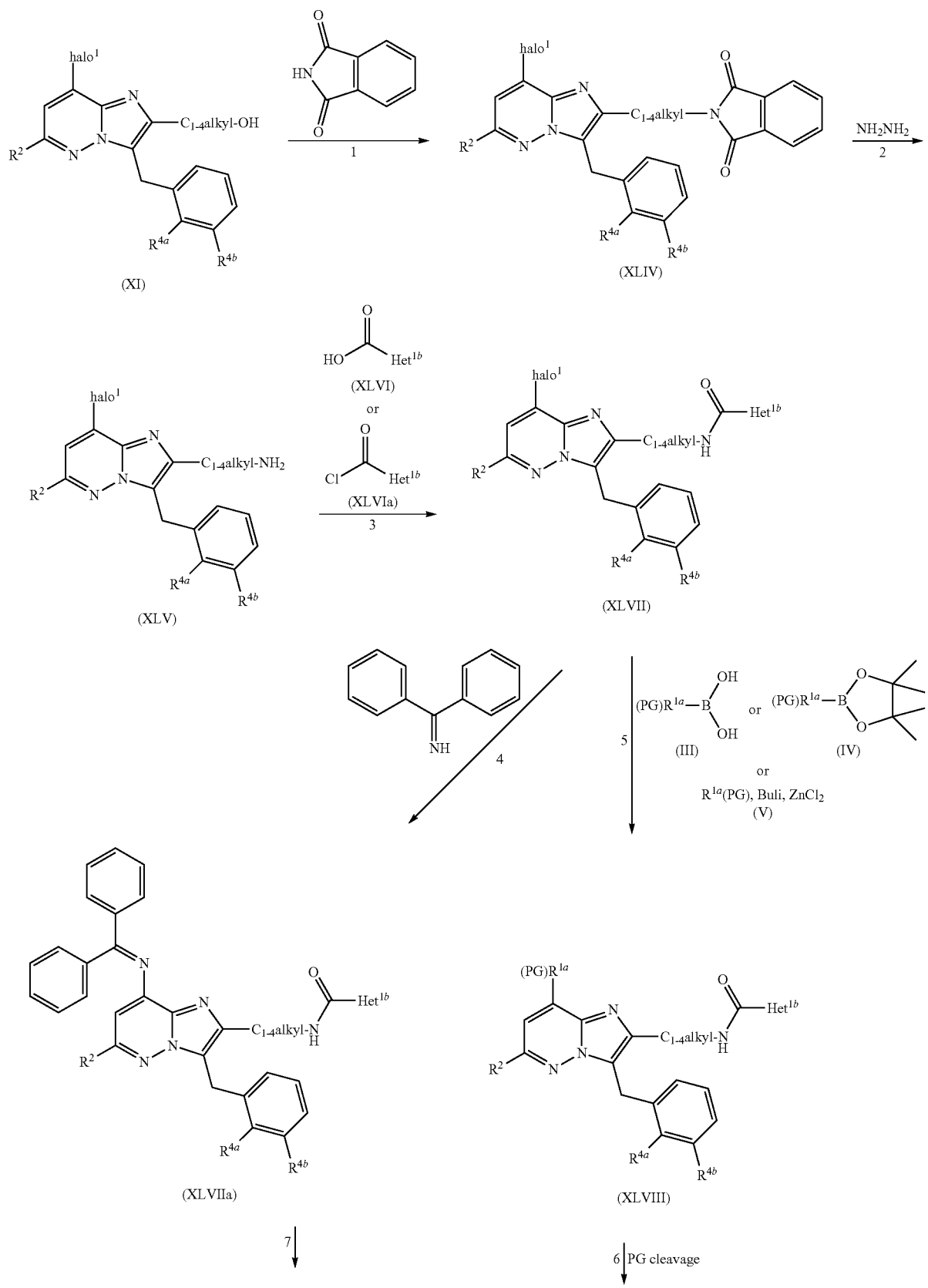

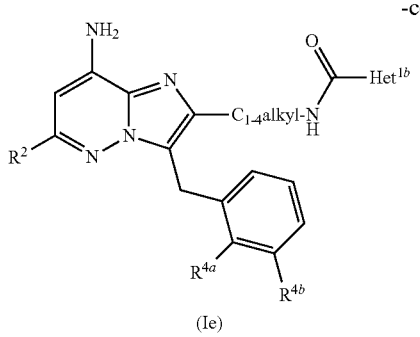

(Ie)

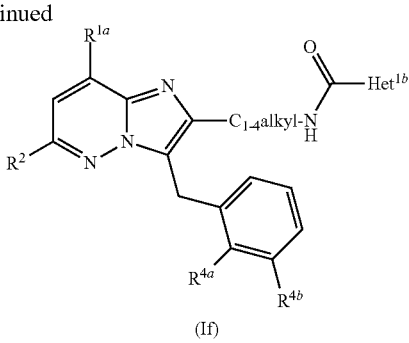

(If)

In Scheme 9, the following reaction conditions apply:

1: in the presence of a suitable reagent such as for example di-tert-butyl azodicarboxylate, a suitable phosphine such as for example triphenylphosphine, and in a suitable solvent such as for example THF;

2: at a suitable temperature such as for example 80° C., in a suitable solvent such as for example ethanol;

3: in case of an acyl chloride, in the presence of a suitable base such as for example diisopropylethylamine, and in a suitable solvent such as for example dichloromethane in case of a carboxylic acid, in the presence of a suitable coupling reagent such as for example 1-(3-dimethyamino-propyl)-3-ethylcarbodiimide hydrochloride, a suitable additive such as for example 1-hydroxybenzotriazole, a suitable base such as for example triethylamine, and in a suitable solvent such as for example a mixture of THF and dichloromethane;

4: in the presence of a suitable catalyst such as for example palladium acetate, in the presence of a suitable ligand such as for example racemic-2,2'-bis(diphenylphosphino)-1,1'-binaphtyl, in the presence of a suitable base such as for example cesium carbonate, and in a suitable solvent such as for example toluene at a temperature of 100° C., optionally in a sealed vessel;

5: in case of (PG)$R^{1a}$B(OH)$_2$ or (PG)$R^{1a}$ (4,4,5,5-tetramethyl-1,3,2-dioxaborolane), in the presence of a suitable catalyst such as for example 1,1'-bis(diphenylphosphino) ferrocene palladium(II)dichloride dichloromethane adduct, a suitable base such as for example potassium carbonate, and a suitable solvent such as for example a mixture of dioxane and water, at a suitable temperature such as for example at 100° C.;

In case of $R^{1a}$(PG), first, in the presence of zinc chloride, a suitable deprotonating agent such as for example butyl lithium, a suitable solvent such as for example THF, at a suitable temperature such as for example −78° C., followed by addition (of/to) this solution (to) a mixture of intermediate (XLVII), optionally in solution in THF, and a suitable catalyst such as for example Pd(PPh$_3$)$_4$, heating at a suitable temperature ranging from 60 to 100° C.;

6: in the presence of a suitable acid such as for example p-toluenesulfonic acid, hydrochloric acid or trifluoroacetic acid, in a suitable solvent such as for example dioxane, methanol or dichloromethane, at a suitable temperature such as for example 50 or 100° C.

7: in the presence of a suitable acid such as for example hydrochloric acid or trifluoroacetic acid, in a suitable solvent such as for example tetrahydrofurane or dichloromethane, at a suitable temperature such as for example room temperature, 50° C. or 70° C.

In general, compounds of Formula (I) wherein $R^1$ is —C(═O)OH, and wherein the other variables are as shown in Formula (Ig); and compounds of Formula (I) wherein $R^1$ is —C(═O)NH$_2$, and wherein the other variables are as shown in Formula (Ih), can be prepared according to the following reaction Scheme 10 wherein all other variables are defined as above or according to the scope of the present invention.

Scheme 10

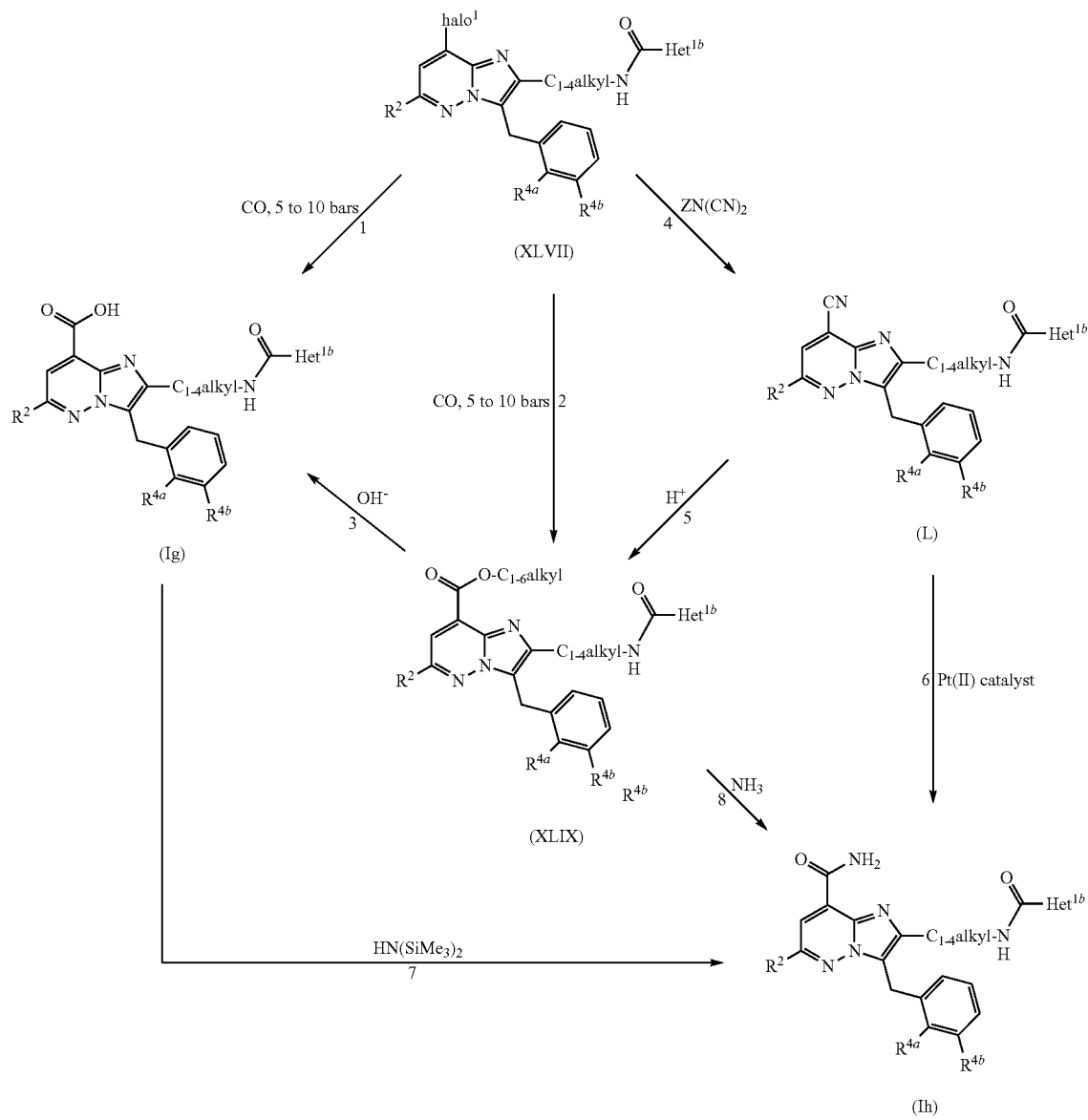

In Scheme 10, the following reaction conditions apply:

1: in the presence of a suitable catalyst such as for example Pd(PPh$_3$)$_4$, a suitable base such as for example an aqueous solution of Na$_2$CO$_3$, and a suitable solvent such as for example N,N-dimethylformamide, at a suitable temperature such as for example at 120° C.;

2: in the presence of a suitable catalyst such as for example Pd(PPh$_3$)$_4$, a suitable base such as for example triethylamine (Et$_3$N), and a suitable solvent such as for example methanol or ethanol, at a suitable temperature such as for example at 100° C. or 120° C.;

3: in the presence of a suitable base such as lithium hydroxide monohydrate, and a suitable solvent or a mixture of solvents such as for example a mixture of THF/water or MeOH/water;

4: in the presence of a suitable catalyst such as for example Pd(PPh$_3$)$_4$, and a suitable solvent such as a for example N,N-dimethylformamide (DMF), at a suitable temperature such as for example at 100° C.;

5: in the presence of a suitable acid such as for example sulphuric acid, and a suitable solvent such as methanol, at a suitable temperature such as for example at 100° C.;

6: in the presence of a suitable catalyst such as for example hydrido(dimethylphosphinous acid-kP)[hydrogen bis(dimethylphosphinito-kP)]platinum(II), and a suitable solvent or a mixture of solvents such as for example a mixture of THF/water, at a suitable temperature such as for example at 95° C.;

7: in the presence of a suitable peptidic coupling reagent such as 1-[bis(dimethylamino)methylene]-1H-[1,2,3]triazolo[4,5-b]pyridin-1-ium 3-oxide hexafluorophosphate (HATU), in the presence of a suitable base such as for example diisopropylamine, and a suitable solvent such as for example DMF;

8: in a suitable solvent such as for example methanol, at a suitable temperature such as for example at 100° C., in a sealed vessel.

In general, compounds of Formula (I) wherein $R^1$ is a —$NH_2$, and wherein the other variables are as shown in Formula (Ii), can be prepared according to the following reaction Scheme 11. All variables in Scheme 11 are defined as above or according to the scope of the present invention.

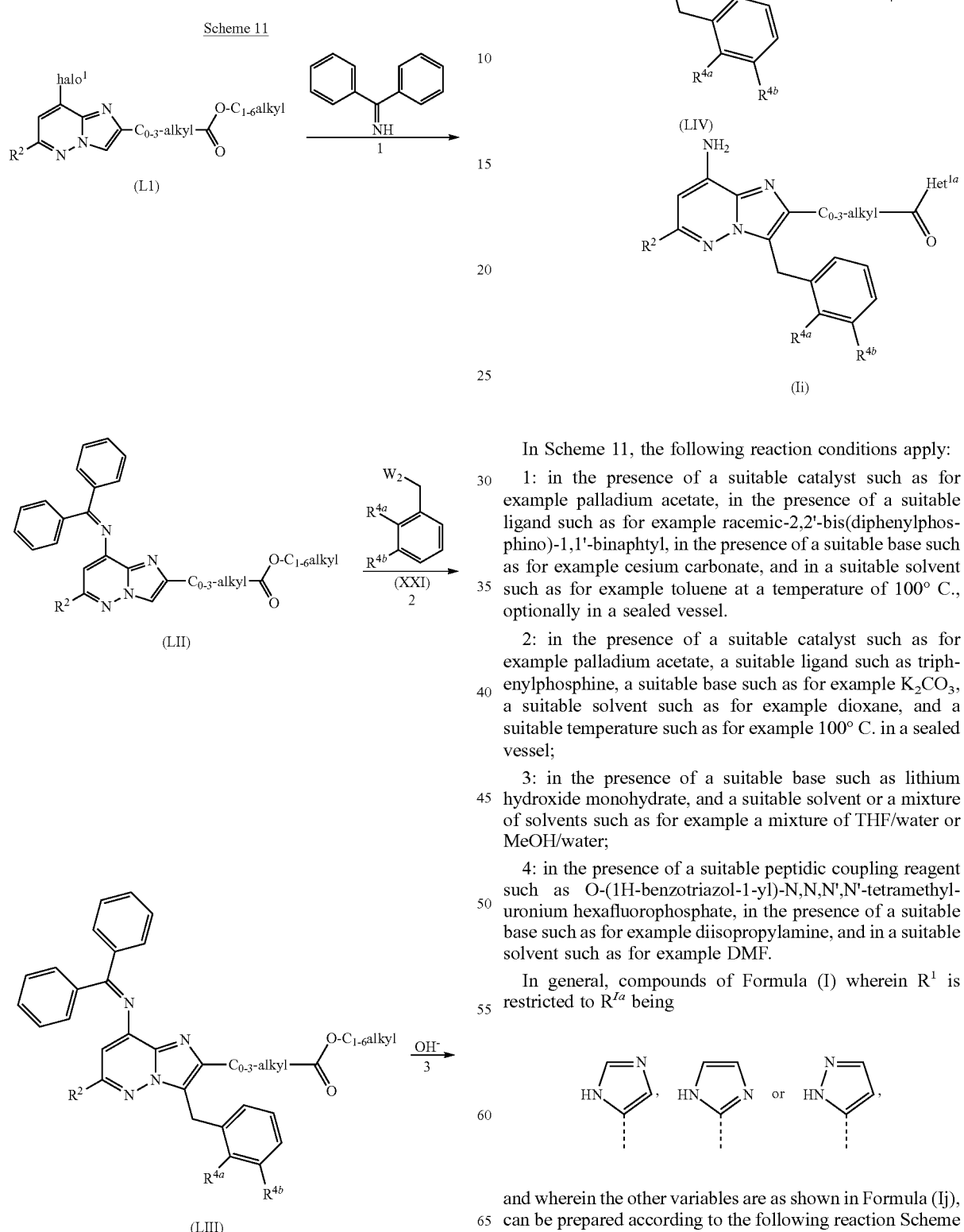

In Scheme 11, the following reaction conditions apply:

1: in the presence of a suitable catalyst such as for example palladium acetate, in the presence of a suitable ligand such as for example racemic-2,2'-bis(diphenylphosphino)-1,1'-binaphtyl, in the presence of a suitable base such as for example cesium carbonate, and in a suitable solvent such as for example toluene at a temperature of 100° C., optionally in a sealed vessel.

2: in the presence of a suitable catalyst such as for example palladium acetate, a suitable ligand such as triphenylphosphine, a suitable base such as for example $K_2CO_3$, a suitable solvent such as for example dioxane, and a suitable temperature such as for example 100° C. in a sealed vessel;

3: in the presence of a suitable base such as lithium hydroxide monohydrate, and a suitable solvent or a mixture of solvents such as for example a mixture of THF/water or MeOH/water;

4: in the presence of a suitable peptidic coupling reagent such as O-(1H-benzotriazol-1-yl)-N,N,N',N'-tetramethyluronium hexafluorophosphate, in the presence of a suitable base such as for example diisopropylamine, and in a suitable solvent such as for example DMF.

In general, compounds of Formula (I) wherein $R^1$ is restricted to $R^{Ia}$ being and wherein the other variables are as shown in Formula (Ij), can be prepared according to the following reaction Scheme 12. All other variables in Scheme 12 are defined as above or according to the scope of the present invention.

Scheme 12

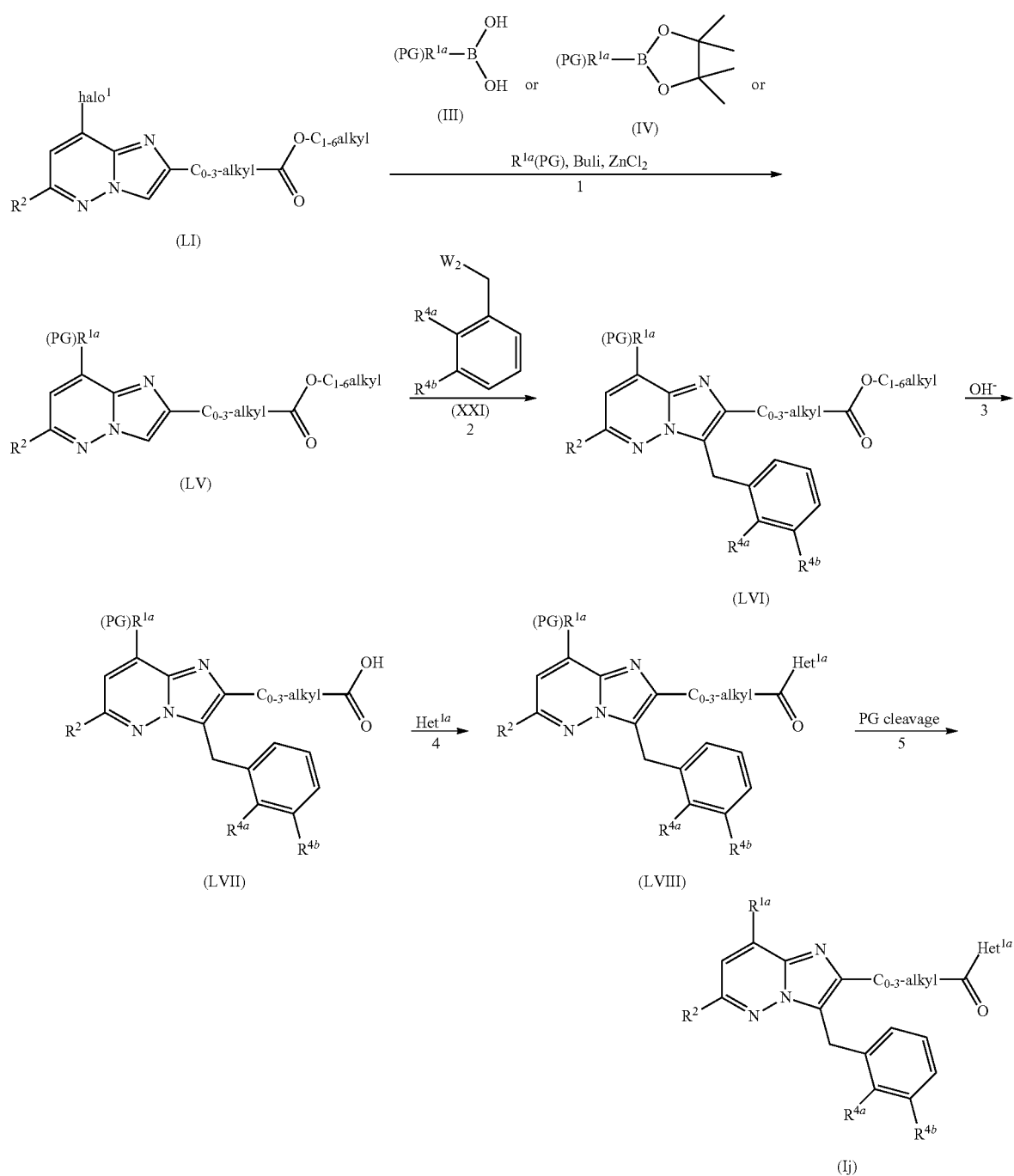

In Scheme 12, the following reaction conditions apply:

1: in case of (PG)R$^{1a}$B(OH)$_2$ or (PG)R$^{1a}$ (4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium carbonate, and a suitable solvent such as for example a mixture of dioxane and water, at a suitable temperature such as for example at 100° C.;

In case of R$^{1a}$(PG), first, in the presence of zinc chloride, a suitable deprotonating agent such as for example butyl lithium, a suitable solvent such as for example THF, at a suitable temperature such as for example −78° C., followed by addition (of/to) this solution (to) a mixture of intermediate (LI), optionally in solution in THF, and a suitable catalyst such as for example Pd(PPh$_3$)$_4$, heating at a suitable temperature ranging from 60 to 100° C.;

2: in the presence of a suitable catalyst such as for example palladium acetate, a suitable ligand such as triphenylphosphine, a suitable base such as for example K$_2$CO$_3$, a suitable solvent such as for example dioxane, and a suitable temperature such as for example 100° C. in a sealed vessel;

3: in the presence of a suitable base such as lithium hydroxide monohydrate, and a suitable solvent or a mixture of solvents such as for example a mixture of THF/water or MeOH/water;

4: in the presence of a suitable peptidic coupling reagent such as O-(1H-benzotriazol-1-yl)-N,N,N',N'-tetramethyl-uronium hexafluorophosphate, in the presence of a suitable base such as for example diisopropylamine, and in a suitable solvent such as for example DMF;

5: in the presence of a suitable acid such as for example p-toluenesulfonic acid, hydrochloric acid or trifluoroacetic acid, in a suitable solvent such as for example dioxane or methanol (MeOH), at a suitable temperature such as for example 50 or 100° C.

In general, compounds of Formula (I) wherein $R^1$ is —C(=O)OH, and wherein the other variables are as shown in Formula (Ik); and compounds of Formula (I) wherein $R^1$ is —C(=O)NH$_2$, and wherein the other variables are as shown in Formula (Im), can be prepared according to the following reaction Scheme 13 wherein all variables in Scheme 13 are defined as above or according to the scope of the present invention.

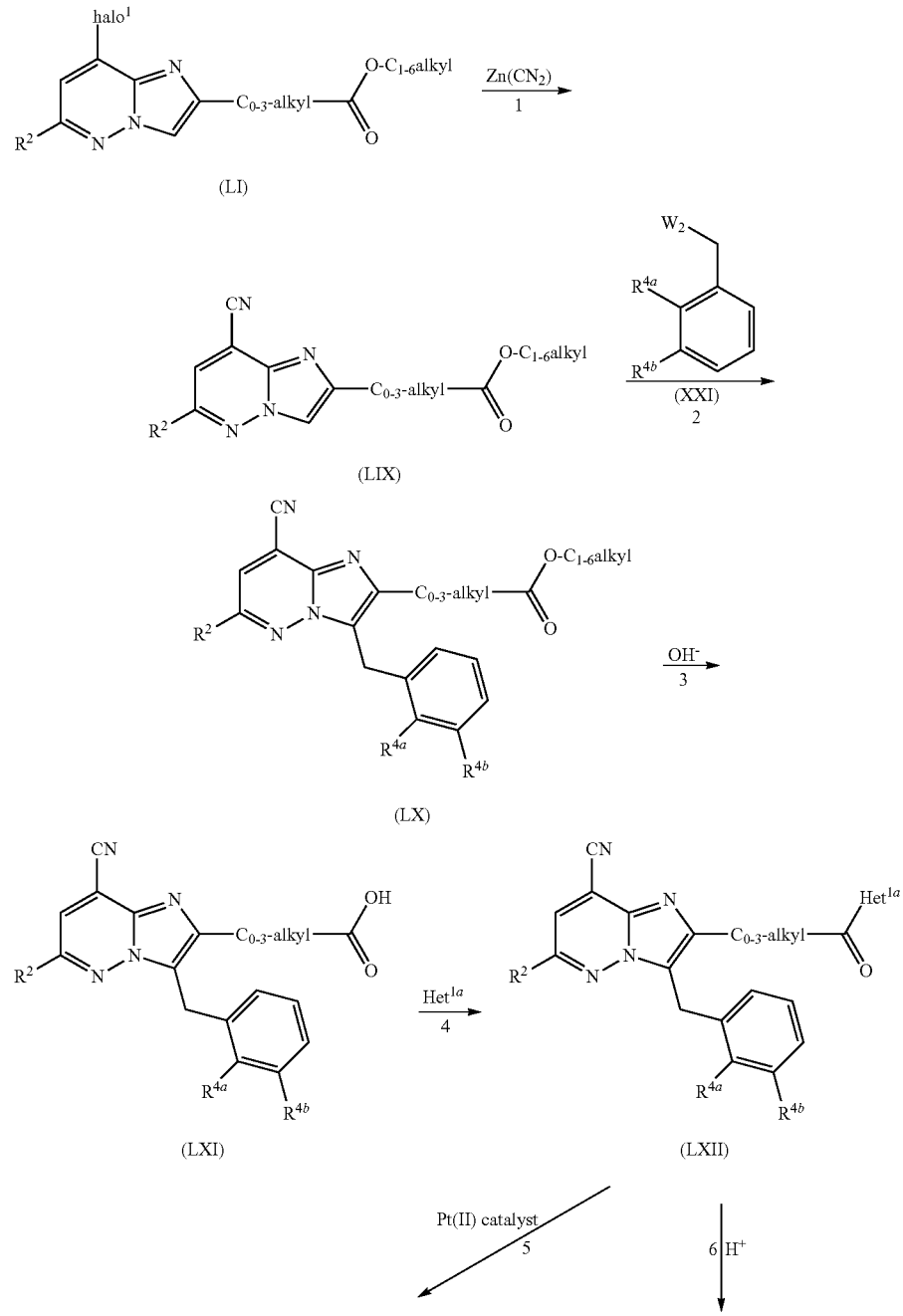

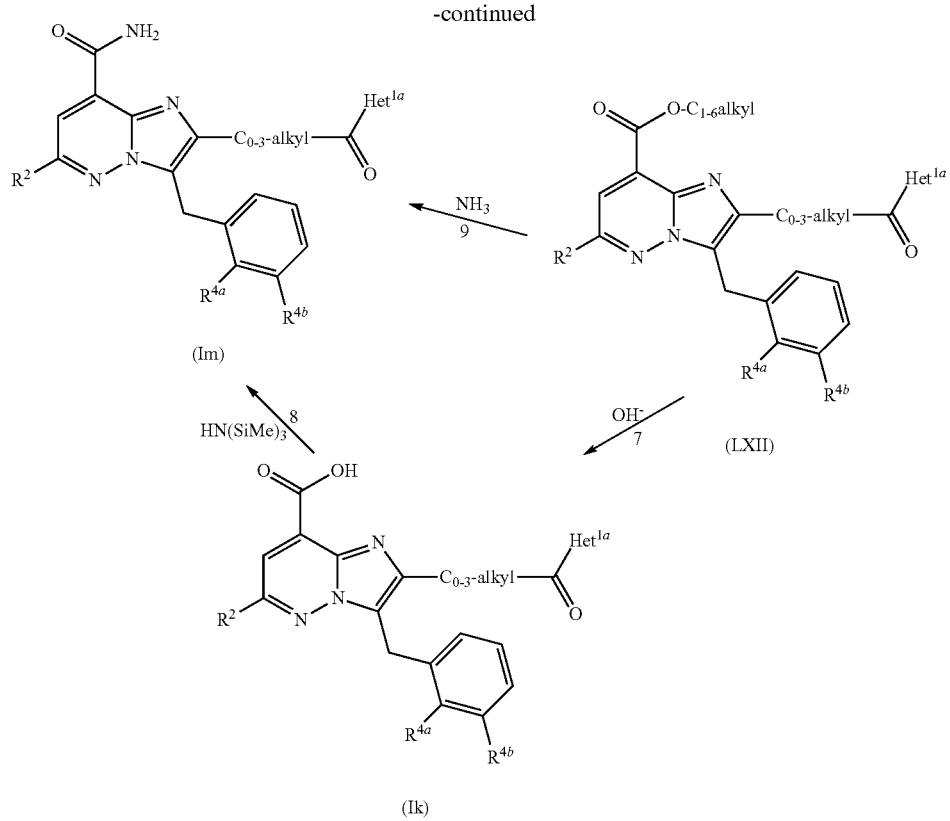

In Scheme 13, the following reaction conditions apply:
1: in the presence of a suitable catalyst such as for example Pd(PPh$_3$)$_4$, and a suitable solvent such as a for example N,N-dimethylformamide (DMF), at a suitable temperature such as for example at 100° C.;
2: in the presence of a suitable catalyst such as for example palladium acetate, a suitable ligand such as triphenylphosphine, a suitable base such as for example K$_2$CO$_3$, a suitable solvent such as for example dioxane, and a suitable temperature such as for example 100° C. optionally in a sealed vessel;
3: in the presence of a suitable base such as lithium hydroxide monohydrate, and a suitable solvent or a mixture of solvents such as for example a mixture of THF/water or MeOH/water;
4: in the presence of a suitable peptidic coupling reagent such as O-(1H-benzotriazol-1-yl)-N,N,N',N'-tetramethyluronium hexafluorophosphate, in the presence of a suitable base such as for example diisopropylamine, and in a suitable solvent such as for example DMF;
5: in the presence of a suitable catalyst such as for example hydrido(dimethylphosphinous acid-kP)[hydrogen bis(dimethylphosphinito-kP)]platinum(II), and a suitable solvent or a mixture of solvents such as for example a mixture of THF/water, at a suitable temperature such as for example at 95° C.;
6: in the presence of a suitable acid such as for example sulphuric acid, and a suitable solvent such as methanol, at a suitable temperature such as for example at 100° C.;
7 in the presence of a suitable base such as lithium hydroxide monohydrate, and a suitable solvent or a mixture of solvents such as for example a mixture of THF/water or MeOH/water;
8: in the presence of a suitable peptidic coupling reagent such as 1-[bis(dimethylamino)methylene]-1H-[1,2,3]triazolo[4,5-b]pyridin-1-ium 3-oxide hexafluorophosphate (HATU), in the presence of a suitable base such as for example diisopropylamine, and a suitable solvent such as for example DMF;
9: in a suitable solvent such as for example methanol, at a suitable temperature such as for example at 100° C., in a sealed vessel.

Intermediates of Formula (LI) used in the above Schemes 11, 12 and 13 can be prepared according to the following reaction Scheme 14 wherein all the variables are defined as above or according to the scope of the present invention.

Scheme 14

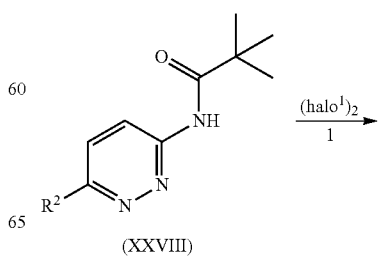

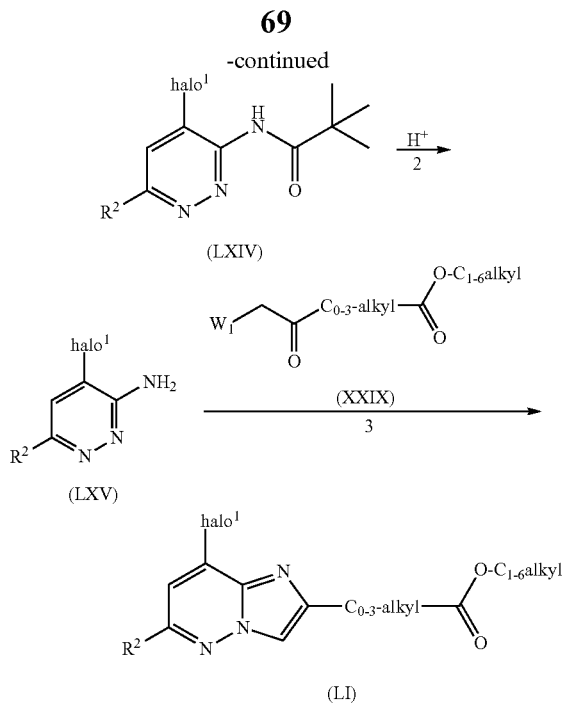

In Scheme 14, the following reaction conditions apply:

1: in the presence of an amine such as for example 2,2,6,6-tetramethylpiperidine, a deprotonating agent such as for example butyl lithium, and a suitable solvent such as for example THF at a suitable temperature ranging for 0 to −78° C.;

2: in the presence of a suitable acid such as for example hydrochloric acid, a suitable solvent such as for example dioxane, and a suitable temperature such as for example 70° C.;

3: at a suitable temperature such as for example 80° C., optionally in the presence of a suitable solvent such as for example N,N-dimethylformamide, dimethoxyethane or ethanol.

In general, compounds of Formula (I) wherein $R^1$ is —$NH_2$, and wherein the other variables are as shown in Formula (In); and compounds of Formula (I) wherein $R^1$ is restricted to $R^{1a}$ being

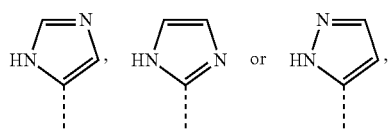

and wherein the other variables are as shown in Formula (Io), can be prepared according to the following reaction Scheme 15. In scheme 15, $Het^1$ is restricted to $Het^{1b}$. $Het^{1b}$ is defined as $Het^1$ provided that $Het^{1b}$ is always attached to the remainder of the molecule of Formula (I) through a ring carbon atom.

All other variables in Scheme 15 are defined as above or according to the scope of the present invention.

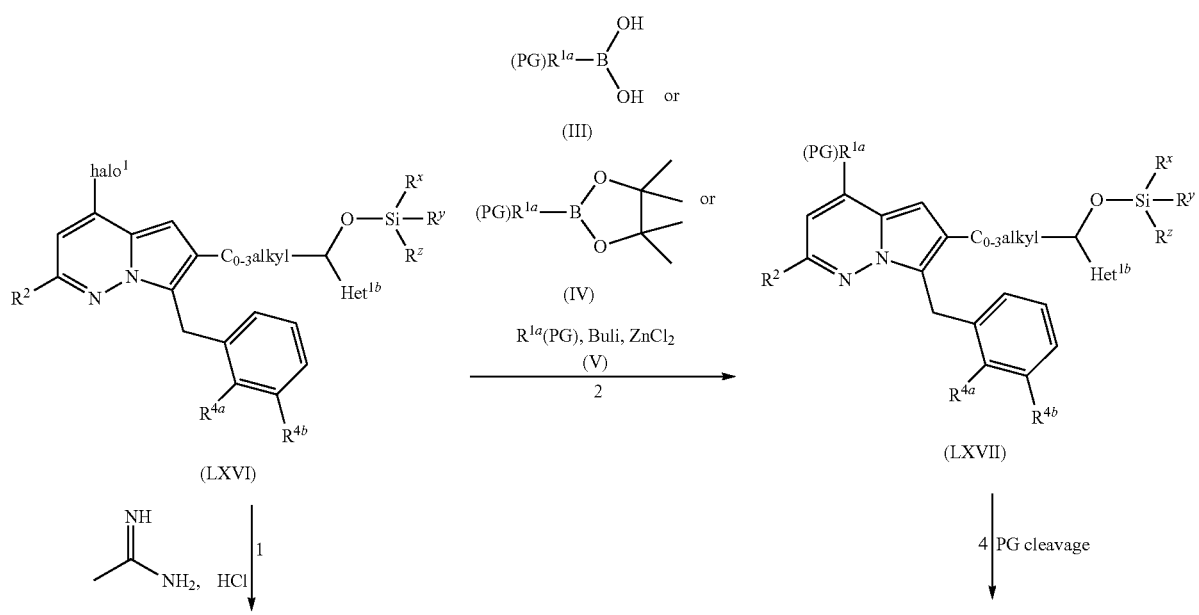

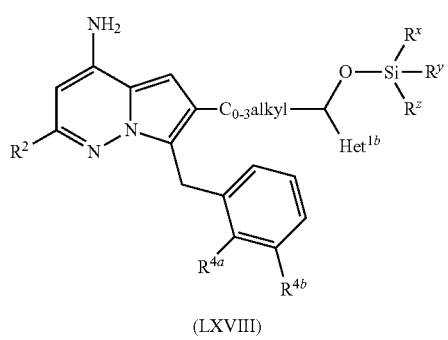

(LXVIII)

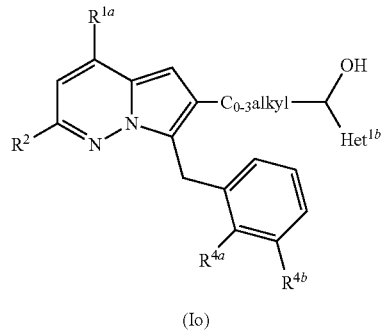

(Io)

TBAF or H⁺ ↓ 3

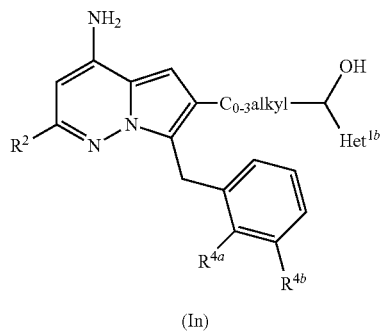

(In)

In Scheme 15, the following reaction conditions apply:

1: in the presence of a suitable catalyst such as for example copper iodide, a suitable ligand such as for example L-proline, a suitable base such as for example cesium carbonate, a suitable solvent such as for example N,N-dimethylformamide, at a suitable temperature such as 110° C. in a sealed vessel;

2: in case of (PG)R$^{1a}$B(OH)$_2$ or (PG)R$^{1a}$ (4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium carbonate, and a suitable solvent such as for example a mixture of dioxane and water, at a suitable temperature such as for example at 100° C.;

In case of R$^{1a}$(PG), first, in the presence of zinc chloride, a suitable deprotonating agent such as for example butyl lithium, a suitable solvent such as for example THF, at a suitable temperature such as for example −78° C., followed by addition (of/to) this solution (to) a mixture of intermediate (II), optionally in solution in THF, and a suitable catalyst such as for example Pd(PPh$_3$)$_4$, heating at a suitable temperature ranging from 60 to 100° C.;

3: in the presence of a suitable reagent such as for example tetrabutylammonium fluoride, hydrochloric acid or trifluoroacetic acid in a suitable solvent such as for example THF, dioxane or dichloromethane;

4: in the presence of a suitable acid such as for example p-toluenesulfonic acid hydrochloric acid or trifluoroacetic acid, in a suitable solvent such as for example dioxane or methanol, at a suitable temperature such as for example 50 or 100° C.

In general, compounds of Formula (I) wherein R$^1$ is —C(═O)OH, and wherein the other variables are as shown in Formula (Ip); and compounds of Formula (I) wherein R$^1$ is —C(═O)NH$_2$, and wherein the other variables are as shown in Formula (Iq), can be prepared according to the following reaction Scheme 16 wherein all variables in Scheme 16 are defined as above or according to the scope of the present invention.

Scheme 16
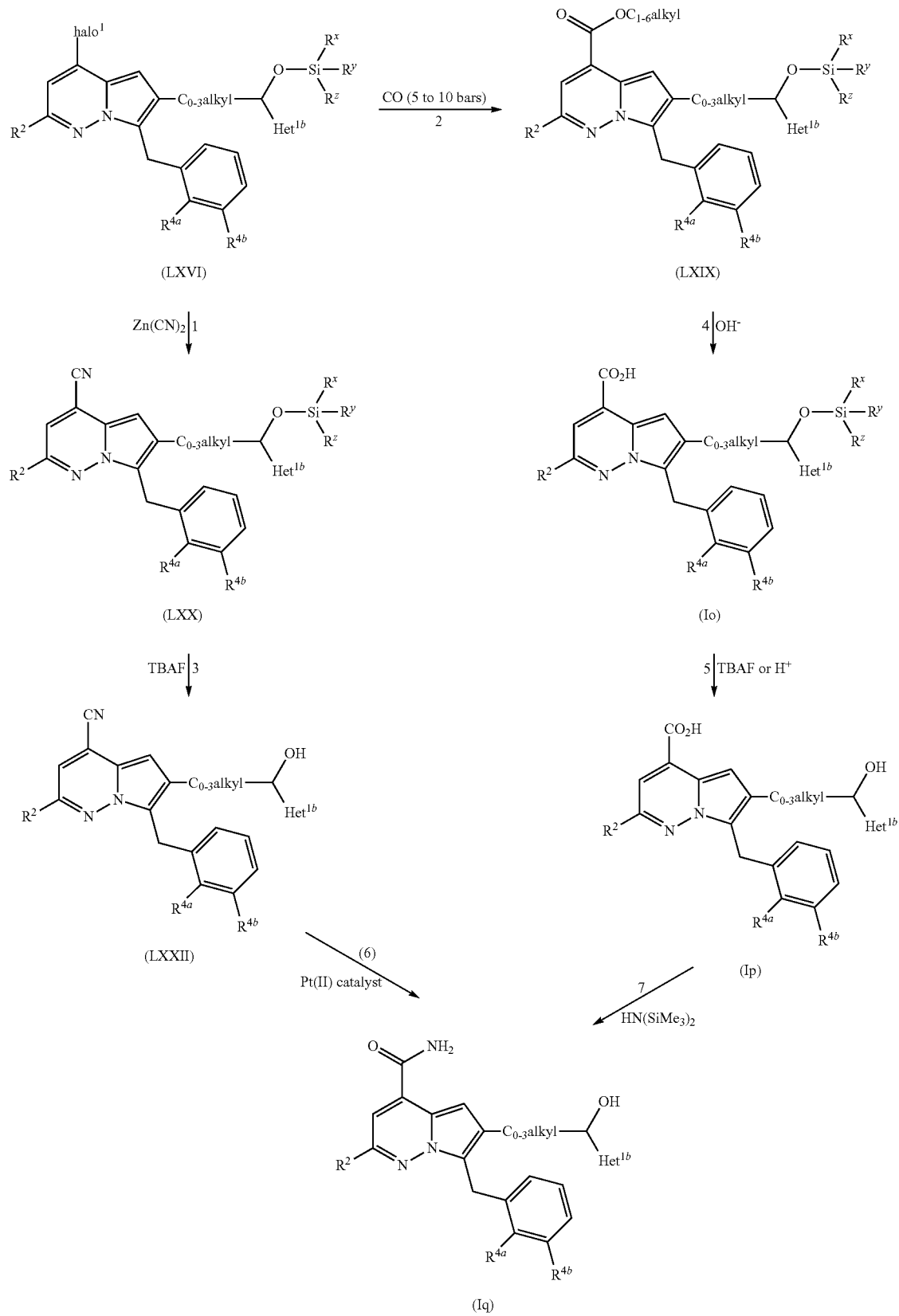

In Scheme 16, the following reaction conditions apply:

1: in the presence of a suitable catalyst such as for example Pd(PPh$_3$)$_4$, and a suitable solvent such as a for example N,N-dimethylformamide (DMF), at a suitable temperature such as for example at 100° C.;

2: in the presence of a suitable catalyst such as for example Pd(PPh$_3$)$_4$, a suitable base such as for example triethylamine (Et$_3$N), and a suitable solvent such as for example methanol or ethanol, at a suitable temperature such as for example at 100° C. or 120° C.;

3: in the presence of a suitable reagent such as for example tetrabutylammonium fluoride, in a suitable solvent such as for example THF;

4: in the presence of a suitable base such as lithium hydroxide monohydrate, and a suitable solvent or a mixture of solvents such as for example a mixture of THF/water or MeOH/water;

5: in the presence of a suitable reagent such as for example tetrabutylammonium fluoride, hydrochloric acid or trifluoroacetic acid in a suitable solvent such as for example THF, dioxane or dichloromethane;

6: in the presence of a suitable catalyst such as for example hydrido(dimethylphosphinous acid-kP)[hydrogen bis(dimethylphosphinito-kP)]platinum(II), and a suitable solvent or a mixture of solvents such as for example a mixture of THF/water, at a suitable temperature such as for example at 95° C.;

7: in the presence of a suitable peptidic coupling reagent such as 1-[bis(dimethylamino)methylene]-1H-[1,2,3]triazolo[4,5-b]pyridin-1-ium 3-oxide hexafluorophosphate (HATU), in the presence of a suitable base such as for example diisopropylamine, and a suitable solvent such as for example DMF.

Intermediates of Formula (LXVI) used in the above Schemes 15 and 16 can be prepared according to the following reaction Scheme 17 wherein halo$^2$ is an halogen defined as Br or I. In scheme 17, all the other variables are defined as above or according to the scope of the present invention.

Scheme 17

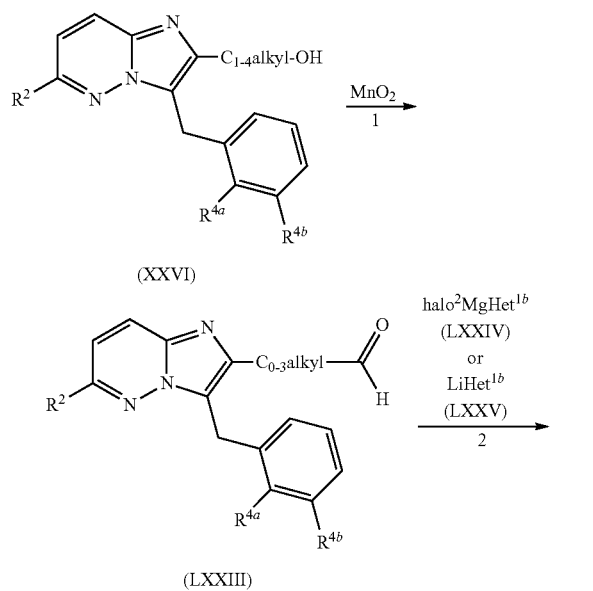

(XXVI)

(LXXIII)

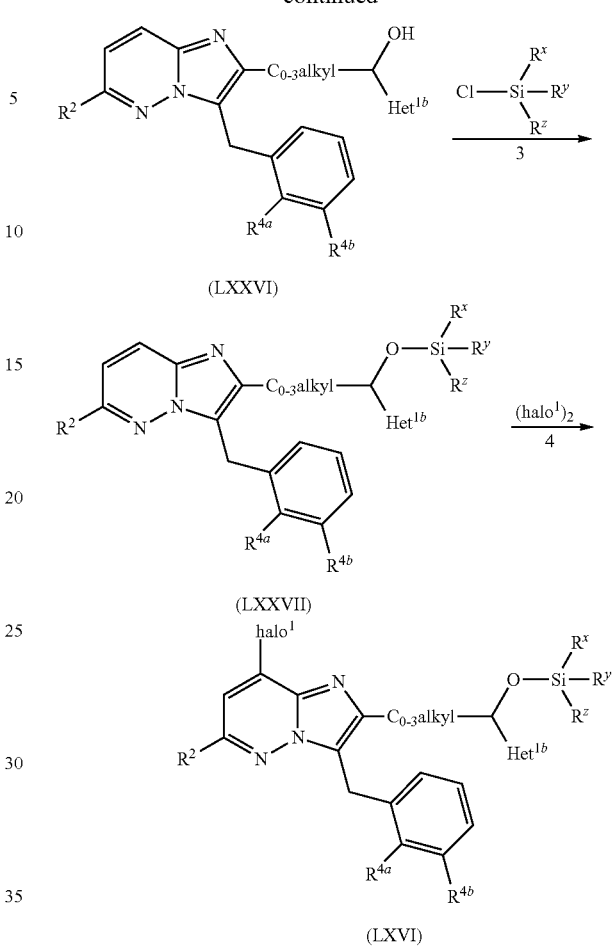

(LXXVI)

(LXXVII)

(LXVI)

In Scheme 17, the following reaction conditions apply:

1: at a suitable temperature such as for example 80° C., in the presence of a suitable oxidative reagent such as for example manganese dioxide, in a suitable solvent such as for example dioxane;

2: in a suitable solvent such as for example THF at a suitable temperature such as for example −78° C. or 0° C.;

3: in the presence of a suitable activating agent such as for example imidazole and a suitable solvent such as for example N,N-dimethylformamide;

4: in the presence of a suitable base, such as for example lithium diisopropylamide, and a suitable solvent such as for example tetrahydrofuran (THF), at a suitable temperature such as for example at −70° C.

In general, compounds of Formula (I) wherein R$^1$ is restricted to R$^{1a}$ being

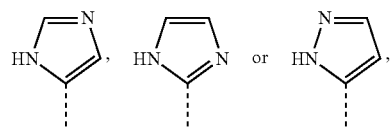

and wherein the other variables are as shown in Formula (Ir), can be prepared according to the following reaction Scheme 18 wherein all variables are defined as above or according to the scope of the present invention.

Scheme 18

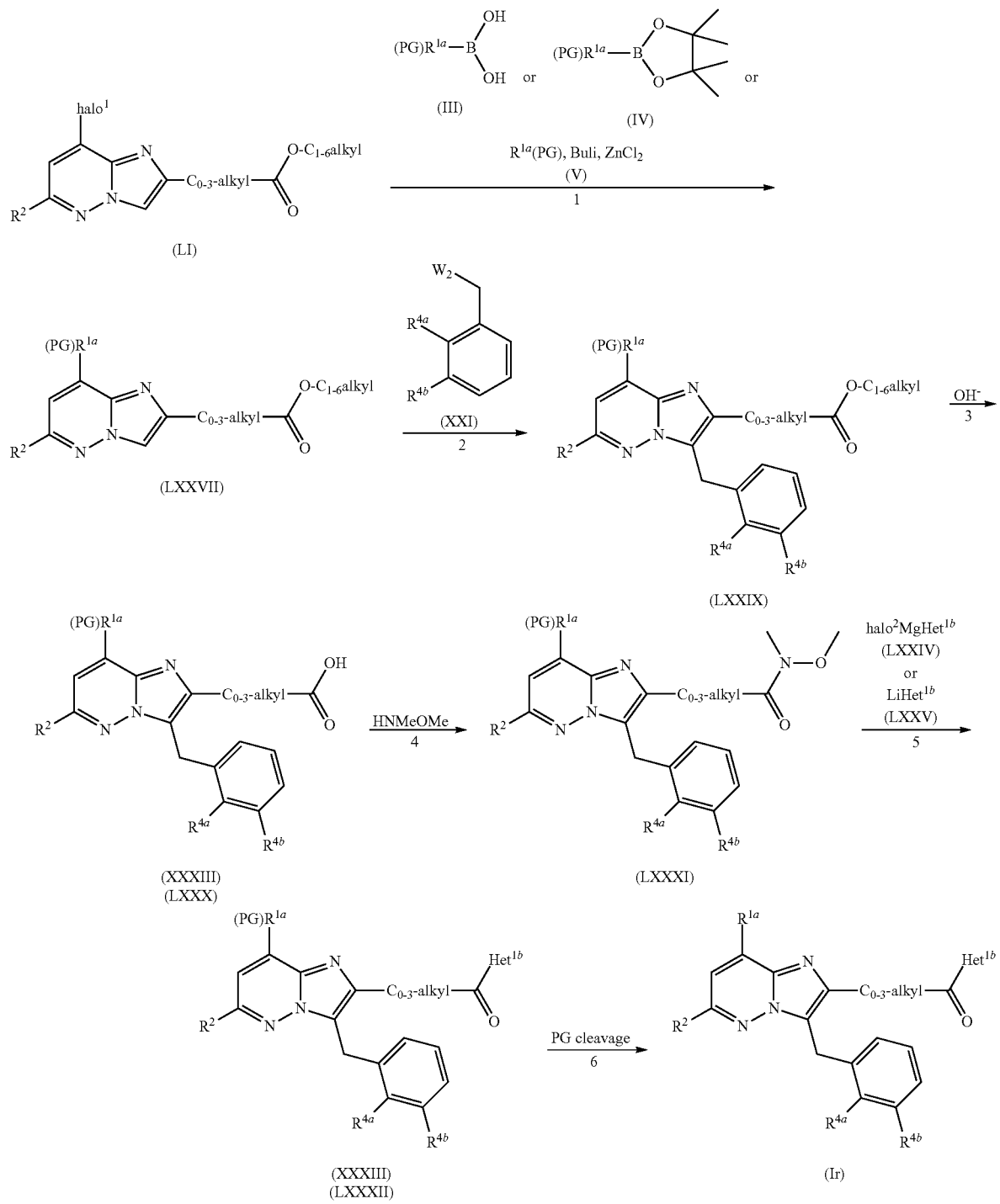

In Scheme 18, the following reaction conditions apply:

1: in case of $(PG)R^{1a}B(OH)_2$ or $(PG)R^{1a}$ (4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium carbonate, and a suitable solvent such as for example a mixture of dioxane and water, at a suitable temperature such as for example at 100° C.;

In case of $R^{1a}(PG)$, first, in the presence of zinc chloride, a suitable deprotonating agent such as for example butyl lithium, a suitable solvent such as for example THF, at a suitable temperature such as for example −78° C., followed by addition (of/to) this solution (to) a mixture of intermediate (LI), optionally in solution in THF, and a suitable catalyst such as for example Pd(PPh$_3$)$_4$, heating at a suitable temperature ranging from 60 to 100° C.;

2: in the presence of a suitable catalyst such as for example palladium acetate, a suitable ligand such as triphenylphosphine, a suitable base such as for example K$_2$CO$_3$, a suitable solvent such as for example dioxane, and a suitable temperature such as for example 100° C., optionally in a sealed vessel;

3 in the presence of a suitable base such as lithium hydroxide monohydrate, and a suitable solvent or a mixture of solvents such as for example a mixture of THF/water or MeOH/water;

4: in the presence of a suitable peptidic coupling reagent such as O-(1H-benzotriazol-1-yl)-N,N,N',N'-tetramethyl-uronium hexafluorophosphate, in the presence of a suitable base such as for example diisopropylamine, and in a suitable solvent such as for example DMF;

5: in a suitable solvent such as for example THF at a suitable temperature such as for example −78° C. or 0° C.;

6: in the presence of a suitable acid such as for example p-toluenesulfonic acid hydrochloric acid or trifluoroacetic acid, in a suitable solvent such as for example dioxane or methanol, at a suitable temperature such as for example 50 or 100° C.

In general, compounds of Formula (I) wherein $R^1$ is NH$_2$, and wherein the other variables are as shown in Formula (Is); and compounds of Formula (I) wherein $R^1$ is restricted to $R^{1a}$ being

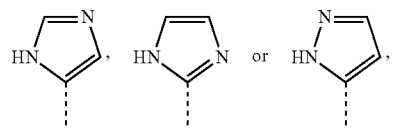

and wherein the other variables are as shown in Formula (It), can be prepared according to the following reaction Scheme 19 wherein all variables in Scheme 19 are defined according to the scope of the present invention.

Scheme 19

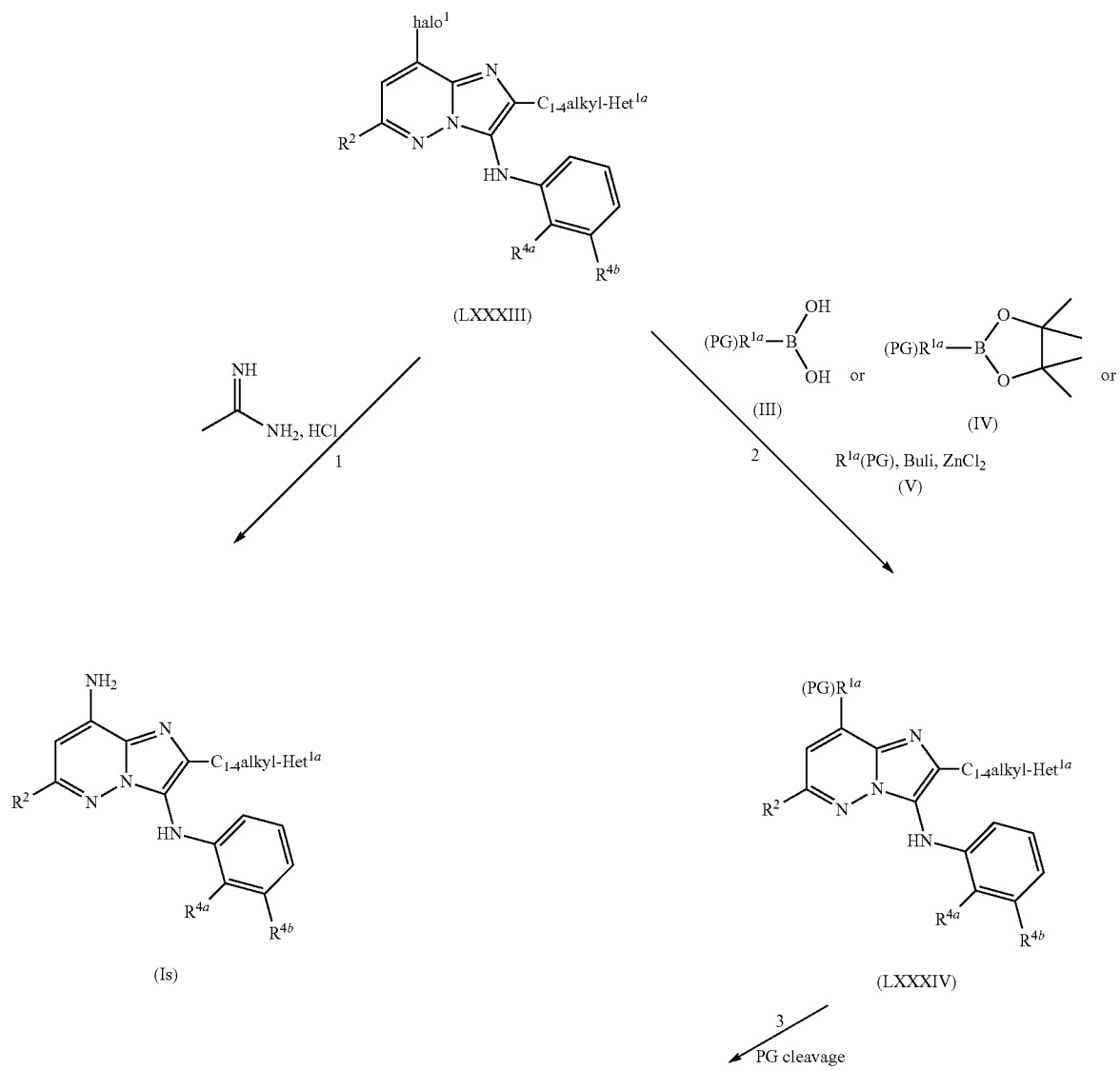

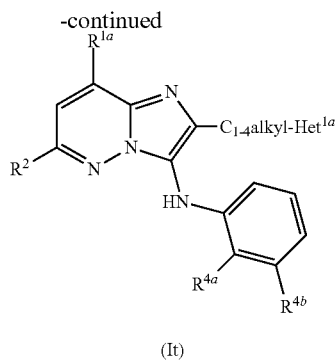

(It)

In Scheme 19, the following reaction conditions apply:

1: in the presence of a suitable catalyst such as for example copper iodide, a suitable ligand such as for example L-proline, a suitable base such as for example cesium carbonate, a suitable solvent such as for example N,N-dimethylformamide, at a suitable temperature such as 110° C. in a sealed vessel;

2: in case of (PG)$R^{1a}$B(OH)$_2$ or (PG)$R^{1a}$ (4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium carbonate, and a suitable solvent such as for example a mixture of dioxane and water, at a suitable temperature such as for example at 100° C.;

In case of $R^{1a}$(PG), first, in the presence of zinc chloride, a suitable deprotonating agent such as for example butyl lithium, a suitable solvent such as for example THF, at a suitable temperature such as for example −78° C., followed by addition (of/to) this solution (to) a mixture of intermediate (LXXXIII), optionally in solution in THF, and a suitable catalyst such as for example Pd(PPh$_3$)$_4$, heating at a suitable temperature ranging from 60 to 100° C.;

4: in the presence of a suitable acid such as for example p-toluenesulfonic acid hydrochloric acid or trifluoroacetic acid, in a suitable solvent such as for example dioxane or methanol, at a suitable temperature such as for example 50 or 100° C.

In general, compounds of Formula (I) wherein $R^1$ is COOH, and wherein the other variables are as shown in Formula (Iu); and compounds of Formula (I) wherein $R^1$ is CONH$_2$, and wherein the other variables are as shown in Formula (Iv), can be prepared according to the following reaction Scheme 20 wherein all other variables in Scheme 20 are defined as above or according to the scope of the present invention.

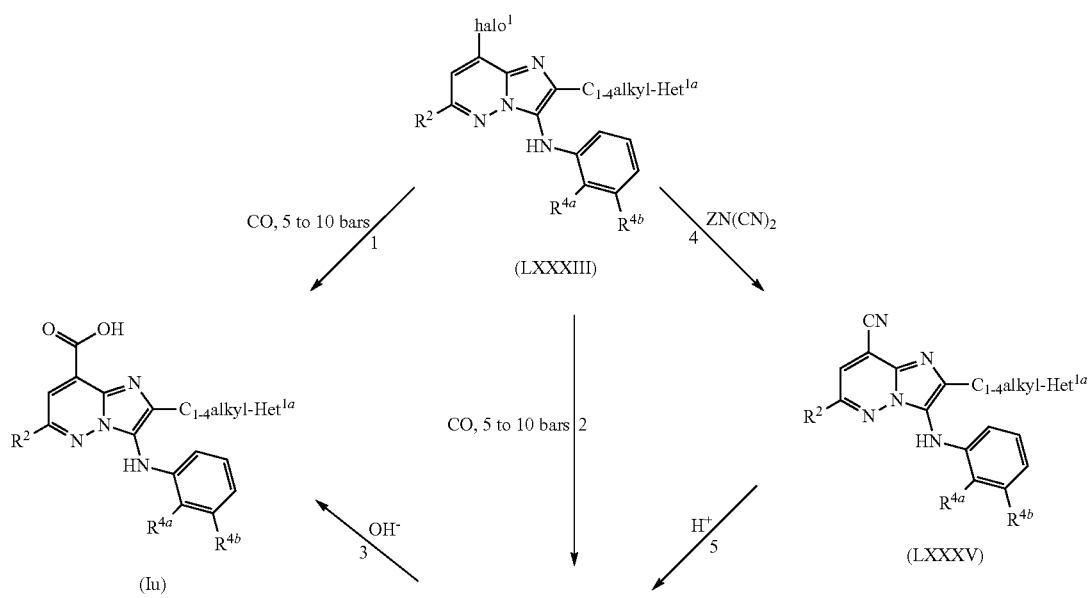

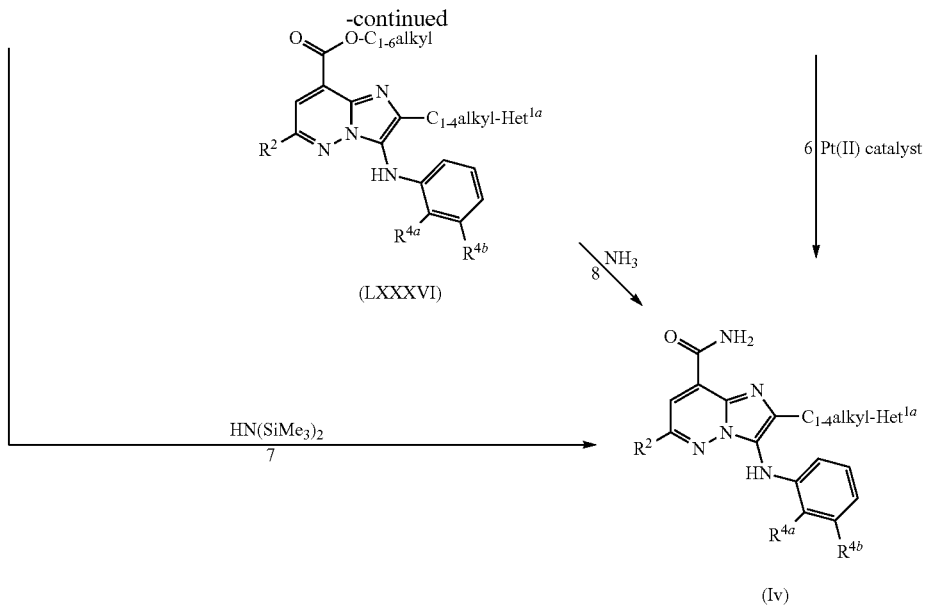

(LXXXVI)

(Iv)

In Scheme 20, the following reaction conditions apply:

1: in the presence of a suitable catalyst such as for example $Pd(PPh_3)_4$, a suitable base such as for example an aqueous solution of $Na_2CO_3$, and a suitable solvent such as for example N,N-dimethylformamide, at a suitable temperature such as for example at 120° C.;

2: in the presence of a suitable catalyst such as for example $Pd(PPh_3)_4$, a suitable base such as for example triethylamine ($Et_3N$), and a suitable solvent such as for example methanol or ethanol, at a suitable temperature such as for example at 100° C. or 120° C.;

3: in the presence of a suitable base such as lithium hydroxide monohydrate, and a suitable solvent or a mixture of solvents such as for example a mixture of THF/water or MeOH/water;

4: in the presence of a suitable catalyst such as for example $Pd(PPh_3)_4$, and a suitable solvent such as a for example N,N-dimethylformamide (DMF), at a suitable temperature such as for example at 100° C.;

5: in the presence of a suitable acid such as for example sulphuric acid, and a suitable solvent such as methanol, at a suitable temperature such as for example at 100° C.;

6: in the presence of a suitable catalyst such as for example hydrido(dimethylphosphinous acid-kP)[hydrogen bis(dimethylphosphinito-kP)]platinum(II), and a suitable solvent or a mixture of solvents such as for example a mixture of THF/water, at a suitable temperature such as for example at 95° C.;

7: in the presence of a suitable peptidic coupling reagent such as 1-[bis(dimethylamino)methylene]-1H-[1,2,3]triazolo[4,5-b]pyridin-1-ium 3-oxide hexafluorophosphate (HATU), in the presence of a suitable base such as for example diisopropylamine, and a suitable solvent such as for example DMF;

8: in a suitable solvent such as for example methanol, at a suitable temperature such as for example at 100° C., in a sealed vessel.

Intermediates of Formula (LXXXIII) used in the above Schemes 19 and 20 can be prepared according to the following reaction Scheme 21. In scheme 21, $halo^3$ is defined as Br or I and all the other variables are defined as above or according to the scope of the present invention.

In Scheme 21, the following reaction conditions apply:

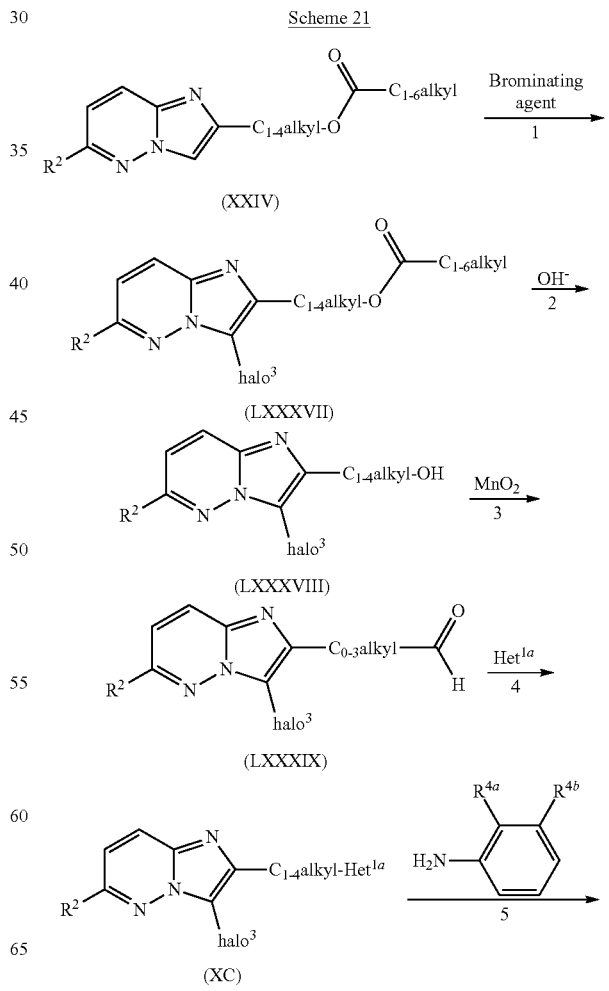

-continued

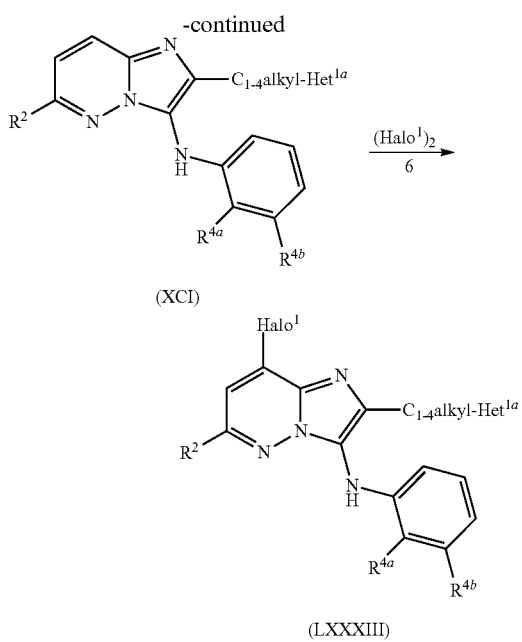

In Scheme 21, the following reaction conditions apply:
1: in the presence of a suitable brominating reagent such as for example N-bromosuccinimide, in a suitable solvent such as for example acetonitrile;

2 in the presence of a suitable base such as lithium hydroxide monohydrate, and a suitable solvent or a mixture of solvents such as for example a mixture of THF/water or MeOH/water;

3: at a suitable temperature such as for example 80° C., in the presence of a suitable oxidative reagent such as for example manganese dioxide, in a suitable solvent such as for example dioxane;

4: in the presence of a suitable reducing agent such as for example sodium triacetoxyborohydride, a suitable additive such as for example sodium acetate, and in a suitable solvent such as for example dichloromethane;

5: at a temperature such as 100° C., in the presence of a suitable catalyst such as for example tris(dibenzylideneacetone)dipalladium(0), a suitable ligand such as for example 2-(di-t-butylphosphino)biphenyl, a suitable base such as for example sodium tert-butoxide, and in a suitable solvent such as for example toluene;

6: in the presence of a suitable base, such as for example lithium diisopropylamide, and a suitable solvent such as for example tetrahydrofuran (THF), at a suitable temperature ranging such for example at −78° C. to −40° C.

In general, compounds of Formula (I) wherein $R^1$ is —$NH_2$, and wherein the other variables are as shown in Formula (Ia) can be prepared according to the following reaction Scheme 22. $Het^{1a}$ is defined as above. All other variables in Scheme 22 are as defined before (e.g. see Scheme 3) or according to the scope of the present invention.

Scheme 22

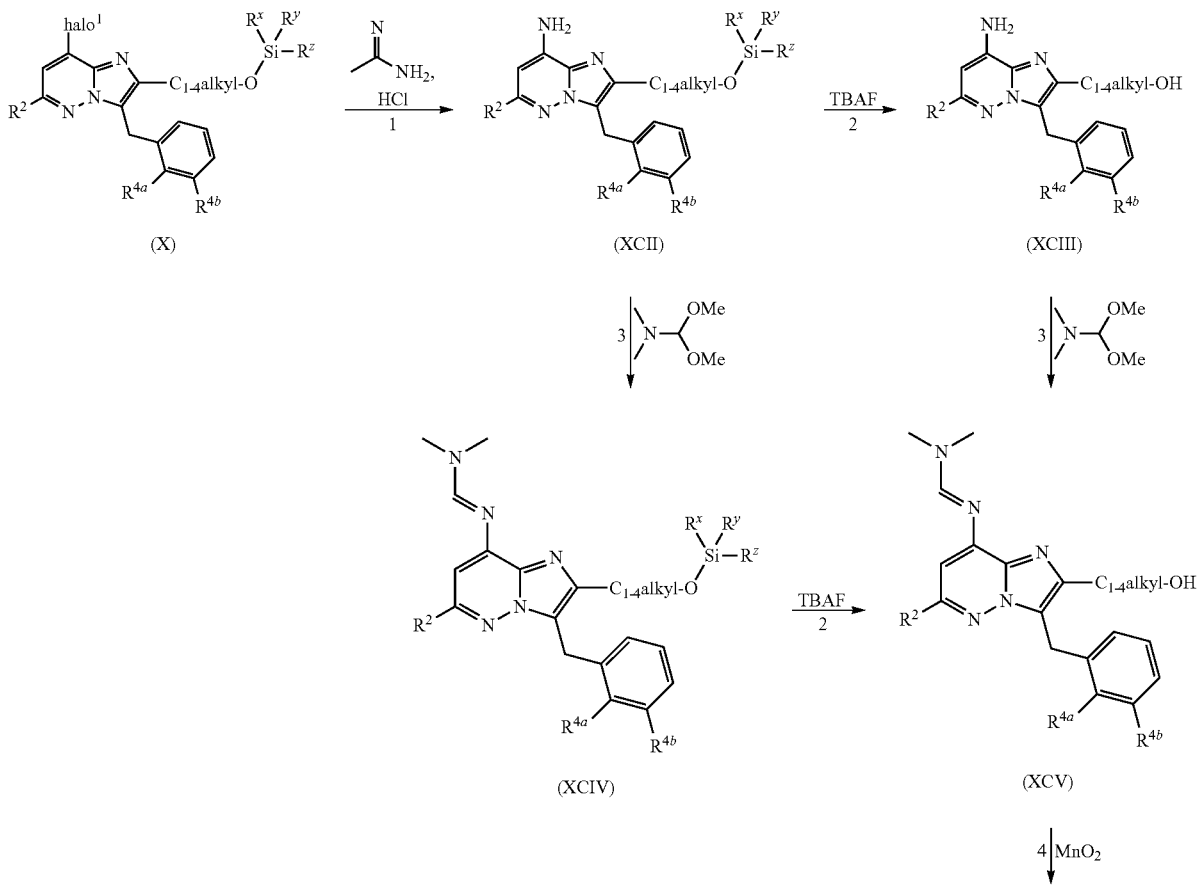

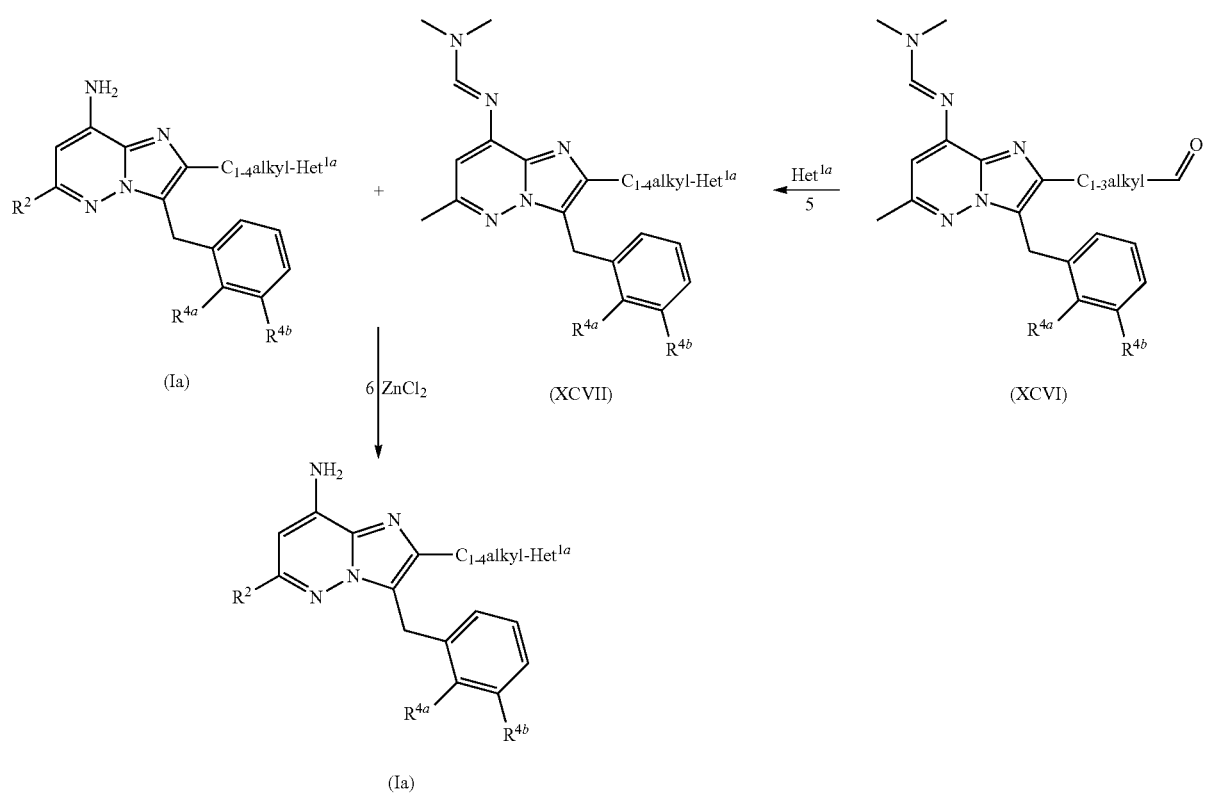

In Scheme 22, the following reaction conditions apply:

1: in the presence of a suitable catalyst such as for example copper iodide, a suitable ligand such as for example L-proline, a suitable base such as for example cesium carbonate, a suitable solvent such as for example N,N-dimethylformamide, at a suitable temperature such as for example 110° C. optionally in a sealed vessel;

2: In the presence of a suitable solvent such as for example tetrahydrofurane, at a suitable temperature such as for example room temperature;

3: In the presence of a suitable solvent such as for example toluene, at a suitable temperature such as for example 120° C.;

4: In the presence of a suitable solvent such as for example toluene, at a suitable temperature such as for example 80° C.;

5: In the presence of a suitable reducing reagent such as for example sodium cyanoborohydride, a suitable acid such as for example acetic acid, a suitable solvent such as for example methanol, at a suitable temperature such as for example room temperature;

6: In the presence of a suitable solvent such as for example ethanol, at a suitable temperature such as for example 90° C.

In general, compounds of Formula (I) wherein $R^1$ is —$NH_2$, and wherein the other variables are as shown in Formula (Iy);

and compounds of Formula (I) wherein $R^1$ is restricted to $R^{1a}$ being

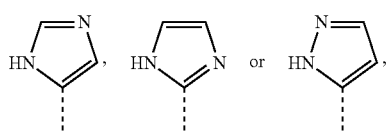

and wherein the other variables are as shown in Formula (Ix), can be prepared according to the following reaction Scheme 23. All other variables in Scheme 23 are defined as above or according to the scope of the present invention.

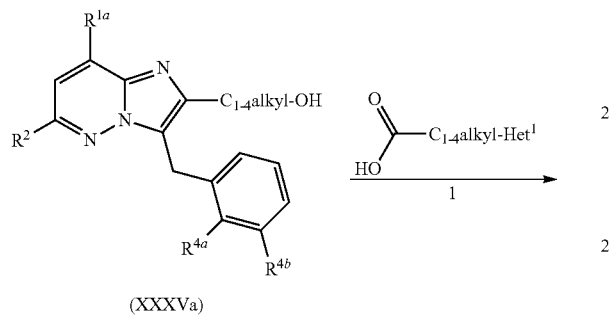

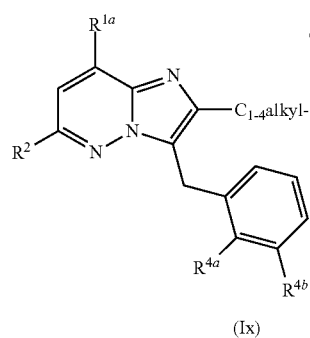

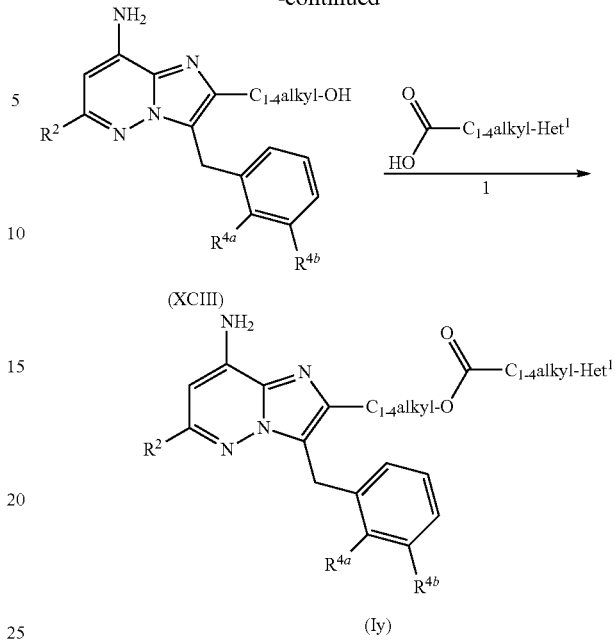

In Scheme 23, the following reaction conditions apply:

1: in the presence of a suitable coupling reagent such as for example 1 [Bis(dimethylamino)methylene]-1H-1,2,3-triazolo[4,5-b]pyridinium 3-oxid hexafluorophosphate, a suitable additive such as for example dimethylaminopyridine, a suitable base such as for example diisopropylethylamine, and in a suitable solvent such as for example dimethylformamide.

In some cases, the reaction might be followed by a deprotective step using classical conditions based on the protective group nature. Then, another reaction such as for example a reductive amination could be used for further functionalization of het$^1$.

In general, compounds of Formula (I) wherein R$^1$ is —NH$_2$, and wherein the other variables are as shown in Formula (Ie), can be prepared according to the following reaction Scheme 24. Het$^{1b}$ is defined as above. All other variables in Scheme 24 are defined as above or according to the scope of the present invention.

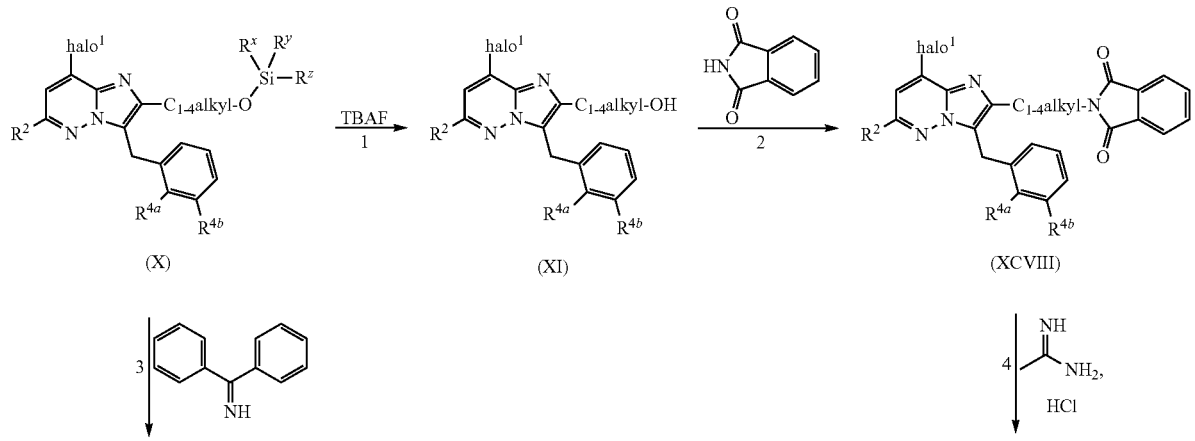

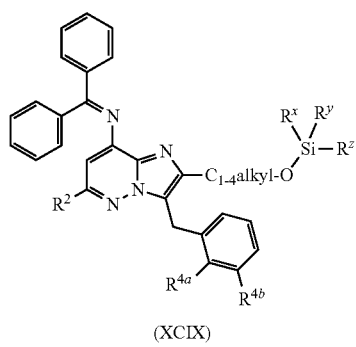

(XCIX)

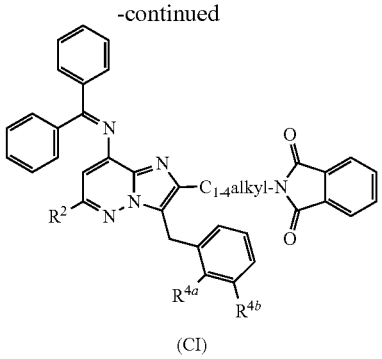

(CI)

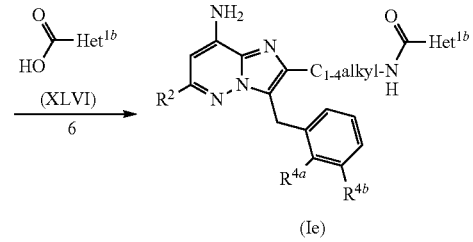

(CII)

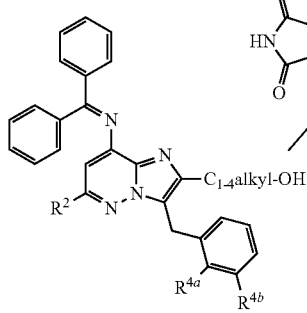

(C)

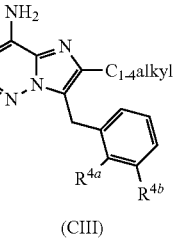

(CIII)

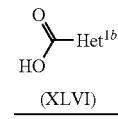

(Ie)

1: in the presence of a suitable reagent such as for example tetrabutylammonium fluoride in a suitable solvent such as tetrahydrofurane;

2: in the presence of a suitable reagent such as for example di-tert-butyl azodicarboxylate, a suitable phosphine such as for example triphenylphosphine, and in a suitable solvent such as for example THF or methyl-THF;

3: in the presence of a suitable catalyst such as for example palladium acetate, in the presence of a suitable ligand such as for example racemic-2,2'-bis(diphenylphosphino)-1,1'-binaphtyl, in the presence of a suitable base such as for example cesium carbonate, and in a suitable solvent such as for example toluene at a temperature of 100° C., in a sealed vessel;

4: in the presence of a suitable catalyst such as for example copper iodide, a suitable ligand such as for example L-proline, a suitable base such as for example cesium carbonate, a suitable solvent such as for example N,N-dimethylformamide, at a suitable temperature such as for example 110° C. in a sealed vessel;

5: at a suitable temperature such as for example 80° C., in a suitable solvent such as for example ethanol;

6: in the presence of a suitable coupling reagent such as for example 1-(3-dimethyaminopropyl)-3-ethylcarbodiimide hydrochloride, a suitable additive such as for example 1-hydroxybenzotriazole, a suitable base such as for example triethylamine, and in a suitable solvent such as for example a mixture of THF and dichloromethane.

In all these preparations, the reaction products may be isolated from the reaction medium and, if necessary, further purified according to methodologies generally known in the art such as, for example, extraction, crystallization, trituration and chromatography.

The chirally pure forms of the compounds of Formula (I) form a preferred group of compounds. It is therefore that the chirally pure forms of the intermediates and their salt forms are particularly useful in the preparation of chirally pure compounds of Formula (I). Also enantiomeric mixtures of the intermediates are useful in the preparation of compounds of Formula (I) with the corresponding configuration.

Pharmacology

It has been found that the compounds of the present invention inhibit PI3Kβ kinase activity, and optionally also have PI3Kδ inhibitory activity. Some of the compounds of the present invention may undergo metabolism to a more active form in vivo (prodrugs).

It is therefore anticipated that the compounds according to the present invention or pharmaceutical compositions thereof may be useful for treating or preventing, in particular treating, of diseases such as cancer, autoimmune disorders, cardiovascular diseases, inflammatory diseases, neurodegenerative diseases, allergy, pancreatitis, asthma, multiorgan failure, kidney diseases, platelet aggregation, sperm motility, transplantation rejection, graft rejection, lung injuries and the like; in particular cancer.

Because the pharmaceutically active compounds of the present invention are active as PI3Kβ inhibitors, they exhibit therapeutic utility in treatment or prevention, in particular treatment, of susceptible neoplasms, particularly those neoplasms that exhibit a PTEN deficiency.

As used herein, the phrase "PTEN deficient" or "PTEN deficiency" shall describe tumors with deficiencies of the tumor suppressor function of PTEN (Phosphatase and Tensin Homolog). Such deficiency includes mutation in the PTEN gene, reduction or absence of PTEN proteins when compared to PTEN wild-type, or mutation or absence of other genes that cause suppression of PTEN function.

"Susceptible neoplasm" as used herein refers to neoplasms which are susceptible to treatment by a kinase inhibitor and particularly neoplasms that are susceptible to treatment by a PI3Kβ inhibitor. Neoplasms which have been associated with inappropriate activity of the PTEN phosphatase and particularly neoplasms which exhibit mutation of PTEN, or mutation of an upstream activator of PI3Kβ kinase or overexpression of an upstream activator of PI3Kβ kinase, and are therefore susceptible to treatment with an PI3Kβ inhibitor, are known in the art, and include both primary and metastatic tumors and cancers. According to an embodiment, description of the treatment of a susceptible neoplasm may be used interchangeably with description of the treatment of a cancer.

According to one embodiment, "susceptible neoplasms" include but are not limited to PTEN-deficient neoplasms listed as follows: brain (gliomas), glioblastomas, leukemias, Bannayan-Zonana syndrome, Cowden disease, Lhermitte-Duclos disease, breast cancer, inflammatory breast cancer, colorectal cancer Wilm's tumor, Ewing's sarcoma, Rhabdomyosarcoma, ependymoma, medulloblastoma colon cancer, head and neck cancer, liver cancer, kidney cancer, lung cancer, melanoma, squamous cell carcinoma, ovarian cancer, pancreatic cancer, prostate cancer, sarcoma cancer, osteosarcoma, giant cell tumor of bone, thyroid cancer, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, Plasmacytoma, immunoblastic large cell leukemia, Mantle cell leukemia, Multiple myeloma, Megakaryoblastic leukemia. Acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, cervical cancer, vulval cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), and testicular cancer.

According to an alternative embodiment, the term "susceptible neoplasm" includes and is limited to hormone refractory prostate cancer, non-small-cell lung cancer, endometrial cancer, gastric cancer, melanoma, head and neck cancer, breast cancer, including tripnegative breast cancer, and glioma.

In an embodiment, the term "susceptible neoplasm" includes and is limited to prostate cancer, in particular hormone refractory prostate cancer.

The compounds of the present invention may also have therapeutic applications in sensitising tumour cells for radiotherapy and chemotherapy.

Hence the compounds of the present invention may be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nitnorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

The invention relates to compounds of Formula (I) and N-oxides, pharmaceutically acceptable addition salts, and solvates thereof, for use as a medicament.

The invention also relates to compounds of Formula (I) and N-oxides, pharmaceutically acceptable addition salts, and solvates thereof, for use in the inhibition of PI3Kβ kinase activity and optionally also for use in the inhibition of PI3Kδ.

The compounds of the present invention can be "anticancer agents", which term also encompasses "anti-tumor cell growth agents" and "anti-neoplastic agents".

The invention also relates to compounds of Formula (I) and N-oxides, pharmaceutically acceptable addition salts, and solvates thereof, for use in the treatment of diseases mentioned above.

The invention also relates to compounds of Formula (I) and N-oxides, pharmaceutically acceptable addition salts, and solvates thereof, for the treatment or prevention, in particular for the treatment, of said diseases.

The invention also relates to compounds of Formula (I) and N-oxides, pharmaceutically acceptable addition salts, and solvates thereof, for the treatment or prevention, in particular in the treatment, of PI3Kβ mediated diseases or conditions.

The invention also relates to compounds of Formula (I) and N-oxides, pharmaceutically acceptable addition salts, and solvates thereof, for the treatment or prevention, in particular in the treatment, of PI3Kβ and optionally PI3Kδ mediated diseases or conditions.

The invention also relates to the use of compounds of Formula (I) and N-oxides, pharmaceutically acceptable addition salts, and solvates thereof, for the manufacture of a medicament.

The invention also relates to the use of compounds of Formula (I) and N-oxides, pharmaceutically acceptable addition salts, and solvates thereof, for the manufacture of a medicament for the inhibition of PI3Kβ.

The invention also relates to the use of compounds of Formula (I) and N-oxides, pharmaceutically acceptable addition salts, and solvates thereof, for the manufacture of a medicament for the inhibition of PI3Kβ and optionally also for the inhibition of PI3Kδ.

The invention also relates to the use of compounds of Formula (I) and N-oxides, pharmaceutically acceptable addition salts, and solvates thereof, for the manufacture of a medicament for the treatment or prevention, in particular for the treatment, of any one of the disease conditions mentioned hereinbefore.

The invention also relates to the use of compounds of Formula (I) and N-oxides, pharmaceutically acceptable addition salts, and solvates thereof, for the manufacture of a medicament for the treatment of any one of the disease conditions mentioned hereinbefore.

The compounds of Formula (I) and N-oxides, pharmaceutically acceptable addition salts, and solvates thereof, can be administered to mammals, preferably humans for the treatment or prevention of any one of the diseases mentioned hereinbefore.

In view of the utility of the compounds of Formula (I) and N-oxides, pharmaceutically acceptable addition salts, and solvates thereof, there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I) or a N-oxide, a pharmaceutically acceptable addition salt, or a solvate thereof, to warm-blooded animals, including humans.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment max also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent cancer or cancer-related conditions, may be administered alone or in combination with one or more additional therapeutic agents. Combination therapy includes administration of a single pharmaceutical dosage formulation which contains a compound of Formula (I), a N-oxide, a pharmaceutically acceptable addition salt, or a solvate thereof, and one or more additional therapeutic agents, as well as administration of the compound of Formula (I), a N-oxide, a pharmaceutically acceptable addition salt, or a solvate thereof, and each additional therapeutic agents in its own separate pharmaceutical dosage formulation. For example, a compound of Formula (I), a N-oxide, a pharmaceutically acceptable addition salt, or a solvate thereof, and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition comprising a pharmaceutically acceptable carrier and, as active ingredient, a therapeutically effective amount of a compound of Formula (I), a N-oxide, a pharmaceutically acceptable addition salt, or a solvate thereof.

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds of Formula (I) and N-oxides, pharmaceutically acceptable addition salts, and solvates thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing a compound of Formula (I), a N-oxide, a pharmaceutically acceptable addition salt, or a solvate thereof, may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable welling agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

In order to enhance the solubility and/or the stability of the compounds of Formula (I) and N-oxides, pharmaceutically acceptable addition salts, and solvates thereof, in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), a N-oxide, a pharmaceutically acceptable addition salt, or a solvate thereof, and from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anti-cancer agent is envisaged, especially for use as a medicine, more specifically for use in the treatment of cancer or related diseases.

For the treatment of the above conditions, the compounds of the invention may be advantageously employed in combination with one or more other medicinal agents, more particularly, with other anti-cancer agents or adjuvants in cancer therapy.

Examples of anti-cancer agents or adjuvants (supporting agents in the therapy) include but are not limited to:
  platinum coordination compounds for example cisplatin optionally combined with amifostine, carboplatin or oxaliplatin;
  taxane compounds for example paclitaxel, paclitaxel protein bound particles (Abraxane™) or docetaxel;
  topoisomerase I inhibitors such as camptothecin compounds for example irinotecan, SN-38, topotecan, topotecan hcl;
  topoisomerase II inhibitors such as anti-tumour epipodophyllotoxins or podophyllotoxin derivatives for example etoposide, etoposide phosphate or teniposide;
  anti-tumour vinca alkaloids for example vinblastine, vincristine or vinorelbine;
  anti-tumour nucleoside derivatives for example 5-fluorouracil, leucovorin, gemcitabine, gemcitabine hcl, capecitabine, cladribine, fludarabine, nelarabine;
  alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil;
  anti-tumour anthracycline derivatives for example daunorubicin, doxorubicin optionally in combination with dexrazoxane, doxil, idarubicin, mitoxantrone, epirubicin, epirubicin hcl, valrubicin;
  molecules that target the IGF-1 receptor for example picropodophilin,
  tetracarcin derivatives for example tetrocarcin A;
  glucocorticoiden for example prednisone;
  antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;
  estrogen receptor antagonists or selective estrogen receptor modulators or inhibitors of estrogen synthesis for example tamoxifen, fulvestrant, toremifene, droloxifene, faslodex, raloxifene or letrozole;
  aromatase inhibitors such as exemestane, anastrozole, letrazole, testolactone and vorozole;
  differentiating agents such as retinoids, vitamin D or retinoic acid and retinoic acid metabolism blocking agents (RAMBA) for example accutane;
  DNA methyl transferase inhibitors for example azacytidine or decitabine;
  antifolates for example premetrexed disodium;

antibiotics for example antinomycin D, bleomycin, mitomycin C, dactinomycin, carminomycin, daunomycin, leyamisole, plicamycin, mithramycin;

antimetabolites for example clofarabine, aminopterin, cytosine arabinoside or methotrexate, azacitidine, cytarabine, floxuridine, pentostatin, thioguanine;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;

famesyltransferase inhibitors for example tipifamib;

histone deacetylase (HDAC) inhibitors for example sodium butyrate, suberoylanilide hydroxamic acid (SAHA), depsipeptide (FR 901228), NVP-LAQ824, R306465, JNJ-26481585, trichostatin A, vorinostat;

Inhibitors of the ubiquitin-proteasome pathway for example PS-341, MLN 0.41 or bortezomib;

Yondelis;

Telomerase inhibitors for example telomestatin;

Matrix metalloproteinase inhibitors for example batimastat, marimastat, prinostat or metastat;

Recombinant interleukins for example aldesleukin, denileukin diftitox, interferon alfa 2a, interferon alfa 2b, peginterferon alfa 2b;

MAPK inhibitors;

Retinoids for example alitretinoin, bexarotene, tretinoin;

Arsenic trioxide;

Asparaginase;

Steroids for example dromostanolone propionate, megestrol acetate, nandrolone (decanoate, phenpropionate), dexamethasone;

Gonadotropin releasing hormone agonists or antagonists for example abarelix, goserelin acetate, histrelin acetate, leuprolide acetate;

Thalidomide, lenalidomide;

Mercaptopurine, mitotane, pamidronate, pegademase, pegaspargase, rasburicase;

BH3 mimetics for example ABT-737;

MEK inhibitors for example PD98059, AZD6244, CI-1040;

colony-stimulating factor analogs for example filgrastim, pegfilarastim, sargramostim; erythropoietin or analogues thereof (e.g. darbepoetin alfa); interleukin 11; oprelvekin; zoledronate, zoledronic acid; fentanyl; bisphosphonate; palifermin;

a steroidal cytochrome P450 17alpha-hydroxylase-17,20-lyase inhibitor (CYP17), e.g. abiraterone, abiraterone acetate;

Glycolysis inhibitors, such as 2-deoxyglucose;

mTOR inhibitors such as rapamycins and rapalogs, and mTOR kinase inhibitors;

PI3K inhibitors and dual mTOR/PI3K inhibitors;

autophagy inhibitors, such as chloroquine and hydroxychloroquine;

androgen receptor antagonist drugs, e.g. enzalutamide or ARN-509;

antibodies that re-activate the immune response to tumors, for example nivolumab (anti-PD-1), lambrolizumab (anti-PD-1), ipilimumab (anti-CTLA4), and MPDL3280A (anti-PD-L1).

The present invention further relates to a product containing as first active ingredient a compound according to the invention and as further active ingredient one or more anticancer agents, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter (mg/m$^2$) of body surface area, for example 50 to 400 mg/m$^2$, particularly for cisplatin in a dosage of about 75 mg/m$^2$ and for carboplatin in about 300 mg/m$^2$ per course of treatment.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$)

of body surface area, particularly for vinblastine in a dosage of about 3 to 12 mg/m², for vincristine in a dosage of about 1 to 2 mg/m², and for vinorelbine in dosage of about 10 to 30 mg/m² per course of treatment.

The anti-tumour nucleoside derivative is advantageously administered in a dosage of 200 to 2500 mg per square meter (mg/m²) of body surface area, for example 700 to 1500 mg/m², particularly for 5-FU in a dosage of 200 to 500 mg/m², for gemcitabine in a dosage of about 800 to 1200 mg/m² and for capecitabine in about 1000 to 2500 mg/m² per course of treatment.

The alkylating agents such as nitrogen mustard or nitrosourea is advantageously administered in a dosage of 100 to 500 mg per square meter (mg/m²) of body surface area, for example 120 to 200 mg/m², particularly for cyclophosphamide in a dosage of about 100 to 500 mg/m², for chlorambucil in a dosage of about 0.1 to 0.2 mg/kg, for carmustine in a dosage of about 150 to 200 mg/m² and for lomustine in a dosage of about 100 to 150 mg/m² per course of treatment.

The anti-tumour anthracycline derivative is advantageously administered in a dosage of 10 to 75 mg per square meter (mg/m²) of body surface area, for example 15 to 60 mg/m², particularly for doxorubicin in a dosage of about 40 to 75 mg/m², for daunorubicin in a dosage of about 25 to 45 mg/m², and for idarubicin in a dosage of about 10 to 15 mg/m² per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m²) of body surface area, or as known in the art, if different. Trastuzumab is advantageously administered in a dosage of 1 to 5 mg per square meter (mg/m²) of body surface area, particularly 2 to 4 mg/m² per course of treatment.

These dosages may be administered for example once, twice or more per course of treatment, which may be repeated for example every 7, 14, 21 or 28 days.

The following examples illustrate the present invention. In case no specific stereochemistry is indicated for a stereocenter of a compound, this means that the compound was obtained as a mixture of the R and the S enantiomers.

EXAMPLES

Hereinafter, the term 'DCM' means dichloromethane, 'Me' means methyl, 'Et' means ethyl, 'MeOH' means methanol, 'DMF' means dimethylformamide, 'Et₂O' means diethyl ether, 'EtOAc' means ethyl acetate, 'THF' means tetrahydrofuran, 'ACN' means acetonitrile. 'EtOH' means ethanol, 'DME' means 1,2-dimethoxyethane, 'SFC' means supercritical fluid chromatography, 'MgSO₄' means magnesium sulfate, 'q.s.' means quantum sufficit, 'M.P.' means melting point, 'iPrNH₂' means isopropylamine, 'DIPE' means diisopropylether, 'K₂CO₃' means potassium carbonate, 'Celite®' means diatomaceous earth, 'NH₄Cl' means ammonium chloride, 'Na₂S₂O₃' means sodium thiosulfate, 'Pd₂dba₃' means Tris(dibenzylideneacetone)dipalladium(0), 'Pd(Ph₃)₄' means tetrakis-(triphenylphosphine)palladium (0), 'PdCl₂dppf.DCM' means (1,1'-bis(diphenylphosphino) ferrocene)dichloropalladium-dichloromethane (1:1), 'Pd/C (10%)' means palladium on carbon (10%), 'TBAF' means tetrabutylammonium fluoride, 'Me-THF' means methyltetrahydrofuran, 'PPh₃' means triphenylphosphine, 'MTBE' means methyl tertiarybutylether, 'TFA' means trifluoroacetic acid, 'Cs₂CO₃' means cesium carbonate, 'NH₄OH' means ammonia aqueous solution, 'NaHCO₃' means sodium bicarbonate. 'NaOH' means sodium hydroxide, 'HCOONH₄' means ammonium formate, 'N₂' means nitrogen, 'HCl' means hydrochloric acid, 'RuPhos' means 2-dicyclohexylphosphino-2',6'-diisopropoxy-1,1'-biphenyl, 'rt' means room temperature.

For intermediates that were used in a next reaction step as a crude or as a partially purified intermediate, theoretical mol amounts are indicated in the reaction protocols described below.

A. Preparation of the Intermediate Compounds

Note: in some preparations of intermediate compounds, final compounds were also obtained during the reaction.

Example A1

Preparation of Intermediate 1:

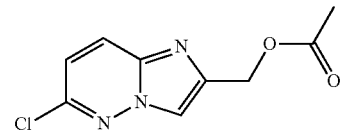

3-Amino-6-chloropyridazine (50 g; 386 mmol) was dissolved in DMF (500 mL). 1-acetoxy-3-chloroacetone was added (80 mL; 680 mmol) and the mixture was heated at 90° C. for 15 hours. The reaction was cooled to room temperature, poured into cooled water and EtOAc, basified with K₂CO₃ powder (pH=10-11). The organic layer was dried over MgSO₄, filtered and evaporated to dryness.

The residue was purified by chromatography over silica gel (irregular SiOH, 50 g; mobile phase: 99% DCM, 1% MeOH). The fractions containing the product were collected and evaporated to dryness yielding 38 g (44%) of intermediate 1.

Alternative Route:

3-Amino-6-chloropyridazine (40 g; 309 mmol) was dissolved in DME (1200 mL). 1-acetoxy-3-chloroacetone (80 mL; 680 mmol) and molecular sieves 4 A (40 g) were added. Then the mixture was heated at 90° C. for 15 hours. The reaction was cooled to room temperature, DCM was added and the mixture was filtered over a pad of Celite®. The filtrate was poured into cooled water, basified with K₂CO₃ powder (pH=10-11). The organic layer was separated dried over MgSO₄, filtered and evaporated to dryness.

The residue (51 g) was purified by chromatography over silica gel (irregular SiOH, 900 g; mobile phase: 60% Heptane, 5% MeOH, 35% EtOAc). The fractions containing the product were collected and evaporated to dryness to afford 26.3 g (38%) of intermediate 1.

Preparation of Intermediate 2:

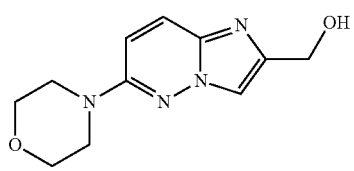 [SMILES: OCc1cn2nc(N3CCOCC3)ccc2n1]

A mixture of intermediate 1 (29.8 g; 132 mmol) and morpholine (330 mL; 375 mmol) was heated at 105° C. for 20 hours. The mixture was cooled and the solvent was evaporated, the residue was poured into cooled water, basified with $K_2CO_3$ powder and DCM was added. The organic layer was separated, dried over $MgSO_4$, filtered and evaporated to dryness.

The residue was crystallized from DCM. The precipitate was filtered and dried to afford 18.8 g (61%) of intermediate 2.

The filtrate was purified by chromatography over silica gel (irregular SiOH, 550 g; gradient from 100% DCM to 90% DCM 10% $CH_3OH$ 0.1% $NH_4OH$). The fractions containing the product were collected and evaporated to dryness yielding 17.3 g (54%) of intermediate 2.

Alternative Route:

Lithium aluminum hydride (7.7 g; 202.7 mmol) was added portionwise to a solution of intermediate 103 (28 g; 101.3 mmol) in THF (300 mL) at 0° C. The reaction mixture was stirred overnight at room temperature. The reaction was quenched with water (7.7 mL) then an aqueous solution of sodium hydroxide 1N (7.7 mL). The precipitate was filtered over a pad of Celite® The filtrate was evaporated to afford 20 g of intermediate 2.

Preparation of Intermediate 3

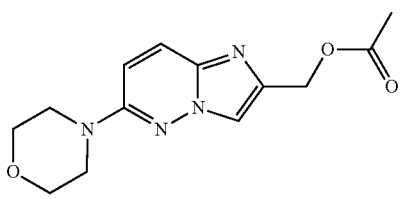 [SMILES: CC(=O)OCc1cn2nc(N3CCOCC3)ccc2n1]

Acetyl chloride (6.8 mL; 96.2 mmol) was added dropwise to a solution of intermediate 2 ((18.8 g; 80.2 mmol), triethylamine (16.8 mL; 0.12 mmol) in DCM (350 mL) at 5° C. The reaction mixture was stirred for 2 hours at room temperature. The solution was poured into water and the organic layer was separated then dried over $MgSO_4$, filtered and evaporated until dryness.

The residue (23 g) was purified by chromatography over silica gel (irregular SiOH, 330 g; gradient from 100% DCM to 95% DCM 5% $CH_3OH$ 0.1% $NH_4OH$). The fractions containing the product were collected and evaporated to dryness yielding 19.4 g (88%) of intermediate 3.

Preparation of Intermediate 4

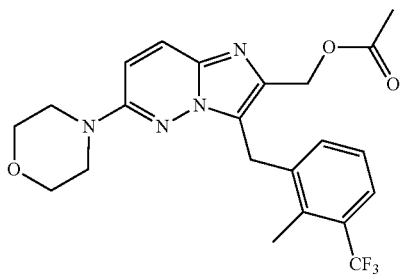 [SMILES: CC(=O)OCc1nc2ccc(N3CCOCC3)nn2c1Cc1cccc(C(F)(F)F)c1C]

A mixture of intermediate 3 (15.5 g; 56.1 mmol), 1-(chloromethyl)-2-methyl-3-(trifluoromethyl)benzene (14 g; 67.3 mmol) and potassium carbonate (11.6 g; 84 mmol) in dioxane (210 mL) was degassed under nitrogen then triphenylphosphine (2.94 g; 11.2 mmol) and palladium acetate (1.4 g; 6.2 mmol) was added and the reaction mixture was heated at 100° C. for 15 hours. The mixture was cooled down to room temperature, poured into water, basified with $K_2CO_3$ solid and extracted with EtOAc. The organic layer was dried over $MgSO_4$, filtered and evaporated to dryness. The residue was purified by chromatography over silica gel (irregular SiOH, 550 g; gradient from 100% DCM to 95% DCM 5% $CH_3OH$ 0.1% $NH_4OH$). The fractions containing the product were collected and evaporated to dryness yielding 21.1 g (84%) of intermediate 4.

Preparation of Intermediate 5:

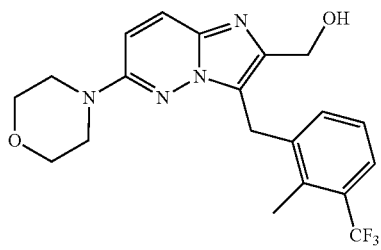 [SMILES: Cc1c(Cc2c(CO)nc3ccc(N4CCOCC4)nn23)cccc1C(F)(F)F]

Lithium hydroxide monohydrate (9.8 g; 234 mmol) was added to a mixture of intermediate 4 (21 g; 47 mmol) in methanol (175 mL) and water (56 mL). Then the reaction was stirred at room temperature for 15 hours and the solvent was evaporated. The residue was taken up with water. The precipitate was filtered, then washed twice with water and dried to afford 43.4 g (98%) intermediate 5.

Alternative Route:

A mixture of intermediate 25 (96 g; 241 mmol) and morpholine (500 mL) was heated at 120° C. overnight. After cooling to room temperature, the reaction mixture was concentrated. The residue was washed with a saturated solution of sodium hydrogencarbonate. The precipitate was filtered, washed with ACN and dried to afford 70 g (71%) of intermediate 5.

Alternative Route:

Under nitrogen, lithium aluminum hydride (0.13 g; 3.3 mmol) was added portionwise to a solution of intermediate 104 (1.25 g; 2.8 mmol) in THF (30 mL) at 0° C. The reaction mixture was stirred for 2 hours at room temperature. The reaction was quenched carefully with water (0.5 mL) then DCM was added. The reaction mixture was dried over $MgSO_4$, filtered and evaporated. The residue (1.2 g) was solubilized in DCM. The insoluble part was filtered off, washed with DCM and dried to give 0.39 g (34%) of intermediate 5. The filtrate was purified by chromatography over silica gel (irregular SiOH 40 g; gradient from 100% DCM to 95% DCM 5% CH₃OH 0.1% NH₄OH). The fractions containing the product were collected and evaporated to dryness yielding 0.12 g (10%) of intermediate 5 and 0.091 g of intermediate 104.

Preparation of Intermediate 6:

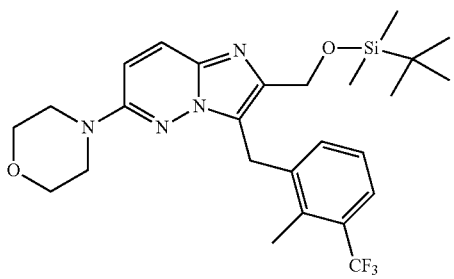 [SMILES: Cc1c(Cc2c(CO[Si](C)(C)C(C)(C)C)nc3ccc(N4CCOCC4)nn23)cccc1C(F)(F)F]

Imidazole (5.34 g; 35.4 mmol) was added to a mixture of intermediate 5 (7.2 g; 17.7 mmol), tert-butyldimethylchlorosilane (5 g; 74.3 mmol) in DMF (25 mL) and the reaction was stirred at room temperature for 15 hours. The mixture was poured into water and extracted with DCM. The organic layer was dried over MgSO₄, filtered and evaporated to dryness.

The residue (12 g) was purified by chromatography over silica gel (irregular SiOH 120 g; gradient from 100% DCM to 95% DCM 5% CH₃OH 0.1% NH₄OH). The fractions containing the product were collected and evaporated to dryness yielding 9.1 g (99%) of intermediate 6.

Preparation of intermediate 7:

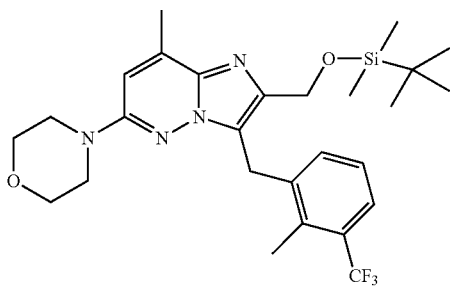 [SMILES: Cc1c(Cc2c(CO[Si](C)(C)C(C)(C)C)nc3c(C)cc(N4CCOCC4)nn23)cccc1C(F)(F)F]

Under nitrogen at −70° C., n-butyllithium 1.6 M in THF (20.6 mL; 33 mmol) was added dropwise to a solution of diisopropylamine (4.5 mL; 31.7 mmol) in THF (35 mL). The solution was stirred at −70° C. for 20 minutes and a solution of intermediate 6 (6.6 g; 12.7 mmol) in THF (70 mL) was added dropwise and the reaction was stirred at −70° C. for 30 minutes. A solution of iodine (3.5 g; 13.9 mmol) in THF (30 mL) was added dropwise and the reaction mixture was stirred 1 hour at −70° C. An aqueous solution of NH₄Cl (10%) was added and the reaction was extracted with EtOAc. The organic layer was separated, dried over MgSO₄, filtered and evaporated to dryness.

The residue (9 g) was purified by chromatography over silica gel (irregular SiOH, 40 g; gradient from 100% DCM to 95% DCM 5% CH₃OH 0.1% NH₄OH). The fractions containing the product were collected and evaporated to dryness yielding 5 g (61%) of intermediate 7.

Preparation of Intermediate 8:

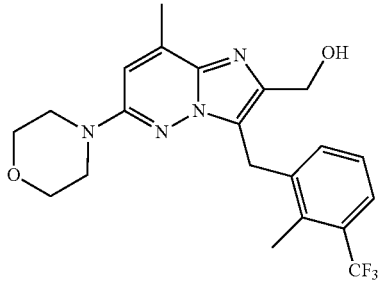

Tetrabutylammonium fluoride (2.3 mL; 2.3 mmol) was added dropwise to a solution of intermediate 7 (1.5 g; 2.3 mmol) in THF (23 mL). The reaction mixture was stirred overnight at room temperature. The reaction mixture was concentrated, taken up with MeOH and the precipitate was filtered and dried to give 0.63 g (51%) of intermediate 8.

The filtrate was purified by chromatography over silica gel (irregular SiOH, 24 g; gradient from 99% DCM 1% CH₃OH 0.1% NH₄OH. to 98% DCM 2% CH₃OH 0.1% NH₄OH). The fractions containing the product were collected and evaporated to dryness yielding 0.6 g (43%) of intermediate 8.

Example A2

Preparation of Intermediate 9:

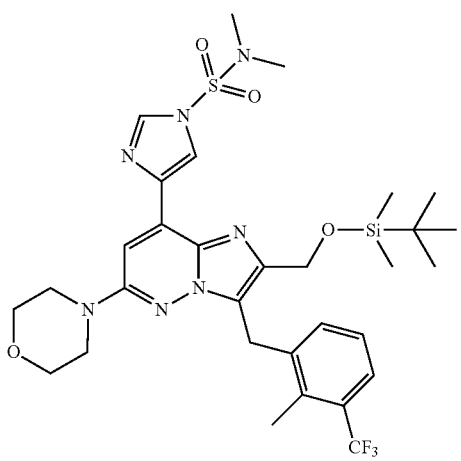 [SMILES: Cc1c(Cc2c(CO[Si](C)(C)C(C)(C)C)nc3c(-c4cn(S(=O)(=O)N(C)C)cn4)cc(N4CCOCC4)nn23)cccc1C(F)(F)F]

In a sealed tube, under nitrogen, PdCl₂dppf.DCM (0.190 g; 0.23 mmol) was added to a mixture of intermediate 7 (1.5 g; 2.3 mmol), N,N-dimethyl-4-(4,4,5,5-tetramethyl-1,3,2-dioxaborolan-2-yl)-1H-imidazole-1-sulfonamide (0.98 g; 3.3 mmol) and potassium carbonate (0.65 g; 4.6 mmol) in dioxane (36 mL) and water (9 mL) was heated at 100° C. for 4 hours. The reaction mixture was cooled to room temperature, poured into water and DCM was added. The suspension was filtered over a pad of Celite®. The organic layer was separated, dried over MgSO₄, filtered and evaporated to dryness to afford 2 g of intermediate 9, which was directly used in the next reaction step without any further purification.

Preparation of Intermediate 10:

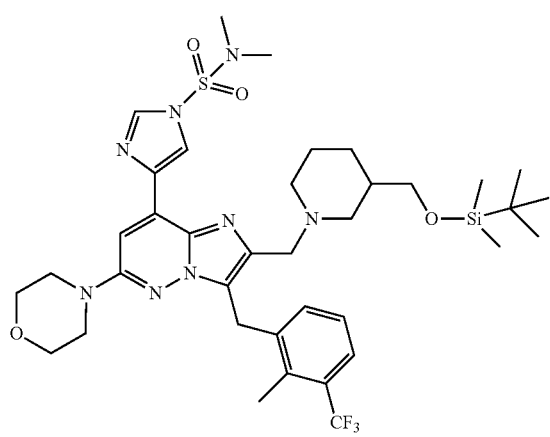 [SMILES: Cc1c(Cc2c(CN3CCCC(CO[Si](C)(C)C(C)(C)C)C3)nc3c(-c4cn(S(=O)(=O)N(C)C)cn4)cc(N4CCOCC4)nn23)cccc1C(F)(F)F]

Intermediate 10 was prepared according to an analogous procedure as described for the synthesis of intermediate 9, using intermediate 39 as starting material (74%).

Preparation of Intermediate 11:

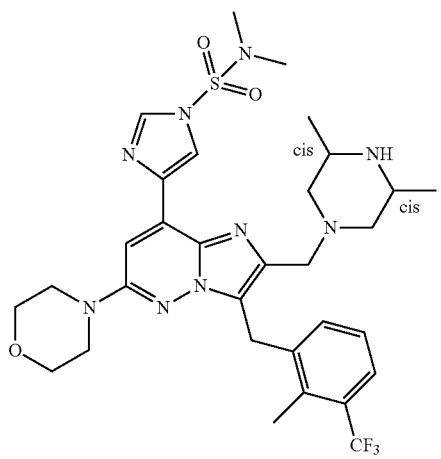 [SMILES: Cc1c(Cc2c(CN3CC(C)NC(C)C3)nc3c(-c4cn(S(=O)(=O)N(C)C)cn4)cc(N4CCOCC4)nn23)cccc1C(F)(F)F]

Intermediate 11 was prepared according to an analogous procedure as described for the synthesis of intermediate 9, using intermediate 24 as starting material. Intermediate 11 was directly used in the next step without any further treatment.

Example A3

Preparation of Intermediate 12:

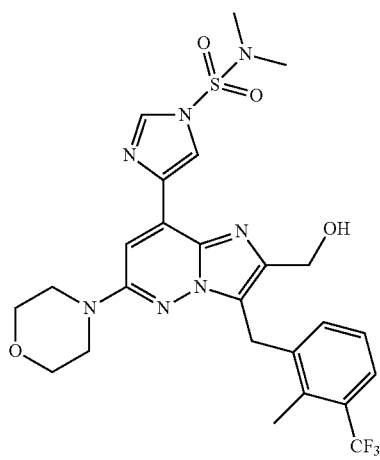 [SMILES: Cc1c(Cc2c(CO)nc3c(-c4cn(S(=O)(=O)N(C)C)cn4)cc(N4CCOCC4)nn23)cccc1C(F)(F)F]

Tetrabutylammonium fluoride (5.8 mL; 5.8 mmol) was added dropwise to a solution of intermediate 9 (2 g; 2.9 mmol) in THF (50 mL). The reaction mixture was stirred for 2 hours at room temperature. The reaction mixture was poured into water and DCM was added. The organic layer was separated, dried over $MgSO_4$, filtered and evaporated.

The residue was taken up with $Et_2O$ and a drop of ACN. The precipitate was filtered and dried to afford 1.23 g (74%) of intermediate 12.

Preparation of Intermediate 13:

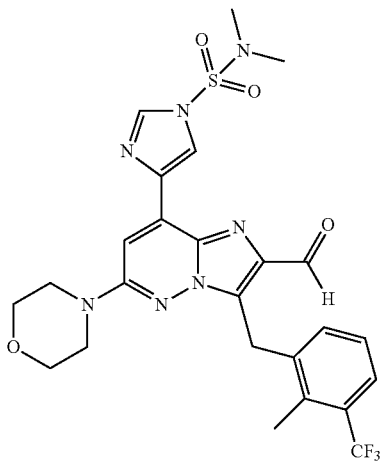 [SMILES: Cc1c(Cc2c(C=O)nc3c(-c4cn(S(=O)(=O)N(C)C)cn4)cc(N4CCOCC4)nn23)cccc1C(F)(F)F]

A mixture of intermediate 12 (1.2 g; 2.2 mmol) and manganese dioxide (1.9 g; 22 mmol) in dioxane (23 mL) was heated at 100° C. for 4 hours. The mixture was cooled, filtered through a pad of Celite® and the product was washed with DCM. The filtrate was evaporated to afford 1.14 g (93%) of intermediate 13.

Example A4

Preparation of Intermediate 14:

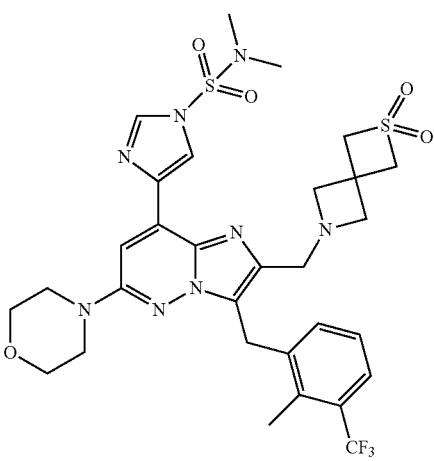 [SMILES: Cc1c(Cc2c(CN3CC4(C3)CS(=O)(=O)C4)nc3c(-c4cn(S(=O)(=O)N(C)C)cn4)cc(N4CCOCC4)nn23)cccc1C(F)(F)F]

A mixture of intermediate 13 (0.3 g; 0.52 mmol) and 2-thia-6-azaspiro[3.3]heptane 2,2-dioxide (0.27 g; 01.1 mmol) in MeOH (3.7 mL) was stirred at room temperature overnight. Sodium triacetoxyborohydride (0.33 g; 1.6 mmol) was added to the reaction mixture and it was stirred 3 hours at room temperature. The solution was poured into cooled water, basified with K₂CO₃ powder and the product was extracted with EtOAc. The organic layer was separated, dried over MgSO₄, filtered and evaporated to dryness. The residue (0.41 g) was purified by chromatography over silica gel (Irregular SiOH, 15-40 μm, 30 g, gradient from 98% DCM 2% CH₃OH 0.2% NH₄OH to 95% DCM 5% CH₃OH 0.5% NH₄OH). The fractions containing the product were collected and evaporated to dryness to afford 0.24 g (59%) of intermediate 14.

Example A5

Preparation of Intermediate 15:

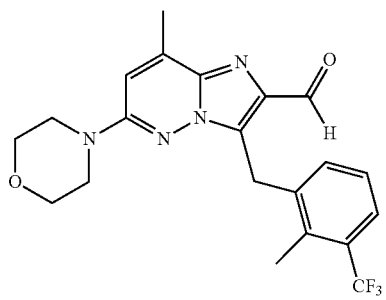 [SMILES: Cc1c(Cc2c(C=O)nc3c(C)cc(N4CCOCC4)nn23)cccc1C(F)(F)F]

A mixture of intermediate 8 (6.1 g; 11 mmol) and manganese dioxide (10 g; 115 mmol) in dioxane (104 mL) was heated at 80° C. for 30 minutes. The mixture was cooled, filtered through a pad of Celite® which was washed with EtOAc. The filtrate was evaporated to afford 4.4 g (73%) of intermediate 15.

Example A6

Preparation of Intermediate 16:

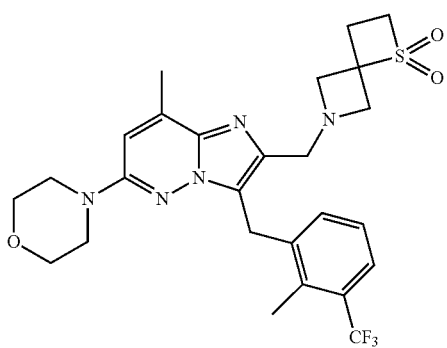 [SMILES: Cc1c(Cc2c(CN3CC4(CCS4(=O)=O)C3)nc3c(C)cc(N4CCOCC4)nn23)cccc1C(F)(F)F]

Sodium triacetoxyborohydride (0.18 g; 0.85 mmol) was added to a mixture of intermediate 15 (0.3 g; 0.57 mmol), 1-thia-6-azaspiro[3.3]heptane-1,1-dioxide (0.085 g; 0.62 mmol) and acetic acid sodium salt (0.070 g; 0.85 mmol) in dichloroethane (15 mL). The reaction mixture was stirred overnight at room temperature. The solution was poured into cooled water and an aqueous solution of sodium hydrogenocarbonate was added. Then the product was extracted with DCM. The organic layer was separated, dried over MgSO₄, filtered and evaporated to dryness. The residue (0.33 g) was purified by chromatography over silica gel (Irregular SiOH, 15-40 μm, 24 g, gradient from 98% DCM 2% CH₃OH 0.1% NH₄OH to 96% DCM 4% CH₃OH 0.1% NH₄OH). The fractions containing the product were collected and evaporated to dryness to afford 0.28 g (73%) of intermediate 16.

Preparation of Intermediate 17:

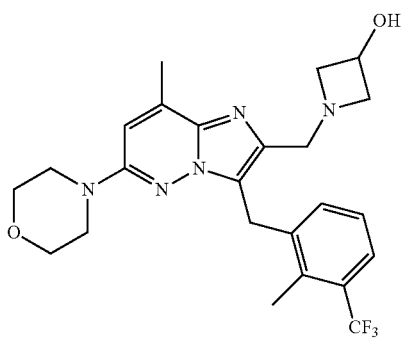 [SMILES: Cc1c(Cc2c(CN3CC(O)C3)nc3c(C)cc(N4CCOCC4)nn23)cccc1C(F)(F)F]

Intermediate 17 was prepared according to an analogous procedure as described for the synthesis of intermediate 16, using intermediate 15 and 3-hydroxyazetidine hydrochloride as starting materials (14%).

Preparation of Intermediate 18:

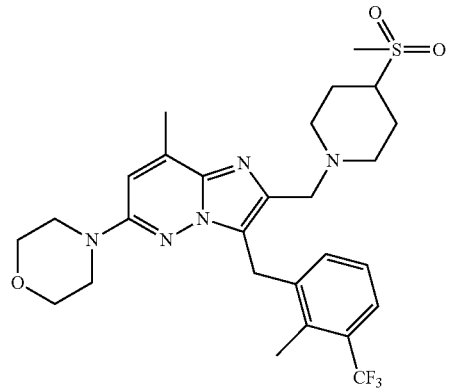 [SMILES: Cc1c(Cc2c(CN3CCC(S(C)(=O)=O)CC3)nc3c(C)cc(N4CCOCC4)nn23)cccc1C(F)(F)F]

Intermediate 18 was prepared according to an analogous procedure as described for the synthesis of intermediate 16, using intermediate 15 and 4-(methylsulfonyl)piperidine as starting materials (81%).

Preparation of Intermediate 19:

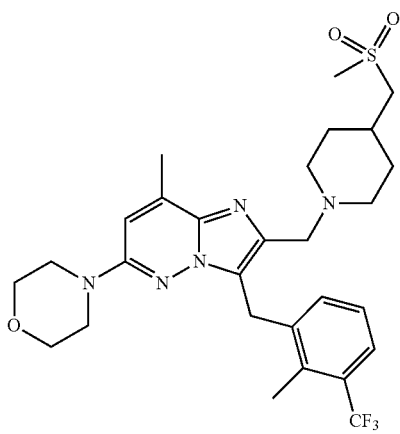 [SMILES: Cc1c(Cc2c(CN3CCC(CS(C)(=O)=O)CC3)nc3c(C)cc(N4CCOCC4)nn23)cccc1C(F)(F)F]

Intermediate 19 was prepared according to an analogous procedure as described for the synthesis of intermediate 16, using intermediate 15 and 4-[(methylsulfonyl)methyl]piperidine hydrochloride as starting materials (59%).

Preparation of Intermediate 20:

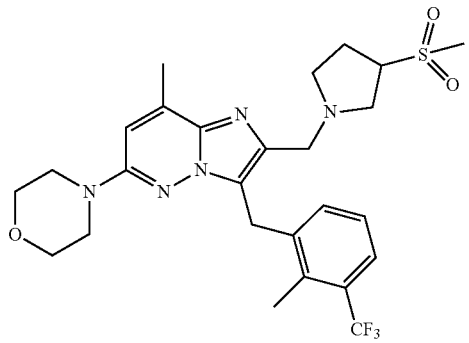 [SMILES: Cc1c(Cc2c(CN3CCC(S(C)(=O)=O)C3)nc3c(C)cc(N4CCOCC4)nn23)cccc1C(F)(F)F]

Intermediate 20 was prepared according to an analogous procedure as described for the synthesis of intermediate 16, using intermediate 15 and 3-(methylsulfonyl)pyrrolidine as starting materials (69%).

Preparation of Intermediate 21:

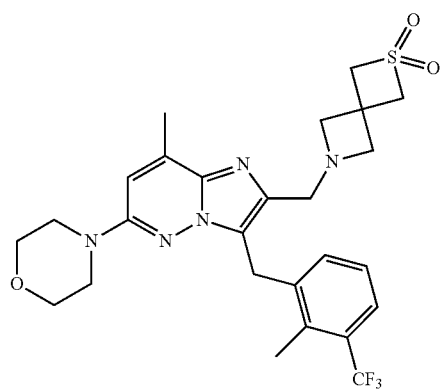 [SMILES: Cc1c(Cc2c(CN3CC4(C3)CS(=O)(=O)C4)nc3c(C)cc(N4CCOCC4)nn23)cccc1C(F)(F)F]

Intermediate 21 was prepared according to an analogous procedure as described for the synthesis of intermediate 16, using intermediate 15 and 2-thia-6-azaspiro[3.3]heptane 2,2-dioxide as starting materials (69%).

Preparation of Intermediate 22:

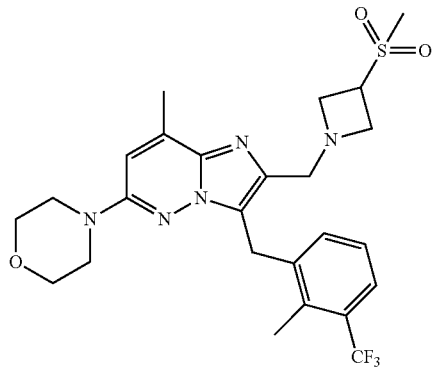 [SMILES: Cc1c(Cc2c(CN3CC(S(C)(=O)=O)C3)nc3c(C)cc(N4CCOCC4)nn23)cccc1C(F)(F)F]

Intermediate 22 was prepared according to an analogous procedure as described for the synthesis of intermediate 16, using intermediate 15 and 3-(methylsulfonyl)azetidine hydrochloride as starting materials (90%).

Preparation of Intermediate 23:

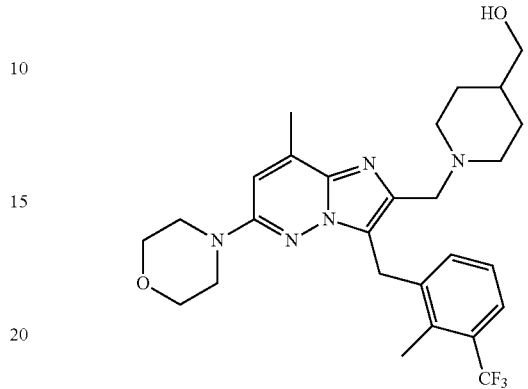

Intermediate 23 was prepared according to an analogous procedure as described for the synthesis of intermediate 16, using intermediate 15 and 4-piperidinemethanol as starting materials (49%).

Preparation of Intermediate 24:

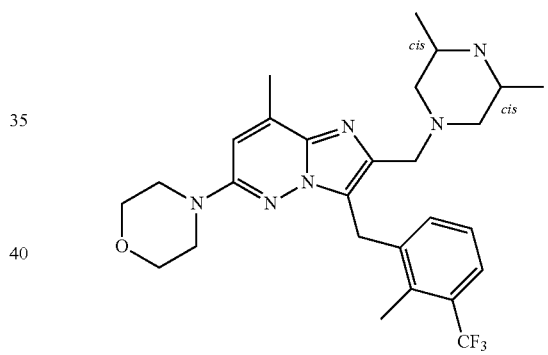

Intermediate 24 was prepared according to an analogous procedure as described for the synthesis of intermediate 16, using intermediate 15 and cis-2,6-dimethylpiperazine as starting materials (quantitative yield).

Preparation of Intermediate 25:

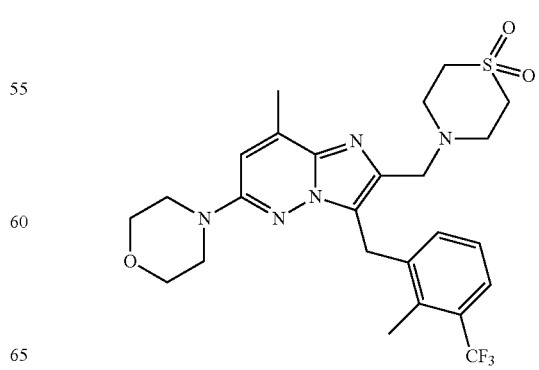

Intermediate 25 was prepared according to an analogous procedure as described for the synthesis of intermediate 16, using intermediate 15 and thiomorpholine-1,1-dioxide as starting materials (85%).

Preparation of Intermediate 26:

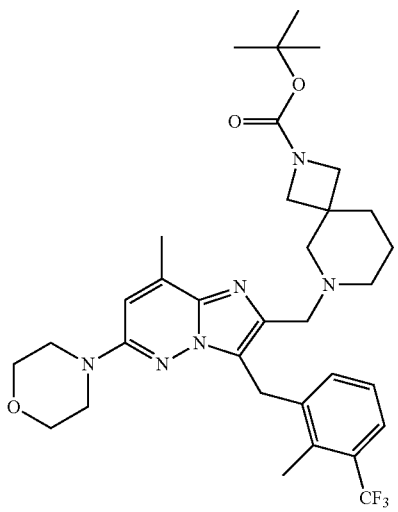 [SMILES: Cc1c(Cc2c(CN3CCCC4(C3)CN(C(=O)OC(C)(C)C)C4)nc3c(C)cc(N4CCOCC4)nn23)cccc1C(F)(F)F]

Intermediate 26 was prepared according to an analogous procedure as described for the synthesis of intermediate 16, using intermediate 15 and 2-boc-2,6-diazaspiro[3.5]nonane-oxalate-2-boc-2,6-diazaspiro[3.5]nonaneoxalate as starting materials. Intermediate 26 was directly used in the next reaction step without any further treatment.

Preparation of Intermediate 27:

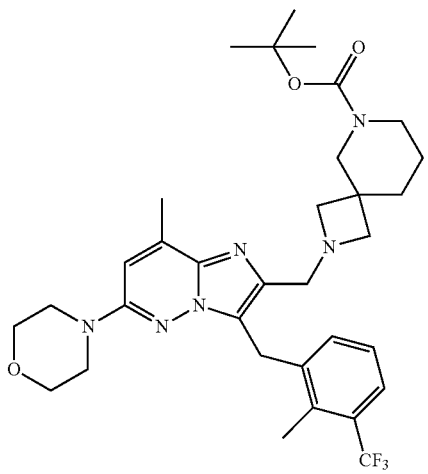 [SMILES: Cc1c(Cc2c(CN3CC4(CCCN(C(=O)OC(C)(C)C)C4)C3)nc3c(C)cc(N4CCOCC4)nn23)cccc1C(F)(F)F]

Intermediate 27 was prepared according to an analogous procedure as described for the synthesis of intermediate 16, using intermediate 15 and tert-butyl-2,6-diazaspiro[3.5]nonane-6-carboxylateoxalate as starting materials. Intermediate 27 was directly used in the next reaction step without any further treatment.

Preparation of Intermediate 28:

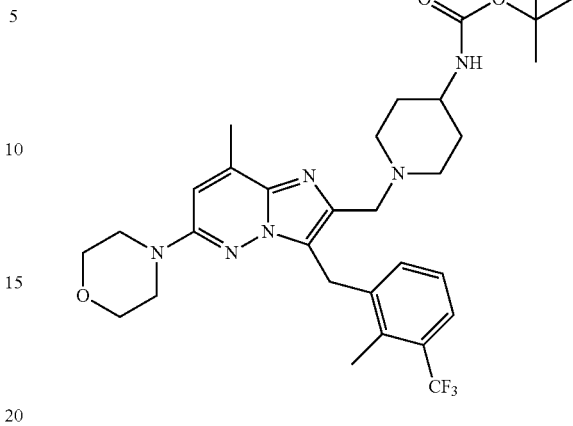

Intermediate 28 was prepared according to an analogous procedure as described for the synthesis of intermediate 16, using intermediate 15 and 4-boc-aminopiperidine as starting materials. Intermediate 28 was directly used in the next reaction step without any further treatment.

Preparation of Intermediate 29:

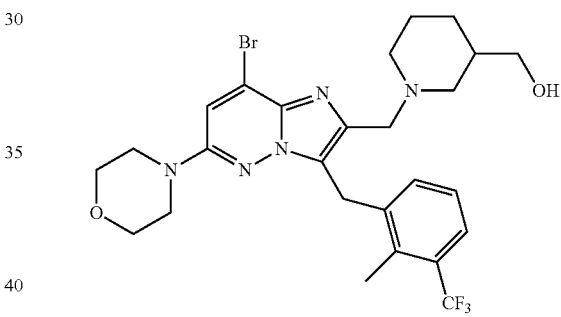

intermediate 29 was prepared according to an analogous procedure as described for the synthesis of intermediate 16, using intermediate 38 and 3-piperine methanol as starting materials (53%).

Preparation of Intermediate 30:

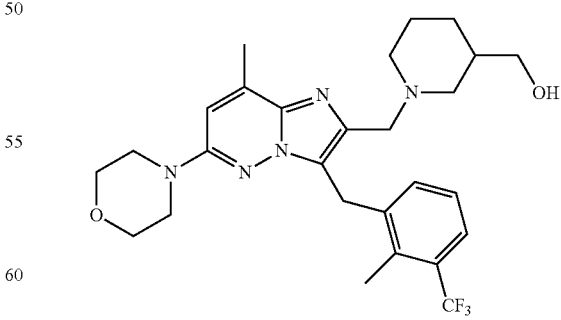

Intermediate 30 was prepared according to an analogous procedure as described for the synthesis of intermediate 16, using intermediate 15 and 3-piperidinemethanol as starting materials (63%).

Preparation of Intermediate 73:

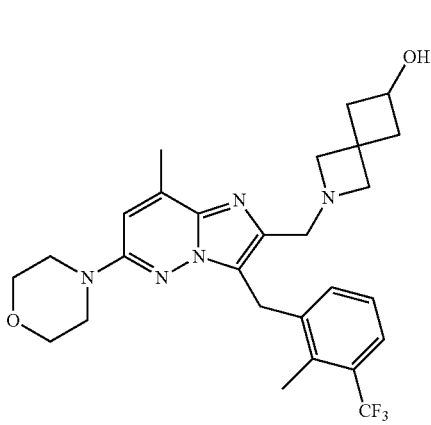 [SMILES: Cc1c(Cc2c(CN3CC4(CC(O)C4)C3)nc3c(C)cc(N4CCOCC4)nn23)cccc1C(F)(F)F]

Intermediate 73 was prepared according to an analogous procedure as described for the synthesis of intermediate 16, using intermediate 15 and 2-azaspiro[3.3]heptan-6-ol (17%) as starting materials.

Example A7

Preparation of Intermediate 31:

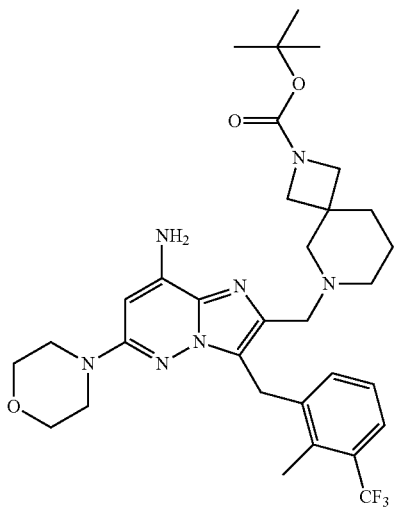 [SMILES: Cc1c(Cc2c(CN3CCCC4(C3)CN(C(=O)OC(C)(C)C)C4)nc3c(N)cc(N4CCOCC4)nn23)cccc1C(F)(F)F]

Under nitrogen, acetamidine hydrochloride (0.047 g; 0.50 mmol) was added to a mixture of intermediate 26 (0.4 g; 0.54 mmol), L-proline (0.0124 g; 0.108 mmol), cesium carbonate (0.53 g; 1.62 mmol) and copper iodide (0.0103 g; 0.054 mmol) in DMF (2.1 mL). The reaction mixture was heated at 110° C. overnight in a sealed tube. The mixture was concentrated and solubilized in EtOAc. The residue was washed with five times with brine. The organic layer was separated, dried over MgSO$_4$, filtered and evaporated to dryness. The residue was purified by chromatography over silica gel (Irregular SiOH, 15-40 μm, 12 g, gradient from 99% DCM 1% CH$_3$OH 0.1% NH$_4$OH. to 97% DCM 3% CH$_3$OH 0.1% NH$_4$OH). The fractions containing the product were collected and evaporated to dryness to afford 0.260 g (76%) of intermediate 31.

Preparation of Intermediate 32:

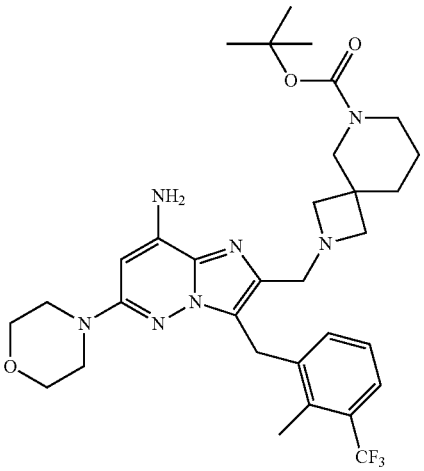 [SMILES: Cc1c(Cc2c(CN3CC4(CCCN(C(=O)OC(C)(C)C)C4)C3)nc3c(N)cc(N4CCOCC4)nn23)cccc1C(F)(F)F]

Intermediate 32 was prepared according to an analogous procedure as described for the synthesis of intermediate 31, using intermediate 27 as starting material (56%).

Preparation of Intermediate 33:

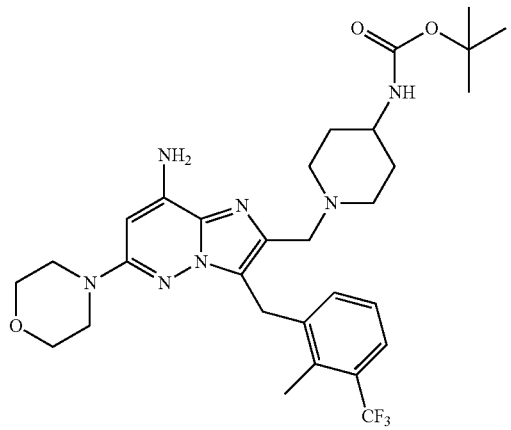 [SMILES: Cc1c(Cc2c(CN3CCC(NC(=O)OC(C)(C)C)CC3)nc3c(N)cc(N4CCOCC4)nn23)cccc1C(F)(F)F]

Intermediate 33 was prepared according to an analogous procedure as described for the synthesis of intermediate 31, using intermediate 28 and 4-boc-aminopiperidine as starting materials. Intermediate 33 was directly used in the next reaction step without any further treatment.

Example A8

Preparation of Intermediate 34:

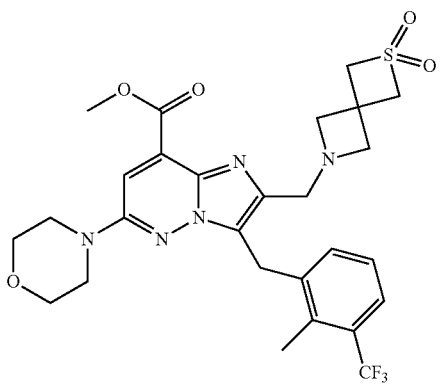 [SMILES: COC(=O)c1cc(N2CCOCC2)nn2c(Cc3cccc(C(F)(F)F)c3C)c(CN3CC4(C3)CS(=O)(=O)C4)nc12]

In sealed tube, to a mixture of intermediate 21 (0.25 g, 0.38 mmol), triethylamine (0.7 mL, 5.3 mmol) in MeOH (5 mL) previously purged with $N_2$ then was added $Pd(PPh_3)_4$ (0.044 g, 0.038 mmol). The reaction was then purged for 5 additional minutes and carbon monoxide was added (5 bars) the reaction was stirred overnight at 120° C. and then concentrated. The residue was purified by chromatography over silica gel (Irregular SiOH, 15-40 μm, 24 g, mobile phase, gradient from 97% DCM 3% $CH_3OH$ 0.1% $NH_4OH$ to 80% DCM 20% $CH_3OH$ 0.4% $NH_4OH$). The frictions containing the product were collected and evaporated to dryness to afford 0.18 g (81%) of intermediate 34.

Example A9

Preparation of Intermediate 35:

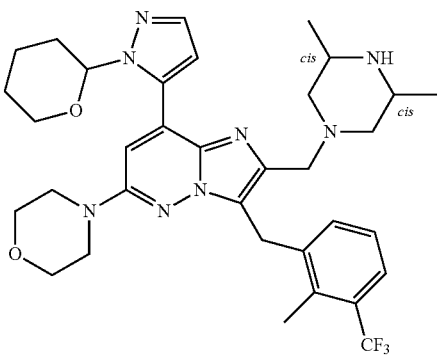 [SMILES: Cc1c(Cc2c(CN3CC(C)NC(C)C3)nc3c(-c4ccnn4C4CCCCO4)cc(N4CCOCC4)nn23)cccc1C(F)(F)F]

$PdCl_2dppf.DCM$ (0.019 g, 0.023 mmol) was added to a solution of intermediate 24 (0.146 g, 0.23 mmol), potassium carbonate (0.064 g, 0.46 mmol) and 1-(tetrahydropyran-2-yl)-1H-pyrazole-5-boronic acid pinacol ester (0.078 g, 0.28 mmol) in dioxane (4 mL) and water (1 mL). The reaction mixture was heated at 100° C. overnight in a sealed tube. The reaction was cooled to room temperature, poured into brine and extracted with EtOAc. The organic layer was separated, dried over $MgSO_4$, filtered and evaporated until dryness. The residue was purified by chromatography over silica gel (irregular SiOH, 24 g; gradient phase 97% DCM 3% $CH_3OH$ 0.1% $NH_4OH$ to 95% DCM 5% $CH_3OH$ 0.1% $NH_4OH$). The fractions containing the product were collected and evaporated to dryness yielding 0.072 g (48%) of intermediate 35.

Example A10

Preparation of Intermediate 36:

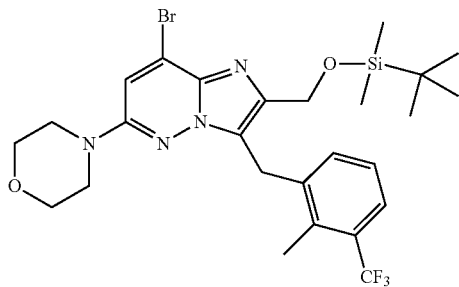 [SMILES: Cc1c(Cc2c(CO[Si](C)(C)C(C)(C)C)nc3c(Br)cc(N4CCOCC4)nn23)cccc1C(F)(F)F]

Under nitrogen at −70° C., n-butyllithium 1.6 M in THF (9.4 mL; 14.9 mmol) was added dropwise to a solution of diisopropylamine (2 mL; 14.4 mmol) in THF (35 mL). The solution was stirred for 20 minutes then a solution of intermediate 6 (3 g; 5.8 mmol) in THF (40 mL) was added dropwise and the reaction was stirred at −70° C. for 1 hour. A solution of bromine (0.36 mL; 6.9 mmol) in THF (30 mL) was added dropwise and the reaction mixture was allowed to warm to −20° C. The reaction mixture was quenched with a 10% aqueous solution of $NH_4Cl$ and EtOAc was added. The organic layer was decanted, separated, washed with brine, dried over $MgSO_4$, filtered and evaporated to dryness. The residue (9 g) was purified by chromatography over silica gel (irregular SiOH, 40 g; gradient from 100% DCM to 95% DCM 5% $CH_3OH$ 0.1% $NH_4OH$). The fractions containing the product were collected and evaporated to dryness yielding 1 g (30%) of intermediate 36.

Preparation of Intermediate 37:

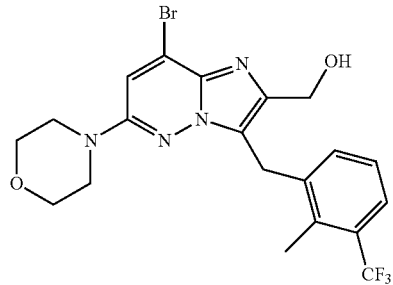 [SMILES: Cc1c(Cc2c(CO)nc3c(Br)cc(N4CCOCC4)nn23)cccc1C(F)(F)F]

Intermediate 37 was prepared according to an analogous procedure as described for the synthesis of intermediate 8, using intermediate 36 as starting material (71%).

Preparation of Intermediate 38:

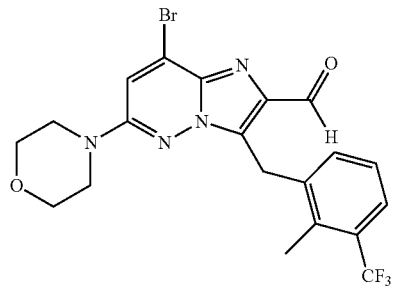 [SMILES: Cc1c(Cc2c(C=O)nc3c(Br)cc(N4CCOCC4)nn23)cccc1C(F)(F)F]

A mixture of intermediate 37 (1.6 g; 2.3 mmol) and manganese dioxide (2.9 g; 32.3 mmol) in dioxane (30 mL) was heated at 80° C. for 1 hour. The mixture was cooled, filtered through a pad of Celite® and the product was washed with EtOAc. The filtrate was evaporated to afford 1.35 g (85%) of intermediate 38.

Example A11

Preparation of Intermediate 39:

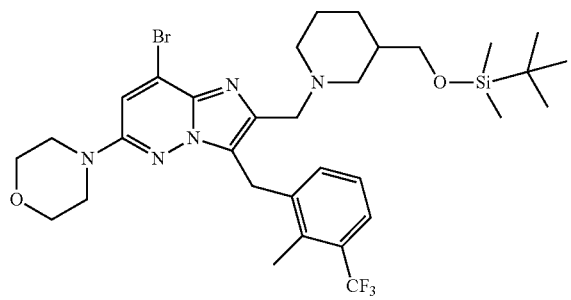 [SMILES: Cc1c(Cc2c(CN3CCCC(CO[Si](C)(C)C(C)(C)C)C3)nc3c(Br)cc(N4CCOCC4)nn23)cccc1C(F)(F)F]

Imidazole (0.204 g; 1.36 mmol) was added to a mixture of intermediate 29 (0.263 g; 0.45 mmol) and tert-butyldimethylchlorosilane (0.19 g; 2.7 mmol) in DMF (3.7 mL). The reaction mixture was stirred at room temperature for 15 hours. The mixture was poured into water and extracted with DCM. The organic layer was separated, dried over $MgSO_4$, filtered and evaporated to dryness.

The residue (0.358 g) was purified by chromatography over silica gel (irregular SiOH, 4 g; mobile phase 97% DCM 3% $CH_3OH$ 0.3% $NH_4OH$). The fractions containing the product were collected and evaporated to dryness yielding 0.252 g (80%) of intermediate 39.

Preparation of Intermediate 40:

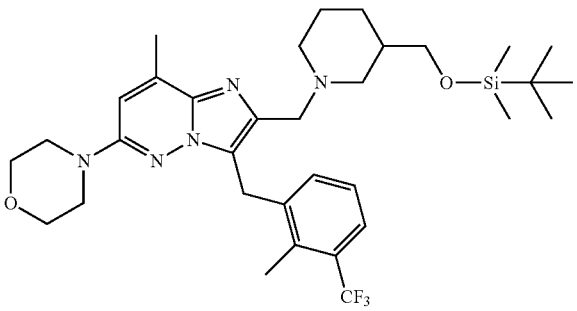 [SMILES: Cc1c(Cc2c(CN3CCCC(CO[Si](C)(C)C(C)(C)C)C3)nc3c(C)cc(N4CCOCC4)nn23)cccc1C(F)(F)F]

Intermediate 40 was prepared according to an analogous procedure as described for the synthesis of intermediate 39, using intermediate 30 as starting material (63%).

Example A12

Preparation of Intermediate 41:

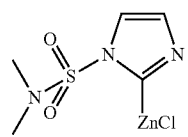

N-butyllithium (9.4 mL (1.6 M in hexanes); 15 mmol) was added dropwise at −78° C., to a solution of N,N-Dimethylimidazole-1-sulfonamide (2.63 g; 15 mmol) in THF (45 mL) and the reaction mixture was stirred for 30 minutes. A solution of zinc chloride (30 mL (1 M in THF); 30 mmol) was added and the reaction mixture was allowed to warm to room temperature over 30 minutes. The reaction mixture containing intermediate 41 [c=0.18 M] was directly used in the next reaction step without any further treatment.

Preparation of Intermediate 42:

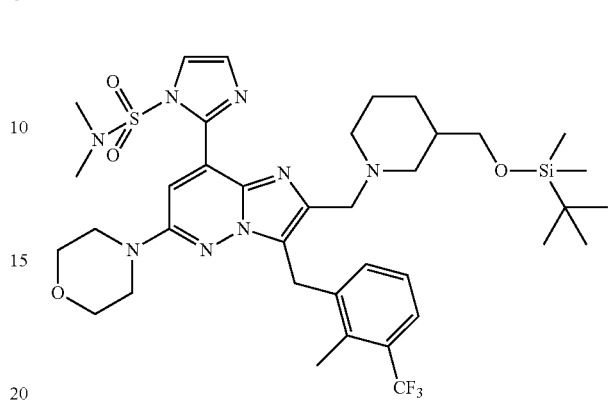

Intermediate 41 (10 mL; 1.9 mmol; 0.18 M) was added dropwise a previously degassed mixture of intermediate 40 (0.275 g; 0.37 mmol) and $Pd(PPh_3)_4$ (0.043 g; 0.037 mmol) in THF (1 mL). The reaction was heated at 100° C. for 1 hour. Additional intermediate 41 (10 mL; 1.9 mmol; 0.18 M) was added and stirring was pursued overnight at 100° C. The reaction mixture was cooled to room temperature, diluted with DCM and quenched with a 10% aqueous solution of $K_2CO_3$. The mixture was filtered through a pad of Celite® which was washed with DCM. The filtrate was extracted with DCM. The organic layer was washed with brine, dried over $MgSO_4$, filtered and the solvent was evaporated. The residue (1.1 g) was purified by chromatography over silica gel (Irregular SiOH, 15-40 µm, 150 g, mobile phase 95% DCM 5% $CH_3OH$ 0.1% $NH_4OH$). The fractions containing the product were collected and evaporated to dryness affording 0.41 g of a mixture containing intermediate 42 and N,N-dimethyl imidazole-1-sulfonamide.

Preparation of Intermediate 43 and 44:

intermediate 43

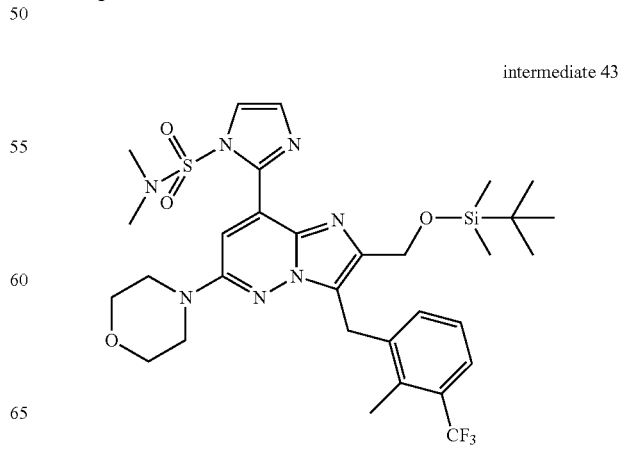

intermediate 44

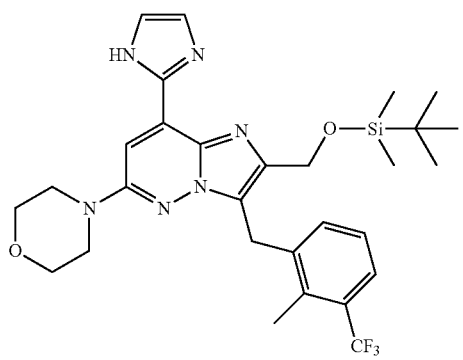

intermediate 46

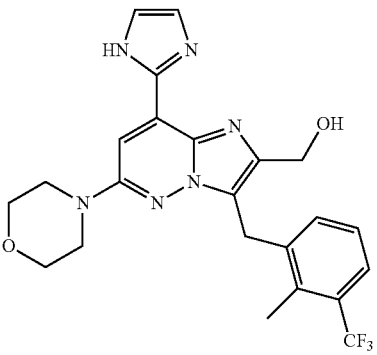

In a sealed tube, intermediate 41 (86 mL; 15.5 mmol; 0.18 M) was added to a previously degassed mixture of intermediate 7 (2 g; 3.1 mmol) and Pd(Ph₃)₄ (3572 mg; 0.31 mmol) and the reaction mixture was heated at 70° C. for 1 hour. Intermediate 41 (86 mL; 15.5 mmol; 0.18 M) was added again and the heating was continued for 1 hour. The reaction mixture was cooled to room temperature, poured onto a 10% aqueous solution of K₂CO₃ and extracted with DCM. The organic layer was decanted, washed with aqueous HCl 1N, then water and finally with a 10% aqueous solution of K₂CO₃. The organic layer was decanted, dried over MgSO₄, filtered and evaporated to dryness. The residue was gathered with another reaction performed in the same conditions on 1 g of intermediate 7.

The combined residues were purified by silica gel chromatography (irregular SiOH, 40 g; mobile phase: gradient from 0% NH₄OH, 0% MeOH, 100% DCM to 1% NH₄OH, 10% MeOH, 90% DCM). The fractions containing the product were collected and evaporated to dryness yielding 2.15 g (67%) of intermediate 43 and 1.3 g of a mixture of intermediate 43 and 44 (77/33 based on LCMS). The final yields are based on 3 g of intermediate 7 as starting material.

Preparation of Intermediate 45 and 46:

Two reactions were run in parallel and mixed for the purification:

Reaction 1:

Tetrabutylammonium fluoride (6.2 mL; 6.2 mmol) was added dropwise to a solution of intermediate 43 (2.16 g; 3.11 mmol) in THF (80 mL). The reaction mixture was stirred for 3 hours at room temperature. The reaction mixture was poured into water and DCM was added and a 10% aqueous solution of K₂CO₃ was added.

Reaction 2:

Tetrabutylammonium fluoride (3.7 mL; 3.7 mmol) was added dropwise to a solution of a mixture intermediate 43 and 44 (1.3 g; 1.87 mmol) in THF (45 mL). The reaction mixture was stirred for 3 hours at room temperature. The reaction mixture was poured into water and DCM was added and a 10% aqueous solution of K₂CO₃ was added.

The organic layers from reaction 1 and reaction 2 were mixed, washed with water, dried over MgSO₄, filtered and evaporated. The residue was purified by chromatography over silica gel (Irregular SiOH, 150 g, gradient from 97% DCM 3% CH₃OH 0.3% NH₄OH. to 85% DCM 15% CH₃OH 1.5% NH₄OH). The fractions containing the product were collected and evaporated to dryness to afford 1.87 g (49%) of intermediate 45 and 725 mg (32%) of intermediate 46.

Example A13

Preparation of Intermediate 47:

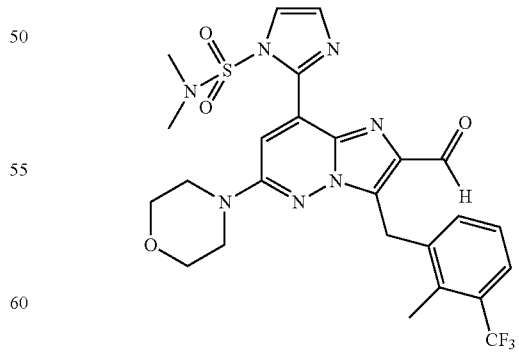

intermediate 45

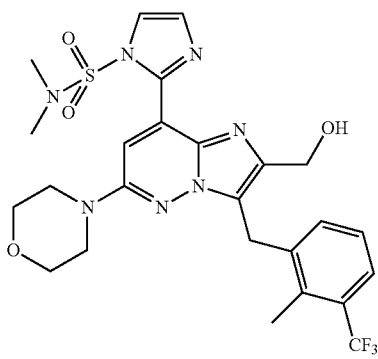 [SMILES: Cc1c(Cc2c(C=O)nc3c(-c4nccn4S(=O)(=O)N(C)C)cc(N4CCOCC4)nn23)cccc1C(F)(F)F]

A mixture of intermediate 45 (0.54 g; 0.9 mmol) and manganese dioxide (0.8 g; 9.3 mmol) in dioxane (10 mL) was heated at 100° C. for 3 hours. The mixture was cooled, filtered through a pad of Celite® and the product was washed with DCM. The filtrate was evaporated to afford 0.49 g (91%) of intermediate 47.

Preparation of Intermediate 48:

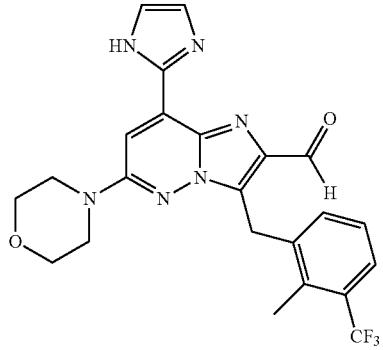 [SMILES: Cc1c(Cc2c(C=O)nc3c(-c4ncc[nH]4)cc(N4CCOCC4)nn23)cccc1C(F)(F)F]

Intermediate 48 was prepared according to an analogous procedure as described for the synthesis of intermediate 47, using intermediate 46 as starting material (69%).

Example A14

Preparation of Intermediate 49:

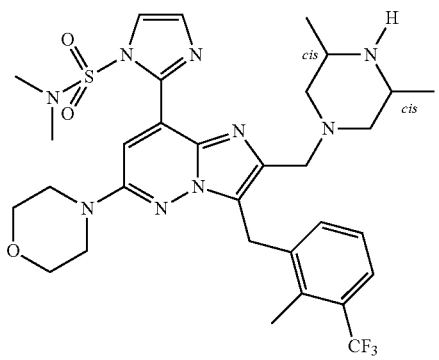 [SMILES: Cc1c(Cc2c(CN3CC(C)NC(C)C3)nc3c(-c4nccn4S(=O)(=O)N(C)C)cc(N4CCOCC4)nn23)cccc1C(F)(F)F]

A mixture of intermediate 47 (0.49 g; 0.85 mmol) and cis 2,6-dimethylpiperazine (0.2 g; 1.7 mmol) in MeOH (6 mL) was stirred at room temperature overnight. Sodium triacetoxyborohydride (0.54 g; 2.6 mmol) was added to the reaction mixture and stirred 3 hours at room temperature. The solution was poured into cooled water and basified with $K_2CO_3$ powder and the product was extracted with EtOAc. The organic layer was separated, dried over $MgSO_4$, filtered and evaporated to dryness. The residue (0.625 g) was purified by chromatography over silica gel (Irregular SiOH, 15-40 µm, gradient from 97% DCM 3% $CH_3OH$ 0.1% $NH_4OH$ to 85% DCM 15% $CH_3OH$ 0.1% $NH_4OH$). The fractions containing the product were collected and evaporated to dryness to afford 0.347 g (61%) of intermediate 49.

Preparation of Intermediate 50:

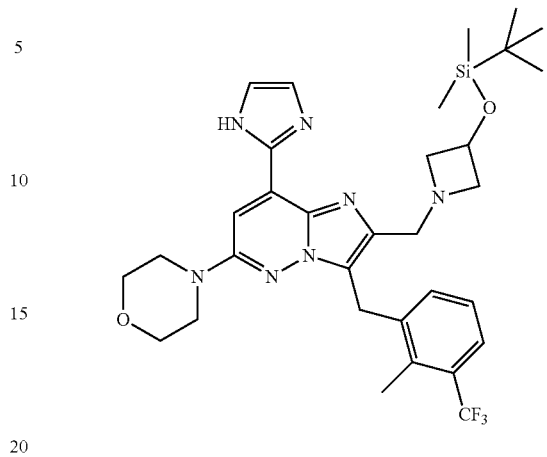

Intermediate 50 was prepared according to an analogous procedure as described for the synthesis of intermediate 49, using intermediate 48 and 3-[(tert-Butyldimethylsilanyl)oxy]azetidine as starting materials (74%).

Example A15

Preparation of Intermediate 51:

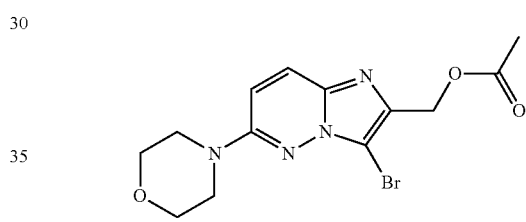

To a solution of intermediate 3 (1.5 g; 5.5 mmol) in ACN (29 mL) was added portionwise N-bromosuccinimide (0.97 g; 5.5 mmol) at room temperature. The solution was stirred overnight.

EtOAc and a saturated aqueous solution of brine were added to the mixture. The organic layer was washed, separated, dried over $MgSO_4$, filtered and evaporated. The residue was purified by chromatography over silica gel (irregular SiOH, 120 g, mobile phase 98% DCM 2% $CH_3OH$ 0.1% $NH_4OH$). The fractions containing the product were collected and evaporated to dryness to afford 1.8 g (93%) of intermediate 51.

Preparation of Intermediate 52:

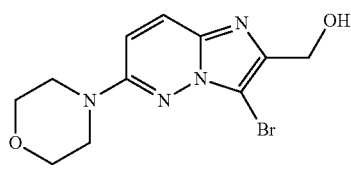 [SMILES: OCc1nc2ccc(N3CCOCC3)nn2c1Br]

Lithium hydroxide monohydrate (0.56 g, 13 mmol) was added to a mixture of intermediate 51 (0.95 g, 2.7 mmol) in water (3.2 mL) and MeOH (9.7 mL). Then, the reaction mixture was stirred at room temperature overnight and the solvent was evaporated. The residue was taken up with water. The precipitate was filtered, then washed with water and dried to give 0.71 g (85%) of intermediate 52.

Preparation of Intermediate 53:

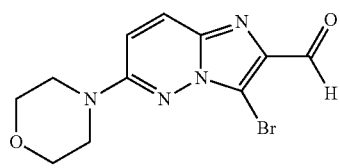 [SMILES: O=Cc1nc2ccc(N3CCOCC3)nn2c1Br]

A mixture of intermediate 52 (4.45 g; 14.2 mmol) and manganese dioxide (12.4 g; 142.1 mmol) in toluene (135 mL) was heated at 80° C. for 30 minutes. The mixture was cooled, solubilized in DCM then filtered through a pad of Celite® and the product was washed with DCM. The filtrate was evaporated to afford 1.9 g (43%) of intermediate 53. The pad of Celite® was washed again with DCM/MeOH 90/10 to give additional 1.5 g (34%) of intermediate 53.

Preparation of Intermediate 54:

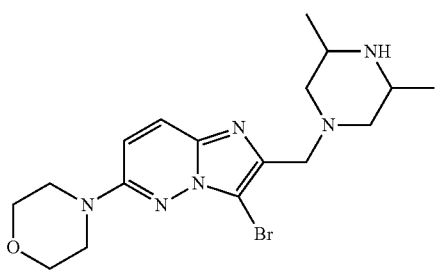 [SMILES: CC1CN(Cc2nc3ccc(N4CCOCC4)nn3c2Br)CC(C)N1]

Intermediate 54 was prepared according to an analogous procedure as described for the synthesis of intermediate 14 using intermediate 53 and 2,6-dimethylpiperazine as starting materials (96%).

Preparation of Intermediate 55:

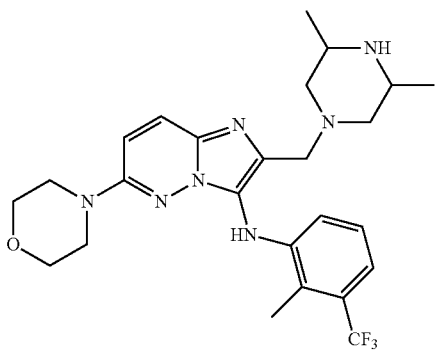 [SMILES: Cc1c(Nc2c(CN3CC(C)NC(C)C3)nc3ccc(N4CCOCC4)nn23)cccc1C(F)(F)F]

Under nitrogen, in a sealed tube, to a mixture of intermediate 54 (1.4 g, 3.4 mmol), 2-methyl-3-(trifluoromethyl)aniline (1.2 g. 6.8 mmol) and sodium tert-butoxide (0.66 g, 6.8 mmol) in toluene (14 mL) degassed with nitrogen, were added $Pd_2dba_3$ (0.31 g, 0.34 mmol) and 2-(di-t-butylphosphino)biphenyl (0.21 g, 0.68 mmol). The reaction mixture was heated at 100° C. overnight. EtOAc and a saturated aqueous solution of brine were added to the mixture. The organic layer was washed, separated, dried on $MgSO_4$, filtered and evaporated. The residue was purified by chromatography over silica gel (irregular SiOH, 40 g; mobile phase gradient from 96% DCM 4% $CH_3OH$ 0.1% $NH_4OH$ to 92% DCM 8% $CH_3OH$ 0.1% $NH_4OH$). The fractions containing the product were collected and evaporated to dryness to afford 0.96 g (56%) of intermediate 55.

Preparation of Intermediate 56:

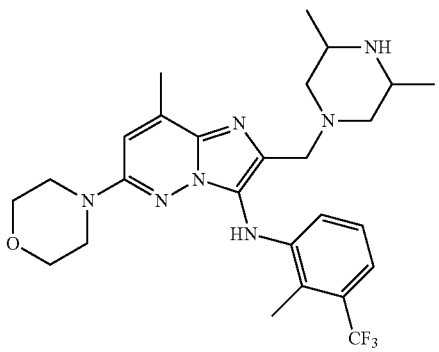 [SMILES: Cc1c(Nc2c(CN3CC(C)NC(C)C3)nc3c(C)cc(N4CCOCC4)nn23)cccc1C(F)(F)F]

Under nitrogen at −70° C., n-butyllithium 1.6 M in THF (5.5 mL; 8.7 mmol) was added dropwise to a solution of diisopropylamine (1.2 mL; 8.6 mmol) in THF (10 mL). The solution was stirred at −40° C. for 20 minutes. Then, a solution of intermediate 55 (0.96 g; 1.9 mmol) in THF (11 mL) was added dropwise and the reaction was stirred at −70° C. for 30 minutes. A solution of iodine (0.53 g; 2.1 mmol) in THF (10 mL) was added dropwise and the reaction mixture was stirred 45 minutes at −70° C. A 10% aqueous solution of $NH_4Cl$ was added and the reaction was extracted with EtOAc. The organic layer was separated, dried over $MgSO_4$, filtered and evaporated to dryness. The residue (9 g) was purified by chromatography over silica gel (irregular SiOH, 40 g; gradient 92% DCM 8% $CH_3OH$ 0.1% $NH_4OH$). The fractions containing the product were collected and evaporated to dryness yielding 0.22 g (19%) of intermediate 56.

Example A16

Preparation of Intermediate 57:

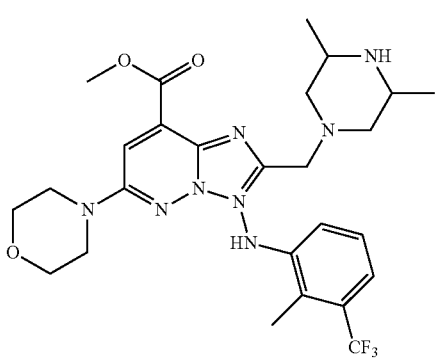

In a sealed tube, a mixture of intermediate 56 (0.21 g, 0.33 mmol) and triethylamine (0.65 mL, 4.7 mmol) in MeOH (4 mL) was degassed with nitrogen. $Pd(PPh_3)_4$ (0.077 g, 0.067 mmol) was added and the reaction was purged with $N_2$ for 5 minutes. Carbon monoxide was added (5 bars) and the reaction was stirred for 5 hours at 120° C. The mixture was concentrated and the residue was purified by chromatography over silica gel (irregular SiOH, 12 g; gradient from 99% DCM 1% $CH_3OH$ 0.1% $NH_4OH$ to 91% DCM 9% $CH_3OH$ 0.1% NH₄OH). The fractions containing the product were collected and evaporated to dryness yielding 0.090 g (48%) of intermediate 57.

Example A17

Preparation of Intermediate 58:

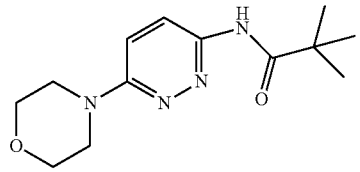 [SMILES: CC(C)(C)C(=O)Nc1ccc(N2CCOCC2)nn1]

A mixture of N-(6-chloro-3-pyridazinyl)-2,2-dimethyl-propionamide (65.3 g; 305.6 mmol) and morpholine (538 mL; 6.1 mmol) was heated at 120° C. for 24 hours. The mixture was cooled and evaporated. The residue was poured into cooled water, basified with K₂CO₃ powder and DCM was added. The organic layer was separated, dried over MgSO₄, filtered and evaporated to dryness. The residue was crystallized from Et₂O. The precipitate was filtered and dried to afford 69.3 g (87%) of intermediate 58.

Preparation of Intermediate 59:

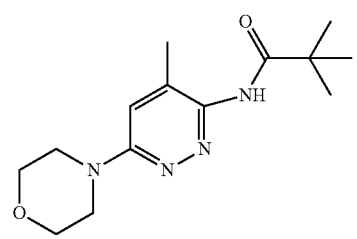 [SMILES: Cc1cc(N2CCOCC2)nnc1NC(=O)C(C)(C)C]

Under nitrogen, at −78° C., n-butyllithium (250 mL 1.6M in hexanes, 0.4 mol) was added to a solution of 2,2,6,6-tetramethylpiperidine (68.1 mL, 0.405 mol) in THF (265 mL) and the solution was stirred at 0° C. for 30 minutes. After cooling to −78° C., a solution of intermediate 58 ((13.2 g, 50 mmol) in THF (265 mL) was added dropwise and the mixture was stirred at −78° C. for 1 hour. Iodine (104.06 g, 0.41 mol) in THF (120 mL) was added dropwise and the reaction mixture was stirred at −78° C. for 2 hours. The reaction mixture was poured into water and basified with NH₄Cl powder. Then, the aqueous layer was extracted with EtOAc. The organic layer was taken up with an aqueous solution of Na₂S₂O₃, separated, dried over MgSO₄, filtered and evaporated. The residue (26 g) was purified by chromatography over silica gel (irregular SiOH, 300 g; gradient from 100% DCM to 90% DCM 10% CH₃OH 0.1% NH₄OH). The fractions containing the product were collected and evaporated to dryness yielding 15.3 g (79%) of intermediate 59.

Preparation of Intermediate 60:

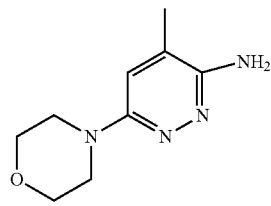

Intermediate 59 (15.3 g; 39.2 mmol) in HCl 6N (140 mL; 0.8 mmol) and dioxane (255 mL) were heated at 70° C. for 9 hours. The reaction was cooled to room temperature, then concentrated and the residue was poured into water. The mixture was basified and saturated with K₂CO₃ powder, extracted with DCM several times. The organic layer was dried over MgSO₄, filtered and evaporated until dryness. The residue (4.5 g) was purified by chromatography over silica gel (irregular SiOH, 80 g; gradient from 100% DCM to 95% DCM 5% CH₃OH 0.1% NH₄OH). The fractions containing the product were collected and evaporated to dryness. The resulting product was crystallized from Et₂O. The precipitate was filtered and dried to give 1.12 g intermediate 60.

Preparation of Intermediate 61:

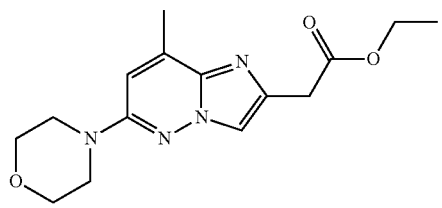 [SMILES: CCOC(=O)Cc1cn2nc(N3CCOCC3)cc(C)c2n1]

Ethyl-4-chloroacetate (6.7 mL; 49 mmol) was added dropwise to a suspension intermediate 60 (5 g; 16.3 mmol) in EtOH (60 mL). Then, the mixture was heated at 80° C. for 15 hours. The solution was cooled to room temperature. The precipitate was filtered and eliminated to afford of intermediate 60. The filtrate was concentrated then the residue was taken up with DCM. The organic layer was separated, washed, dried over MgSO₄, filtered and evaporated. The residue (60 g) was purified by chromatography over silica gel (irregular SiOH, 450 g; mobile phase 65% Heptane 5% CH₃OH (0.1% NH₄OH), 35% EtOAc). The fractions containing the product were collected and evaporated to dryness to afford 2.7 g (40%) of intermediate 61.

Example A18

Preparation of Intermediate 62:

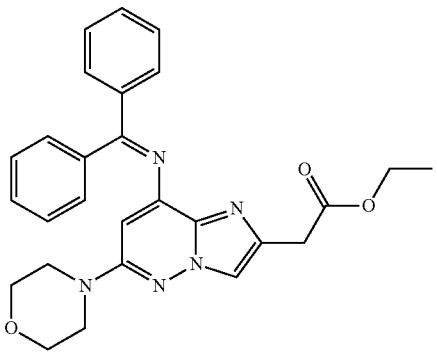 [SMILES: CCOC(=O)Cc1cn2nc(N3CCOCC3)cc(N=C(c3ccccc3)c3ccccc3)c2n1]

The reaction was realized 6 times on 1 g (2.4 mmol) of intermediate 61. Then, the 6 reactions were combined for the work up and the purification.

Under nitrogen and in a sealed tube, a mixture of intermediate 61 (1 g; 2.4 mmol), benzophenone imine (0.6 mL; 3.6 mmol), $Cs_2CO_3$ (2.35 g; 7.2 mmol), racemic-2,2'-bis(diphenylphosphino)-1,1'-binaphtyl (0.075 g; 0.12 mmol) and palladium acetate (0.026 g; 0.12 mmol) in toluene (10 mL) was degassed for 10 minutes and then, was heated at 100° C. The 6 reaction mixtures were cooled to room temperature, combined, poured into water and the product was extracted with EtOAc. The organic layer was separated, washed with a saturated solution of brine, dried over $MgSO_4$, filtered and evaporated. The residue (8.4 g) was purified by chromatography over silica gel (Irregular SiOH, 15-40 μm, 450 g, mobile phase 62% Heptane, 3% MeOH (+10% $NH_4OH$), 35% EtOAc). The fractions containing the product were collected and evaporated to dryness to afford 2 g (29%) of intermediate 62.

Preparation of Intermediate 63:

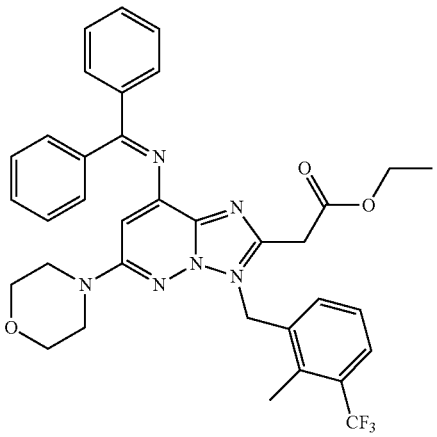

The reaction was realized 2 times on 1 g (2.1 mmol) of intermediate 62. Then, the 2 reactions were combined for the work up and the purification.

Under nitrogen and in sealed tube, to a mixture of intermediate 62 (1 g; 2.13 mmol), 1-(chloromethyl)-2-methyl-3-(trifluoromethylbenzene) (0.8 g; 3.85 mmol) and potassium carbonate (0.75 g; 5.32 mmol) in dioxane (10 mL), previously degassed under nitrogen, were added triphenylphosphine (0.056 g; 0.215 mmol) and palladium acetate (0.048 g; 0.215 mmol). The reaction mixture was heated to 100° C. for 15 hours.

The 2 reaction mixtures were cooled down to room temperature, combined and poured into ice water. EtOAc was added and the resulting mixture was filtered through a pad of Celite®. The organic layer was separated, washed with brine, dried over $MgSO_4$, filtered and evaporated till dryness. The residue (4.15 g) was purified by chromatography over silica gel (Irregular SiOH, 15-40 μm, 450 g, mobile phase 62% Heptane, 3% MeOH (+10% $NH_4OH$), 35% EtOAc). The fractions containing the product were collected and evaporated to dryness to afford 0.7 g (25%) of intermediate 63.

Preparation of Intermediate 64:

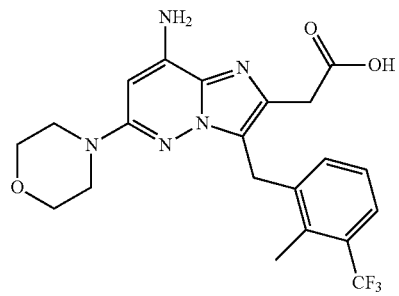 [SMILES: Cc1c(Cc2c(CC(=O)O)nc3c(N)cc(N4CCOCC4)nn23)cccc1C(F)(F)F]

Lithium hydroxide monohydrate (0.23 g; 5.5 mmol) was added to a mixture of intermediate 63 (0.7 g; 1.1 mmol), in methanol (11 mL) and water (1.3 mL). The reaction mixture was stirred at room temperature for 15 hours. A solution of HCl 3N was added dropwise to the reaction mixture and it was stirred 3 hours at room temperature. The precipitate was filtered and dried to afford 0.323 g (66%) of intermediate 64.

Example A19

Preparation of Intermediate 65:

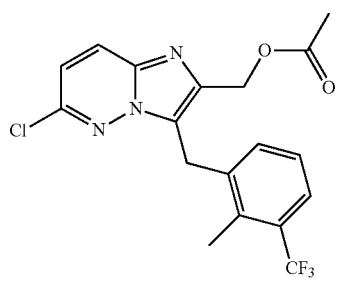 [SMILES: CC(=O)OCc1nc2ccc(Cl)nn2c1Cc1cccc(C(F)(F)F)c1C]

Intermediate 65 was prepared according to an analogous procedure as described for the synthesis of intermediate 4, using intermediate I as starting material (55%).

Example A20

Preparation of Intermediate 66:

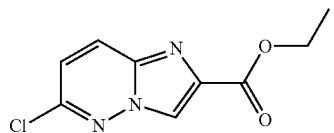

3-amino-6-chloropyridazine (20 g; 154.4 mmol) and ethyl bromopyruvate (38.9 mL; 308.8 mmol) in EtOH (90 mL) were refluxed overnight. The reaction mixture was cooled to room temperature, water and DCM were added. The organic layer was separated, dried over MgSO$_4$, filtered and evaporated. The residue was purified by chromatography over silica gel (Irregular SiOH, 15-40 µm, 300 g, gradient from 97% heptane 30% EtOAc to 50% Heptane 50% EtOAc). The fractions containing the product were collected and evaporated to dryness to afford 13.5 g (39%) of intermediate 66.

Preparation of Intermediate 67:

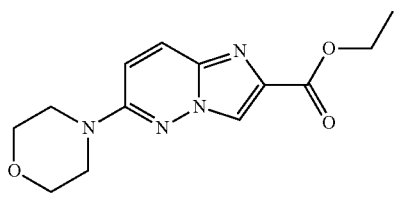 [SMILES: CCOC(=O)c1cn2nc(N3CCOCC3)ccc2n1]

A mixture of intermediate 66 and morpholine (84 mL; 0.96 mmol) was heated at 90° C. for 4 hours. The reaction mixture was cooled to room temperature and the solvent was evaporated, the residue was poured into water and DCM was added. The organic layer was separated, dried over MgSO$_4$, filtered and evaporated. DCM was added then the solution was stirred overnight. The precipitate was filtered to eliminate morpholine excess. The filtrate was purified by chromatography over silica gel (Irregular SiOH, 15-40 µm, 300 g, gradient from 99% DCM 1% CH$_3$OH 0.1% NH$_4$OH to 97% DCM 3% CH$_3$OH 0.1% NH$_4$OH). The fractions containing the product were collected and evaporated to dryness to afford 6.9 g (71%) of intermediate 67.

Preparation of Intermediate 68:

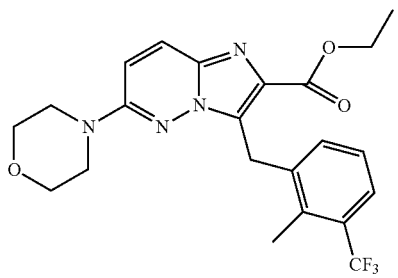 [SMILES: CCOC(=O)c1nc2ccc(N3CCOCC3)nn2c1Cc1cccc(C(F)(F)F)c1C]

A mixture of intermediate 67 (2 g; 7.2 mmol), 1-(chloromethyl)-2-methyl-3-(trifluoromethyl)benzene (1.7 g; 7.96 mmol) and potassium carbonate (1.5 g; 10.9 mmol) in dioxane (29 mL) was degassed under nitrogen then triphenylphosphine (0.38 g; 1.45 mmol) and palladium acetate (0.16 g; 0.72 mmol) was added and the reaction mixture was heated at 100° C. for 15 hours. The mixture was cooled down to room temperature, poured into water, basified with K$_2$CO$_3$ solid and extracted with EtOAc. The organic layer was dried over MgSO$_4$, filtered and evaporated to dryness. The residue (6 g) was purified by chromatography over silica gel (irregular SiOH, 550 g; gradient from 100% DCM to 95% DCM 5% CH$_3$OH 0.1% NH$_4$OH). The fractions containing the product were collected, evaporated to dryness and crystallized in acetone. The precipitate was filtered and dried to give 1.5 g (46%) of intermediate 68.

Example A21

Preparation of Intermediate 69:

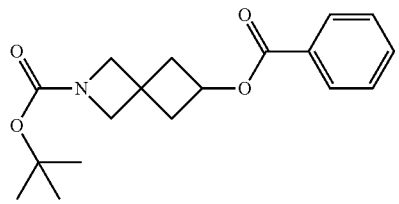 [SMILES: CC(C)(C)OC(=O)N1CC2(CC(OC(=O)c3ccccc3)C2)C1]

Benzoyl chloride (0.33 mL; 2.81 mmol) was added to a solution of 6-hydroxy-2-aza-spiro[3.3]heptane-2-carboxylic acid tert-butyl ester (500 mg; 2.34 mmol) and triethylamine (0.52 mL; 3.75 mmol) in DCM (10 mL) at room temperature. The reaction mixture was stirred overnight at the room temperature, diluted with DCM and washed with a 10% aqueous solution of K$_2$CO$_3$. The organic layer was decanted, dried over MgSO$_4$, filtered and evaporated to dryness. The crude residue was purified by chromatography over silica gel (irregular SiOH, 12 g; gradient 100% DCM to 2% MeOH, 98% DCM). The pure fractions were collected and evaporated to dryness yielding 395 mg (53%) of intermediate 69.

Preparation of Intermediate 70:

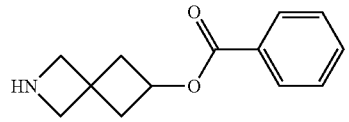 [SMILES: O=C(OC1CC2(CNC2)C1)c1ccccc1]

TFA (2.5 mL; 32.669 mmol) was added dropwise to a solution of intermediate 69 (345 mg; 1.09 mmol) in DCM (25 mL) at 0° C. and the reaction mixture was stirred at rt for 2 hours. A 10% aqueous solution of K$_2$CO$_3$ was added and the organic layer was decanted, dried over MgSO$_4$, filtered and evaporated to dryness yielding 334 mg (quantitative) of intermediate 70. The product was used without purification in the next reaction step.

Preparation of Intermediate 71:

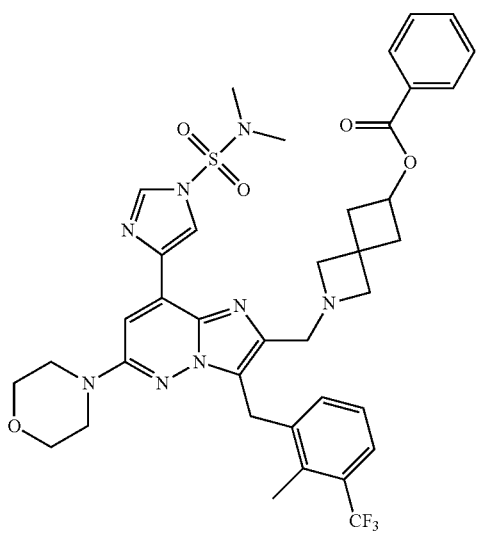 [SMILES: Cc1c(Cc2c(CN3CC4(CC(OC(=O)c5ccccc5)C4)C3)nc3c(-c4cn(S(=O)(=O)N(C)C)cn4)cc(N4CCOCC4)nn23)cccc1C(F)(F)F]

A mixture of intermediate 13 (388 mg; 0.67 mmol), intermediate 70 (292 mg; 1.344 mmol) in MeOH/DCM (80/20) (8 mL) was stirred at room temperature all over the weekend. Sodium triacetoxyborohydride (427 mg; 2.02 mmol) was added and stirred overnight. The reaction mixture was diluted with DCM and poured onto a 10% aqueous solution of $K_2CO_3$. The organic layer was decanted, dried over $MgSO_4$, filtered and evaporated to dryness. The residue was purified by chromatography over silica gel (irregular SiOH, 10 g; gradient from 2% MeOH, 98% DCM to 7% MeOH, 93% DCM). The pure fractions were collected and evaporated to dryness yielding 329 mg (63%) of intermediate 71.

Preparation of Intermediate 72:

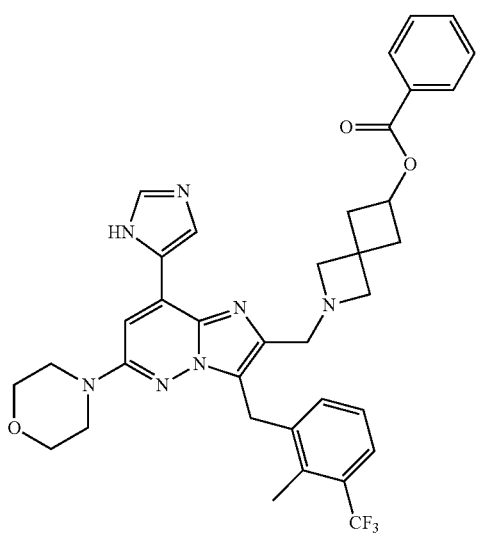 [SMILES: Cc1c(Cc2c(CN3CC4(CC(OC(=O)c5ccccc5)C4)C3)nc3c(-c4cnc[nH]4)cc(N4CCOCC4)nn23)cccc1C(F)(F)F]

TFA (700 µL; 9.15 mmol) was added dropwise at 5° C. to a suspension of intermediate 71 (329 mg; 0.42 mmol) in 1,4-dioxane (7 mL) and the reaction mixture was stirred at 70° C. for 6 hours. TFA (700 µL; 9.15 mmol) was added again and the reaction mixture was stirred at 70° C. over- night. TFA (700 µL; 9.15 mmol) was added again to complete the reaction and the reaction mixture was stirred at 70° C. overnight. The reaction mixture was diluted with DCM and poured onto a 10% aqueous solution of $K_2CO_3$. The organic layer was decanted, dried over $MgSO_4$, filtered and evaporated to dryness. The residue was purified by chromatography over silica gel (irregular SiOH, 24 g; gradient from 0.5% $NH_4OH$, 5% MeOH, 95% DCM to 1.5% $NH_4OH$, 15% MeOH, 85% DCM). The pure fractions were collected and evaporated to dryness yielding 139 mg (49%) of intermediate 72.

Example A22

Preparation of Intermediate 74:

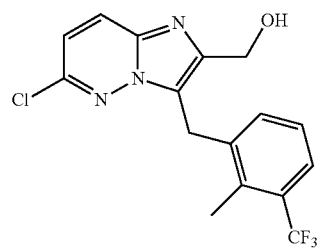 [SMILES: Cc1c(Cc2c(CO)nc3ccc(Cl)nn23)cccc1C(F)(F)F]

NaOH (1M in water) (26.6 mL; 26.6 mmol) was added dropwise to a solution of intermediate 1 (5.3 g; 13.3 mmol) in THF (65 mL) and EtOH (65 mL). The reaction mixture was stirred at rt for 2 hours. The mixture was evaporated under vacuum and the residue was taken up in DCM and water. The layers were separated and the aqueous layer was extracted with DCM. The combined organic layers were dried o$MgSO_4$, filtered off and evaporated in vacuo to give 4.54 g (95%; brown solid) of intermediate 74.

Preparation of Intermediate 75:

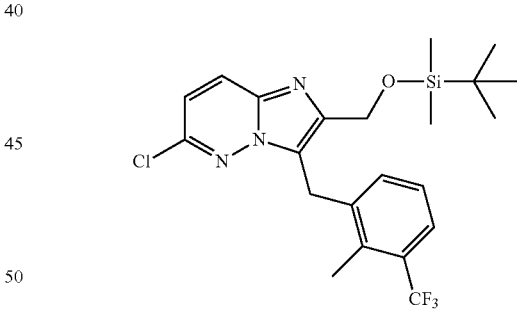

Imidazole (2.58 g; 37.9 mmol) and tert-butyldimethylchlorosilane (3.81 g; 25.3 mmol) were added to a solution of intermediate 74 (4.54 g; 12.6 mmol) in DMF (65 mL). The reaction mixture was stirred at rt overnight. The mixture was evaporated under vacuum and the residue was taken-up in EtOAc. A 10% aqueous solution of $NaHCO_3$ was added and the layers were separated. The aqueous layer was extracted with EtOAc. The combined organic layers was washed with brine (3×), dried over $MgSO_4$, filtered off and evaporated in vacuo. The residue (6.39 g; beige solid) was purified by chromatography over silica gel (regular SiOH 30 µm, 200 g, gradient: from 100% DCM to 90% DCM, 10% EtOAc). The pure fractions were collected and the solvent was evaporated to give 4.94 g (83%; off-white solid) of intermediate 75.

Preparation of Intermediate 76:

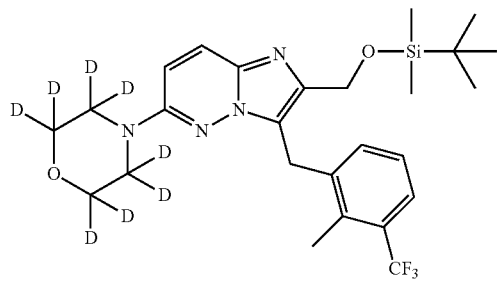 [SMILES: [2H]C1([2H])OC([2H])([2H])C([2H])([2H])N(c2ccc3nc(CO[Si](C)(C)C(C)(C)C)c(Cc4cccc(C(F)(F)F)c4C)n3n2)C1([2H])[2H]]

In sealed tube, a mixture of intermediate 75 (500 mg; 1.06 mmol), morpholine-2,2,3,3,5,5,6,6-d$_8$ (182 mg; 1.92 mmol) and Cs$_2$CO$_3$ (693 mg; 2.13 mmol) in 2-methyl-2-butanol (4 mL) was purged with N$_2$. Pd$_2$(dba)$_3$ (97 mg; 0.11 mmol) and RuPhos (99 mg; 0.21 mmol) were added. The reaction mixture was purged with N$_2$ and heated at 110° C. in a one single mode microwave (biotage initiator EXP60) with a power output ranging from 0 to 400 W for 30 min. After cooling down to rt, the mixture was poured into water and EtOAc and filtered through a pad of Celite®. The organic layer was separated, dried over MgSO$_4$, filtered off and evaporated under vacuum. The residue (954 mg, red oil) was purified by chromatography over silica gel (Irregular SiOH 15-40 μm, 30 g, gradient: from 100% DCM to 90% DCM, 10% acetone). The pure fractions were collected and the solvent was evaporated to give 459 mg (82%, orange foam) of intermediate 76.

Preparation of Intermediate 77:

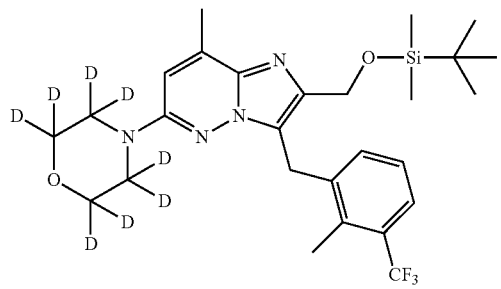 [SMILES: [2H]C1([2H])OC([2H])([2H])C([2H])([2H])N(c2cc(C)c3nc(CO[Si](C)(C)C(C)(C)C)c(Cc4cccc(C(F)(F)F)c4C)n3n2)C1([2H])[2H]]

To a solution of diisopropylamine (307 μL; 2.17 mmol) THF (6 mL), at −78° C. under N$_2$, was added n-butyllithium (1.41 mL, 2.26 mmol). The mixture was stirred at −40° C. for 20 min and then cooled down to −78° C. A solution of intermediate 76 (459 mg; 0.87 mmol) in THF (4 mL) was added dropwise and the mixture was stirred at −78° C. for 30 min. Then, a solution of iodide (242 mg; 0.96 mmol) in THF (4 mL) was added dropwise and the mixture was stirred at −78° C. for 1 h. After warming up to rt, the reaction mixture was slowly quenched with a 10% aqueous solution of NH$_4$Cl and EtOAc was added. The layers were separated and the aqueous layer was extracted with EtOAc. The combined organic layers were dried over MgSO$_4$, filtered off and evaporated under vacuum. The residue (brown oil) was purified by chromatography over silica gel (irregular SiOH, 15-40 μm, 24 g, gradient: from 100% DCM to 95% DCM, 5% EtOAc). The pure fractions were collected and the solvent was evaporated to give 279 mg (49%, colourless oil which crystallized) of intermediate 77.

Preparation of Intermediate 78:

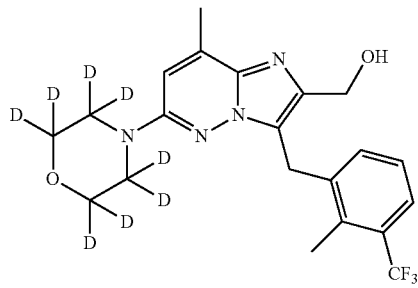 [SMILES: [2H]C1([2H])OC([2H])([2H])C([2H])([2H])N(c2cc(C)c3nc(CO)c(Cc4cccc(C(F)(F)F)c4C)n3n2)C1([2H])[2H]]

To a solution of intermediate 77 (279 mg; 0.43 mmol) in THF (4.30 mL) was added HCl (3M in water) (284 μL; 0.85 mmol). The solution was stirred for 3 hours then cooled down to 0° C. and slowly neutralized with solid K$_2$CO$_3$. The mixture was extracted with DCM (2×). The combined organic layers were dried over MgSO$_4$, filtered off and evaporated in vacuo to give 233 mg (quant., off-white solid) of intermediate 78. The product was used without purification in the next step.

Preparation of Intermediate 79:

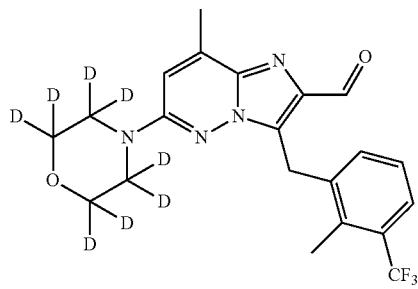 [SMILES: [2H]C1([2H])OC([2H])([2H])C([2H])([2H])N(c2cc(C)c3nc(C=O)c(Cc4cccc(C(F)(F)F)c4C)n3n2)C1([2H])[2H]]

To a suspension of intermediate 78 (233 mg; 0.43 mmol) DCM (8 mL) was added manganese oxide (375 mg; 4.31 mmol). The reaction mixture was stirred at rt for 18 hours and filtered on a pad of Celite®. The Celite® was rinsed with DCM and the filtrate was evaporated in vacuum to give 202 mg (87%, grey solid) of intermediate 79. The product was used without purification in the next step.

Preparation of Intermediate 80:

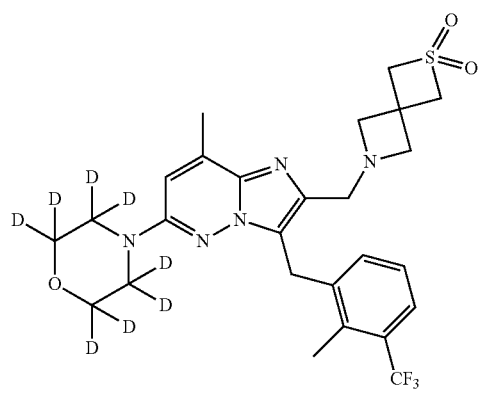 [SMILES: [2H]C1([2H])OC([2H])([2H])C([2H])([2H])N(c2cc(C)c3nc(CN4CC5(C4)CS(=O)(=O)C5)c(Cc4cccc(C(F)(F)F)c4C)n3n2)C1([2H])[2H]]

Intermediate 80 was prepared according to an analogous procedure as described for the synthesis of intermediate 16, using intermediate 79 and 2-thia-6-azaspiro[3.3]heptane 2,2-dioxide (47%) as starting materials.

Example A23

Preparation of Intermediate 81:

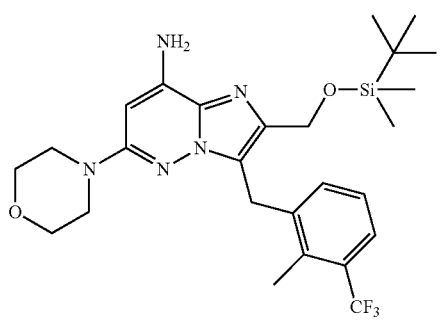 [SMILES: Cc1c(Cc2c(CO[Si](C)(C)C(C)(C)C)nc3c(N)cc(N4CCOCC4)nn23)cccc1C(F)(F)F]

Acetamidine hydrochloride (87.7 mg; 9.28 mmol) was added under nitrogen to a flask charged with copper iodide (147 mg; 0.77 mmol). L-proline (178 mg; 1.55 mmol), intermediate 7 (5 g; 7.73 mmol) and $Cs_2CO_3$ (7.56 g; 23.2 mmol) in DME (40 mL). The reaction mixture was stirred at 110° C. overnight. The mixture was concentrated, then solubilized in EtOAc and washed with brine. The organic layer was dried over $MgSO_4$, filtered and concentrated. The residue (4.2 g) was purified by chromatography over silica gel (Irregular SiOH 20-45 µm; 450 g; mobile phase: 60% heptane, 5% MeOH (+10% $NH_4OH$), 35% EtOAc). The pure fractions were collected and the solvent was evaporated to give 2.2 g (53%) of intermediate 81.

Preparation of Intermediate 81a:

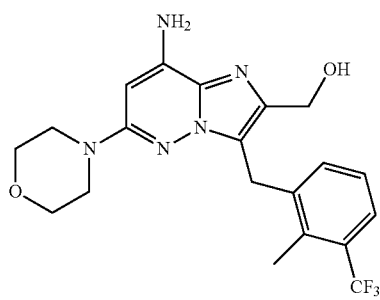 [SMILES: Cc1c(Cc2c(CO)nc3c(N)cc(N4CCOCC4)nn23)cccc1C(F)(F)F]

Tetrabutylammonium fluoride (2.99 mL, 2.99 mmol) was added dropwise to a solution of intermediate 81 (1.6 g, 2.99 mmol) in THE (26.67 mL) at room temperature. The mixture was stirred overnight and poured onto ice water. The precipitate was filtered, washed with water, dried and purified by chromatography over silica gel (Irregular SiOH, 40 µm, 200 g, gradient from 97% DCM 3% $CH_3OH$ 0.1% $NH_4OH$. to 95% DCM 5% $CH_3OH$ 0.1% $NH_4OH$). The fractions containing the product were collected and evaporated to dryness yielding 0.537 g (43%) of intermediate 81a. M.P.: 241° C. (DSC).

Preparation of Intermediate 82:

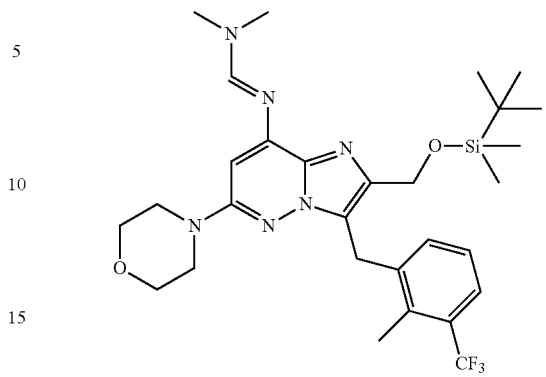

A mixture of intermediate 81 (2.9 g; 5.41 mmol) and N,N-dimethylformamide dimethyl acetal (2.16 mL; 16.24 mmol) in toluene (75 mL) was heated at 120° C. for 4 h. The reaction mixture was concentrated until dryness to give 3.3 g of intermediate 82. This compound was used without any further purification in the next reaction step.

Preparation of Intermediate 83:

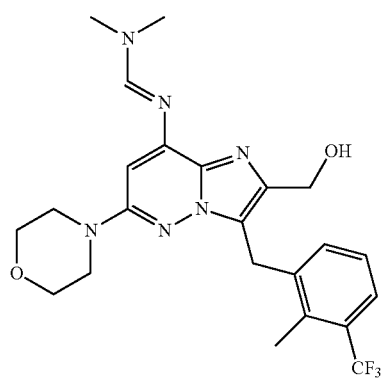 [SMILES: Cc1c(Cc2c(CO)nc3c(/N=C/N(C)C)cc(N4CCOCC4)nn23)cccc1C(F)(F)F]

TBAF (5.58 mL; 5.58 mmol) was added dropwise to a solution of intermediate 82 (3.3 g; 5.58 mmol) in THF (50 mL) at rt. The reaction mixture was stirred overnight at rt. The solution was poured into ice water, extracted with DCM and washed with brine. The organic layer was dried over $MgSO_4$, filtered and evaporated to dryness. The residue was crystallized from DIPE. The precipitate was filtered off and dried under vacuum to give 235 g (88%) of intermediate 83.

Alternative Pathway:

A mixture of intermediate 81a (2.4 g; 5.69 mmol) and N,N-dimethylformamide dimethyl acetal (2.27 mL; 17.09 mmol) in toluene (70 mL) was heated at 120° C. for 4 h. The reaction mixture was concentrated until dryness. The residue was crystallized from DIPE and EtOH (50/50). The precipitate was filtered off and dried in vacuum to give 1.1 g (41%) of intermediate 83.

Preparation of Intermediate 84:

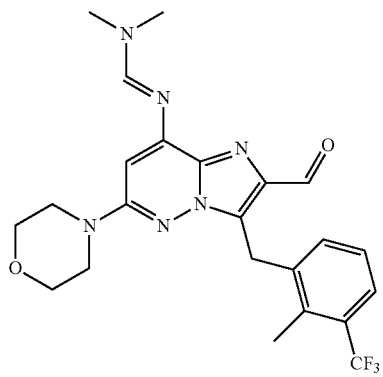 [SMILES: Cc1c(Cc2c(C=O)nc3c(/N=C/N(C)C)cc(N4CCOCC4)nn23)cccc1C(F)(F)F]

A mixture of intermediate 83 (1.1 g; 2.31 mmol) and manganese oxide (1.41 g; 16.16 mmol) in toluene (20 mL) was heated at 80° C. for 1 h. The reaction mixture was cooled down to rt, diluted in DCM and filtered through a pad of Celite®. Celite® was washed with DCM and the filtrate was evaporated until dryness. The residue (1.2 g) was crystallized from DIPE. The precipitate was filtered off and dried under vacuum to give 0.785 g (72%) of intermediate 84.

Preparation of Intermediate 85 and Compound 31:

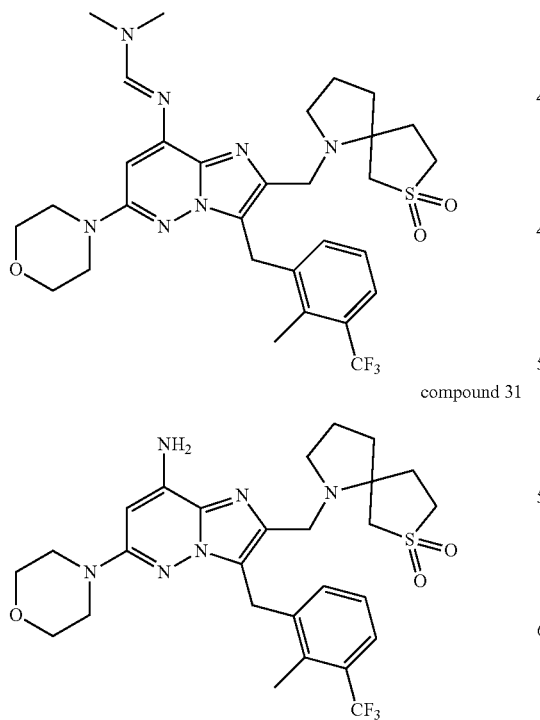

intermediate 85 compound 31

6-thia-1-azaspiro[4.4]nonane 7,7-dioxide (112 mg; 0.53 mmol) and acetic acid (615 μL; 10.74 mmol) were added to a solution of intermediate 84 (250 mg; 0.53 mmol) in MeOH (15 mL). The reaction mixture was stirred at rt for 15 min. Then, sodium cyanoborohydride (33 mg; 0.53 mmol) was added. The reaction mixture was stirred at rt for 18 h. The reaction mixture was poured on a 10% aqueous solution of $K_2CO_3$ and extracted with DCM. The organic layer was dried over $MgSO_4$, filtered off and the solvent was evaporated under vacuum. The residue (300 mg) was purified by chromatography over silica gel (SiOH 20-45 μm; 24 g; gradient: from 98% DCM, 2% MeOH, 0.1% $NH_4OH$ to 90% DCM, 10% MeOH, 0.1% $NH_4OH$). The pure fractions were collected and the solvent was evaporated to give 280 mg of a mixture of intermediate 85 and compound 31. The mixture was used without further purification in the next reaction step.

Preparation of Intermediate 86 and Compound 32:

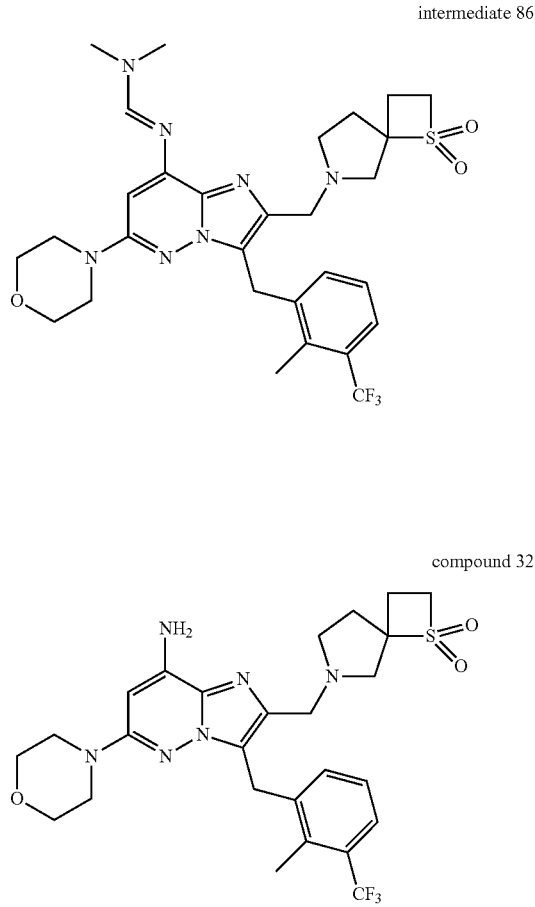

intermediate 86 compound 32

A mixture of intermediate 86 and compound 32 was prepared according to an analogous procedure as described for the synthesis of intermediate 85, using intermediate 84 and 1-Thia-6-azaspiro[3.4]octane1,1dioxide hydrochloride as starting materials. The mixture was used for the next step.

Preparation of Intermediate 87 and Compound 33:

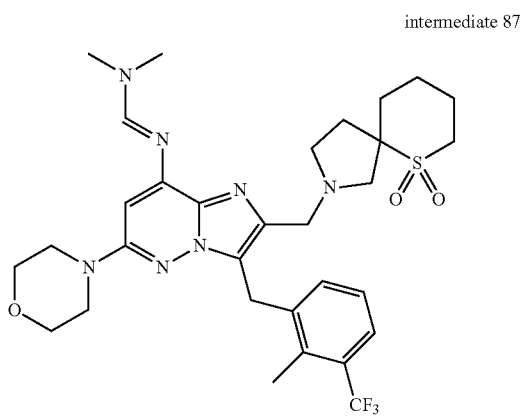
intermediate 87

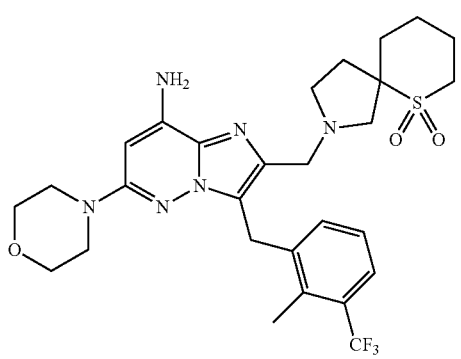
compound 33

A mixture of intermediate 87 and compound 33 was prepared according to an analogous procedure as described for the synthesis of intermediate 85, using intermediate 84 and 6-thia-2-azaspiro[4.5]decane 6,6-dioxide hydrochloride as starting materials. The mixture was used as such in the next reaction step.

Preparation of Intermediate 88 and Compound 34:

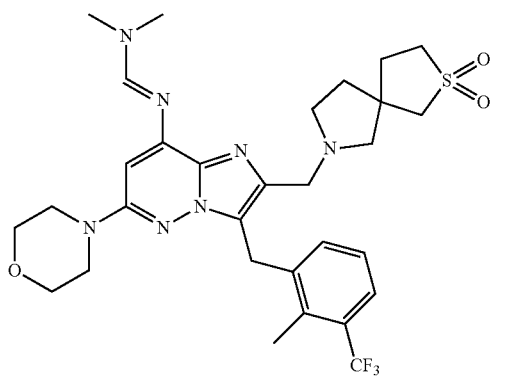
intermediate 88

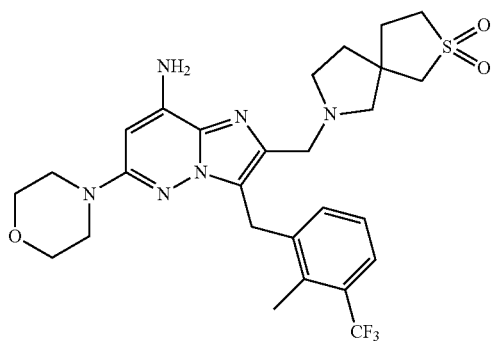
compound 34

A mixture of intermediate 88 and compound 34 was prepared according to an analogous procedure as described for the synthesis of intermediate 85, using intermediate 84 and 2-thia-7-azaspiro[4.4]nonane 2,2-dioxide hydrochloride as starting materials. The mixture was used as such in the next reaction step.

Example A24

Preparation of Intermediate 90:

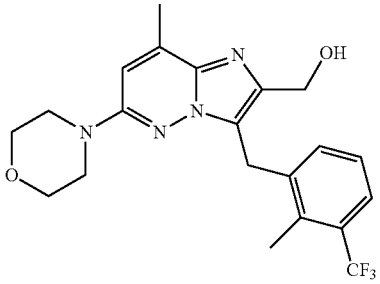 [SMILES: Cc1c(Cc2c(CO)nc3c(C)cc(N4CCOCC4)nn23)cccc1C(F)(F)F]

Tetrabutylammonium fluoride (2.3 mL; 2.3 mmol) was added dropwise to a solution of intermediate 7 (1.5 g; 2.3 mmol) in THF (23 mL). The reaction mixture was stirred overnight at room temperature. The reaction mixture was concentrated, taken up with MeOH and the precipitate was filtered and dried to give 0.63 g (51%) of intermediate 90. The filtrate was purified by chromatography over silica gel (irregular SiOH, 24 g; gradient from 99% DCM 1% $CH_3OH$ 0.1% $NH_4OH$ to 98% DCM 2% $CH_3OH$ 0.1% $NH_4OH$). The fractions containing the product were collected and evaporated to dryness yielding additional 0.54 g (43%) of intermediate 90.

Preparation of Intermediate 91:

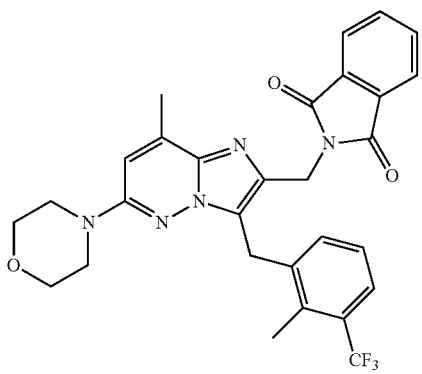 [SMILES: Cc1c(Cc2c(CN3C(=O)c4ccccc4C3=O)nc3c(C)cc(N4CCOCC4)nn23)cccc1C(F)(F)F]

Di-tert-butyl azodicarboxylate (0.454 g; 1.97 mmol) was added portionwise to a solution of intermediate 90 (0.7 g; 1.32 mmol), phtalimide (0.23 g; 1.58 mmol) and triphenylphosphine (0.52 g; 1.97 mmol) in THF (20 mL) at room temperature under nitrogen. The reaction mixture was stirred at room temperature overnight. The reaction mixture was diluted with DCM and washed with a 10% aqueous solution of $K_2CO_3$. The organic layer was dried over $MgSO_4$, filtered and evaporated. The residue was taken up with $Et_2O$, filtered and dried to afford 0.83 mg of intermediate 91.

Preparation of Intermediate 92:

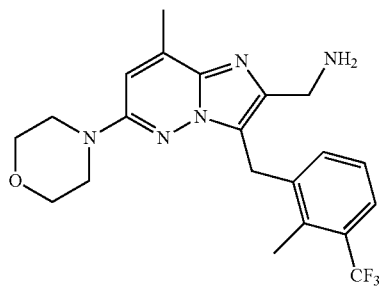 [SMILES: Cc1c(Cc2c(CN)nc3c(C)cc(N4CCOCC4)nn23)cccc1C(F)(F)F]

Hydrazine monohydrate (0.17 mL; 2.84 mmol) was added to a suspension of intermediate 91 (0.51 g; 0.78 mmol) in EtOH (11 mL) at room temperature. The reaction mixture was heated at 80° C. overnight. The mixture was cooled down to room temperature. Then, DCM was added and the mixture was stirred at room temperature for 10 minutes. The insoluble was filtered and washed with DCM. The filtrate was evaporated to give 0.25 g (61%) of intermediate 92.

Preparation of Intermediate 93:

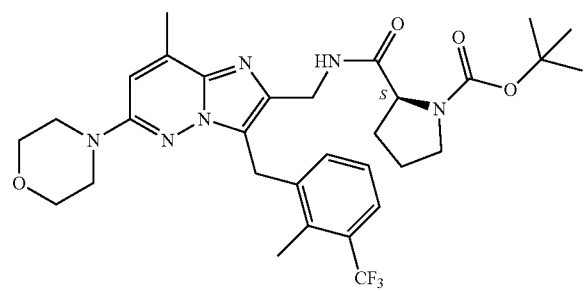

1-Hydroxybenzotriazole (114 mg; 0.85 mmol) and 1-(3-dimethylaminopropyl)-3-ethylcarbodiimide hydrochloride (162 mg; 0.85 mmol) were added to a solution of intermediate 92 (500 mg; 0.71 mmol), Boc-L-proline (152 mg; 0.71 mmol) and triethylamine (342 µL; 2.47 mmol) in DCM (3.38 mL) and THF (3.38 mL) at rt. The reaction mixture was stirred at room temperature overnight. A saturated solution of $NaHCO_3$ and DCM were added. The organic layer was separated, dried over $MgSO_4$ and the solvent was evaporated. The residue was purified by chromatography over silica gel (irregular bare silica 150 g, gradient from 0.1% $NH_4OH$ 9% DCM, 1% MeOH to 0.2% $NH_4OH$, 98% DCM, 2% MeOH). The pure fractions were collected and the solvent was evaporated to give 428 mg (73%; white foam) of intermediate 93.

Preparation of Intermediate 95:

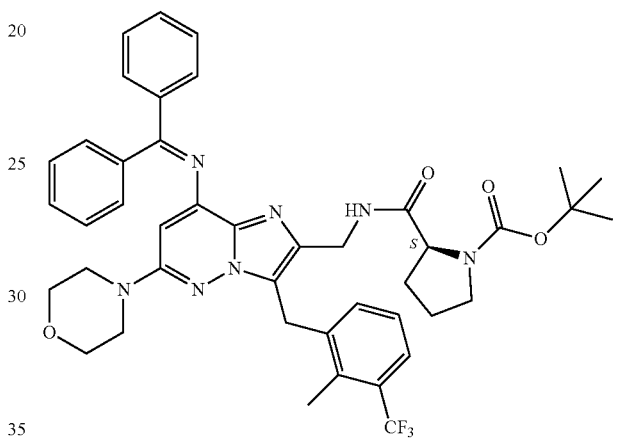

In a sealed tube, intermediate 93 (0.261 g; 0.36 mmol), benzophenone imine (90 µL; 0.54 mmol), $Cs_2CO_3$ (0.35 g; 1.08 mmol), racemic 2-2'-bis(diphenylphosphino)-1,1'-binaphthyl (22 mg; 0.04 mmol) and palladium(II) acetate (8 mg; 0.04 mmol) in 1,4-dioxane (5.5 mL) were heated at 100° C. overnight. The reaction mixture was combined with a test reaction performed on 50 mg of intermediate 93 and partitioned between water and DCM. The organic layer was separated, dried over $MgSO_4$, filtered and the solvent was evaporated. The residue was purified by silica gel chromatography (irregular SiOH, 40 g, gradient from 99% DCM 1% MeOH 0.1% $NH_4OH$ to 97% DCM 3% MeOH 0.3% $NH_4OH$). The fractions containing the product were mixed and the solvent was evaporated to afford 307 mg (92% combined yield) of intermediate 95.

Preparation of Intermediate 96:

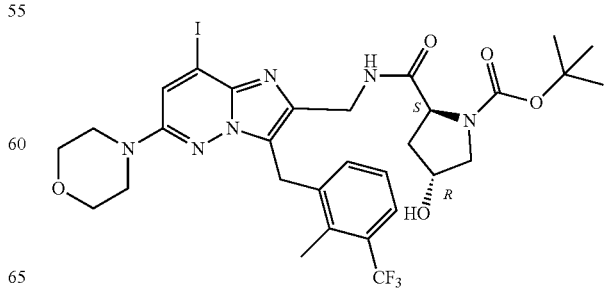

Intermediate 96 was prepared according to an analogous procedure as described for the synthesis of intermediate 93, using intermediate 92 and Boc-trans-4-hydroxy-L-proline as starting materials (64%).

Preparation of Intermediate 97:

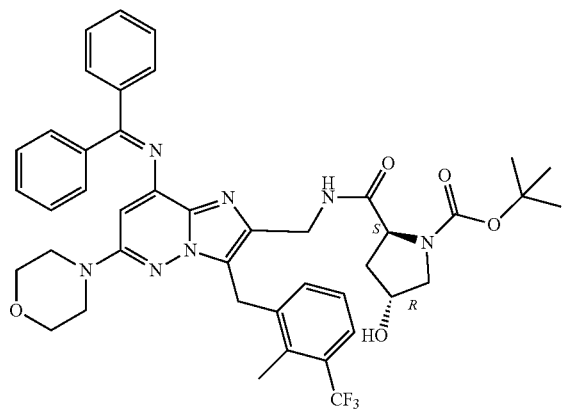

Intermediate 97 was prepared according to an analogous procedure as described for the synthesis of intermediate 95, using intermediate 96 as starting material (63%).

Preparation of Intermediate 98:

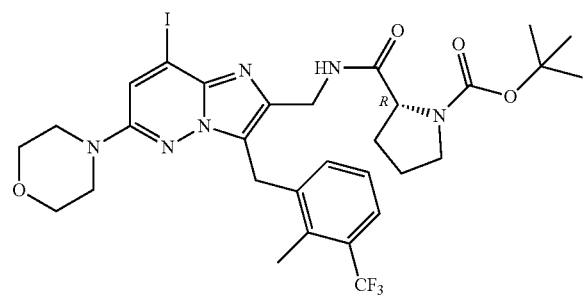

Intermediate 98 was prepared according to an analogous procedure as described for the synthesis of intermediate 93, using intermediate 92 and Boc-D-proline as starting materials (230 mg, 86%, yellow foam).

Preparation of Intermediate 99:

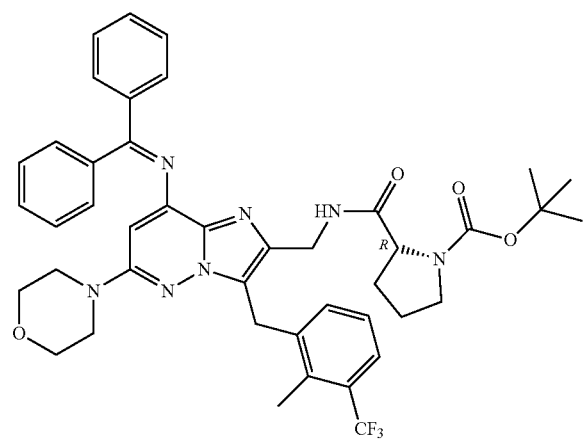

Intermediate 99 was prepared according to an analogous procedure as described for the synthesis of intermediate 95, using intermediate 98 as starting material (242 mg; 81%).

Preparation of Intermediate 100:

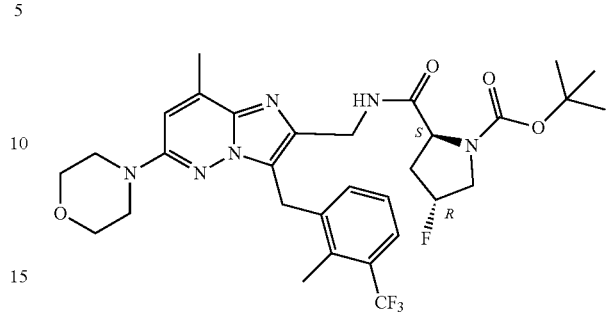

Intermediate 100 was prepared according to an analogous procedure as described for the synthesis of intermediate 93, using intermediate 92 and 4-fluoro-, 1-(1,1-dimethylethyl) ester (2S,4R)-1,2-Pyrrolidinedicarboxylic acid as starting material (550 mg, 85%, yellow foam).

Preparation of Intermediate 101:

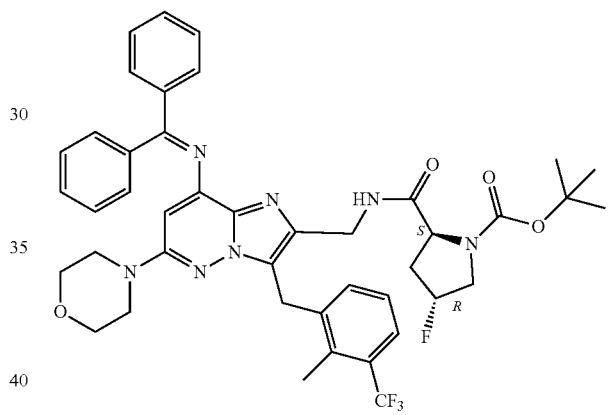

Intermediate 101 was prepared according to an analogous procedure as described for the synthesis of 95, using intermediate 100 and benzophenone imine as starting material (450 mg, 66%).

Preparation of Intermediate 102:

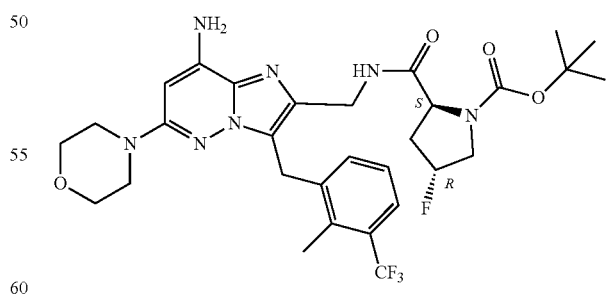

In a round bottom flask, intermediate 101 (0.45 g; 0.49 mmol) was diluted in THF (22 mL) and DCM (22 mL). Then, at room temperature, HCl (1M in water) (9.8 mL; 9.88 mmol) was added and the reaction mixture was stirred for 3 hours at 70° C. Additional HCl (1M in water) (9.8 mL; 9.88 mmol) was added and the reaction mixture was stirred at 70°

C. for 3 additional hours. Then, the reaction mixture was quenched with a saturated solution of Na₂CO₃. The aqueous layer was twice extracted with DCM. The organic layers were mixed, dried over MgSO₄ and the solvent was evaporated to afford 188 mg (52%) of intermediate 102. The product was used without purification in the next reaction step.

Preparation of Intermediate 103:

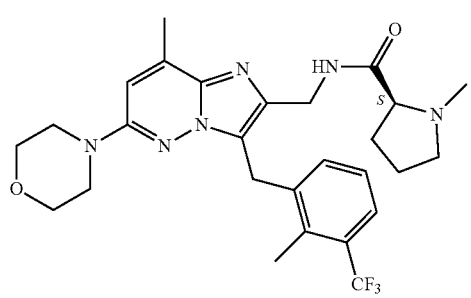

Intermediate 103 was prepared according to an analogous procedure as described for the synthesis of intermediate 93, using intermediate 92 and N-methyl-L-proline as starting materials (1.14 g, 45%, yellow solid), M.P.: 193° C., (Kofler).

Preparation of Intermediate 104:

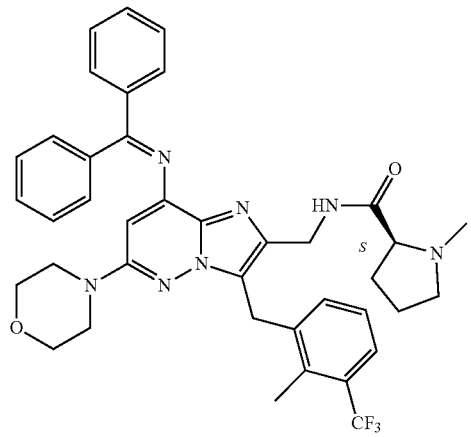

In a sealed tube, a mixture of intermediate 103 (1.14 g; 1.77 mmol), benzophenone imine (447 µL; 2.66 mmol), Cs₂CO₃ (1.73 g; 5.32 mmol), racemic-2,2'-Bis(diphenylphosphino)-1,1'-binaphtyl (111 mg; 0.18 mmol) and Palladium(II) acetate (40 mg; 0.18 mmol) in 1,4-dioxane (27 mL) was heated at 100° C. over the weekend. The reaction mixture was partitioned between a saturated aqueous solution of NaHCO₃ and EtOAc. The organic layer was separated, dried over MgSO₄, filtered and the solvent was evaporated. The residue (2.0 g, yellow oil) was purified by chromatography over silica gel (irregular SiOH; 120 g; gradient: from 99% DCM, 1% MeOH, 0.1% NH₄OH to 95% DCM, 5% MeOH, 0.5% NH₄OH). Everything was flushed. The compound was purified again by chromatography over silica gel (irregular SiOH, 120 g, gradient: from 100% DCM to 98% DCM, 2% MeOH). The pure fractions were collected and the solvent was evaporated to give 2 fractions of intermediate 104:

670 mg (38%; 70% of purity evaluated by LCMS, yellow oil)

420 mg (34%, yellow oil).

Example A25

Preparation of Intermediate 105:

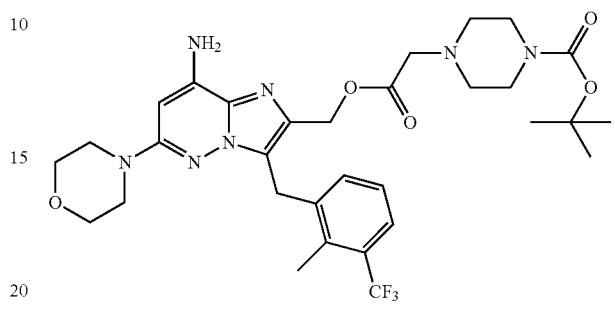

Under N₂ at room temperature, 4-dimethylaminopyridine (10 mg; 0.08 mmol), 1 [Bis(dimethylamino)methylene]-1H-1,2,3-triazolo[4,5-b]pyridinium 3-oxid hexafluorophosphate (1.35 g; 3.6 mmol) and diisopropylethylamine (1.3 mL; 7.1 mmol) were added to a solution of 4-Boc-1-piperazineacetic acid (0.35 g; 1.4 mmol) in DMF (18 mL). After 10 minutes, intermediate 81a (0.6 g; 1.4 mmol) was added and the solution was stirred at room temperature for 64 hours. The solution was poured out into cooled water and EtOAc was added. The organic layer was extracted, washed with water, dried with MgSO₄ and evaporated to dryness. The resulting residue was mixed with another crude coming from a reaction performed on 200 mg of intermediate 81a. A purification was then performed via silica gel chromatography (Stationary phase: irregular SiOH 15-40 µm, Mobile phase: 96% DCM, 4% MeOH, 0.1% NH₄OH). The fractions containing the product were mixed and the solvent was evaporated to afford 440 mg of intermediate 105 (36%).

Example A26

Preparation of Intermediate 107:

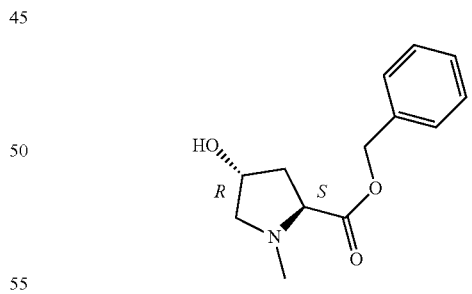

(2S,4R)-benzyl-4-hydroxypyrrolidine-2-carboxyatehydrochloride (2 g; 7.76 mmol) was dissolved in MeOH (31 mL) and, then formaldehyde (37% in water) (15.1 mL; 202 mmol) was added while stirring. The reaction mixture was heated at reflux for 30 min and allowed to cool to room temperature. Then, the reaction was cooled to 0° C. and sodium borohydride (1.02 g; 26.90 mmol) was added. The reaction mixture was stirred for 3 h, then evaporated to dryness under vaccum. The residue (1.5 g, colourless oil) was purified by chromatography over silica gel (irregular SiOH; 40 g; mobile phase: from 100% DCM to 1% NH₄OH, 10% MeOH, 90% DCM). The pure fractions were collected and the solvent was evaporated to give 192 mg (11%, colourless oil) of intermediate 107.

Preparation of Intermediate 108:

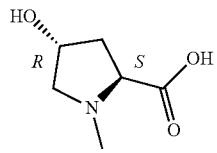

Intermediate 107 (0.19 g; 0.81 mmol) was dissolved in MeOH (3.9 mL) under $N_2$. Pd/C (10%) (8.6 mg; 0.008 mmol) was added. The reaction mixture was hydrogenated at room temperature for 2 h. The catalyst was filtered through a pad of Celite® which was washed with MeOH. The filtrate was evaporated to give 104 mg (89%) of intermediate 108.

Example A27

Preparation of Intermediate 109:

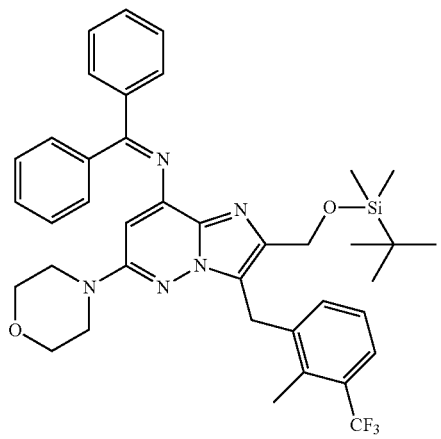 [SMILES: Cc1c(Cc2c(CO[Si](C)(C)C(C)(C)C)nc3c(N=C(c4ccccc4)c4ccccc4)cc(N4CCOCC4)nn23)cccc1C(F)(F)F]

The reaction was performed twice from respectively on (8 g; 12.37 mmol) and (10 g; 5.65 mmol) of intermediate 7:

In a sealed vessel with good stirring, $N_2$ was bubbled in a mixture of intermediate 7 (10 g; 15.47 mmol) and benzophenone imine (3.89 mL; 23.2 mmol) in 1,4-dioxane (81 mL). Then, $Cs_2CO_3$ (15.12 g; 46.4 mmol) was added and the reaction mixture was degassed again with $N_2$. Finally, rac-bis(diphenylphosphino)-1,1'-binaphtyl (481.5 mg; 0.77 mmol) and palladium(II) acetate (173.6 mg; 0.77 mmol) were added and the reaction mixture was heated at 100° C. for 18 h. The reaction mixtures coming from the 2 reactions were combined for the work-up and partitioned between water and EtOAc. The organic layer was decanted, washed with brine, dried over $MgSO_4$, filtered and evaporated to dryness. The residue (29.6 g) was purified by successive chromatography over silica gel (Irregular SiOH; 450 g; gradient: from 100% heptane to 80% heptane, 20% EtOAc). The pure fractions were collected and evaporated to dryness yielding 2 batches of intermediate 109 respectively 16.7 g (85%) and 3.6 g (18%). The 2 batches were directly used in the next reaction step without any further purification.

Preparation of Intermediate 110:

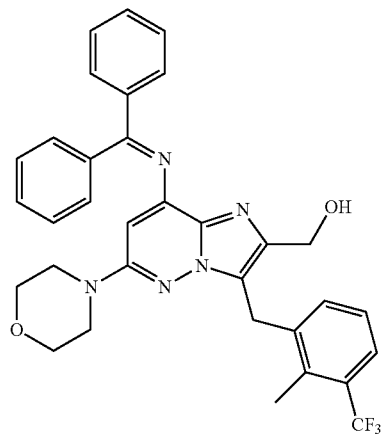 [SMILES: Cc1c(Cc2c(CO)nc3c(N=C(c4ccccc4)c4ccccc4)cc(N4CCOCC4)nn23)cccc1C(F)(F)F]

TBAF (1M in THF) (8.28 mL; 8.28 mmol) was added dropwise to a solution of intermediate 109 (5.8 g; 8.29 mmol) in THF (70 mL) at room temperature. The reaction mixture was stirred for 3 h at room temperature. The solution was poured into ice water, extracted with EtOAc and washed with brine. The organic layer was dried over $MgSO_4$, filtered and evaporated to dryness. The residue was crystallized from diisopropylethylether. The precipitate was filtered and dried under vacuum to yield 2.7 g (55%) of intermediate 110. The filtrate was purified by chromatography over silica gel (irregular SiOH; 80 g; gradient: from 100% DCM to 90% DCM, 10% MeOH, 0.1% $NH_4OH$). The pure fractions were collected and evaporated to dryness to give additional 0.4 g (8%) of intermediate 110.

Preparation of Intermediate 111:

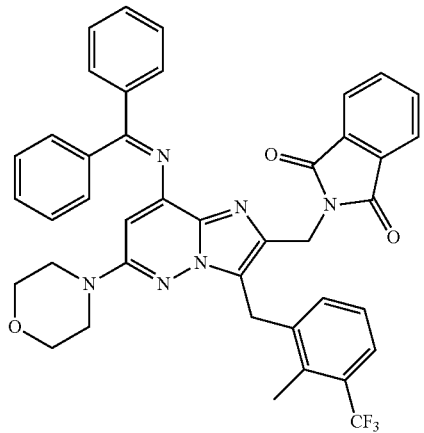 [SMILES: Cc1c(Cc2c(CN3C(=O)c4ccccc4C3=O)nc3c(N=C(c4ccccc4)c4ccccc4)cc(N4CCOCC4)nn23)cccc1C(F)(F)F]

Di-tert-butyl azodicarboxylate (337 mg; 1.46 mmol) was added portionwise to a solution of intermediate 111 (571 mg; 0.98 mmol), phtalimide (172 mg; 1.17 mmol), $PPh_3$ (384 mg; 1.463 mmol) in Me-THF (15 mL) at room temperature under $N_2$. The reaction mixture was stirred at room temperature for overnight, diluted with DCM and washed with 10% aqueous solution of $K_2CO_3$. The organic layer was decanted, dried over $MgSO_4$, filtered and evaporated to dryness. The residue was purified by chromatography over silica gel (irregular SiOH; 50 g; gradient: from 100% DCM to 95% DCM, 5% MeOH, 0.5% $NH_4OH$). The pure fractions were collected and evaporated to dryness yielding 800 mg (quant.) of intermediate 111. The product was used without purification in the next reaction step.

Preparation of Intermediate 113:

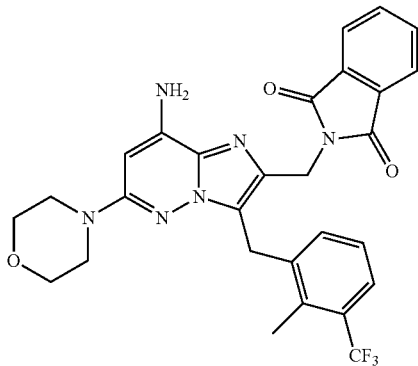 [SMILES: Cc1c(Cc2c(CN3C(=O)c4ccccc4C3=O)nc3c(N)cc(N4CCOCC4)nn23)cccc1C(F)(F)F]

In sealed tube, acetamidine hydrochloride (86 mg; 0.91 mmol) was added under $N_2$ to a mixture of copper(I) iodide (14 mg; 0.08 mmol), L-proline (17 mg; 0.15 mmol), intermediate 91 (0.5 g; 0.76 mmol) and $Cs_2CO_3$ (0.74 g; 2.27 mmol) in DMF (2.9 mL). The reaction mixture was stirred at 110° C. overnight. The mixture was concentrated, then solubilized in EtOAc and washed fifth times with brine. The organic layer was dried and evaporated. The residue (beige solid) was purified by chromatography over silica gel (SiOH; 30 μm; 24 g; mobile phase: from 99% DCM, 1% MeOH 0.1% $NH_4OH$ to 96% DCM, 4% MeOH 0.1% $NH_4OH$). The pure fractions were collected and the solvent was evaporated to give 76 mg (18%, white solid) of intermediate 113.

Alternative Pathway:

Di-tert-butyl azodicarboxylate (446 mg; 1.94 mmol) was added portionwise to a solution of intermediate 81a (371 mg; 0.88 mmol), phtalimide (155 mg; 1.06 mmol), $PPh_3$ (508 mg; 1.94 mmol) in DMF (12 mL) at room temperature under $N_2$. The reaction mixture was stirred at room temperature for 2 h. and combined with a batch coming from a reaction performed on 50 mg of intermediate 81a for the treatment. Water and EtOAc were added. The mixture was extracted with EtOAc (3×). The organic layer was washed with brine (2×), dried over $MgSO_4$, filtered and the solvent was evaporated. The residue (1.95 g, brown oil) was purified by chromatography over silica gel (irregular bare silica 150 g; mobile phase: 98% DCM, 2% MeOH, 0.1% $NH_4OH$). The pure fractions were collected and the solvent was evaporated to give 137 mg (25%, yellow foam) of intermediate 113.

Preparation of Intermediate 114:

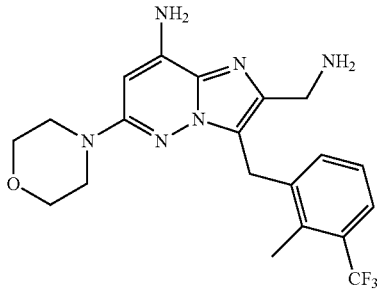

Hydrazine monohydrate (55 μL; 0.90 mmol) was added to a suspension of intermediate 113 (135 mg; 0.25 mmol) in EtOH (3.5 mL) at room temperature. The reaction mixture was heated at 80° C. overnight. The mixture was cooled down to room temperature. Then, DCM was added and the mixture was stirred for 10 min. The insoluble was filtered and washed with DCM/MeOH (90/10) (3 times). The filtrate was evaporated. The residue (93 mg, brown solid) was purified by chromatography over silica gel (Spherical bare silica 5 μm 150×30.0 mm; gradient: from 98% DCM, 2% MeOH, 0.2% $NH_4OH$ to 87% DCM, 13% MeOH, 1.3% $NH_4OH$). The pure fractions were collected and the solvent was evaporated to give 23 mg (22%) of intermediate 114. M.P.: 191° C. (Kofler).

Alternative pathway: Hydrazine monohydrate (0.93 mL; 9.75 mmol) was added to a suspension of intermediate 111 (697 mg; 0.98 mmol) in EtOH (10 mL) at room temperature. The reaction mixture was heated at 80° C. overnight, cooled down to room temperature and diluted with DCM. The organic layer was washed with water, dried over $MgSO_4$, filtered and evaporated to dryness. The residue was taken up with acetonitrile and the precipitate was filtered, washed with diethylether and dried to give 210 mg (51%) of intermediate 114.

Example A28

Preparation of Intermediate 115:

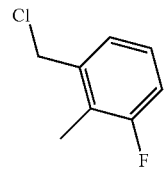

Lithium chloride (1.25 g; 29.55 mmol) was added to a solution of 3-fluoro-2-methylbenzyl bromide (1 g; 4.93 mmol) in DMF (5 mL) at room temperature. The reaction mixture was stirred at room temperature for 24 h, poured into water and extracted with $Et_2O$. The organic layer was decanted, washed with water and brine, dried over $MgSO_4$, filtered and evaporated to dryness to give 762 mg (97%) of intermediate 115.

Preparation of Intermediate 116:

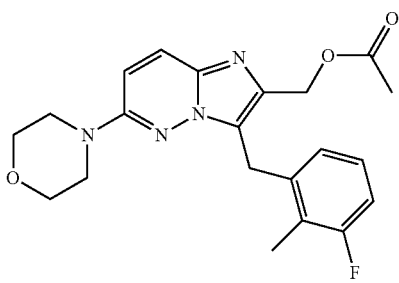 [SMILES: CC(=O)OCc1nc2ccc(N3CCOCC3)nn2c1Cc1cccc(F)c1C]

In a sealed tube, a mixture of intermediate 3 (300 mg; 1.09 mmol), intermediate 115 (206 mg; 1.30 mmol) and $K_2CO_3$ (225 mg; 1.63 mmol) in 1,4-dioxane (4 mL) was bubbled with $N_2$ for 15 min. Then, $PPh_3$ (57 mg; 0.22 mmol) and palladium(II) acetate (Aldrich, 98%) (27 mg; 0.12 mmol) were added. The reaction mixture was stirred at 100° C.

overnight, cooled down to room temperature, poured into water and extracted with DCM. The organic layer was decanted, dried over MgSO₄, filtered and evaporated to give 543 mg of mixture of intermediate 116 and intermediate 117. The mixture of two products was used without purification in the next reaction step.

Preparation of Intermediate 117:

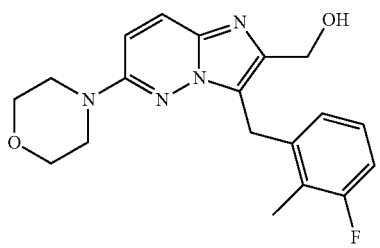 [SMILES: Cc1c(F)cccc1Cc1c(CO)nc2ccc(N3CCOCC3)nn12]

Lithium hydroxide monohydrate (228 mg; 5.43 mmol) (227 mg; 5.43 mmol) was added to a mixture of intermediate 116 (mixed with 50% of intermediate 117) (432 mg; 1.09 mmol) in water (1.3 mL) and MeOH (4 mL) at room temperature. The reaction mixture was stirred at room temperature all over the week end. Water was added to the mixture. The precipitate was filtered, washed with water (twice) and dissolved in DCM/MeOH. The organic layer was washed with water, dried over MgSO₄, filtered and evaporated to dryness. The residue was purified by chromatography over silica gel (irregular SiOH; 24 g; gradient: from 0.3% NH₄OH, 3% MeOH, 97% DCM to 0.6% NH₄OH, 6% MeOH, 94% DCM). The pure fractions were collected and evaporated to dryness. The residue (320 mg; 83%) was taken up with diethylether. The precipitate was filtered and dried to give 305 mg (79%) of intermediate 117. M.P.: 184° C. (Kofler).

Preparation of Intermediate 118:

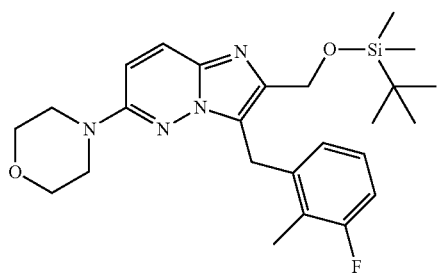 [SMILES: Cc1c(F)cccc1Cc1c(CO[Si](C)(C)C(C)(C)C)nc2ccc(N3CCOCC3)nn12]

Ter-butyldimethylsilyl chloride (4.4 g; 29.18 mmol) was added to a mixture of intermediate 117 (5.2 g; 14.59 mmol), imidazole (4 g; 58.36 mmol) in DMF (100 mL) at room temperature and the reaction mixture was stirred for 2 h at this temperature. The reaction mixture was poured into H₂O and extracted with EtOAc/diethylether. The organic layer was washed with H₂O, dried over MgSO₄, filtered and evaporated to dryness. The residue was purified by chromatography over silica gel (gradient: from 100% DCM to 0.3% NH₄OH, 3% MeOH, 97% DCM). The pure fractions were collected and evaporated to dryness. The residue (7 g) was purified by chromatography over silica gel (gradient: from 100% DCM to 7% MeOH, 93% DCM). The pure fractions were collected and evaporated to give 5.55 g (81%) of intermediate 118.

Preparation of Intermediate 119:

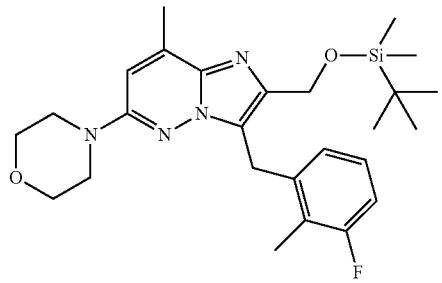 [SMILES: Cc1c(F)cccc1Cc1c(CO[Si](C)(C)C(C)(C)C)nc2c(C)cc(N3CCOCC3)nn12]

n-butyllithium (18.5 mL; 29.67 mmol) was added dropwise to a solution of diisopropyl amine (4 mL; 28.52 mmol) in Me-THF (54 ml) at −78° C. under N₂. The reaction mixture was stirred for 15 min at −78° C. Then, a solution of intermediate 118 (5.37 g; 11.41 mmol) in Me-THF (18 mL) was added dropwise (15 min) and the reaction mixture was stirred at this temperature for 30 min. A solution of iodine (3.18 g; 12.55 mmol) in Me-THF (18 mL) was added dropwise at −70° C. (15 min). The reaction mixture was stirred at this temperature for 30 min and poured onto a mixture of a 10% aqueous solution of NH₄Cl. The reaction mixture was diluted with EtOAc. Then, the organic layer was decanted, washed with a saturated solution of sodium thiosulfate, water then brine, dried over MgSO₄, filtered and evaporated to dryness. The residue was purified by chromatography over silica gel (irregular SiOH; 80 g; gradient: from 15% EtOAc, 85% heptane to 40% EtOAc, 60% heptane). The pure fractions were collected and evaporated to give 2.46 g (36%) of intermediate 119.

Preparation of Intermediate 120:

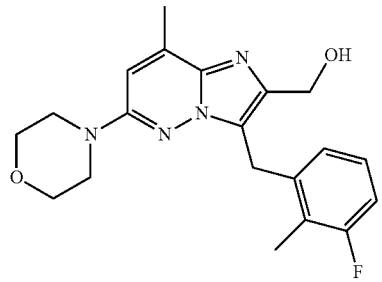 [SMILES: Cc1c(F)cccc1Cc1c(CO)nc2c(C)cc(N3CCOCC3)nn12]

Intermediate 120 was prepared according to an analogous procedure as described for the synthesis of intermediate 110, using intermediate 119 as starting material (1.27 g, 64%), The reaction was performed in Me-THF.

Preparation of Intermediate 121:

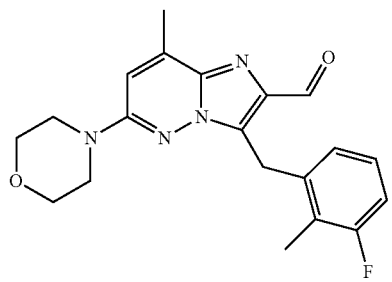 [SMILES: Cc1c(F)cccc1Cc1c(C=O)nc2c(C)cc(N3CCOCC3)nn12]

Intermediate 121 was prepared according to an analogous procedure as described for the synthesis of intermediate 84, using intermediate 120 as starting material (1.15 g, quant.). The reaction mixture was performed in 1,4-dioxane.

Preparation of Intermediate 122:

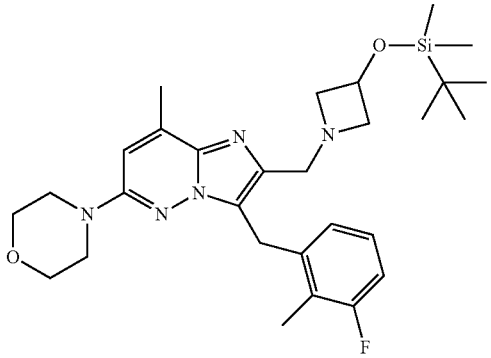 [SMILES: Cc1c(F)cccc1Cc1c(CN2CC(O[Si](C)(C)C(C)(C)C)C2)nc2c(C)cc(N3CCOCC3)nn12]

A mixture of intermediate 121 (300 mg; 0.63 mmol), 3-[[(1,1-dimethylethyl)dimethylsilyl]oxy]-azetidine (234 mg; 1.25 mmol) in MeOH (6 mL) was stirred at room temperature overnight. Sodium triacetoxyborohydride (397 mg; 1.87 mmol) was added and stirred at room temperature for 3 h. The reaction mixture was poured into water, basified with K$_2$CO$_3$ solid and extracted with EtOAc (3×). The organic layer was washed with brine, dried over MgSO$_4$, filtered and the solvent was evaporated to dryness. The residue was purified by chromatography over silica gel (irregular SiOH, 24 g; mobile phase: gradient from 1% MeOH, 30% EtOAc, 70% heptane to 1% MeOH, 60% EtOAc, 40% heptane). The pure fractions were collected and evaporated to give 263 mg (65%) of intermediate 122.

Preparation of Intermediate 123:

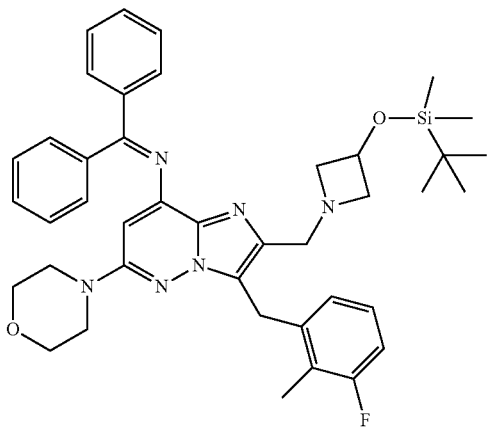 [SMILES: Cc1c(F)cccc1Cc1c(CN2CC(O[Si](C)(C)C(C)(C)C)C2)nc2c(N=C(c3ccccc3)c3ccccc3)cc(N3CCOCC3)nn12]

Intermediate 123 was prepared according to an analogous procedure as described for the synthesis of intermediate 95, using 122 and benzophenone imine as starting materials (231 mg, 81%).

Preparation of Intermediate 124:

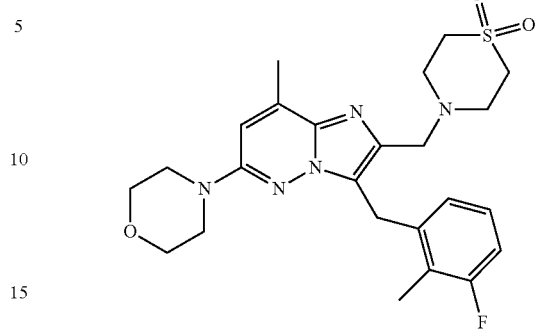

Intermediate 124 was prepared according to an analogous procedure as described for the synthesis of intermediate 122, using intermediate 121 and 1,1-dioxide thiomorpholine as starting material (364 mg, 87%).

Preparation of Intermediate 125:

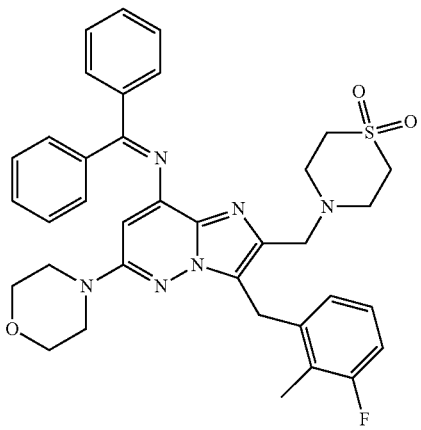 [SMILES: Cc1c(F)cccc1Cc1c(CN2CCS(=O)(=O)CC2)nc2c(N=C(c3ccccc3)c3ccccc3)cc(N3CCOCC3)nn12]

Intermediate 125 was prepared according to an analogous procedure as described for the synthesis of intermediate 95, using 124 and benzophenone imine as starting material (375 mg, 95%).

Preparation of Intermediate 126:

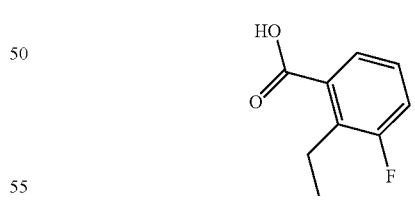

N-butyllithium (188.4 mL; 471.05 mmol) was added to a solution of 2,2,6,6-tetramethylpiperidine (79.5 mL; 471.05 mmol) in THF (600 mL) at −20° C. 3-fluorobenzoic acid (30 g; 214.11 mmol) in THF (150 mL) was added dropwise at −50° C. and the mixture was stirred for 4 h at −50° C. Then, iodoethane (68.8 mL; 856.46 mmol) was added at −50° C. The reaction mixture was warmed to room temperature and stirred overnight. Water (300 mL) was added. The aqueous layers were washed with MTBE (400 mL) and acidified with a 4M aqueous solution of HCl to pH 2. The mixture was separated and the aqueous layer was extracted with MTBE (2×400 mL). The combined organic layers were washed with brine and dried over MgSO₄. The solvent was removed under vacuum. The residue was purified by flash column chromatography over silica gel (eluent: from 100% petroleum ether from to 80% petroleum ether, 20% EtOAc). The pure fractions were collected and the solvent was evaporated to give 19 g (53%) of intermediate 126.

Preparation of Intermediate 127:

Intermediate 126 (19.62 g; 116.67 mmol) was dissolved in THF (200 mL). Borane tetrahydrofuran complex (1M in THF) (233.3 mL; 233.34 mmol) was added dropwise at 0° C. The reaction mixture was stirred overnight at 50° C. The mixture was quenched with a saturated aqueous solution of NaHCO₃ (300 mL) and extracted with EtOAc (3×400 mL). The mixture was washed with brine and dried over Na₂SO₄. The solvent was evaporated under vacuum to give 17.9 g (100%) of intermediate 127.

Preparation of Intermediate 128:

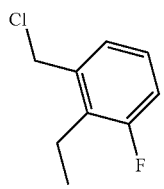

Thionyle chloride (12.6 mL, 174.15 mmol) was added to a solution of intermediate 127 (17.9 g; 116.10 mmol) in DCM (335 mL) at 0° C. The reaction mixture was warmed to room temperature and stirred overnight. The solvent was evaporated under vacuum. The residue was purified by chromatography over silica gel (Max-RP; 250*50 min*10 μm; eluent: ACN/H₂O from 40% to 80%). The pure fractions were collected and the solvent was evaporated under vacuum. The residue was freeze-dried to give 6.7 g (32%) of intermediate 128.

Preparation of Intermediate 129:

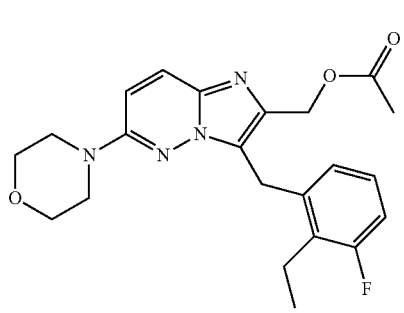 [SMILES: CCc1c(F)cccc1Cc1c(COC(C)=O)nc2ccc(N3CCOCC3)nn12]

Intermediate 129 was prepared according to an analogous procedure as described for the synthesis of intermediate 116, using intermediate 3 and intermediate 128 as starting materials (10.9 g). The product was used without purification for the next step.

Preparation of Intermediate 130:

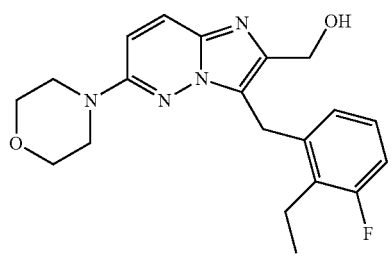 [SMILES: CCc1c(F)cccc1Cc1c(CO)nc2ccc(N3CCOCC3)nn12]

Intermediate 130 was prepared according to an analogous procedure as described for the synthesis of 117, using intermediate 129 as starting material (6.04 g. 90%). M.P.: 170° C., (Kofler).

Preparation of Intermediate 131:

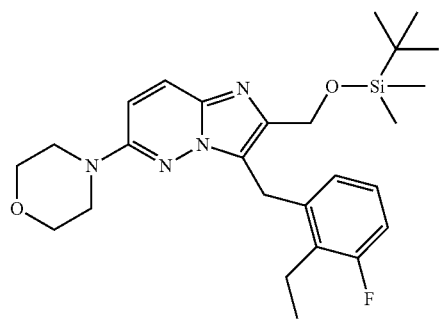 [SMILES: CCc1c(F)cccc1Cc1c(CO[Si](C)(C)C(C)(C)C)nc2ccc(N3CCOCC3)nn12]

Intermediate 131 was prepared according to an analogous procedure as described for the synthesis of intermediate 118, using intermediate 130 as starting material (6.6 g, 86%).

Preparation of Intermediate 132:

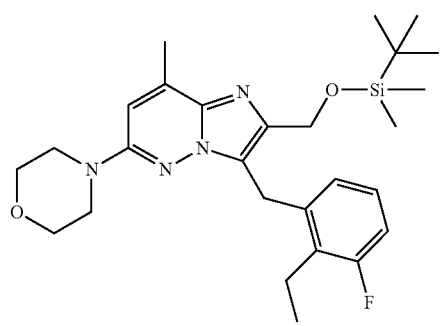 [SMILES: CCc1c(F)cccc1Cc1c(CO[Si](C)(C)C(C)(C)C)nc2c(C)cc(N3CCOCC3)nn12]

Intermediate 132 was prepared according to an analogous procedure as described for the synthesis of intermediate 119, using intermediate 131 as starting material (4.1 g, 51%).

Preparation of Intermediate 133:

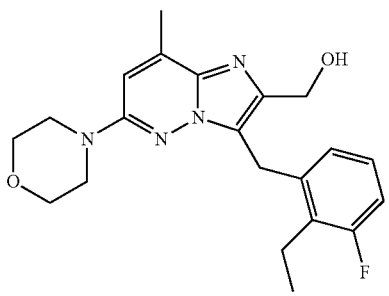 [SMILES: CCc1c(F)cccc1Cc1c(CO)nc2c(C)cc(N3CCOCC3)nn12]

Intermediate 133 was prepared according to an analogous procedure as described for the synthesis of intermediate 110, using intermediate 132 as starting material (2.39 g, 79%, M.P.: 198° C. (K)). The reaction mixture was performed in Me-THF.

Preparation of Intermediate 134:

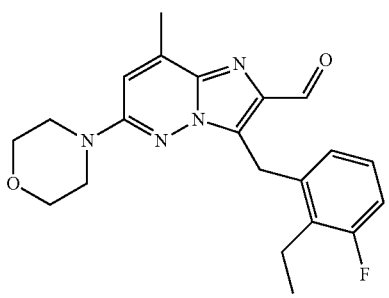 [SMILES: CCc1c(F)cccc1Cc1c(C=O)nc2c(C)cc(N3CCOCC3)nn12]

Intermediate 134 was prepared according to an analogous procedure as described for the synthesis of intermediate 84, using intermediate 133 as starting material (1.97 g, 88%, M.P.: 151° C. (K)). The reaction mixture was performed in 1,4-dioxane.

Preparation of Intermediate 135:

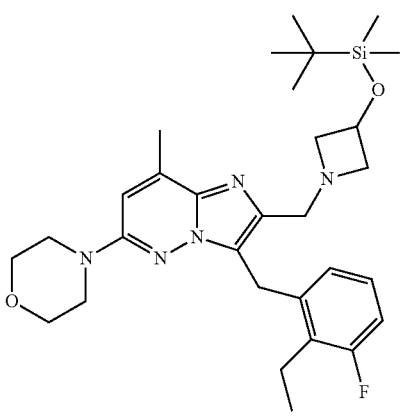 [SMILES: CCc1c(F)cccc1Cc1c(CN2CC(O[Si](C)(C)C(C)(C)C)C2)nc2c(C)cc(N3CCOCC3)nn12]

Intermediate 135 was prepared according to an analogous procedure as described for the synthesis of intermediate 122, using intermediate 134 and 3-[[(1,1-dimethylethyl)dimethylsilyl]oxy]-azetidine as starting materials (526 mg, 79%).

Preparation of Intermediate 136:

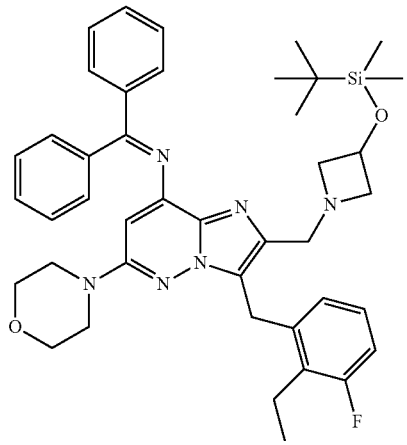 [SMILES: CCc1c(F)cccc1Cc1c(CN2CC(O[Si](C)(C)C(C)(C)C)C2)nc2c(N=C(c3ccccc3)c3ccccc3)cc(N3CCOCC3)nn12]

Intermediate 136 was prepared according to an analogous procedure as described for the synthesis of intermediate 95, using intermediate 135 and benzophenone imine as starting materials (438 mg, 77%).

Preparation of Intermediate 137:

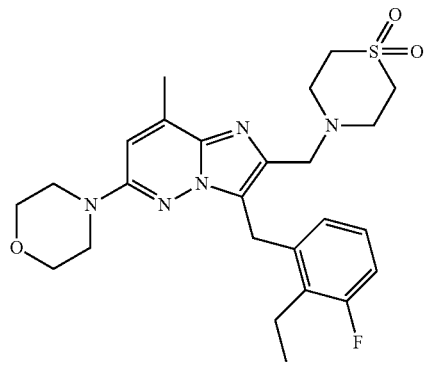 [SMILES: CCc1c(F)cccc1Cc1c(CN2CCS(=O)(=O)CC2)nc2c(C)cc(N3CCOCC3)nn12]

Intermediate 137 was prepared according to an analogous procedure as described for the synthesis of intermediate 122, using intermediate 134 and thiomorpholine 1,1-dioxide as starting materials (600 mg, 99%).

Preparation of Intermediate 138:

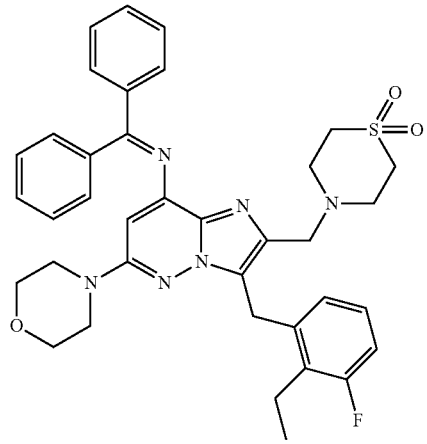 [SMILES: CCc1c(F)cccc1Cc1c(CN2CCS(=O)(=O)CC2)nc2c(N=C(c3ccccc3)c3ccccc3)cc(N3CCOCC3)nn12]

Intermediate 138 was prepared according to an analogous procedure as described for the synthesis of intermediate 95, using intermediate 137 and benzophenone imine as starting material (358 mg, 55%).

B. Preparation of the Final Compounds

Example B1

Preparation of Compound 1:

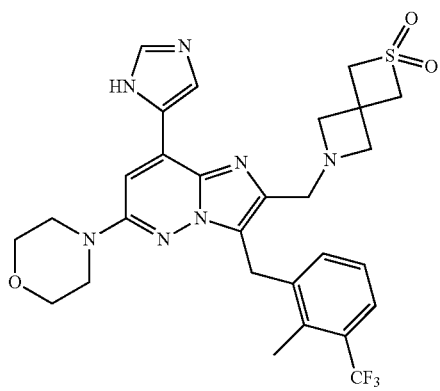 [SMILES: Cc1c(Cc2c(CN3CC4(C3)CS(=O)(=O)C4)nc3c(-c4cnc[nH]4)cc(N4CCOCC4)nn23)cccc1C(F)(F)F]

Trifluoroacetic acid (0.206 mL; 2.69 mmol) was added dropwise at 5° C. to a suspension of intermediate 14 (0.106 g; 0.14 mmol) in dioxane (2.3 mL). The reaction mixture was stirred at 70° C. overnight. Trifluoroacetic acid (0.206 mL; 2.69 mmol) was added at room temperature and the reaction mixture was stirred at 70° C. overnight. The reaction mixture was diluted with ice-water, a 10% aqueous solution of $K_2CO_3$ and DCM were added. The organic layer was dried over $MgSO_4$, filtered and evaporated. The residue (0.46 g) was purified by chromatography over silica gel (Irregular SiOH, 15-40 µm, gradient from 97% DCM 3% $CH_3OH$ 0.3% $NH_4OH$. to 85% DCM 15% $CH_3OH$ 1.5% $NH_4OH$). The fractions containing the product were collected, evaporated to dryness and was recrystallized with ACN. The precipitate was filtered and dried to give 0.024 g (15%) of compound 1, M.P.: 217° C., (Kofler).

Example B2

Preparation of Compound 2:

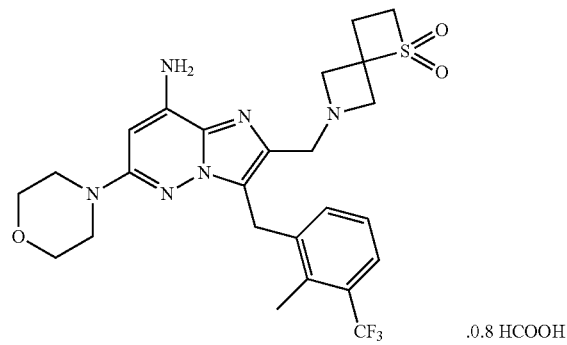 [SMILES: Cc1c(Cc2c(CN3CC4(CCS4(=O)=O)C3)nc3c(N)cc(N4CCOCC4)nn23)cccc1C(F)(F)F]

Under nitrogen, acetamidine hydrochloride (0.047 g; 0.50 mmol) was added to a mixture of intermediate 16 (0.27 g; 0.42 mmol). L-proline (0.010 g; 0.083 mmol), cesium carbonate (0.41 g; 1.25 mmol) and copper iodide (0.008 g; 0.042 mmol) in DMF (1.6 mL). The reaction mixture was heated at 110° C. overnight in a sealed tube. The mixture was concentrated and solubilized in EtOAc. The residue was washed with brine. The organic layer was separated, dried over $MgSO_4$, filtered and evaporated to dryness. The residue (0.31 g) was purified by chromatography over silica gel (Irregular SiOH, 15-40 µm, 12 g, gradient from 99% DCM 1% $CH_3OH$ 0.1% $NH_4OH$. to 98% DCM 2% $CH_3OH$ 0.1% $NH_4OH$). The fractions containing the product were collected and evaporated to dryness. The resulting mixture (0.1 g) was purified by reverse phase Chromatography (C18 5 µm 30*150 mm, Mobile phase: Gradient from 75% $HCOONH_4$ 0.5% PH=4.5, 25% ACN to 35% $HCOONH_4$ 0.5% PH=4.5, 65% ACN). The fractions containing the product were collected and evaporated. The resulting residue was taken up with DCM/MeOH and concentrated to afford 0.049 g of compound 2 (0.8 HCOOH; formate). M.P.: 180° C., (Kofler).

Preparation of Compound 3:

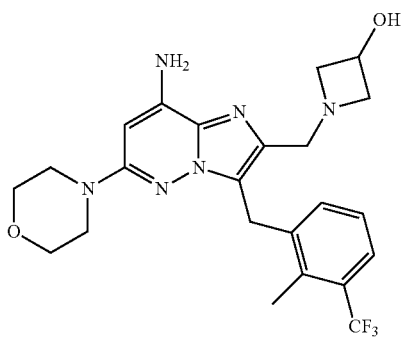 [SMILES: Cc1c(Cc2c(CN3CC(O)C3)nc3c(N)cc(N4CCOCC4)nn23)cccc1C(F)(F)F]

Compound 3 was prepared according to an analogous procedure as described for the synthesis of compound 2, using intermediate 17 as starting material (9%).

Preparation of Compound 4:

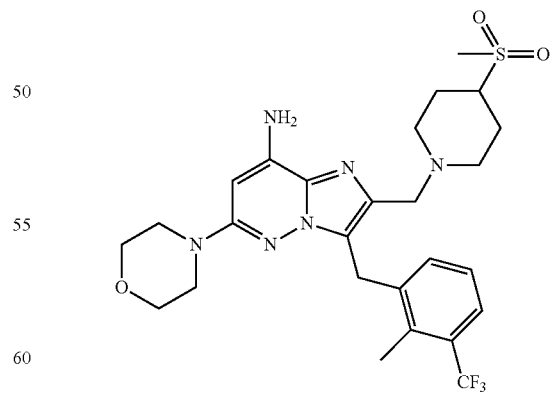

Compound 4 was prepared according to an analogous procedure as described for the synthesis of compound 2, using intermediate 18 as starting material (31%). M.P.: 188° C. (Kofler).

Preparation of Compound 5:

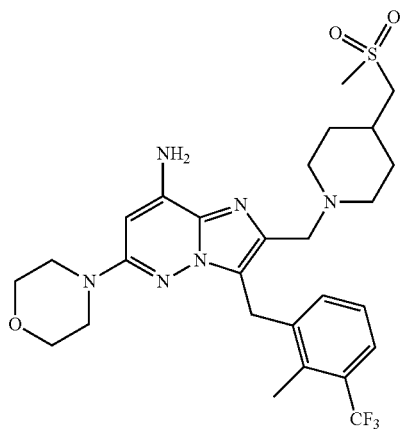 [SMILES: Cc1c(Cc2c(CN3CCC(CS(C)(=O)=O)CC3)nc3c(N)cc(N4CCOCC4)nn23)cccc1C(F)(F)F]

Compound 5 was prepared according to an analogous procedure as described for the synthesis of compound 2, using intermediate 19 as starting material (15%).

Preparation of Compound 6:

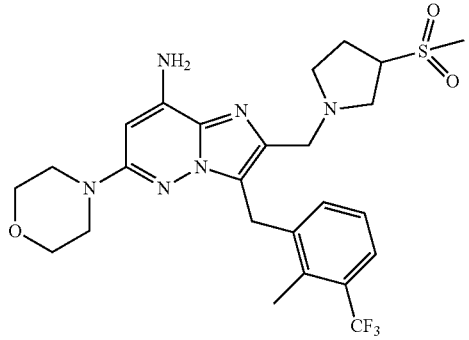 [SMILES: Cc1c(Cc2c(CN3CCC(S(C)(=O)=O)C3)nc3c(N)cc(N4CCOCC4)nn23)cccc1C(F)(F)F]

Compound 6 was prepared according to an analogous procedure as described for the synthesis of compound 2, using intermediate 20 as starting material (14%). M.P.: 159° C. (Kofler).

Preparation of Compound 7:

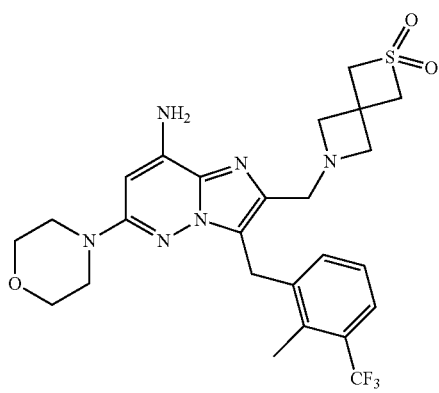 [SMILES: Cc1c(Cc2c(CN3CC4(C3)CS(=O)(=O)C4)nc3c(N)cc(N4CCOCC4)nn23)cccc1C(F)(F)F]

Compound 7 was prepared according to an analogous procedure as described for the synthesis of compound 2, using intermediate 21 as starting material (42%). M.P.: gum between 110-113° C. (Kofler).

Preparation of Compound 8:

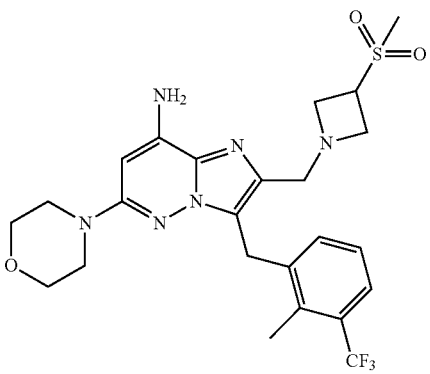 [SMILES: Cc1c(Cc2c(CN3CC(S(C)(=O)=O)C3)nc3c(N)cc(N4CCOCC4)nn23)cccc1C(F)(F)F]

Compound 8 was prepared according to an analogous procedure as described for the synthesis of compound 2, using intermediate 22 as starting material (30%). M.P.: 210° C. (Kofler).

Preparation of Compound 9:

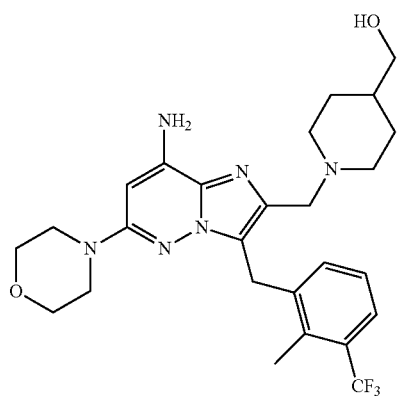 [SMILES: Cc1c(Cc2c(CN3CCC(CO)CC3)nc3c(N)cc(N4CCOCC4)nn23)cccc1C(F)(F)F]

Compound 9 was prepared according to an analogous procedure as described for the synthesis of compound 2, using intermediate 23 as starting material (21%). M. P.: 215° C. (Kofler).

Preparation of Compound 10:

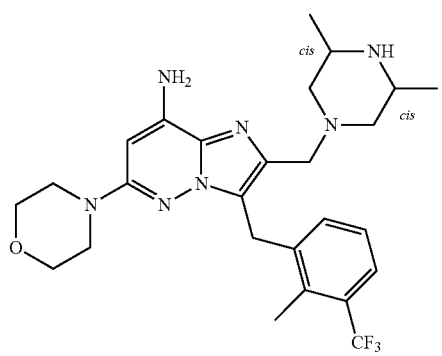 [SMILES: Cc1c(Cc2c(CN3CC(C)NC(C)C3)nc3c(N)cc(N4CCOCC4)nn23)cccc1C(F)(F)F]

Compound 10 was prepared according to an analogous procedure as described for the synthesis of compound 2, using intermediate 24 as starting material (38%). M.P.: gum between 92-97° C. (Kofler).

Preparation of Compound 11:

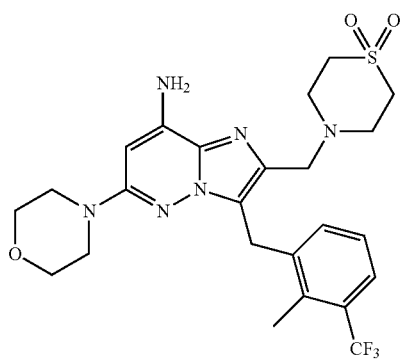 [SMILES: Cc1c(Cc2c(CN3CCS(=O)(=O)CC3)nc3c(N)cc(N4CCOCC4)nn23)cccc1C(F)(F)F]

Compound 11 was prepared according to an analogous procedure as described for the synthesis of compound 2, using intermediate 25 and thiomorpholine-1,1-dioxide as starting materials (17%), M.P.: 214° C. (Kofler).

Preparation of Compound 30:

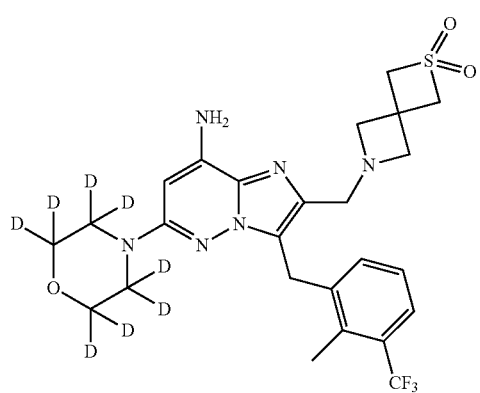 [SMILES: [2H]C1([2H])OC([2H])([2H])C([2H])([2H])N(c2cc(N)c3nc(CN4CC5(C4)CS(=O)(=O)C5)c(Cc4cccc(C(F)(F)F)c4C)n3n2)C1([2H])[2H]]

Compound 30 was prepared according to an analogous procedure as described for the synthesis of compound 2, using intermediate 80 as starting material. The product was solubilized in ACN (2 mL), water (8 mL) was added to the solution and the product was freeze-dried to afford 20 mg (25%, white fluffy solid) of compound 30. M.P: 207° C. (DSC).

Example B3

Preparation of Compound 12:

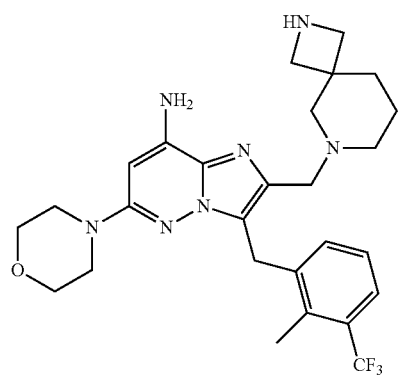 [SMILES: Cc1c(Cc2c(CN3CCCC4(CNC4)C3)nc3c(N)cc(N4CCOCC4)nn23)cccc1C(F)(F)F]

Trifluoroacetic acid (2.3 mL, 30 mmol) was added dropwise to a solution of intermediate 31 (0.26 g, 0.41 mmol) in DCM (5.0 mL) at 0° C. The mixture was slowly warmed from 0° C. to room temperature and stirred overnight at room temperature. The solvent was evaporated. The residue was purified by chromatography over silica gel (Irregular SiOH, 15-40 μm, 12 g, gradient from 96% DCM 4% CH$_3$OH 1% NH$_4$OH. to 92% DCM 8% CH$_3$OH 1% NH$_4$OH). The fractions containing the product were collected and evaporated to dryness to afford 0.137 g (63%) of compound 12. M.P.: gum at 122° C. (Kofler).

Preparation of Compound 13:

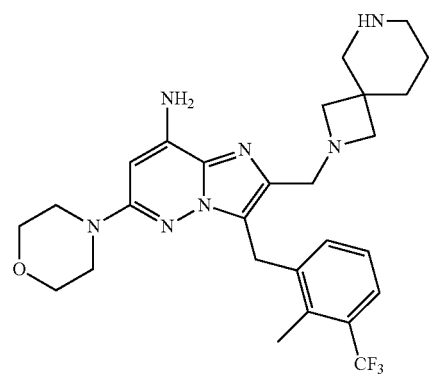 [SMILES: Cc1c(Cc2c(CN3CC4(CCCNC4)C3)nc3c(N)cc(N4CCOCC4)nn23)cccc1C(F)(F)F]

Compound 13 was prepared according to an analogous procedure as described for the synthesis of compound 12, using intermediate 32 as starting material (63%). M.P.: gum between 87-90° C. (Kofler).

Preparation of Compound 14:

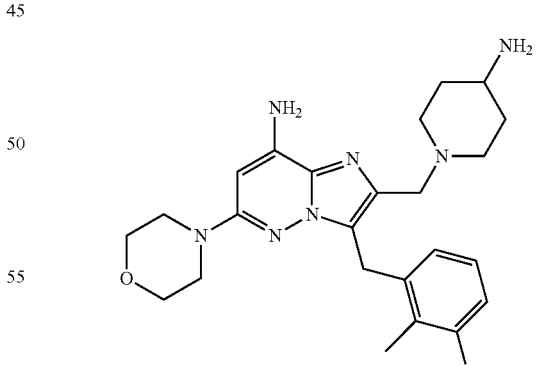

Compound 14 was prepared according to an analogous procedure as described for the synthesis of compound 12, using intermediate 33 as starting material (61%). M.P.: gum between 96-104° C. (Kofler).

Example B4

Preparation of Compound 15:

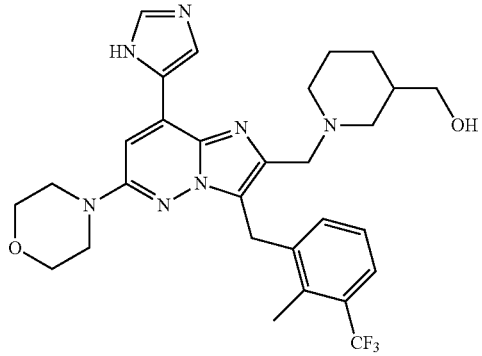 [SMILES: Cc1c(Cc2c(CN3CCCC(CO)C3)nc3c(-c4cnc[nH]4)cc(N4CCOCC4)nn23)cccc1C(F)(F)F]

Intermediate 10 (0.204 g; 0.26 mmol) was dissolved in dioxane (4.4 mL) and an aqueous solution of HCl 6N (1.7 mL) was added. The reaction mixture was heated at 100° C. for 2 hours. The reaction mixture was cooled to room temperature, diluted with EtOAc and basified with a 10% aqueous solution of $K_2CO_3$. The organic layer was separated, washed with brine, dried over $MgSO_4$, filtered and evaporated to dryness. The residue (0.198 g) was purified by chromatography over silica gel (Irregular SiOH, 15-40 µm, 12 g, gradient from 95% DCM 5% $CH_3OH$ 0.5% $NH_4OH$ to 90% DCM 10% $CH_3OH$ 0.1% $NH_4OH$). The fractions containing the product were collected, evaporated to dryness. The resulting residue was recrystallized from $Et_2O$/$CH_3CN$. The precipitate was filtered and dried to afford 0.086 g (59%) of compound 15. M.P.: gum at 160° C. (Kofler).

Preparation of Compound 16:

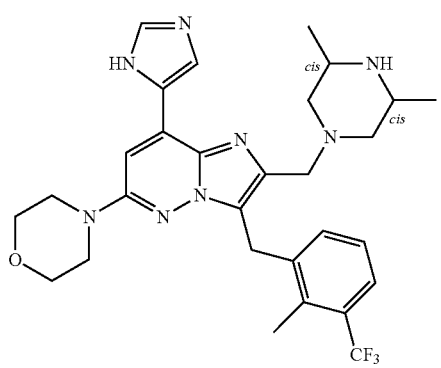

Compound 16 was prepared according to an analogous procedure as described for the synthesis of compound 15, using intermediate 11 as starting material (55%). M.P.: gum at 148° C. (Kofler).

Preparation of Compound 17:

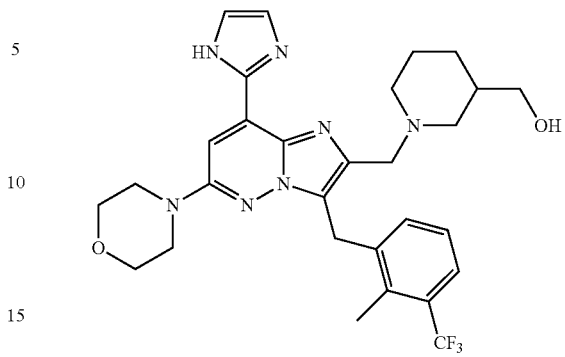

Compound 17 was prepared according to an analogous procedure as described for the synthesis of compound 15, using intermediate 42 as starting material (9%). M.P.: 171° C. (Kofler).

Example B5

Preparation of Compound 18:

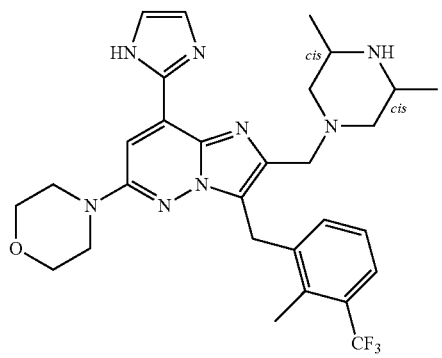 [SMILES: Cc1c(Cc2c(CN3CC(C)NC(C)C3)nc3c(-c4ncc[nH]4)cc(N4CCOCC4)nn23)cccc1C(F)(F)F]

Intermediate 49 (0.337 g; 0.5 mmol) was dissolved in dioxane (8.4 mL) and an aqueous solution of HCl 6N (3.2 mL) was added. The reaction mixture was heated at 100° C. for 2 hours. The reaction mixture was cooled to room temperature, diluted with DCM/MeOH (80/20) and basified with a 10% aqueous solution of $K_2CO_3$. The organic layer was separated, washed with brine, dried over $MgSO_4$, filtered and evaporated to dryness. The residue (0.336 g) was recrystallized from $Et_2O$. The precipitate was filtered and dried to afford 0.175 g (62%) of compound 18. M.P.: gum at 100° C. (Kofler).

Alternative Route

Intermediate 24 (0.31 g, 0.5 mmol), imadazole (0.84 g, 12.3 mmol) copper iodine (0.19 g, 0.9 mmol) in DMF (5 mL) were degassed under nitrogen for 15 minutes. Palladium acetate (0.033 g, 0.15 mmol) was added and the reaction mixture was stirred at 185° C. using one single mode microwave with a power output ranging from 0 to 400 W for 15 min. Water and DCM were added. The reaction mixture was filtered through a pad of Celite®, which was washed with DCM. The filtrate was extracted then the organic layer was separated, dried over $MgSO_4$, filtered and evaporated. The residue (0.6 g) was purified by chromatography over silica gel (Irregular SiOH, 15-40 µm, 24 g, mobile phase gradient from 96% DCM 4% $CH_3OH$ 0.1% $NH_4OH$ to 83% DCM 17% $CH_3OH$ 1.7% $NH_4OH$). The fractions containing the product were collected and evaporated to dryness. The residue (0.060 g) was purified by reverse phase chromatography (C18 5 μm 30*150 min, gradient from 70% NH₄HCO₃ 0.5%, 30% ACN to 0% NH₄HCO₃ 0.5%, 100% ACN). The resulting residue was crystallized from DIPE and the precipitate was filtered and dried yielding 0.020 g (7%) of compound 18.

Example B6

Preparation of Compound 19:

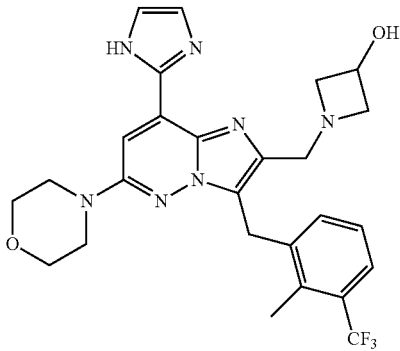 [SMILES: Cc1c(Cc2c(CN3CC(O)C3)nc3c(-c4ncc[nH]4)cc(N4CCOCC4)nn23)cccc1C(F)(F)F]

Compound 19 can be prepared according to an analogous reaction procedure as described for the synthesis of compound 18, using intermediate 17 as starting material.

Alternative Route

Compound 19 was prepared according to the following method:

Tetrabutylammonium fluoride (0.73 mL; 0.73 mmol) was added to a solution of intermediate 50 (0.235 g; 0.37 mmol) in THF (10 mL) and the reaction mixture was stirred for 3 hours. The reaction mixture was diluted with DCM and a 10% aqueous solution of K₂CO₃ was added. The mixture was filtered through a phase separator system and the organic layer was evaporated. The residue was taken up with ACN. The precipitate was filtered and dried to afford 0.091 g (47%) of compound 19. M.P.: 198° C. (Kofler).

Example B7

Preparation of Compound 20:

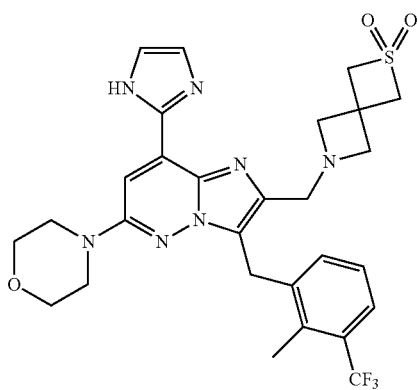 [SMILES: Cc1c(Cc2c(CN3CC4(C3)CS(=O)(=O)C4)nc3c(-c4ncc[nH]4)cc(N4CCOCC4)nn23)cccc1C(F)(F)F]

Compound 20 can be prepared according to an analogous reaction procedure as described for the synthesis of compound 18, using intermediate 21 as starting material.

Alternative Route

Compound 20 was prepared according to the following method:

A mixture of intermediate 48 (0.24 g; 0.51 mmol) and 2-thia-6-azaspiro[3,3]heptane 2,2-dioxide (0.27 g; 1.1 mmol) in MeOH (5 mL) was stirred at room temperature overnight. Sodium triacetoxyborohydride (0.33 g; 1.6 mmol) was added to the reaction mixture and it was stirred 3 hours at room temperature. The solution was poured into cooled water, basified with K₂CO₃ powder and the product was extracted with DCM. The organic layer was separated, dried over MgSO₄, filtered and evaporated to dryness. The residue (0.3 g) was purified by chromatography over silica gel (Irregular SiOH, 15-40 μm, gradient from 98% DCM 2% CH₃OH 0.2% NH₄OH to 88% DCM 12% CH₃OH 1.2% NH₄OH). The fractions containing the product were collected and evaporated to dryness. The resulting residue was taken up with Et₂O, the precipitate was filtered and dried to afford 0.062 g (20%) of compound 20. M.P.: 150° C. (Kofler).

Example B8

Preparation of Compound 21:

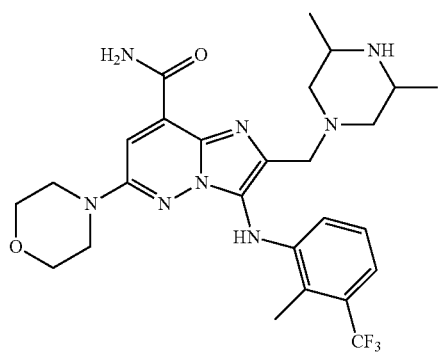 [SMILES: Cc1c(Nc2c(CN3CC(C)NC(C)C3)nc3c(C(N)=O)cc(N4CCOCC4)nn23)cccc1C(F)(F)F]

In a sealed tube, intermediate 57 (0.09 g, 0.16 mmol) in ammonia in MeOH 7N (0.92 mL) was stirred overnight at 100° C. The mixture was cooled to room temperature and then concentrated. A solid was obtained, washed with Et₂O, filtered and dried to give a yellow solid 0.015 g of impure solid. The filtrate was concentrated. The precipitate and the filtrate were combined and the resulting residue was purified by chromatography over silica gel (Irregular SiOH, 15-40 μm, 12 g, mobile phase gradient from 97% DCM 3% CH₃OH 0.1% NH₄OH to 91% DCM 9% CH₃OH 0.1% NH₄OH). The fractions containing the product were collected and evaporated to dryness to afford 0.060 g (68%) of compound 21, M.P: gum between 105-113° C. (Kofler).

Preparation of Compound 26:

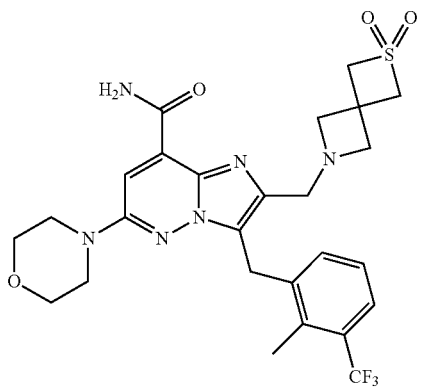 [SMILES: Cc1c(Cc2c(CN3CC4(C3)CS(=O)(=O)C4)nc3c(C(N)=O)cc(N4CCOCC4)nn23)cccc1C(F)(F)F]

Compound 26 was prepared according to an analogous procedure as described for the synthesis of compound 21, using intermediate 34 as starting material (68%). M.P.: 216° C. (Kofler).

Example B9

Preparation of Compound 22:

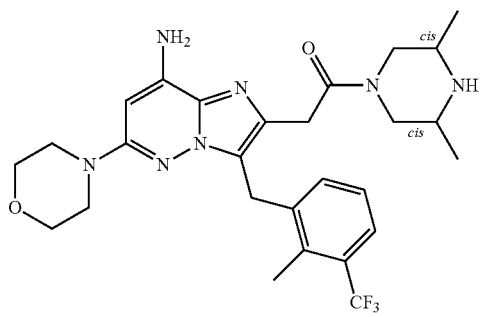 [SMILES: Cc1c(Cc2c(CC(=O)N3CC(C)NC(C)C3)nc3c(N)cc(N4CCOCC4)nn23)cccc1C(F)(F)F]

O-(1H-benzotriazol-1-yl)-N,N,N',N'-tetramethyluronium hexafluorophosphate (0.13 g; 0.34 mmol) was added to a solution of diisopropylamine (0.090 mL; 0.51 mmol), cis-2,6-dimethylpiperazine (0.058 g; 0.51 mmol) and intermediate 64 (0.153 g; 0.34 mmol) in DMF (3 mL). The solution was stirred at room temperature overnight. The solution was poured into cooled water and the product was extracted with EtOAc. The organic layer was separated, washed with brine, dried over MgSO$_4$, filtered and evaporated till dryness. The residue (0.2 g) was purified by chromatography over silica gel (Irregular SiOH, 15-40 µm, 24 g, gradient from 95% DCM 5% CH$_3$OH 0.1% NH$_4$OH. to 80% DCM 20% CH$_3$OH 0.1% NH$_4$OH). The fractions containing the product were collected and evaporated to dryness. The residue (0.068 g; 27%) was freeze-dried with Acetonitrile/water 20/80 to give 0.062 g (33%) of compound 22. M.P: 110° C. (Kofler).

Preparation of Compound 23:

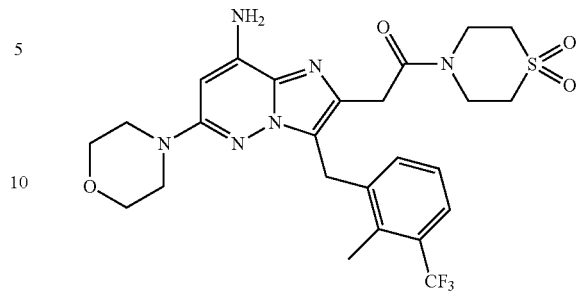

Compound 23 was prepared according to an analogous procedure as described for the synthesis of compound 22, using intermediate 64 as starting material and thiomorpholine-1,1-dioxide (25%). M. P: 226° C. (Kofler).

Preparation of Compound 24:

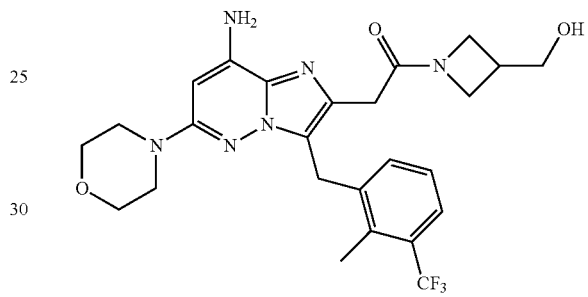

Compound 24 was prepared according to an analogous procedure as described for the synthesis of compound 22, using intermediate 64 and 3-(hydromethyl)azetidine as starting materials (13%). M.P: 130° C. (Kofler).

Example B10

Preparation of Compound 25:

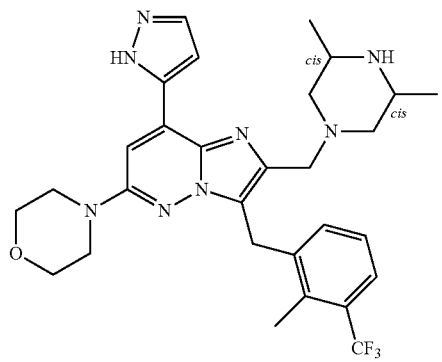 [SMILES: Cc1c(Cc2c(CN3CC(C)NC(C)C3)nc3c(-c4ccn[nH]4)cc(N4CCOCC4)nn23)cccc1C(F)(F)F]

Intermediate 35 (0.072 g, 0.11 mmol) and a 37% aqueous solution of HCl (0.046 mL, 0.55 mmol) in MeOH (5 mL) were stirred at room temperature for 4 hours in a sealed tube. The mixture was poured into water, basified with an aqueous solution of sodium hydrogenocarbonate and extracted with DCM. The organic layer was separated, dried over MgSO$_4$, filtered and evaporated to afford 0.062 g (99%) of compound 25. M.P: 159° C. (Kofler).

Example B11

Preparation of Compound 27:

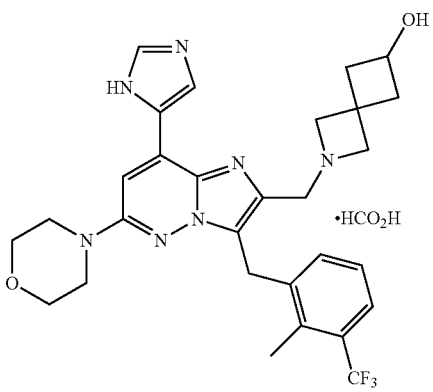 [SMILES: Cc1c(Cc2c(CN3CC4(CC(O)C4)C3)nc3c(-c4cnc[nH]4)cc(N4CCOCC4)nn23)cccc1C(F)(F)F ; "·HCO2H"]

A mixture of intermediate 72 (139 mg; 0.21 mmol) and lithium hydroxide monohydrate (35 mg; 0.83 mmol) in MeOH (3 mL) was stirred at room temperature overnight. The reaction mixture was diluted with DCM and water was added. The organic layer was decanted, dried over MgSO$_4$, filtered and evaporated to dryness. The residue was crystallized from ACN and the precipitate was filtered, washed with Et$_2$O and dried yielding 69 mg (59%). of fraction 1. The filtrate was evaporated to dryness and gathered with fraction 1. Then, the residue (139 mg) was purified by reverse phase Chromatography (X-Bridge-C18 5 μm 30*150 mm; gradient from 75% NH$_4$HCOOH 0.6 g/L, 25% ACN to 35% NH$_4$HCOOH 0.6 g/L, 65% ACN). The pure fractions were collected and evaporated to dryness. The residue (42 mg; 36%) was taken up with Et$_2$O and the precipitate was filtered and dried yielding 33 mg (26%) of compound 27. M.P.: gum 120° C. (Kofler).

Example B12

Preparation of Compound 28:

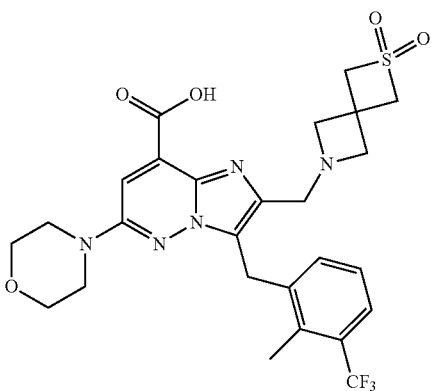 [SMILES: Cc1c(Cc2c(CN3CC4(C3)CS(=O)(=O)C4)nc3c(C(=O)O)cc(N4CCOCC4)nn23)cccc1C(F)(F)F]

A solution of lithium hydroxide monohydrate (17 mg; 0.40 mmol) in water (0.25 mL) was added to a mixture of intermediate 34 (80 mg; 0.14 mmol) in THF (0.74 mL) at rt. The reaction mixture was stirred at rt overnight. The solution was neutralized with HCl 3N until pH=7 and THF was evaporated. The residue was taken in water and extracted with DCM. The organic layer was dried over MgSO$_4$, filtered and concentrated under vacuum. The residue (44 mg) was purified by reverse phase (C18 5 μm 30*150 mm, gradient from 85% TFA 0.05%, 15% ACN to 45% TFA 0.05%, 55% ACN). The pure fractions were collected and the solvent was evaporated to give 24 mg (31%) of compound 28.

Example B13

Preparation of Compound 29:

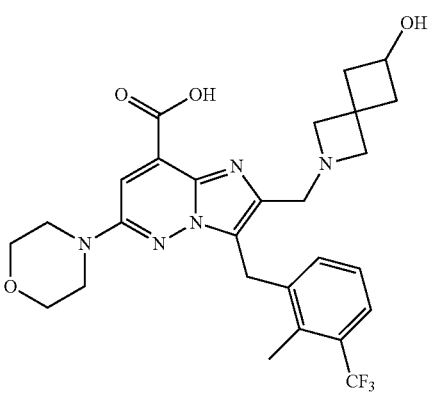 [SMILES: Cc1c(Cc2c(CN3CC4(CC(O)C4)C3)nc3c(C(=O)O)cc(N4CCOCC4)nn23)cccc1C(F)(F)F]

A mixture of intermediate 73 (0.08 g; 0.13 mmol) and triethylamine (0.25 mL, 1.79 mmol) in MeOH (5 mL) was purged with N$_2$ in a sealed cylinder and Pd(PPh$_3$)$_4$ (0.015 g, 0.013 mmol) was added. The reaction mixture was then purged for 5 additional minutes and carbon monoxide was added (5 bars). The reaction was stirred overnight at 120° C. and then concentrated. The residue was purified by chromatography over silica gel (Irregular SiOH, 15-40 μm, 24 g, eluent 99% DCM, 1% MeOH, 0.1% NH$_4$OH). The desired fractions were collected and evaporated to give 34 mg of residue. This residue was washed with Et$_2$O and dried under vacuum. The resulting residue (18 mg) was further purified by reverse phase (C18 5 μm 30*150 mm, gradient from 90% TFA 0.05%, 10% MeOH to 50% TFA 0.05%, 50% MeOH). The pure fractions were collected and the solvent was evaporated to give 14 mg (20%) of compound 29.

Example B14

Compounds 31, 32, 33 and 34 were already obtained as a mixture together with their intermediates, respectively intermediates 85, 86, 87 and 88 (see A23), Example B14 describes how these intermediate mixtures were converted to the compounds.

Preparation of Compound 31:

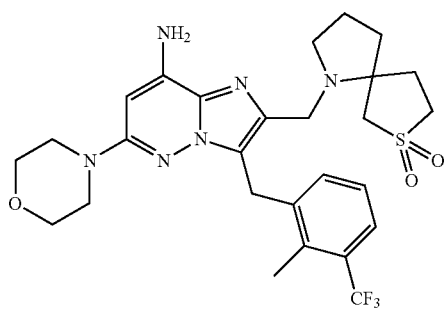 [SMILES: Cc1c(Cc2c(CN3CCCC34CCS(=O)(=O)C4)nc3c(N)cc(N4CCOCC4)nn23)cccc1C(F)(F)F]

A mixture of intermediate 85 (280 mg; 0.44 mmol) and zinc chloride (181 mg; 1.33 mmol) in EtOH (3 mL) was stirred at 90° C. overnight. The reaction mixture was poured into water and filtered through a pad of Celite®. The organic layer was extracted with DCM, separated, dried over MgSO₄, filtered and the solvent was evaporated. The residue (0.26 g) was crystallized from DIPE. The precipitate was filtered off and dried in vacuum to give 0.18 g (63%) of compound 31.

Preparation of Compound 32:

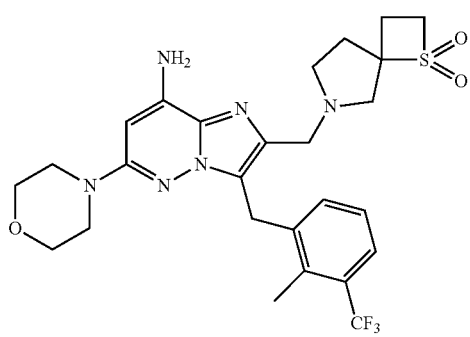 [SMILES: Cc1c(Cc2c(CN3CCC4(CCS4(=O)=O)C3)nc3c(N)cc(N4CCOCC4)nn23)cccc1C(F)(F)F]

Compound 32 was prepared according to an analogous procedure as described for the synthesis of compound 31, using intermediate 86 as starting material. The residue (280 mg) was purified by chromatography over silica gel (SiOH 15 μm; 25 g; gradient: from 100% DCM to 95% DCM, 5% MeOH, 0.1% NH₄OH). The pure fractions were collected and the solvent was evaporated. The residue was crystallized from diethyl ether. The precipitate was filtered off and dried under vacuum to give 120 mg (51%) of compound 32. M.P: 214° C. (DSC).

Preparation of Compound 33:

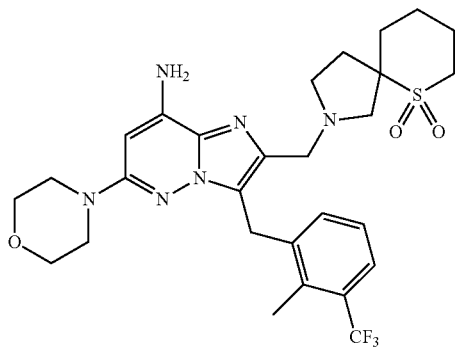 [SMILES: Cc1c(Cc2c(CN3CCC4(CCCCS4(=O)=O)C3)nc3c(N)cc(N4CCOCC4)nn23)cccc1C(F)(F)F]

Compound 33 was prepared according to an analogous procedure as described for the synthesis of compound 31, using intermediate 87 as starting material. The residue (180 mg) was purified by chromatography over silica gel (SiOH 15 μm; 25 g; gradient: from 100% DCM to 95% DCM, 5% MeOH, 0.1% NH₄OH). The pure fractions were collected and the solvent was evaporated. The residue was crystallized from diethyl ether. The precipitate was filtered off and dried under vacuum to give 50 mg (55%) of compound 33. M.P: 228° C. (DSC).

Preparation of Compound 34:

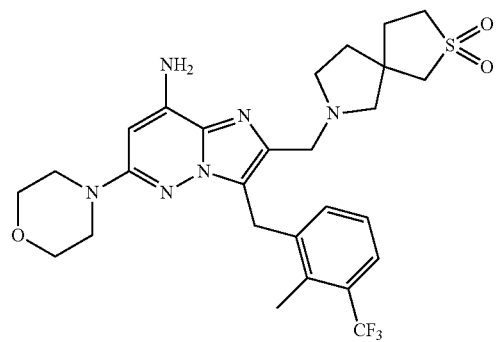 [SMILES: Cc1c(Cc2c(CN3CCC4(CCS(=O)(=O)C4)C3)nc3c(N)cc(N4CCOCC4)nn23)cccc1C(F)(F)F]

Compound 34 was prepared according to an analogous procedure as described for the synthesis of compound 31, using intermediate 88 as starting material. The residue (180 mg) was purified by chromatography over silica gel (SiOH 15 μm; 25 g; gradient: from 98% DCM, 2% MeOH, 0.1% NH₄OH to 90% DCM, 10% MeOH, 0.1% NH₄OH). The pure fractions were collected and the solvent was evaporated to give 97 mg (100%) of compound 34.

Example B15

Preparation of Compound 35:

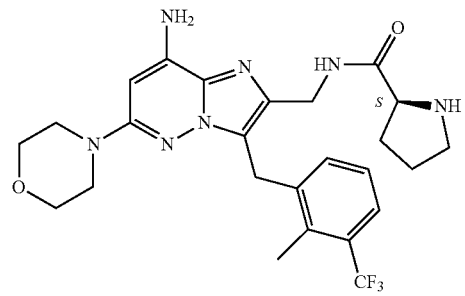

In a round bottom flask, intermediate 95 (0.306 mg; 0.33 mmol) was diluted in THF (15 mL). Then, at room temperature. HCl (1M in water) (3.3 mL, 3.28 mmol) was added and the reaction mixture was stirred for 3 hours. Additional HCl (1M in water) (3.3 mL; 3.28 mmol) was added and the reaction mixture was stirred at 60° C. for 16 hours. The reaction mixture was cooled down to room temperature and basified with a saturated solution of NaHCO₃. The aqueous layer was extracted twice with DCM. The organic layer was dried over MgSO₄, filtered and the solvent was evaporated. The residue was purified by silica gel chromatography (irregular SiOH, 40 g, gradient from 99% DCM 1% MeOH 0.1% NH₄OH to 90% DCM 10% MeOH 1% NH₄OH). The pure fractions were collected and the solvent was evaporated to afford an intermediate fraction which was taken up with ACN. The precipitate was filtered and dried to afford 75 mg (44%; white solid) of compound 35. M.P.: 211° C. (Kofler).

Preparation of Compound 36:

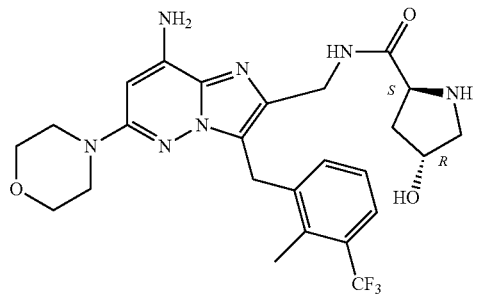

In a round bottom flask, intermediate 97 (0.26 g; 0.13 mmol) was diluted in DCM (10 mL). Then, TFA (1 mL) was added and the reaction mixture was stirred at room temperature overnight. The reaction mixture was carefully quenched with an aqueous saturated solution of NaHCO₃. The aqueous layer was extracted with DCM. The organic layer was separated, dried over MgSO₄ filtered and the solvent was evaporated. The residue was purified by silica gel chromatography (irregular SiOH, 40 g, gradient from 99% DCM, 1% MeOH, 0.1% NH₄OH to 90% DCM, 10% MeOH, 1% NH₄OH). The fractions containing the product were mixed and evaporated. The residue (62 mg) was purified by Reverse phase (X-Bridge-C18 5 μm 30*150 mm, Mobile phase: Gradient from 85% NH₄HCO₃ 0.5%, 15% ACN to 45% NH₄HCO₃ 0.5%, 55% ACN). The pure fractions were mixed and the solvent was evaporated to afford 42 mg (60%) which was taken up with diethylether. The precipitate was filtered and dried to afford 24 mg (34%) of compound 36. M.P.: 140° C. (gum) (K).

Preparation of Compound 37:

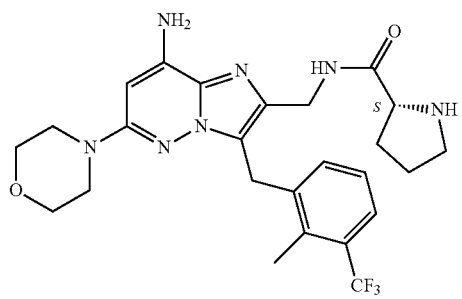

In a round bottom flask, intermediate 99 (0.242 g; 0.26 mmol) was diluted in THF (11.7 mL). Then, at room temperature, HCl (1M in water) (5.1 mL; 5.1 mmol) was added and the reaction mixture was stirred at 70° C. for 16 hours. The reaction mixture was cooled down to room temperature and basified with a saturated solution of NaHCO₃. The aqueous layer was extracted twice with DCM/MeOH (9/1). The organic layer was dried over MgSO₄, filtered and evaporated.

The residue was purified by chromatography over silica gel (irregular bare silica 150 g; gradient: from 100% DCM to 0.8% NH₄OH, 92% DCM, 8% MeOH). The fractions containing the product were mixed and evaporated. The residue (70 mg) was taken up with ACN. The precipitate was filtered and dried to afford 58 mg (43%) of compound 37. M.P.: 212° C. (DSC).

Preparation of Compound 38:

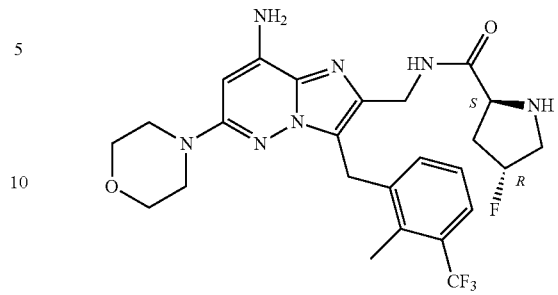

Compound 38 was prepared according to an analogous procedure as described for the synthesis of compound 37, using intermediate 102 as starting material (110 mg, 80%).

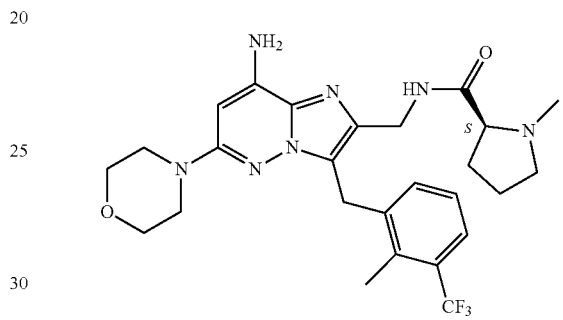

Preparation of Compound 39:

Compound 39 was prepared by 2 reactions from respectively 0.67 g (0.96 mmol) and 0.37 g (0.63 mmol) of intermediate 104:

In a round bottom flask, intermediate 104 (0.67 g; 096 mmol) was diluted in DCM (24 mL). Then, TFA (7.39 mL; 97 mmol) was added and the reaction mixture was stirred at room temperature for two days. The reaction mixture was carefully quenched with an aqueous saturated solution of NaHCO₃. The aqueous layer was extracted with DCM. The organic layer was separated, dried over MgSO₄, filtered and the solvent was evaporated. The residue was purified by chromatography over silica gel (irregular SiOH; 40 g; gradient: from 100% DCM to 95% DCM, 5% MeOH, 0.5% NH₄OH). The pure fractions were collected and the solvent was evaporated to give 275 mg (55%, pink powder) of fraction A.

In a round bottom flask, intermediate 104 (0.37 g; 0.53 mmol) was diluted in DCM (14 mL), Then, TFA (4.08 mL; 53.31 mmol) was added and the reaction mixture was stirred at room temperature for two days. The reaction mixture was carefully quenched with an aqueous saturated solution of NaHCO₃. The aqueous layer was extracted with DCM. The organic layer was separated, dried over MgSO₄, filtered and the solvent was evaporated. The residue (360 mg, brown oil) was purified by chromatography over silica gel (irregular SiOH: 24 g; gradient: from 99% DCM, 1% MeOH, 0.1% NH₄OH to 90% DCM, 10% MeOH, 1% NH₄OH). The pure fractions were collected and the solvent was evaporated to give 70 mg (25%, colorless oil) of fraction B and 121 mg (43%, yellow oil) of fraction C.

Fractions A, B and C were gathered to give 470 mg (brown powder) which were purified by chromatography over silica gel (irregular hare silica 40 g, mobile phase: 42% heptane, 8% MeOH (+10% NH₄OH), 50% EtOAc). The pure fractions were collected and the solvent was evaporated. The residue (370 mg, white powder) was taken up with diethylether. The solid was filtered and dried to give 270 mg (white powder). A recristallisation on 220 mg of this white powder was performed in ACN to give 163 mg (white powder) of compound 39. M.P.: 101° C. (DSC).

Example B16

Preparation of Compound 40a:

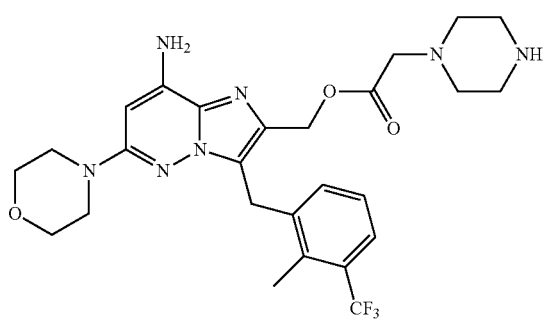 [SMILES: Cc1c(Cc2c(COC(=O)CN3CCNCC3)nc3c(N)cc(N4CCOCC4)nn23)cccc1C(F)(F)F]

A solution of intermediate 105 (0.44 g; 0.68 mmol) and TFA (0.7 mL; 9 mmol) in DCM (7 mL) was stirred at room temperature overnight. The solution was poured into cooled water, basified with $K_2CO_3$ and the product was extracted with DCM. The organic layer was dried over $MgSO_4$, filtered and the solvent was evaporated to give 360 mg (96%) of compound 40a which was not further purified and was used as such in the next reaction step.

Preparation of Compound 40b:

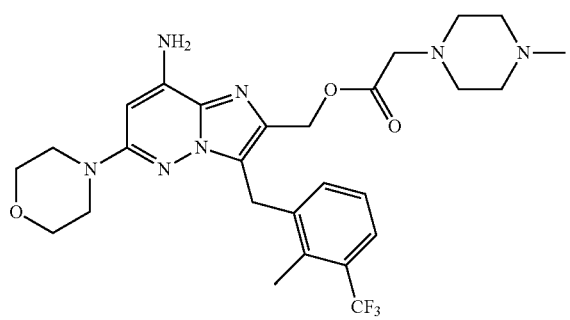 [SMILES: Cc1c(Cc2c(COC(=O)CN3CCN(C)CC3)nc3c(N)cc(N4CCOCC4)nn23)cccc1C(F)(F)F]

Sodium cyanoborohydride (0.11 g; 1.75 mmol) was added to a stirred suspension of compound 40a (0.4 g; 0.73 mmol) and formaldehyde (37% in $H_2O$) (0.11 mL, 1.46 mmol) MeOH (7 mL) and acetic acid (0.7 mL) at room temperature under $N_2$. The reaction mixture was stirred at this temperature for 2 h. The mixture was poured onto iced water and basified with $K_2CO_3$ powder. The aqueous layer was extracted with EtOAc. The organic layer was separated, dried over $MgSO_4$, filtered and evaporated to dryness. The residue (440 mg) was purified by chromatography over silica gel (irregular SiOH 40 µm; 120 g; mobile phase: 90% DCM, 10% MeOH, 0.1% $NH_4OH$). The pure fractions were collected and the solvent was evaporated. The residue (278 mg) was taken up with DCM. The organic layer was washed with 10% aqueous solution of $K_2CO_3$, dried over $MgSO_4$ and evaporated to dryness. The residue (255 mg) was taken up with ACN. HCl (4M in dioxane) (0.55 mL; 2.2 mmol)) was added at 10° C. and the solution was stirred for 1 h. The mixture was evaporated to dryness, then diethylether was added. The precipitate was filtered, dried. As it was not pure enough, it (259 mg) was taken up with $H_2O$, basified with $NaHCO_3$ and extracted with DCM. The organic layer was dried over $MgSO_4$ and evaporated to dryness. The residue (210 mg) was purified by reverse phase (X-Bridge-C18 5 µm; 30*150 mm; gradient: from 75% ($NH_4HCO_3$ 0.5%), 25% ACN to 35% ($NH_4HCO_3$ 0.5%), 65% ACN). The pure fractions were collected and the solvent was evaporated. The residue (172 mg) was crystallized from diethylether. The precipitate was filtered and dried to give 114 mg (28%) of compound 40b. M.P.: 99° C. (DSC).

Example B17

Preparation of compound 41:

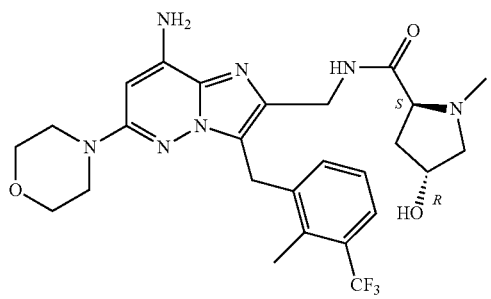

1-Hydroxybenzotriazole (77 mg; 0.57 mmol) and 1-(3-dimethylaminopropyl)-3-ethylcarbodiimide hydrochloride (109 mg; 0.57 mmol) were added to a solution of intermediate 114 (200 mg; 0.48 mmol), intermediate 108 (69 mg; 0.48 mmol) and triethylamine (231 µL; 1.67 mmol) in DCM (2.3 mL) and THF (2.3 mL) at room temperature. The reaction mixture was stirred at this temperature for 72 h. A saturated solution of $NaHCO_3$ and DCM were added. The organic layer was separated, dried over $MgSO_4$ and the solvent was evaporated. The residue (550 mg, yellow powder) was purified by chromatography over silica gel (irregular SiOH; 12 g, gradient: from 100% DCM to 2% $NH_4OH$, 80% DCM, 20% MeOH). The pure fractions were collected and the solvent was evaporated. The residue (142 mg) was taken-up in diethylether. The precipitate was filtered to give 131 mg (50%, white powder) of compound 41. M.P.: 183° C. (DSC).

Example B18

Preparation of compound 42:

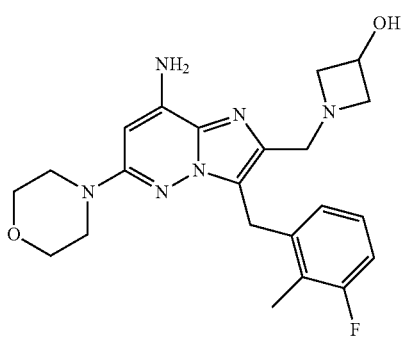 [SMILES: Cc1c(F)cccc1Cc1c(CN2CC(O)C2)nc2c(N)cc(N3CCOCC3)nn12]

HCl (1M in $H_2O$) (3.4 mL; 3.4 mmol) was added at 5° C. to a solution of intermediate 123 (225 mg; 0.319 mmol) in Me-THF (12 mL) and the reaction mixture was stirred overnight at room temperature. The reaction mixture was poured onto ice water, basified with an aqueous solution of NaHCO3 and extracted with EtOAc. The aqueous layer was extracted twice with EtOAc. The combined organic layers were decanted, washed with brine, dried over $MgSO_4$, filtered and evaporated to dryness.

The residue was taken up with a mixture of $EtOH/Et_2O$ and the precipitate was filtered yielding 45 mg (33%) of compound 42. M.P.: 214° C. (K).

Preparation of Compound 43:

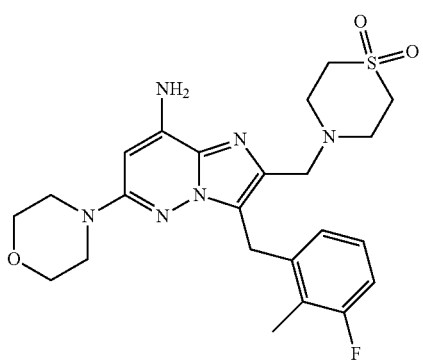 [SMILES: Cc1c(F)cccc1Cc1c(CN2CCS(=O)(=O)CC2)nc2c(N)cc(N3CCOCC3)nn12]

Compound 43 was prepared according to an analogous procedure as described for the synthesis of compound 42, using intermediate 125 as starting material (144 mg, 51%). M.P.: 130° C. (gum, K).

Preparation of Compound 44:

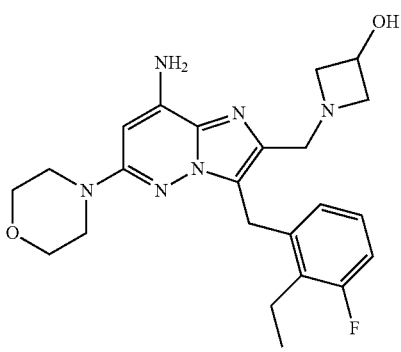 [SMILES: CCc1c(F)cccc1Cc1c(CN2CC(O)C2)nc2c(N)cc(N3CCOCC3)nn12]

Compound 44 was prepared according to an analogous procedure as described for the synthesis of compound 42, using intermediate 136 as starting material (63 mg, 23%). M.P.: 172° C. (K).

Preparation of Compound 45:

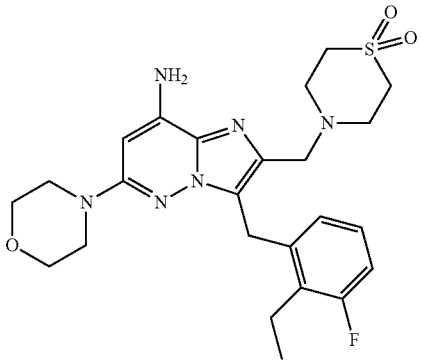 [SMILES: CCc1c(F)cccc1Cc1c(CN2CCS(=O)(=O)CC2)nc2c(N)cc(N3CCOCC3)nn12]

Compound 45 was prepared according to an analogous procedure as described for the synthesis of compound 42, using intermediate 138 as starting material (212 mg, 79%). M.P.: 240° C. (K).

Analytical Part

LCMS (Liquid Chromatography/Mass Spectrometry)

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl), the reported value is the one obtained for the lowest isotope mass. All results were obtained with experimental uncertainties that are commonly associated with the method used.

Hereinafter, "SQD" means Single Quadrupole Detector, "BEH" bridged ethylsiloxane/silica hybrid, "DAD" Diode Array Detector.

TABLE

LCMS Method codes (Flow expressed in mL/min; column temperature (T) in ° C.; Run time in minutes).

| Method code | Instrument | Column | Mobile phase | gradient | Flow Column T | Run time |
|---|---|---|---|---|---|---|
| Method 1 | Waters: Acquity UPLC ®-DAD and Quattro Micro ™ | Waters: BEH C18 (1.7 μm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 40 | 6.2 |

TABLE-continued

LCMS Method codes (Flow expressed in mL/min; column temperature (T) in °C.; Run time in minutes).

| Method code | Instrument | Column | Mobile phase | gradient | Flow Column T | Run time |
|---|---|---|---|---|---|---|
| Method 2 | Waters: Acquity UPLC® H-Class-DAD and SQD 2 | Waters: BEH C18 (1.7 μm, 2.1 × 100 mm) | A: 95% CH$_3$COONH$_4$ 7 mM/5% CH$_3$CN, B: CH$_3$CN | From 84.2% A to 10.5% A in 2.18 min, held for 1.94 min, back to 84.2% A in 0.73 min, held for 0.73 min. | 0.343 40 | 6.1 |

DSC/Kofler

For a number of compounds, melting points (M.P.) were determined with a DSC1 (Mettler-Toledo). Melting points were measured with a temperature gradient of 10° C./minute. Maximum temperature was 350° C. Values are peak values.

For a number of compounds, melting points were obtained with a Kofler hot bench, consisting of a heated plate with linear temperature gradient, a sliding pointer and a temperature scale in degrees Celsius.

NMR

The NMR experiments were carried out using a Bruker Avance 500 III using internal deuterium lock and equipped with reverse triple-resonance ($^1$H, $^{13}$C, $^{15}$N TXI) probe head. Chemical shifts (δ) are reported in parts per million (ppm). DMSO-d$_6$ (deuterated DMSO, dimethyl-d6 sulfoxide) was used as solvent.

OR:

Optical Rotation is measured with a polarimeter 341 Perkin Elmer. The polarized light is passed through a sample with a path length of 1 decimeter and a sample concentration of 0.2 to 0.4 gram per 100 milliliters.

2 to 4 mg of the product in vial are weight, then dissolved with 1 to 1.2 ml of spectroscopy solvent (Dimethylformamide for example). The cell is filled with the solution and put into the polarimeter at a temperature of 20° C. The OR is read with 0.004° of precision.

Calculation of the concentration: weight in gram×100/volume in ml $[\alpha]_d^{20}$: (read rotation×100)/(1.000 dm×concentration).

$^d$ is sodium D line (589 nanometer).

TABLE

Co. No. means compound number; Retention time (R$_t$) in min; MP means melting point (° C.); dec means decomposition; n.d. means not determined.

| Co No. | Compound | MP | Kofler (K) or DSC | Rt | [M + H]$^+$ | LCMS Method |
|---|---|---|---|---|---|---|
| 1 | 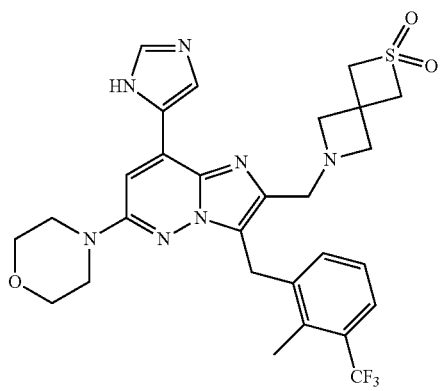 [SMILES: Cc1c(Cc2c(CN3CC4(C3)CS(=O)(=O)C4)nc3c(-c4cnc[nH]4)cc(N4CCOCC4)nn23)cccc1C(F)(F)F] | 217 | K | 2.74 | 6.02 | Method 1 |

TABLE-continued
*Co. No. means compound number; Retention time ($R_t$) in min; MP means melting point (° C.); dec means decomposition; n.d. means not determined.*
| Co No. | Compound | MP | Kofler (K) or DSC | Rt | [M + H]+ | LCMS Method |
|---|---|---|---|---|---|---|
| 2 | 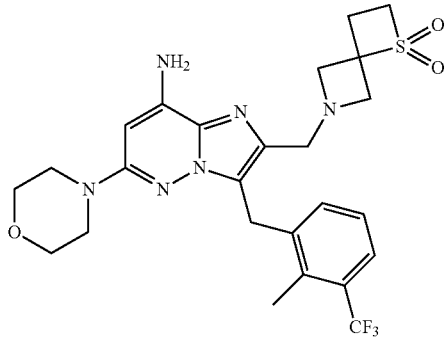 .0.8 HCOOH | 180 | K | 2.83 | 551 | Method 1 |
| 3 | 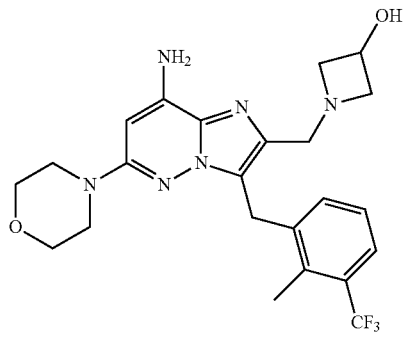 [SMILES: Cc1c(Cc2c(CN3CC(O)C3)nc3c(N)cc(N4CCOCC4)nn23)cccc1C(F)(F)F] | n.d. | | 2.49 | 477 | Method 1 |
| 4 | 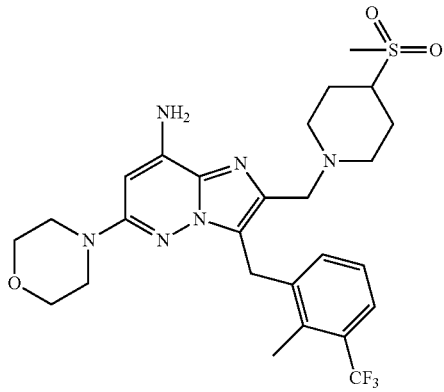 [SMILES: Cc1c(Cc2c(CN3CCC(S(C)(=O)=O)CC3)nc3c(N)cc(N4CCOCC4)nn23)cccc1C(F)(F)F] | 188 | K | 2.80 | 567 | Method 1 |

TABLE-continued
Co. No. means compound number; Retention time (R$_t$) in min; MP means melting point (° C.); dec means decomposition; n.d. means not determined.
| Co No. | Compound | MP | Kofler (K) or DSC | Rt | [M + H]⁺ | LCMS Method |
|---|---|---|---|---|---|---|
| 5 | 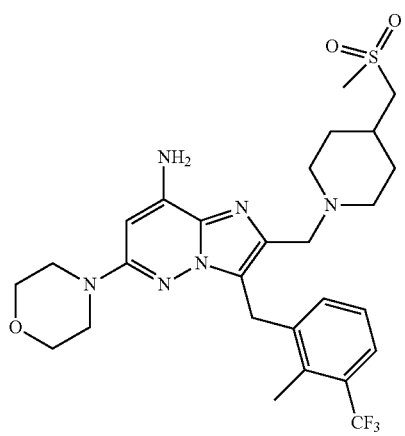 [SMILES: Cc1c(Cc2c(CN3CCC(CS(C)(=O)=O)CC3)nc3c(N)cc(N4CCOCC4)nn23)cccc1C(F)(F)F] | n.d. | | 2.73 | 581 | Method 1 |
| 6 | 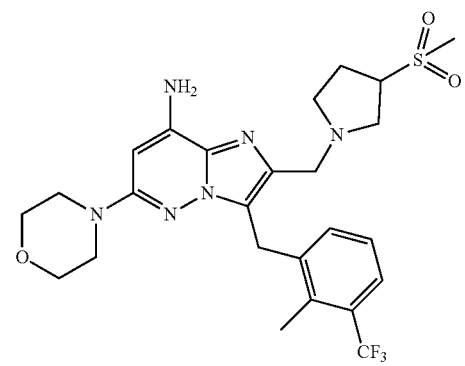 [SMILES: Cc1c(Cc2c(CN3CCC(S(C)(=O)=O)C3)nc3c(N)cc(N4CCOCC4)nn23)cccc1C(F)(F)F] | 159 | K | 2.80 | 553 | Method 1 |
| 7 | 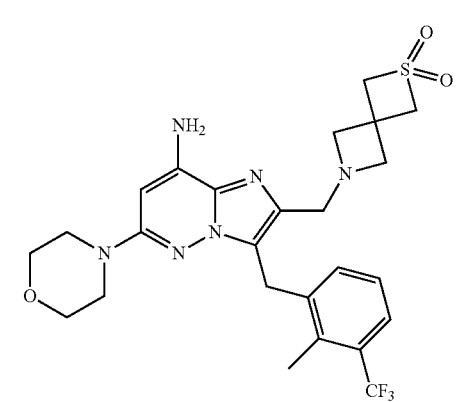 [SMILES: Cc1c(Cc2c(CN3CC4(C3)CS(=O)(=O)C4)nc3c(N)cc(N4CCOCC4)nn23)cccc1C(F)(F)F] | 110-113 gum | K | 2.77 | 551 | Method 1 |

| Co No. | Compound | MP | Kofler (K) or DSC | Rt | [M + H]+ | LCMS Method |
|---|---|---|---|---|---|---|
| 8 | | 210 | K | 2.72 | 539 | Method 1 |
| 9 | | 215 | K | 2.56 | 519 | Method 1 |
| 10 | | 92-97 gum | K | 2.56 | 518 | Method 1 |
| 11 | | 214 | K | 3.29 | 539 | Method 2 |

TABLE-continued
Co. No. means compound number; Retention time (R$_t$) in min; MP means melting point (° C.); dec means decomposition; n.d. means not determined.
| Co No. | Compound | MP | Kofler (K) or DSC | Rt | [M + H]$^+$ | LCMS Method |
|---|---|---|---|---|---|---|
| 12 | 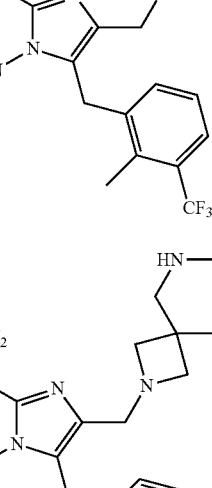 | 122 gum | K | 2.66 | 530 | Method 1 |
| 13 | 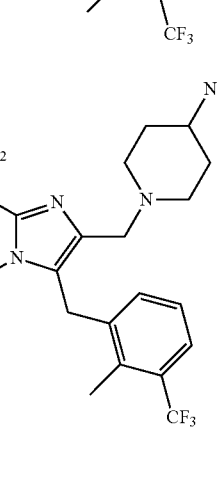 | 87-90 gum | K | 2.57 | 530 | Method 1 |
| 14 | 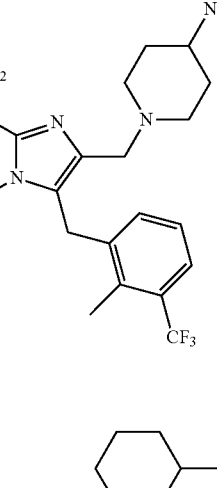 | 96-104 gum | K | 2.51 | 504 | Method 1 |
| 15 | 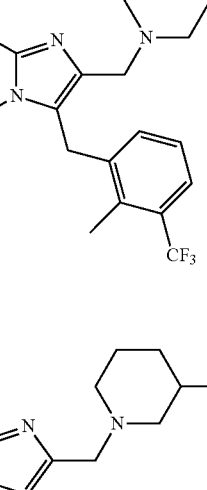 | 160 gum | K | 2.63 | 570 | Method 1 |

TABLE-continued

Co. No. means compound number; Retention time (R_t) in min; MP means melting point (° C.); dec means decomposition; n.d. means not determined.

| Co No. | Compound | MP | Kofler (K) or DSC | Rt | [M + H]+ | LCMS Method |
|---|---|---|---|---|---|---|
| 16 | | 148 | K | 2.56 | 569 | Method 1 |
| 17 | | 171 | K | 2.88 | 570 | Method 1 |
| 18 | | 100 gum | K | 2.68 | 569 | Method 1 |
| 19 | | 198 | K | 2.61 | 528 | Method 1 |

TABLE-continued

*Co. No. means compound number; Retention time (R$_t$) in min; MP means melting point (° C.); dec means decomposition; n.d. means not determined.*

| Co No. | Compound | MP | Kofler (K) or DSC | Rt | [M + H]⁺ | LCMS Method |
|---|---|---|---|---|---|---|
| 20 | | 150 | K | 2.91 | 602 | Method 1 |
| 21 | | 105-113 gum | K | 2.46 | 433 | Method 1 |
| 22 | | 110 | K | 2.55 | 546 | Method 1 |
| 23 | | 226 | K | 2.69 | 567 | Method 1 |

TABLE-continued
Co. No. means compound number; Retention time (R$_t$) in min; MP means melting point (° C.); dec means decomposition; n.d. means not determined.
| Co No. | Compound | MP | Kofler (K) or DSC | Rt | [M + H]$^+$ | LCMS Method |
|---|---|---|---|---|---|---|
| 24 | 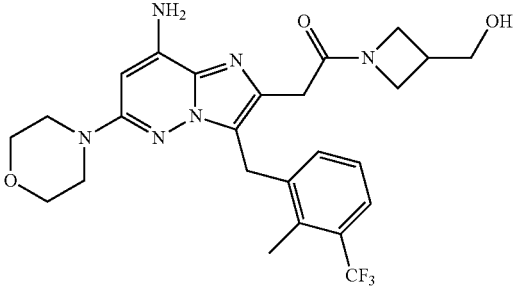 [SMILES: Cc1c(Cc2c(CC(=O)N3CC(CO)C3)nc3c(N)cc(N4CCOCC4)nn23)cccc1C(F)(F)F] | 130 | K | 2.48 | 519 | Method 1 |
| 25 | 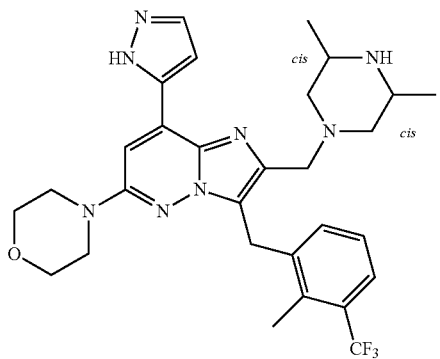 [SMILES: Cc1c(Cc2c(CN3CC(C)NC(C)C3)nc3c(-c4ccn[nH]4)cc(N4CCOCC4)nn23)cccc1C(F)(F)F] | 159 | K | 2.71 | 569 | Method 1 |
| 26 | 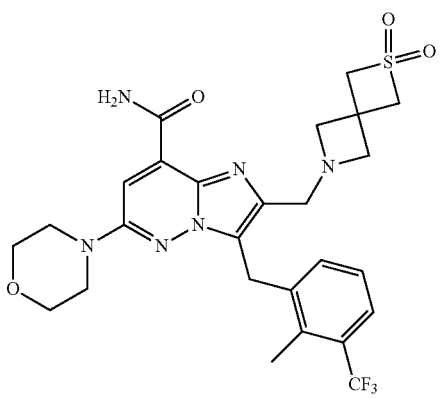 [SMILES: Cc1c(Cc2c(CN3CC4(C3)CS(=O)(=O)C4)nc3c(C(N)=O)cc(N4CCOCC4)nn23)cccc1C(F)(F)F] | 216 | K | 2.79 | 579 | Method 1 |
| 27 | 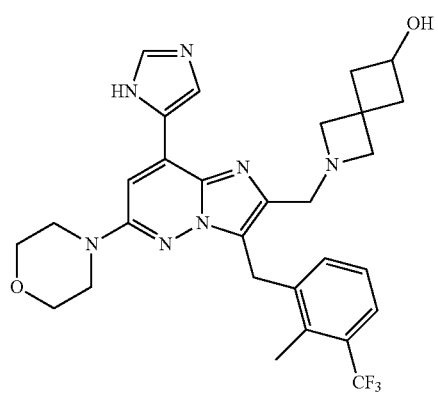 •HCOOH | Gum 120 | K | 2.47 | 568 | Method 1 |

TABLE-continued
Co. No. means compound number; Retention time (R_t) in min; MP means melting point (° C.); dec means decomposition; n.d. means not determined.
| Co No. | Compound | MP | Kofler (K) or DSC | Rt | [M + H]+ | LCMS Method |
|---|---|---|---|---|---|---|
| 28 | 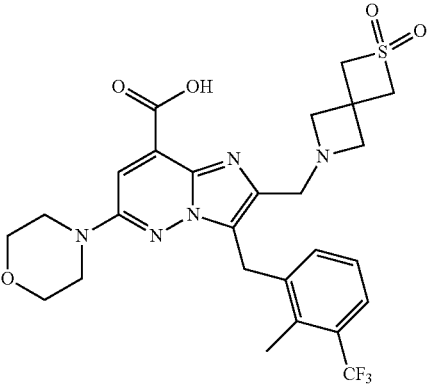 [SMILES: Cc1c(Cc2c(CN3CC4(C3)CS(=O)(=O)C4)nc3c(C(=O)O)cc(N4CCOCC4)nn23)cccc1C(F)(F)F] | n.d. | | 2.21 | 580 | Method 1 |
| 29 | 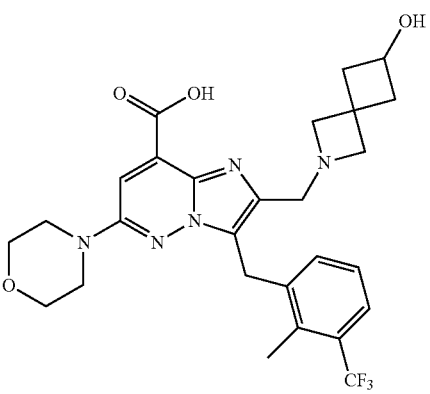 [SMILES: Cc1c(Cc2c(CN3CC4(CC(O)C4)C3)nc3c(C(=O)O)cc(N4CCOCC4)nn23)cccc1C(F)(F)F] | n.d. | | 2.12 | 546 | Method 1 |
| 30 | 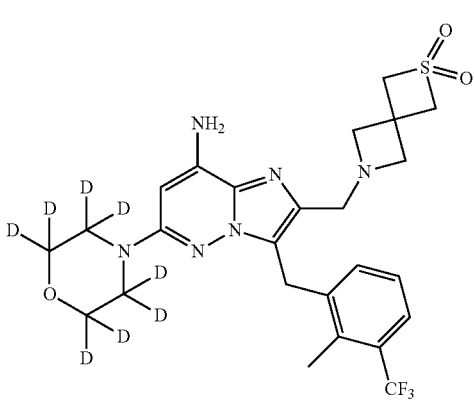 [SMILES: [2H]C1([2H])OC([2H])([2H])C([2H])([2H])N(c2cc(N)c3nc(CN4CC5(C4)CS(=O)(=O)C5)c(Cc4cccc(C(F)(F)F)c4C)n3n2)C1([2H])[2H]] | 207 | DSC | 2.79 | 559 | Method 1 |
| 31 | 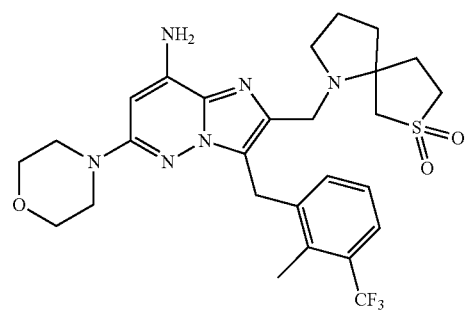 [SMILES: Cc1c(Cc2c(CN3CCCC34CCS(=O)(=O)C4)nc3c(N)cc(N4CCOCC4)nn23)cccc1C(F)(F)F] | n.d. | | 2.97 | 579 | Method 1 |

TABLE-continued

*Co. No. means compound number; Retention time (R$_t$) in min; MP means melting point (° C.); dec means decomposition; n.d. means not determined.*

| Co No. | Compound | MP | Kofler (K) or DSC | Rt | [M + H]$^+$ | LCMS Method |
|---|---|---|---|---|---|---|
| 32 | | 214 | DSC | 2.95 | 565 | Method 1 |
| 33 | | 228 | DSC | 3.02 | 593 | Method 1 |
| 34 | | n.d. | | 2.90 | 579 | Method 1 |
| 35 | | 211 | K | 2.52 | 518 | Method 1 |

TABLE-continued

Co. No. means compound number; Retention time (R_t) in min; MP means melting point (° C.); dec means decomposition; n.d. means not determined.

| Co No. | Compound | MP | Kofler (K) or DSC | Rt | [M + H]+ | LCMS Method |
|---|---|---|---|---|---|---|
| 36 | | 140 (gum) | K | 2.42 | 534 | Method 1 |
| 37 | | 212 | DSC | 2.54 | 518 | Method 1 |
| 38 | | n.d. | | 2.72 | 536 | Method 1 |
| 39 | | 101 | DSC | 2.88 | 532 | Method 1 |
| 40a | | n.d. | | — | — | — |

TABLE-continued

*Co. No. means compound number; Retention time (R_t) in min; MP means melting point (° C.); dec means decomposition; n.d. means not determined.*

| Co No. | Compound | MP | Kofler (K) or DSC | Rt | [M + H]⁺ | LCMS Method |
|---|---|---|---|---|---|---|
| 40b | | 99° C. | DSC | 2.63 | 562 | Method 1 |
| 41 | | 183 | DSC | 2.28 | 548 | Method 2 |
| 42 | | 214 | K | 2.28 | 427 | Method 1 |
| 43 | | 130 (gum) | K | 2.62 | Fragment m/z 357 (peak 489) | Method 1 |

TABLE-continued

Co. No. means compound number; Retention time (R$_t$) in min; MP means melting point (° C.); dec means decomposition; n.d. means not determined.

| Co No. | Compound | MP | Kofler (K) or DSC | Rt | [M + H]$^+$ | LCMS Method |
|---|---|---|---|---|---|---|
| 44 | 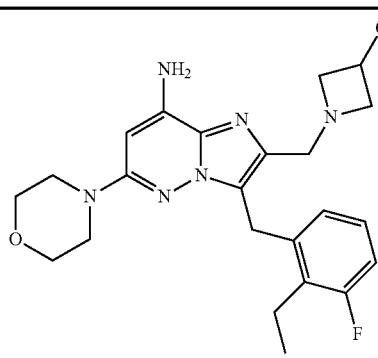 | 172 | K | 2.37 | 441 | Method 1 |
| 45 | 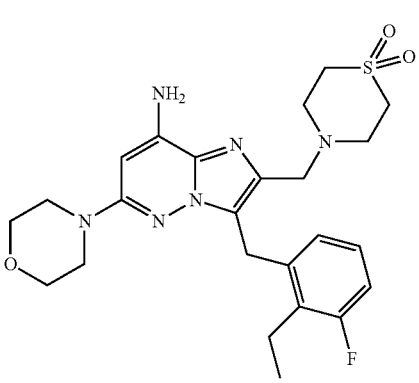 [SMILES: CCc1c(F)cccc1Cc1c(CN2CCS(=O)(=O)CC2)nc2c(N)cc(N3CCOCC3)nn12] | 240 | K | 2.73 | 503 | Method 1 |

OR data: Solvent: DMF; temperature: 20° C.; wavelength: 589 nm

| Compound number | OR | Concentration (g/100 mL) |
|---|---|---|
| 35 | −20.8 | 0.250 |
| 36 | −17.16 | 0.326 |
| 37 | +19.86 | 0.262 |
| 38 | −15.23 | 0.263 |
| 39 | −8.35 | 0.215 |

1H NMR data:

Compound 7:
$^1$H NMR (DMSO-d$_6$): 7.45-7.54 (m, 1H), 7.17-7.28 (m, 2H), 6.51 (s, 2H), 5.86 (s, 1H), 4.23-4.33 (m, 6H), 3.58-3.67 (m, 4H), 3.57 (s, 2H), 3.28 (s, 4H), 3.11-3.20 (m, 4H), 2.45 (s, 3H)

Compound 2 (0.8 HCOOH based on $^1$H NMR):
$^1$H NMR (DMSO-d$_6$): 8.14 (s, 1H), 7.50 (d, J=7.3 Hz, 1H), 7.19-7.30 (m, 2H), 6.53 (s, 2H), 5.86 (s, 1H), 4.25 (s, 2H), 3.92-4.02 (m, 2H), 3.57-3.71 (m, 8H), 3.24-3.28 (m, 2H), 3.11-3.19 (m, 4H), 2.46 (s, 3H), 2.11-2.21 (m, 2H).

Compound 1:
$^1$H NMR (DMSO-d$_6$): 12.56 (br. s., 1H), 8.39 (br. s., 1H), 7.89 (s, 1H), 7.52 (t, J×4.6 Hz, 1H), 7.44 (s, 1H), 7.25 (d, J=4.6 Hz, 2H), 4.34 (s, 2H), 4.27 (s, 4H), 3.63-3.71 (m, 6H), 3.45 (s, 4H), 3.29-3.36 (m, 4H—partially obscured by solvent peak), 2.45 (s, 3H—partially obscured by solvent peak).

Pharmacology

Enzyme Binding Assays (KINOMEscan®)

Kinase enzyme binding affinities of compounds disclosed herein were determined using the KINOMEscan technology performed by DiscoveRx Corporation, San Diego, Calif., USA (www.kinomescan.com). Table A reports the obtained Kd values (nM), with the Kd being the inhibitor binding constant:

| Compound | Kd PIK3Cα_h (nM) | Kd PIK3Cβ_h (nM) | Kd PIK3Cδ_h (nM) | Kd PIK3Cγ_h (nM) | Kd MTOR_h (nM) |
|---|---|---|---|---|---|
| 26 | 692 | 3.0 | 372 | 10715 | >30200 |
| 24 | 3162 | 0.5 | 52 | 16982 | 3981 |
| 23 | 2239 | 1.5 | 240 | >30200 | >30200 |
| 1 | 162 | 1.2 | 12 | 933 | 3162 |
| 20 | 275 | 1.3 | 32 | 1549 | 9333 |
| 22 | 2239 | 0.5 | 56 | 8913 | 10715 |
| 3 | 11482 | 1.7 | 191 | 16218 | 10965 |

-continued

| Compound | Kd PIK3Cα_h (nM) | Kd PIK3Cβ_h (nM) | Kd PIK3Cδ_h (nM) | Kd PIK3Cγ_h (nM) | Kd MTOR_h (nM) |
|---|---|---|---|---|---|
| 19 | 513 | 1.6 | 52 | 891 | 4365 |
| 2 | 5495 | 2.1 | 23 | >30200 | 21380 |
| 4 | 3981 | 2.3 | 166 | >30200 | >30200 |
| 5 | 12023 | 3.6 | 219 | >30200 | >30200 |
| 17 | 813 | <1.5 | 79 | 6761 | >30200 |
| 15 | 537 | 1.4 | 22 | 2188 | 7762 |
| 6 | 7079 | 2.4 | 263 | >30200 | 21878 |
| 7 | 436 | 0.5 | 8 | 27608 | 11366 |
| 8 | 11482 | 1.6 | 195 | 30903 | 15488 |
| 9 | 14454 | 0.6 | 65 | >30200 | >30200 |
| 10 | 4786 | 0.6 | 52 | >30200 | 5754 |
| 11 | 1862 | 0.7 | 81 | >30200 | 11749 |
| 12 | 18621 | 1.7 | 89 | 8511 | 10965 |
| 13 | 1380 | 0.2 | 7 | 977 | 3548 |
| 14 | 7413 | 0.3 | 40 | 4898 | 13804 |
| 16 | 453 | 0.7 | 17 | 5697 | 2005 |
| 18 | 475 | 0.8 | 14 | 3893 | 6069 |
| 25 | 1148 | 2.0 | 98 | 5248 | 407 |
| 21 | 1288 | 1.1 | 129 | 4169 | 19953 |
| 27 | 240 | 0.4 | 10 | 589 | 1549 |
| 29 | 6310 | 0.7 | 112 | 28184 | >30200 |
| 28 | 372 | 0.2 | 13 | 15136 | 21380 |
| 30 | 617 | 0.3 | 12 | 19953 | 8128 |
| 35 | 2054 | 0.2 | 7 | 8641 | 3217 |
| 36 | 1386 | 0.1 | 5 | 3003 | 3143 |
| 37 | 5495 | 0.8 | 68 | 4898 | 5129 |
| 38 | 1000 | 0.2 | 14 | >30200 | 355 |
| 39 | 3548 | 0.3 | 82 | 11683 | 7392 |
| 40b | 25119 | 2.8 | 479 | >30200 | 21878 |
| 31 | >30200 | 4.8 | 479 | >30200 | >30200 |
| 32 | 15136 | 2.5 | 251 | >30200 | >30200 |
| 33 | 13490 | 3.0 | 398 | >30200 | >30200 |
| 34 | 6310 | 1.5 | 224 | >30200 | 18197 |
| 41 | 5370 | 0.4 | 48 | 21380 | 6761 |
| 42 | 4467 | 1.1 | 123 | 2692 | 1230 |
| 43 | 2042 | 0.4 | 62 | >30200 | 1380 |
| 44 | 1698 | 5.4 | 275 | 537 | 1047 |
| 45 | 2399 | 1.1 | 178 | >30200 | 1995 |

Cellular Assays

Cellular activity of PI3Kβ inhibitors was determined by quantifying the phosphorylation of Akt in PC-3 cells. Akt phosphorylated at Ser473 and Thr308 were measured using an enzyme-linked immunosorbent assay (ELISA; Meso Scale Discovery (MSD). Gaithersburg, Md.) and specific primary antibodies from MSD.

On day 1, PC3 cells (ATCC #CRL-14351) were seeded into PerkinElmer MW96 plates at 25.000 cells per well, in 75 μl complete culture medium (DMEM (Dulbecco's Modified Eagle's Medium) high glucose. AQmedia™, D0819, Sigma-Aldrich) containing 10% heat inactivated FCS (Fetal Bovine Serum) and incubated at 37° C., 5% $CO_2$ during 24 hours. On day 2, compound or DMSO (dimethyl sulfoxide) (0.3%) was added and cells were further incubated for 60 min at 37° C., 5% $CO_2$ in a total volume of 100 μl of medium.

The phosphoprotein assay was executed according to vendor instructions in the Phospho-Akt (Ser473) Assay Whole Cell Lysate Kit (MSD #K15100D-3) and the Phospho-Akt (Thr308) Assay Whole Cell Lysate Kit (MSD #K151DYD-3) using the lysis, blocking and wash buffer provided.

Briefly, at the end of the cell treatment period, media were removed by aspiration and adherent cells were lysed in 50 μl ice-cold lysis buffer. MSD plates are supplied pre-coated with capture antibodies for Phospho-Akt (Ser473 and Thr308). After blocking, lysates from tissue culture plates were added and plates were washed. Then, a solution containing the detection antibody (anti-total Akt conjugated with an electrochemiluminescent compound-MSD Sulfo-tag label) was added. The signals were detected using an MSD SECTOR Imager 6000 and are proportional to the phospho-Akt titres.

Data were processed. The percentage of inhibition was plotted against the log concentration of test compounds, and the sigmoidal log concentration-effect curve of best fit was calculated by nonlinear regression analysis. From these concentration-response curves, the $IC_{50}$ values were calculated. Five concentrations were used for curve fitting.

Table B reports the obtained $IC_{50}$ values (nM):

| Compound | $IC_{50}$ pAkt_S473 (nM) | $IC_{50}$ pAkt_Thr308 (nM) | Compound | $IC_{50}$ pAkt_S473 (nM) | $IC_{50}$ pAkt_Thr308 (nM) |
|---|---|---|---|---|---|
| 26 | 275 | ~62 | 18 | 95 | 51 |
| 24 | 49 | 15 | 25 | 214 | 234 |
| 23 | ~79 | ~68 | 21 | 107 | ~69 |

-continued

| Compound | IC$_{50}$ pAkt_S473 (nM) | IC$_{50}$ pAkt_Thr308 (nM) | Compound | IC$_{50}$ pAkt_S473 (nM) | IC$_{50}$ pAkt_Thr308 (nM) |
|---|---|---|---|---|---|
| 1  | 9    | ~4  | 27  | 62   | 43   |
| 20 | ~34  | ~20 | 29  | >513 | >513 |
| 22 | 45   | ~26 | 28  | >513 | >513 |
| 3  | ~89  | 66  | 30  | 4    | 4    |
| 19 | 50   | 54  | 35  | 27   | 18   |
| 2  | 6    | ~4  | 36  | ~73  | ~50  |
| 4  | 18   | ~33 | 37  | 158  | 141  |
| 5  | ~132 | 71  | 38  | 54   | 31   |
| 17 | 65   | 58  | 39  | 44   | 38   |
| 15 | 30   | ~41 | 40b | 214  | 105  |
| 6  | 40   | ~13 | 31  | 117  | 66   |
| 7  | 4    | 3   | 32  | 91   | 74   |
| 8  | 25   | ~20 | 33  | 120  | 100  |
| 9  | 76   | ~39 | 34  | 87   | ~74  |
| 10 | ~42  | ~48 | 41  | 60   | 18   |
| 11 | 10   | 7   | 42  | 117  | 55   |
| 12 | 85   | ~87 | 43  | 10   | 17   |
| 13 | 28   | 44  | 44  | 316  | 145  |
| 14 | 68   | 69  | 45  | >513 | >513 |
| 16 | 38   | 28  |     |      |      |

Composition Examples

"Active ingredient" (a.i.) as used throughout these examples relates to a compound of Formula (I), including any tautomer or stereoisomeric form thereof, or a N-oxide, a pharmaceutically acceptable addition salt or a solvate thereof; in particular to any one of the exemplified compounds.

Typical examples of recipes for the formulation of the invention are as follows:

1. Tablets

| | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:

1. A compound of Formula (I)

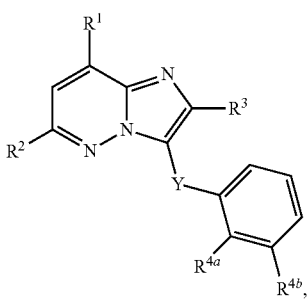

a tautomer or a stereoisomeric form thereof, wherein
R$^1$ represents —C(=O)OH, —C(=O)NH$_2$, —NH$_2$,

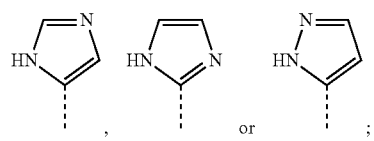

R$^2$ represents

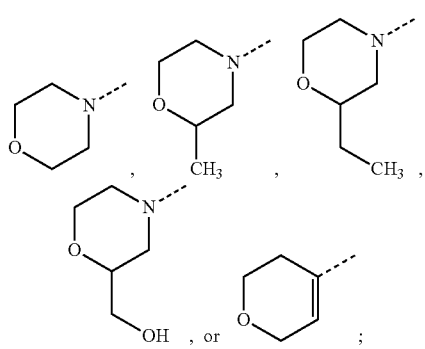

R³ represents C₁₋₄alkyl substituted with one substituent selected from the group consisting of Het¹, —O—C(=O)—C₁₋₄alkyl-Het¹, —C(=O)-Het¹, and —NH—C(=O)-Het¹; —CH(OH)—CH₂-Het¹; or C₁₋₄alkyl substituted on the same carbon atom with one —OH and with one Het¹;

Het¹ represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of halo, —NH₂, C₁₋₄alkyl, —S(=O)₂—C₁₋₆alkyl, —C₁₋₄alkyl-S(=O)₂—C₁₋₆alkyl, hydroxy and C₁₋₄alkyl substituted with one hydroxy; or two substituents on the same carbon atom of said 4-, 5- or 6-membered saturated heterocyclyl are taken together to form together with the common carbon atom to which they are attached Ring A;

Ring A represents cyclobutyl, cyclopentyl, cyclohexyl or a 4-, 5- or 6-membered saturated heterocyclyl containing at least one heteroatom each independently selected from O, S, S(=O)$_p$ and N; said cyclobutyl, cyclopentyl, cyclohexyl or 4-, 5- or 6-membered saturated heterocyclyl is optionally substituted with one or two C₁₋₄alkyl substituents, with one C₁₋₄alkyl and one hydroxy substituent, or with one hydroxy substituent;

Y represents —CH₂— or —NH—;

R⁴ᵃ represents hydrogen, C₁₋₄alkyl, Hetᵃ, or C₁₋₄alkyl substituted with one or more substituents each independently selected from the group consisting of —OH, —NR⁵R⁶ and Hetᵃ;

R⁴ᵇ represents hydrogen, halo, C₁₋₄alkyl, or C₁₋₄alkyl substituted with one or more halo substituents;

or R⁴ᵃ and R⁴ᵇ are taken together to form together with the phenyl ring to which they are attached a structure of Formula (a-1), (a-2), (a-3), (a-4) or (a-5):

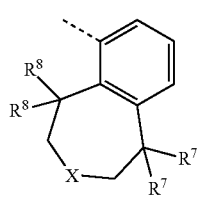

(a-1)

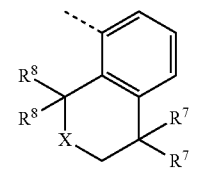

(a-2)

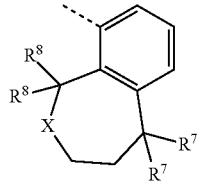

(a-3)

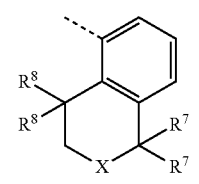

(a-4)

-continued

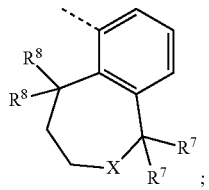

(a-5)

X represents —NH—, —O— or —N(C₁₋₃alkyl)-;

both R⁷ substituents are the same and are selected from the group consisting of hydrogen, fluoro and methyl; or both R⁷ substituents are taken together to form together with the common carbon atom to which they are attached a cyclopropyl, cyclobutyl or oxetanyl;

both R⁸ substituents are the same and are selected from the group consisting of hydrogen and methyl; or both R⁸ substituents are taken together to form together with the common carbon atom to which they are attached a cyclopropyl, cyclobutyl or oxetanyl;

R⁵ represents hydrogen, C₁₋₆alkyl, or C₁₋₆alkyl substituted with one OH;

R⁶ represents hydrogen, C₁₋₆alkyl, or C₁₋₆alkyl substituted with one OH;

each Hetᵃ independently represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of C₁₋₄alkyl, —S(=O)₂—C₁₋₆alkyl, hydroxy, —C₁₋₄alkyl-S(=O)₂—C₁₋₆alkyl, and C₁₋₄alkyl substituted with one hydroxy; or two substituents on the same carbon atom of said 4-, 5- or 6-membered saturated heterocyclyl are taken together to form together with the common carbon atom to which they are attached Ring B;

Ring B represents cyclobutyl, cyclopentyl, cyclohexyl or a 4-, 5- or 6-membered saturated heterocyclyl containing at least one heteroatom each independently selected from O, S, S(=O)$_p$ and N; said cyclobutyl, cyclopentyl, cyclohexyl or 4-, 5- or 6-membered saturated heterocyclyl is optionally substituted with one or two C₁₋₄alkyl substituents, with one C₁₋₄alkyl and one hydroxy substituent, or with one hydroxy substituent;

p represents 1 or 2;

or a N-oxide, a pharmaceutically acceptable addition salt or a solvate thereof.

2. The compound according to claim 1, wherein

R⁴ᵃ represents hydrogen, C₁₋₄alkyl, or C₁₋₄alkyl substituted with one or more —NR⁵R⁶ substituents;

R⁵ represents hydrogen, C₁₋₆alkyl, or C₁₋₆alkyl substituted with one OH;

R⁶ represents hydrogen, C₁₋₆alkyl, or C₁₋₆alkyl substituted with one OH.

3. The compound according to claim 1, wherein

R² represents

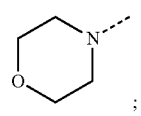

;

R³ represents C₁₋₄alkyl substituted with one substituent selected from the group consisting of Het¹, —O—C(=O)—C₁₋₄alkyl-Het¹, —C(=O)-Het¹, and —NH—C(=O)—Het¹; or —CH(OH)—CH₂-Het¹;

Het¹ represents a 4-, 5- or 6-membered saturated heterocyclyl containing at least one heteroatom each independently selected from S(=O)$_p$ and N; said 4-, 5- or 6-membered saturated heterocyclyl is optionally substituted with one or two substituents each independently selected from the group consisting of halo, —NH₂, C₁₋₄alkyl, —S(=O)₂—C₁₋₆alkyl, —C₁₋₄alkyl-S(=O)₂—C₁₋₆alkyl, hydroxy and C₁₋₄alkyl substituted with one hydroxy; or two substituents on the same carbon atom of said 4-, 5- or 6-membered saturated heterocyclyl are taken together to form together with the common carbon atom to which they are attached Ring A;

Ring A represents cyclobutyl, cyclopentyl, cyclohexyl or a 4-, 5- or 6-membered saturated heterocyclyl containing at least one heteroatom each independently selected from S(=O)$_p$ and N; said cyclobutyl, cyclopentyl, cyclohexyl or 4-, 5- or 6-membered saturated heterocyclyl is optionally substituted with one hydroxy substituent;

R$^{4a}$ represents C₁₋₄alkyl;
R$^{4b}$ represents C₁₋₄alkyl substituted with one or more halo substituents;
p represents 2.

4. The compound according to claim 1, wherein
R¹ represents —C(=O)NH₂, —NH₂,

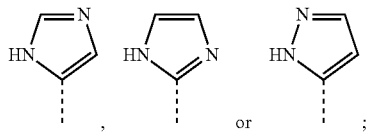

R² represents

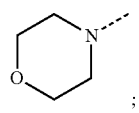

R³ represents C₁₋₄alkyl substituted with one substituent selected from the group consisting of Het¹ and —C(=O)—Het¹;

Het¹ represents a 4-, 5- or 6-membered saturated heterocyclyl containing at least one heteroatom each independently selected from S(=O)$_p$ and N; said 4-, 5- or 6-membered saturated heterocyclyl is optionally substituted with one or two substituents each independently selected from the group consisting of —NH₂, C₁₋₄alkyl, —S(=O)₂—C₁₋₆alkyl, hydroxy and C₁₋₄alkyl substituted with one hydroxy; or two substituents on the same carbon atom of said 4-, 5- or 6-membered saturated heterocyclyl are taken together to form together with the common carbon atom to which they are attached Ring A;

Ring A represents a 4-, 5- or 6-membered saturated heterocyclyl containing at least one heteroatom each independently selected from S(=O)$_p$ and N;

R$^{4a}$ represents C₁₋₄alkyl;

R$^{4b}$ represents C₁₋₄alkyl substituted with one or more halo substituents;
p represents 2.

5. The compound according to claim 1, wherein
R¹ represents —NH₂, or

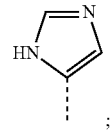

R² represents

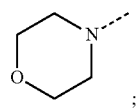

R³ represents C₁₋₄alkyl substituted with one Het¹;
Het¹ represents

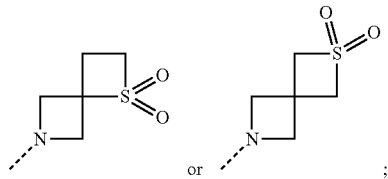

R$^{4a}$ represents C₁₋₄alkyl;
R$^{4b}$ represents C₁₋₄alkyl substituted with one or more halo substituents.

6. The compound according to claim 1, wherein Y represents —CH₂—.

7. The compound according to claim 1, wherein R¹ represents —C(=O)OH, —C(=O)NH₂, or —NH₂.

8. The compound according to claim 1, wherein
R$^{4a}$ represents C₁₋₄alkyl;
R$^{4b}$ represents C₁₋₄alkyl substituted with one or more halo substituents.

9. The compound according to claim 1, wherein
R¹ represents —NH₂;
R² represents

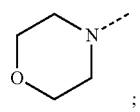

R³ represents C₁₋₄alkyl substituted with one substituent selected from the group consisting of —O—C(=O)—C₁₋₄alkyl-Het¹, and —NH—C(=O)—Het¹; or —CH(OH)—CH₂-Het¹;

Het¹ represents a 4-, 5- or 6-membered saturated heterocyclyl containing one or two heteroatoms each independently selected from S(=O)$_p$ and N; said 4-, 5- or 6-membered saturated heterocyclyl is optionally substituted with one or two substituents each independently selected from the group consisting of C₁₋₄alkyl, and hydroxy; or two substituents on the same carbon atom of said 4-, 5- or 6-membered saturated heterocyclyl are taken together to form together with the common carbon atom to which they are attached Ring A;

Ring A represents a 4-, 5- or 6-membered saturated heterocyclyl containing one or two heteroatoms each independently selected from $S(=O)_p$ and N;

Y represents —CH$_2$—;

$R^{4a}$ represents C$_{1-4}$alkyl;

$R^{4b}$ represents C$_{1-4}$alkyl substituted with one or more halo substituents;

p represents 2.

10. The compound according to claim 1, wherein
Y represents —NH—.

11. A pharmaceutical composition comprising a pharmaceutically acceptable carrier and, as active ingredient, a therapeutically effective amount of a compound according to claim 1.

12. A method of treating a disease or condition selected from the group consisting of cancer, autoimmune disorders, cardiovascular diseases, inflammatory diseases, neurodegenerative diseases, allergy, pancreatitis, asthma, multiorgan failure, kidney diseases, platelet aggregation, sperm motility, transplantation rejection, graft rejection, and lung injuries in a human, comprising administering a therapeutically effective amount of a compound of claim 1.

13. The method according to claim 12 wherein the disease or condition is cancer.

14. The method according to claim 13 wherein the disease or condition is prostate cancer.

* * * * *